(12) United States Patent
Stoessel et al.

(10) Patent No.: US 9,273,080 B2
(45) Date of Patent: Mar. 1, 2016

(54) METAL COMPLEXES

(75) Inventors: Philipp Stoessel, Frankfurt am Main (DE); Holger Heil, Frankfurt am Main (DE); Dominik Joosten, Frankfurt am Main (DE); Christof Pflumm, Darmstadt (DE); Anja Gerhard, Egelsbach (DE); Esther Breuning, Ober-Ramstadt (DE)

(73) Assignee: Merek Patent GmbH (DE)

( * ) Notice: Subject to any disclaimer, the term of this patent is extended or adjusted under 35 U.S.C. 154(b) by 465 days.

(21) Appl. No.: 13/703,683

(22) PCT Filed: May 18, 2011

(86) PCT No.: PCT/EP2011/002467
§ 371 (c)(1),
(2), (4) Date: Dec. 12, 2012

(87) PCT Pub. No.: WO2011/157339
PCT Pub. Date: Dec. 22, 2011

(65) Prior Publication Data
US 2013/0082209 A1    Apr. 4, 2013

(30) Foreign Application Priority Data

Jun. 15, 2010  (EP) .................................... 10006208

(51) Int. Cl.
*C07F 15/00*    (2006.01)
*C07F 19/00*    (2006.01)
*C09K 11/06*    (2006.01)
*H05B 33/14*    (2006.01)
*H01L 51/50*    (2006.01)

(52) U.S. Cl.
CPC ......... *C07F 15/0033* (2013.01); *C07F 15/0086* (2013.01); *C07F 19/00* (2013.01); *C09K 11/06* (2013.01); *H05B 33/14* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *C09K 2211/185* (2013.01); *H01L 51/5016* (2013.01)

(58) Field of Classification Search
None
See application file for complete search history.

(56) References Cited

U.S. PATENT DOCUMENTS

2007/0190359 A1* 8/2007 Knowles et al. ............. 428/690
2011/0284799 A1  11/2011 Stoessel et al.

FOREIGN PATENT DOCUMENTS

WO   WO-2007/095118 A2   8/2007
WO   WO-2010/086089 A1   8/2010

OTHER PUBLICATIONS

International Search Report for PCT/EP2011/002467 mailed Aug. 8, 2011.

* cited by examiner

*Primary Examiner* — Ling Choi
*Assistant Examiner* — Catherine S Branch
(74) *Attorney, Agent, or Firm* — Drinker Biddle & Reath LLP

(57) ABSTRACT

The present invention relates to metal complexes and to electronic devices, in particular organic electroluminescent devices, containing these metal complexes. M(L)n(L')m (formula 1), where the compound of the general formula (1) contains a moiety M(L)n of the formula (2).

18 Claims, No Drawings

METAL COMPLEXES

CROSS-REFERENCE TO RELATED APPLICATIONS

This application is a national stage application (under 35 U.S.C. §371) of PCT/EP2011/002467, filed May 18, 2011, which claims benefit of European application 10006208.2, filed Jun. 15, 2010 which are both incorporated by reference.

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold energy and power efficiency is possible using organometallic compounds as phosphorescent emitters. In general, there is still a need for improvement in OLEDs which exhibit triplet emission, in particular with respect to efficiency, operating voltage and lifetime. This applies, in particular, to OLEDs which emit in the relatively short-wave region, i.e. green and in particular blue.

In accordance with the prior art, iridium complexes, in particular, are employed as triplet emitters in phosphorescent OLEDs. It has been possible to achieve an improvement in these OLEDs by employing metal complexes with polypodal ligands or cryptates, causing the complexes to have higher thermal stability, which results in a longer lifetime of the OLEDs (WO 2004/081017, WO 2005/113563, WO 2006/008069). For blue emission, in particular for saturated deep-blue emission, however, these complexes are less suitable, as are the unbridged complexes.

The prior art furthermore discloses iridium complexes which contain imidazophenanthridine derivatives or diimidazoquinazoline derivatives as ligands (WO 2007/095118). These complexes may result in blue phosphorescence on use in organic electroluminescent devices, depending on the precise structure of the ligand. Here too, further improvements with respect to efficiency, operating voltage and lifetime are still desirable. Furthermore, there is also still a need for improvement here with respect to the colour coordinates in order to be able to achieve deep-blue emission.

WO 2010/086089 discloses metal complexes which contain imidazoisoquinoline derivatives as ligands. Good advances in the development of blue triplet emitters have already been achieved using complexes of this type. However, further improvements with respect to efficiency, operating voltage and lifetime are also still desirable here. In particular, there is also still a need for improvement here with respect to the colour coordinates in order to be able to achieve deep-blue emission, and with respect to the yield with which the complexes can be synthesised.

The object of the present invention is therefore the provision of novel metal complexes which are suitable as emitters for use in OLEDs. In particular, the object is to provide emitters which are suitable for blue-phosphorescent OLEDs and which exhibit improved properties with respect to efficiency, operating voltage, lifetime and/or colour coordinates and/or which can be prepared with improved yield.

Surprisingly, it has been found that certain metal chelate complexes described in greater detail below achieve this object and result in improvements in the organic electroluminescent device. Furthermore, these metal complexes are accessible in high yield. The present invention therefore relates to these metal complexes and to organic electroluminescent devices which comprise these complexes.

The invention thus relates to a compound of the formula (1),

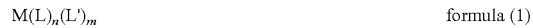

$$M(L)_n(L')_m \quad \text{formula (1)}$$

where the compound of the general formula (1) contains a moiety $M(L)_n$ of the formula (2):

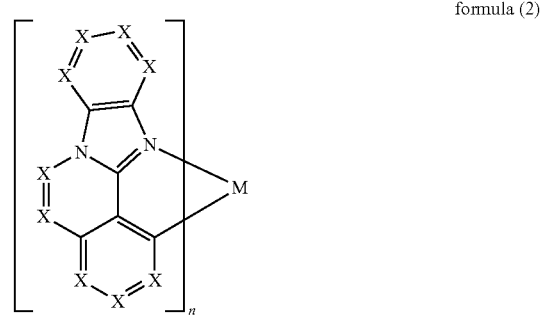

formula (2)

where the following applies to the symbols and indices used:

M is a metal;

X is selected on each occurrence, identically or differently, from the group consisting of CR, CR$^1$ and N, with the proviso that at least one X=N and that at least one X which is adjacent to this N stands for CR$^1$;

R is on each occurrence, identically or differently, H, D, F, Cl, Br, I, N(R$^2$)$_2$, CN, NO$_2$, OH, COOH, C(=O)N(R$^2$)$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals R$^2$, where one or more non-adjacent CH$_2$ groups may be replaced by R$^2$C=CR$^2$, C≡C, Si(R$^2$)$_2$, C=O, NR$^2$, O, S or CONR$^2$ and where one or more H atoms may be replaced by D, F, Cl, Br, I or CN, or an aromatic or heteroaromatic ring system having 5 to 60 aromatic ring atoms, which may in each case be substituted by one or more radicals R$^2$, or an aryloxy or heteroaryloxy group having 5 to 40 aromatic ring atoms, which may be substituted by one or more radicals R$^2$, or an aralkyl or heteroaralkyl group having 5 to 40 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$; two adjacent radicals R or R with R$^1$ here may also form a mono- or polycyclic, aliphatic ring system with one another;

R$^1$ is on each occurrence, identically or differently, CF$_3$, OCF$_3$, a branched or cyclic alkyl or alkoxy group having 3 to 20 C atoms, which may in each case be substituted by one or more radicals R$^2$, where one or more non-adjacent CH$_2$ groups which are not bonded directly to the aromatic carbon atom of the ligand may be replaced by R$^2$C=CR$^2$, C≡C, Si(R$^2$)$_2$, C=O, NR$^2$, O, S or CONR$^2$ and where one or more H atoms may be replaced by D, F, Cl, Br, I or CN, or Si(R$^2$)$_3$, where R$^2$ is not equal to H or D, a dialkylamino group, where the alkyl groups each have 1 to 10 C atoms and may be linear, branched or cyclic, or an aromatic or heteroaromatic ring system having 5 to 60 aromatic ring atoms, which may in each case be substituted by one or more radicals R², or an aralkyl or heteroaralkyl group having 5 to 40 aromatic ring atoms, which may be substituted by one or more radicals R²;

R² is on each occurrence, identically or differently, H, D, F, Cl, Br, I, N(R³)₂, CN, NO₂, Si(R³)₃, B(OR³)₂, C(=O)R³, P(=O)(R³)₂, S(=O)R³, S(=O)₂R³, OSO₂R³, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals R³, where one or more non-adjacent CH₂ groups may be replaced by R³C=CR³, C≡C, Si(R³)₂, C=O, NR³, O, S or CONR³ and where one or more H atoms may be replaced by D, F, Cl, Br, I, CN or NO₂, or an aromatic or heteroaromatic ring system having 5 to 60 aromatic ring atoms, which may in each case be substituted by one or more radicals R³, or an aryloxy or heteroaryloxy group having 5 to 40 aromatic ring atoms, which may be substituted by one or more radicals R³, or an aralkyl or heteroaralkyl group having 5 to 40 aromatic ring atoms, which may be substituted by one or more radicals R³, or a diarylamino group, diheteroarylamino group or arylheteroarylamino group having 10 to 40 aromatic ring atoms, which may be substituted by one or more radicals R³; two or more adjacent radicals R³ here may form a mono- or polycyclic, aliphatic ring system with one another;

R³ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R³ here may also form a mono- or polycyclic, aliphatic ring system with one another;

L' is, identically or differently on each occurrence, any desired co-ligand;

n is 1, 2 or 3;

m is 0, 1, 2, 3 or 4;

a plurality of ligands L may also be linked to one another or L may be linked to L' via a single bond or any desired bridge V and thus form a tridentate, tetradentate, pentadentate or hexadentate ligand system;

a substituent R or R¹ may also additionally be coordinated to the metal;

with the proviso that R¹ stands for a branched or cyclic alkyl group having 4 to 20 C atoms, which may in each case be substituted by one or more radicals R², where one or more non-adjacent CH₂ groups which are not bonded directly to the aromatic carbon atom of the ligand may be replaced by R²C=CR², C≡C, Si(R²)₂, C=O, NR², O, S or CONR² and where one or more H atoms may be replaced by D, F, Cl, Br, I or CN, or for a bi- or oligoaryl or -heteroaryl group having 10 to 60 aromatic ring atoms or for an aryl or heteroaryl group which is substituted by a radical R² other than H or D in at least one ortho-position to the link to the ligand if the moiety conforms to one of the following formulae (3), (4), (5) or (6):

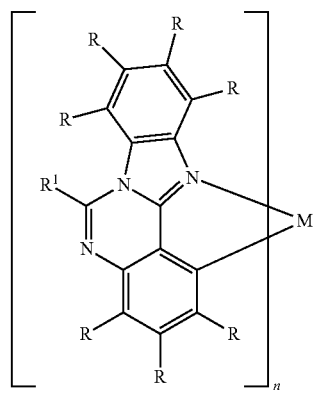

formula (3)

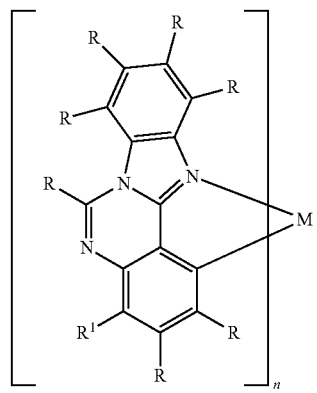

formula (4)

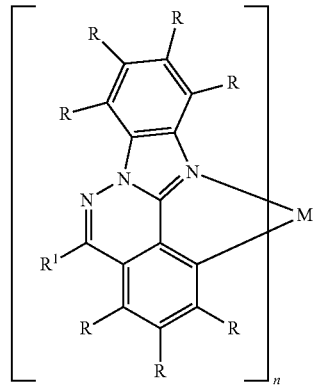

formula (5)

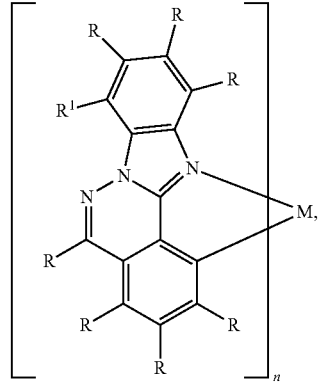

formula (6)

where the symbols and indices used have the above-mentioned meanings.

In the definition of X, "at least one X which is adjacent to this N" means that this X may be bonded directly to the nitrogen or it is the next-possible position in which an X is present in formula (2). This is explained again in the diagrammatic representation below with reference to two specific ligands:

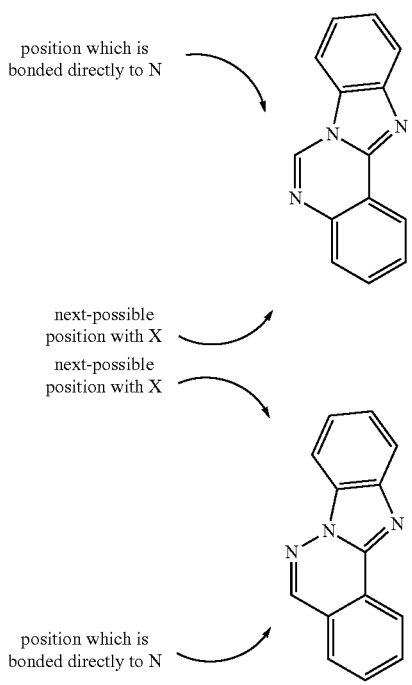

In this representation, both the position which is bonded directly to the nitrogen and also the next-possible position in which an X is present is marked. Both positions are regarded as adjacent positions to the nitrogen atom in the sense of the present application.

As defined above for the symbol X, it is essential to the invention that at least one group X stands for N and that a further group X which is adjacent to this nitrogen atom stands for a group $CR^1$, i.e. for a carbon atom which is substituted by one of the groups $R^1$ defined above.

In the complexes of the formula (1), the indices n and m are selected so that the coordination number on the metal M in total, depending on the metal, corresponds to the coordination number which is usual for this metal. For transition metals, this is usually the coordination number 4, 5 or 6, depending on the metal. It is generally known that metal coordination compounds have different coordination numbers, i.e. bind a different number of ligands, depending on the metal and on the oxidation state of the metal. Since the preferred coordination numbers of metals or metal ions in various oxidation states belong to the general expert knowledge of the person skilled in the art in the area of organometallic chemistry or coordination chemistry, it is straightforward for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S.

An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or transdibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charge of the ligands L and L' in such a way that they compensate for the charge of the complexed metal atom M.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal or for a main-group metal. If M stands for a main-group metal, it then preferably stands for a metal from the third, fourth or fifth main group, in particular for tin.

Preference is given to compounds of the formula (1) in which M stands for a transition metal, where lanthanides and actinides are excluded, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(O), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V). Particular preference is given to Mo(0), W(0), Re(I), Ru(II), Os(II), Rh(III), Cu(I), Ir(III) and Pt(II). Very particular preference is given to Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0. A preferred tetracoordinated metal is Pt(II).

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0. A preferred hexacoordinated metal is Ir(III).

In the ligand L, preferably one, two, three or four groups X, particularly preferably one, two or three groups X, very particularly preferably one or two groups X, stand for N.

In a further preferred embodiment of the invention, for each X which stands for N, at least one X which is adjacent to this N stands for $CR^1$.

If precisely one group X stands for N, preferred moieties of the formula (2) are the moieties of the following formulae (7) to (13),

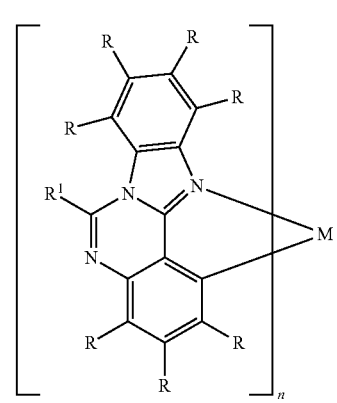

formula (7)

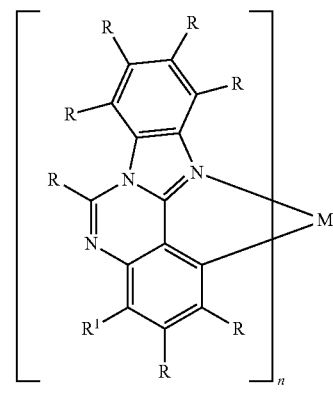

formula (8)

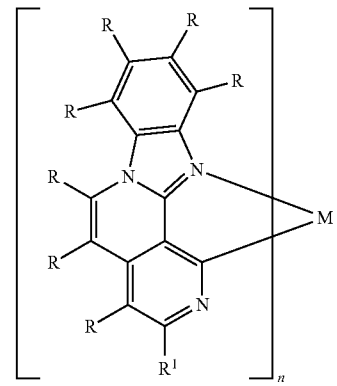

formula (9)

-continued
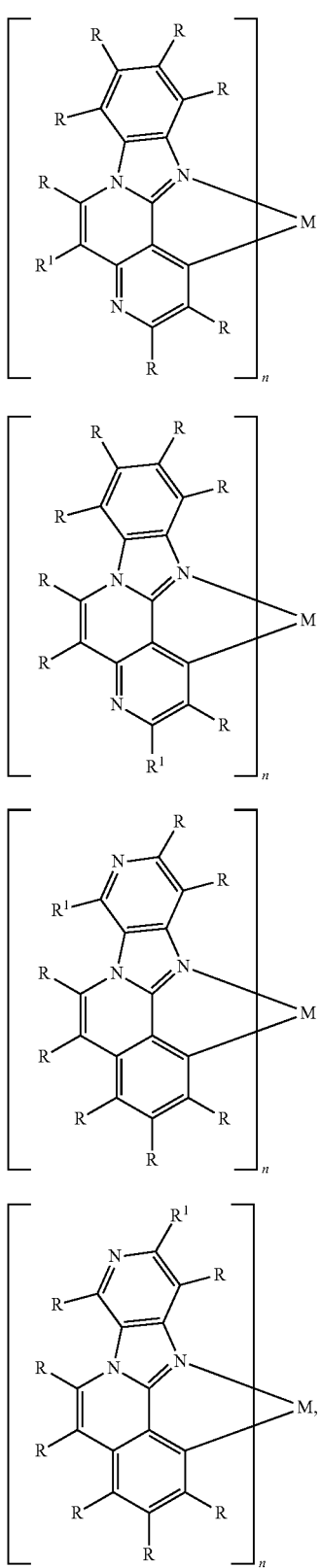
formula (10)
formula (11)
formula (12)
formula (13)
where the symbols and indices used have the above-mentioned meanings, and $R^1$ in formulae (7) and (8) has the narrower meaning defined above in the case of formula (1).
If two groups X stand for N, preferred moieties of the formula (2) are the moieties of the following formulae (14) to (27),
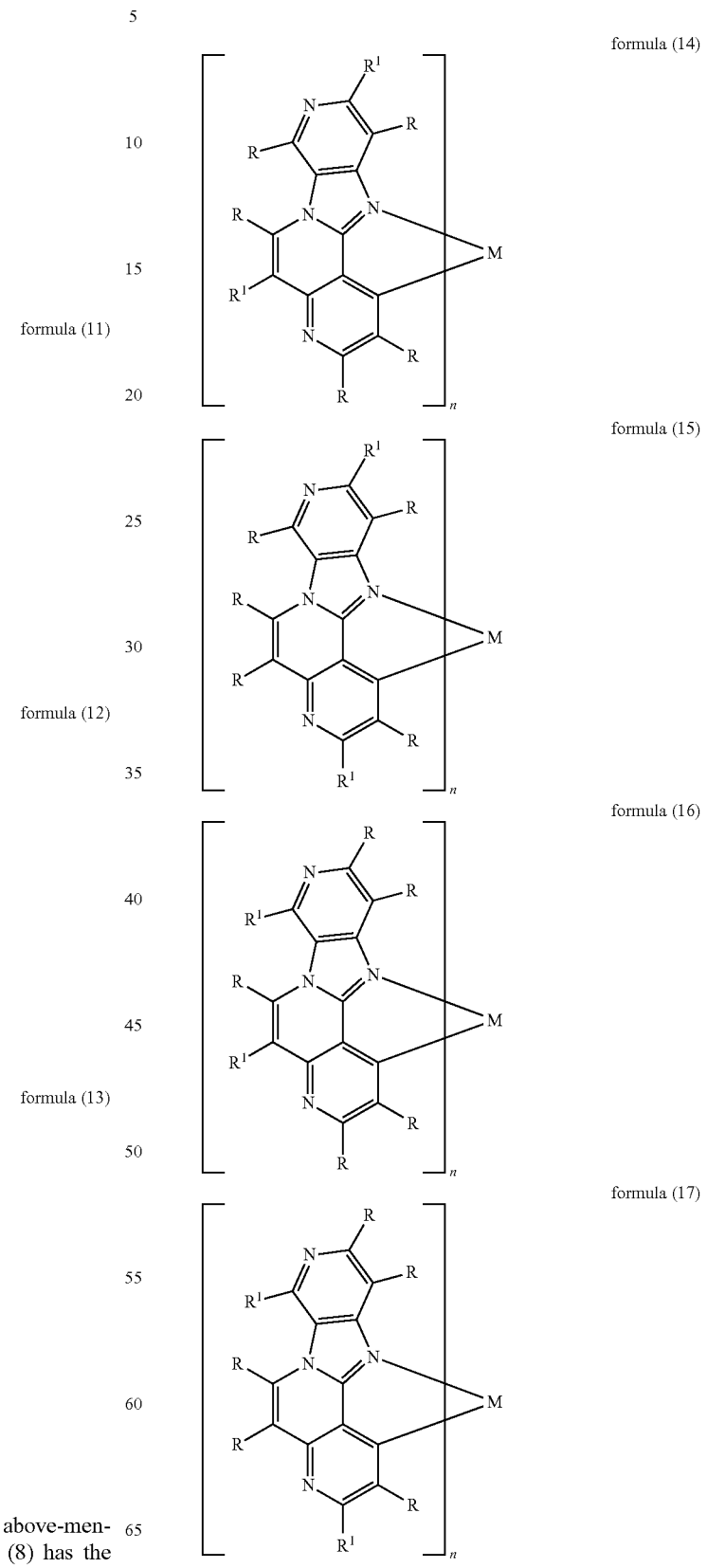
formula (14)
formula (15)
formula (16)
formula (17)

formula (18)
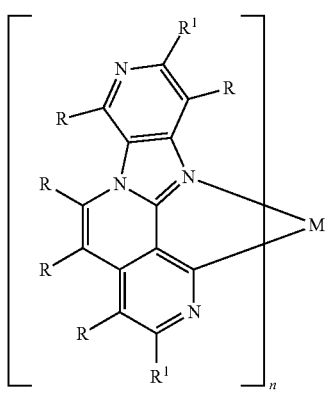
formula (19)
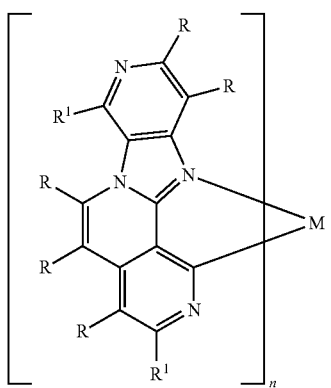
formula (20)
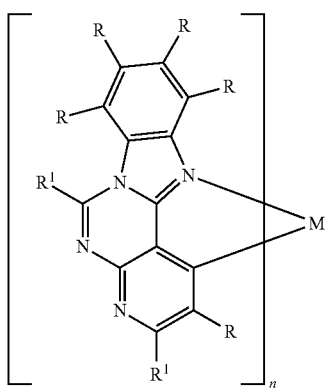
formula (21)
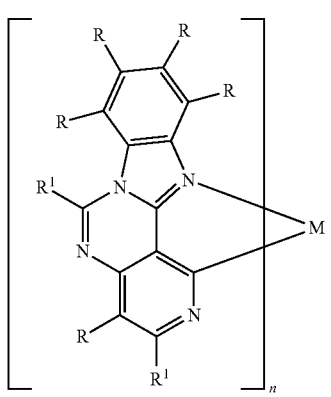
formula (22)
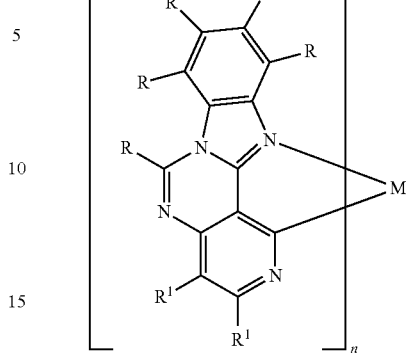
formula (23)
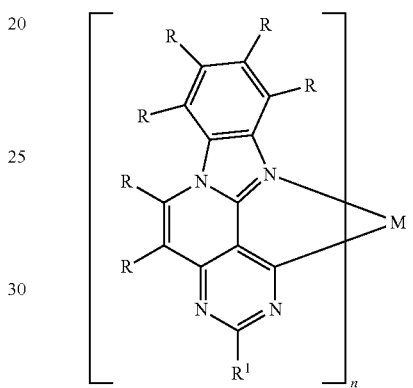
formula (24)
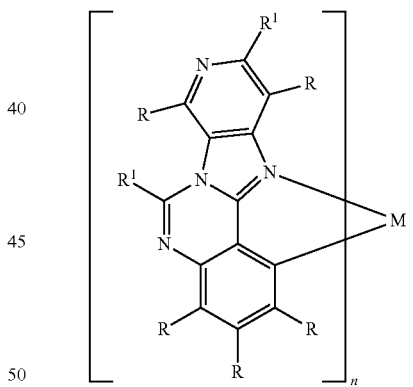
formula (25)
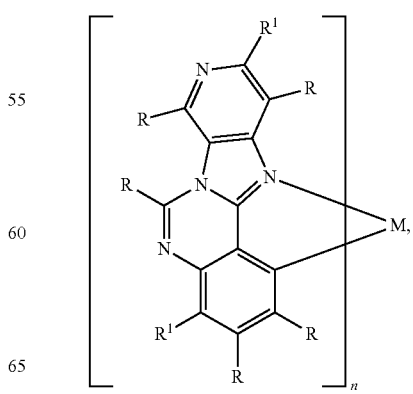

formula (26)
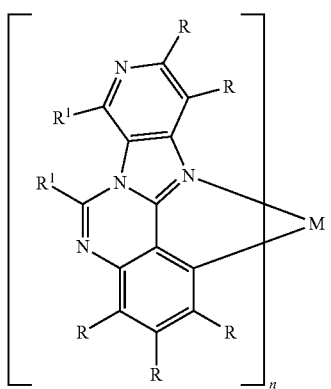
formula (27)
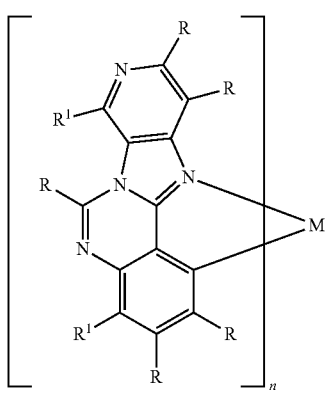
where the symbols and indices used have the above-mentioned meanings.
If three groups X stand for N, preferred moieties of the formula (2) are the moieties of the following formulae (28) to (36),
formula (28)
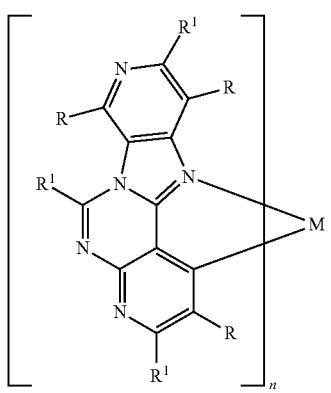
formula (29)
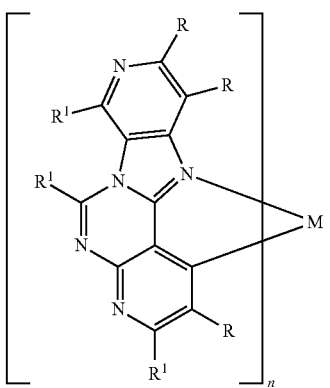
formula (30)
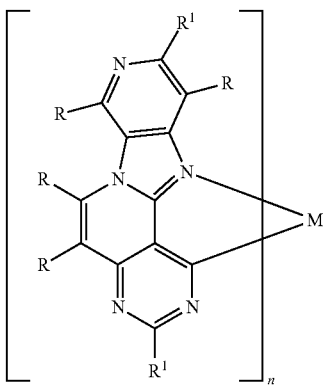
formula (31)
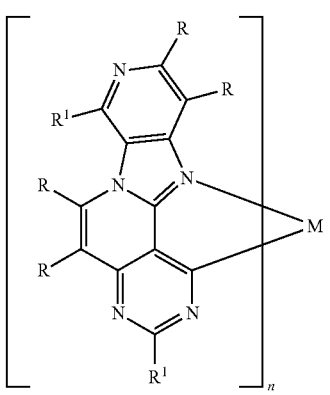
formula (32)
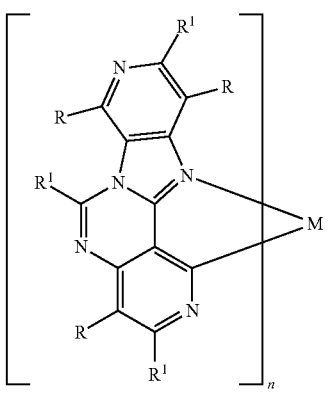

-continued

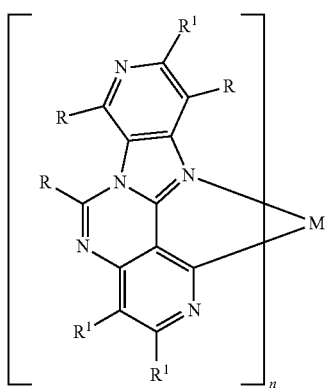
formula (33)

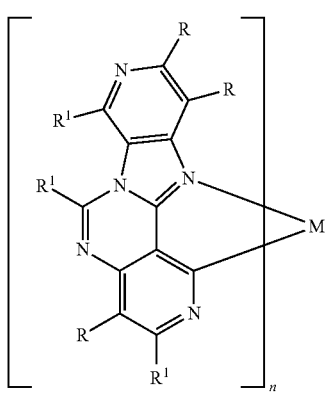
formula (34)

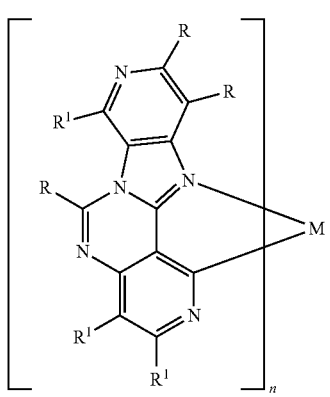
formula (35)

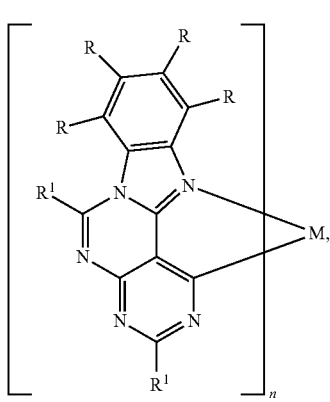
formula (36)

where the symbols and indices used have the above-mentioned meanings.

If four groups X stand for N, preferred moieties of the formula (2) are the moieties of the following formulae (37) and (38),

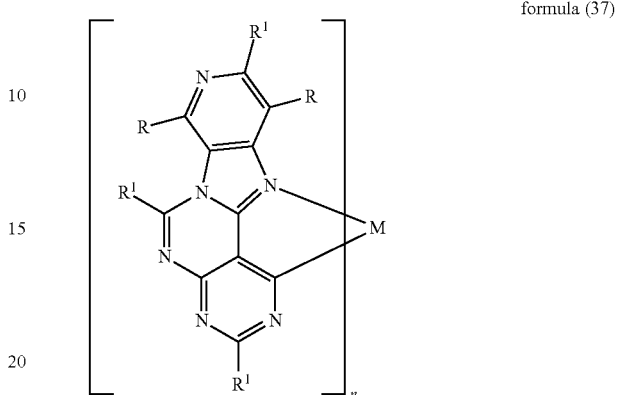
formula (37)

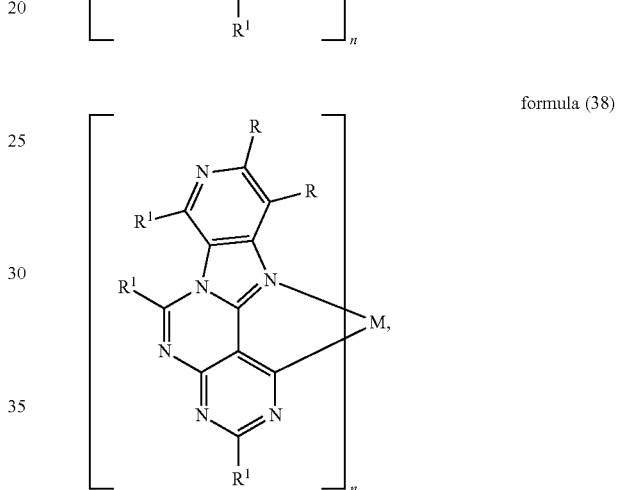
formula (38)

where the symbols and indices used have the above-mentioned meanings.

In a preferred embodiment of the invention, the groups $R^1$ in the formulae (26), (29), (34) and (38) do not both stand for a tertiary alkyl group.

As defined above, a group R al is bonded as substituent adjacent to at least one X which stands for nitrogen. In particular, a group $R^1$ is bonded as substituent adjacent to each X which stands for nitrogen. $R^1$ here, as defined above, is a group selected from $CF_3$, $OCF_3$, branched or cyclic alkyl or alkoxy groups having at least 3 C atoms, trisubstituted silyl groups, aromatic or heteroaromatic ring systems or aralkyl or heteroaralkyl groups. These groups are sterically bulky groups.

If $R^1$ stands for an alkyl group, this alkyl group then preferably has 4 to 10 C atoms. It is furthermore preferably a secondary or tertiary alkyl group in which the secondary or tertiary C atom is either bonded directly to the ligand or is bonded to the ligand via a $CH_2$ group. This alkyl group is particularly preferably selected from the structures of the following formulae ($R^1$-1) to ($R^1$-33), where the linking of these groups to the ligand is in each case also drawn in:

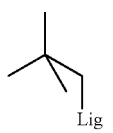 (R¹-1)
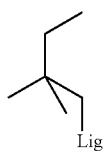 (R¹-2)
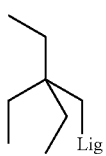 (R¹-3)
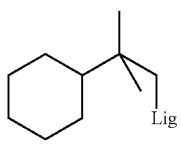 (R¹-4)
 (R¹-5)
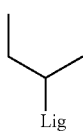 (R¹-6)
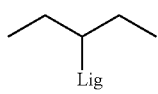 (R¹-7)
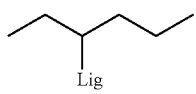 (R¹-8)
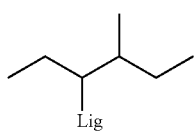 (R¹-9)
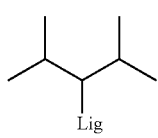 (R¹-10)
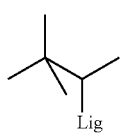 (R¹-11)
-continued
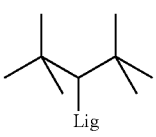 (R¹-12)
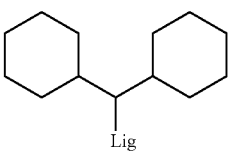 (R¹-13)
 (R¹-14)
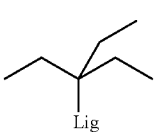 (R¹-15)
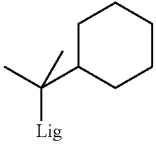 (R¹-16)
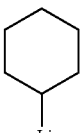 (R¹-17)
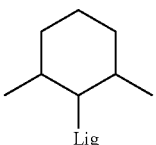 (R¹-18)
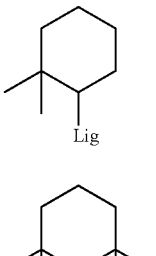 (R¹-19)
(R¹-20)
(R¹-21)
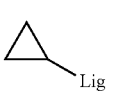 (R¹-22)

(R¹-23) 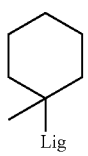
(R¹-24) 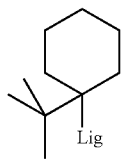
(R¹-25) 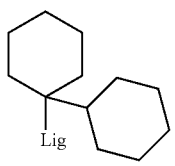
(R¹-26) 
(R¹-27) 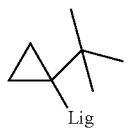
(R¹-28) 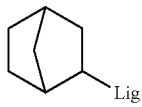
(R¹-29) 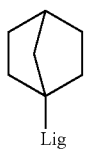
(R¹-30) 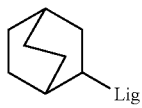
(R¹-31) 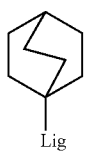
(R¹-32) 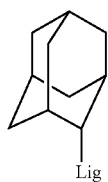
(R¹-33) 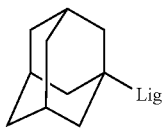
where Lig denotes the link of the alkyl group to the ligand.
If $R^1$ stands for an alkoxy group, this alkoxy group then preferably has 3 to 10 C atoms. This alkoxy group is preferably selected from the structures of the following formulae (R¹-34) to (R¹-47), where the linking of these groups to the ligand is in each case also drawn in:
(R¹-34) 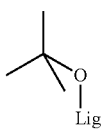
(R¹-35) 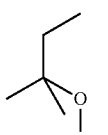
(R¹-36) 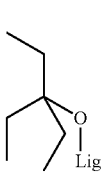
(R¹-37) 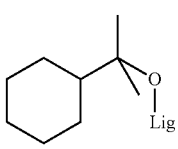
(R¹-38) 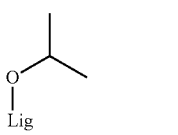
(R¹-39) 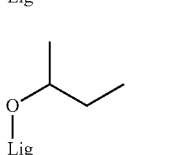
(R¹-40) 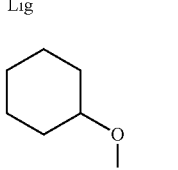
(R¹-41) 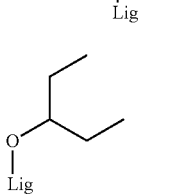

-continued

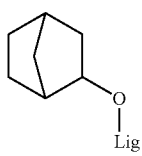
(R¹-42)

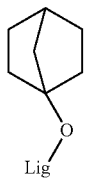
(R¹-43)

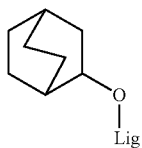
(R¹-44)

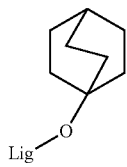
(R¹-45)

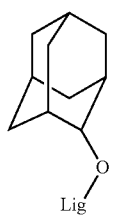
(R¹-46)

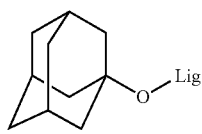
(R¹-47)

where Lig denotes the link of the alkyl group to the ligand.

If R¹ stands for a dialkylamino group, each of these alkyl groups then preferably has 1 to 8 C atoms, particularly preferably 1 to 6 C atoms. Examples of suitable alkyl groups are methyl, ethyl or the structures shown above as groups (R¹-1) to (R¹-33). The dialkylamino group is particularly preferably selected from the structures of the following formulae (R¹-48) to (R¹-55), where the linking of these groups to the ligand is in each case also drawn in:

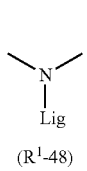 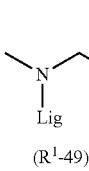 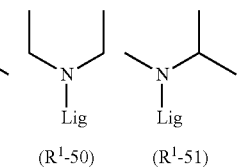 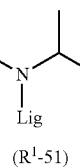
(R¹-48)   (R¹-49)   (R¹-50)   (R¹-51)

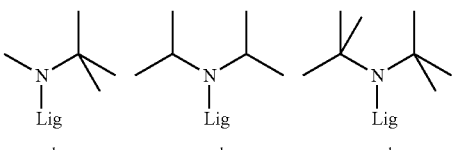
(R¹-52)   (R¹-53)   (R¹-54)

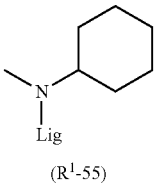
(R¹-55)

where Lig denotes the link of the alkyl group to the ligand.

If R¹ stands for an aralkyl group, this aralkyl group is then preferably selected from the structures of the following formulae (R¹-56) to (R¹-69), where the linking of these groups to the ligand is in each case also drawn in:

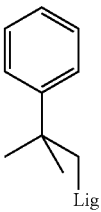
(R¹-56)

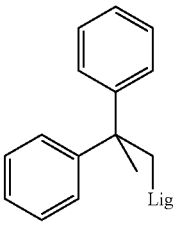
(R¹-57)

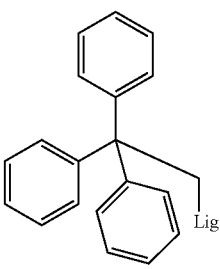
(R¹-58)

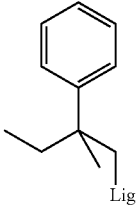
(R¹-59)

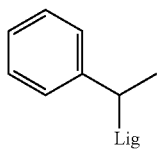 (R¹-60)

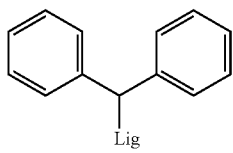 (R¹-61)

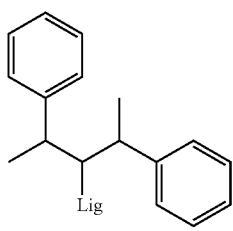 (R¹-62)

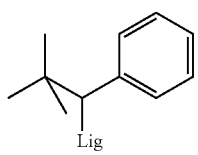 (R¹-63)

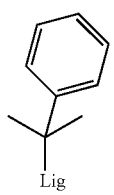 (R¹-64)

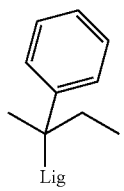 (R¹-65)

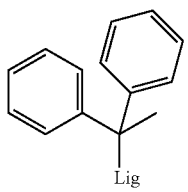 (R¹-66)

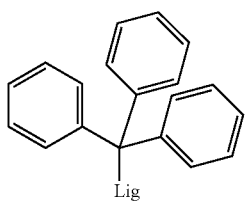 (R¹-67)

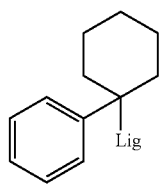 (R¹-68)

 (R¹-69)

where Lig denotes the link of the aralkyl group to the ligand, and the phenyl groups may each be substituted by one or more radicals $R^2$.

The alkyl, alkoxy, dialkylamino and aralkyl groups may, depending on the precise structure, also have one or more stereocentres. Since the basic structure of the complex may also be a chiral structure, the formation of diastereomers is possible, in particular also if a plurality of such alkyl, alkoxy, dialkylamino and aralkyl groups having stereocentres are present. The complexes according to the invention then include both the mixtures of the various diastereomers or the corresponding racemates and also the individual isolated diastereomers or enantiomers.

If $R^1$ stands for an aromatic or heteroaromatic ring system, this aromatic or heteroaromatic ring system then preferably has 5 to 30 aromatic ring atoms, particularly preferably 5 to 24 aromatic ring atoms. This aromatic or heteroaromatic ring system furthermore preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae ($R^1$-70) to ($R^1$-84), where the linking of these groups to the ligand is in each case also drawn in:

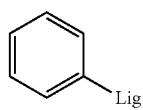 (R¹-70)

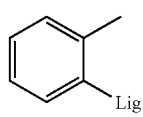 (R¹-71)

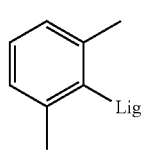 (R¹-72)

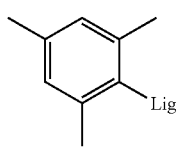
(R¹-73)

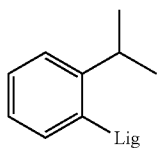
(R¹-74)

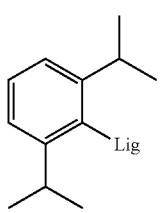
(R¹-75)

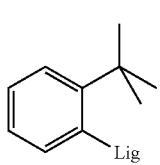
(R¹-76)

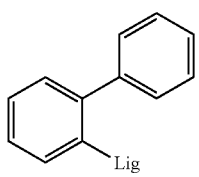
(R¹-77)

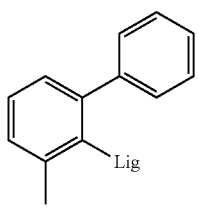
(R¹-78)

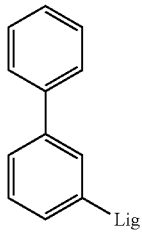
(R¹-79)

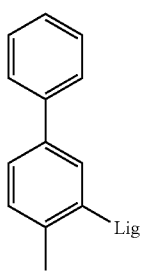
(R¹-80)

(R¹-81)

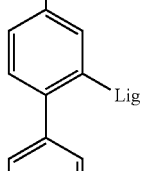

(R¹-82)

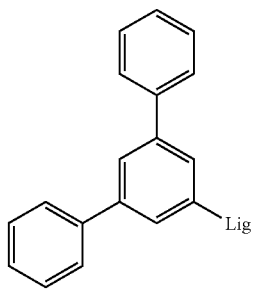

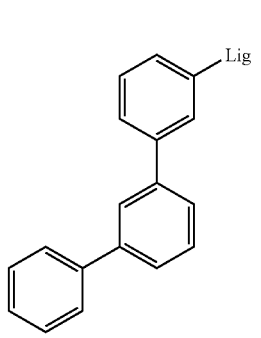
(R¹-83)

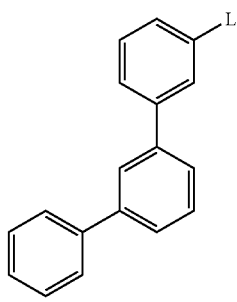

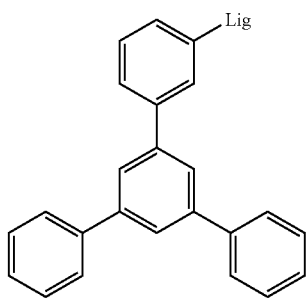
(R¹-84)

where Lig denotes the link of the aromatic or heteroaromatic ring system to the ligand, and the phenyl groups may each be substituted by one or more radicals $R^2$.

The heteroaromatic ring system is furthermore preferably selected from the structures of the following formulae (R¹-85) to (R¹-112), where the linking of these groups to the ligand is in each case also drawn in:

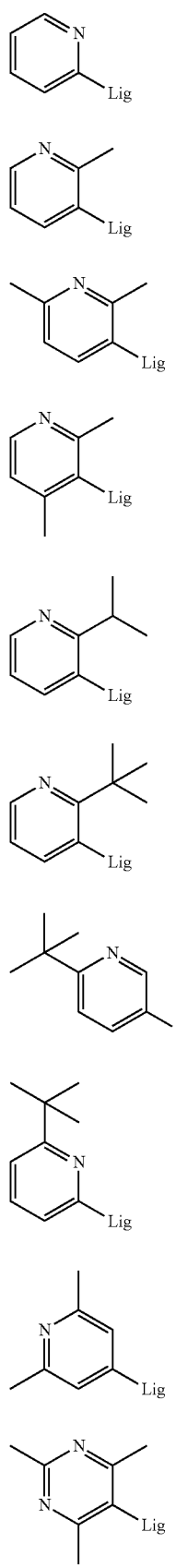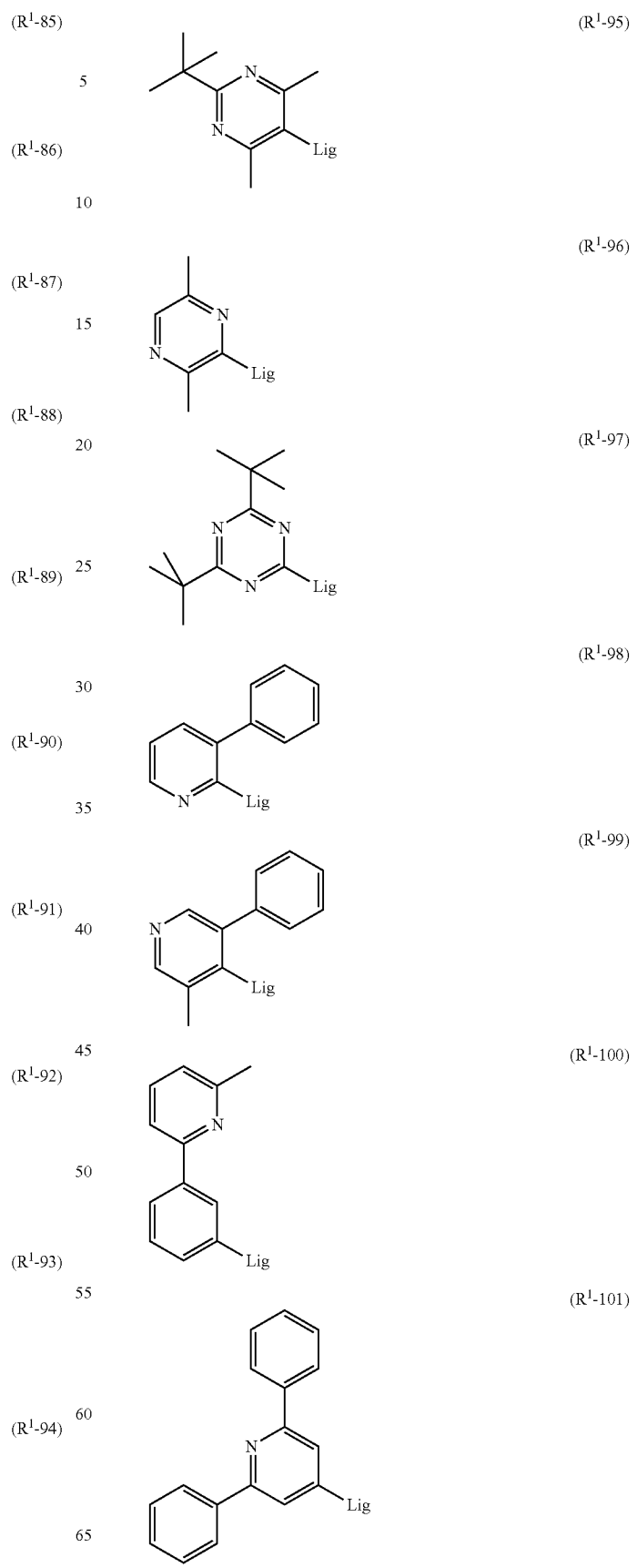

(R¹-102)
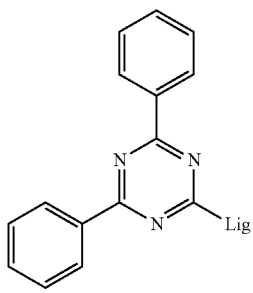

(R¹-103)
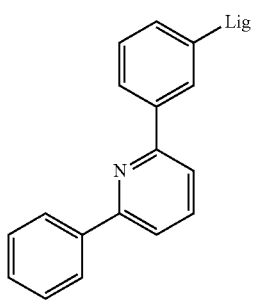

(R¹-104)
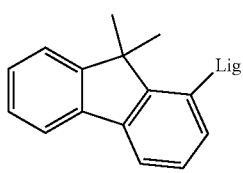

(R¹-105)
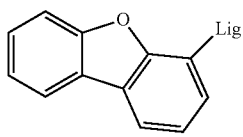

(R¹-106)
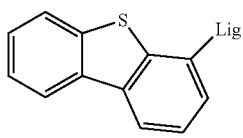

(R¹-107)
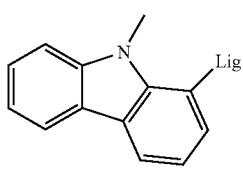

(R¹-108)
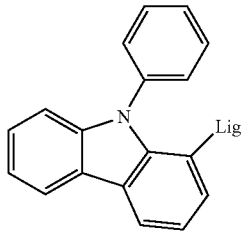

(R¹-109)
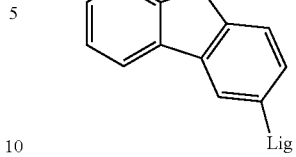

(R¹-110)
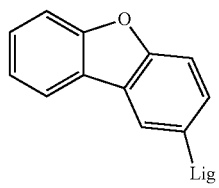

(R¹-111)
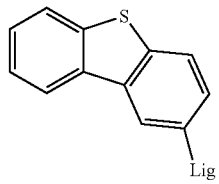

(R¹-112)
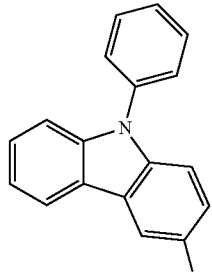

where Lig denotes the link of the aromatic or heteroaromatic ring system to the ligand, and the aromatic and heteroaromatic groups may each be substituted by one or more radicals $R^2$.

If further radicals R are bonded in the moiety of the formula (2) in addition to the radicals $R^1$, these radicals R are preferably selected on each occurrence, identically or differently, from the group consisting of H, D, F, Br, I, $N(R^2)_2$, CN, $Si(R^2)_3$, $B(OR^2)_2$, $C(=O)R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$; two adjacent radical R or R with $R^1$ here may also form a mono- or polycyclic, aliphatic ring system with one another. These radicals R are particularly preferably selected on each occurrence, identically or differently, from the group consisting of H, D, F, $N(R^2)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$; two adjacent radicals R or R with $R^1$ here may also form a mono- or polycyclic, aliphatic ring system with one another.

If substituents R which have a +M or −M effect are bonded in the moiety of the formula (2) of the complex according to the invention, these are preferably bonded in the following positions:

If it is a substituent R which has a +M effect, this is preferably bonded to the ring which is bonded to the metal via the carbon in the meta-position to the metal.

If it is a substituent R which has a −M effect, this is preferably bonded to the ring which is bonded to the metal via the carbon in the para-position to the metal.

What substituents have a +M effect and what substituents have a −M effect is known to the person skilled in the art of organic chemistry. Examples of substituents which have a +M effect are F, Cl, Br, I, amines, alkoxy groups, OH, $N(R^2)_2$ or thioalkoxy groups. Examples of substituents which have a −M effect are CN, $NO_2$, ketones, aldehydes, phosphine oxide groups, sulfoxide groups or sulfones.

The preferred positions at which substituents having +M effect and −M effect are bonded are depicted diagrammatically below:

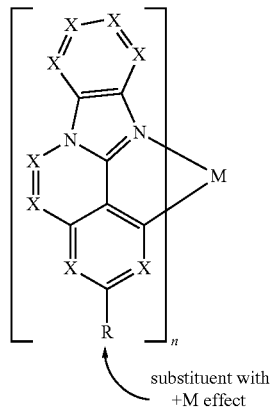
substituent with +M effect

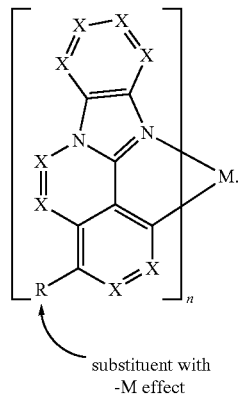
substituent with −M effect

It is furthermore possible for substituent R, which is bonded in the ortho-position to the metal coordination, to represent a coordinating group which is likewise coordinated or bonded to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties $M(L)_n$ of the following formulae (39) to (44), for example, are accessible here:

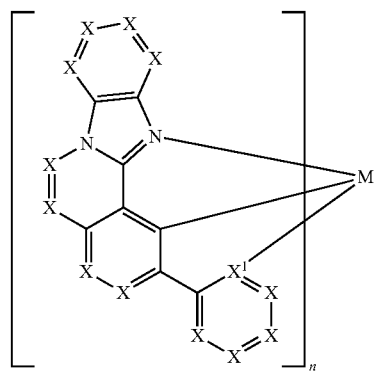
formula (39)

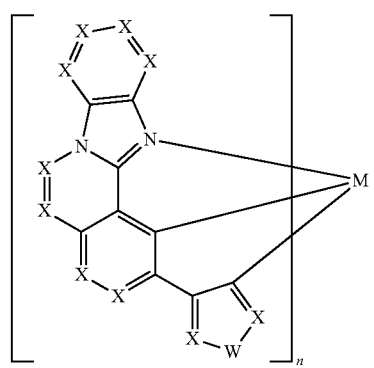
formula (40)

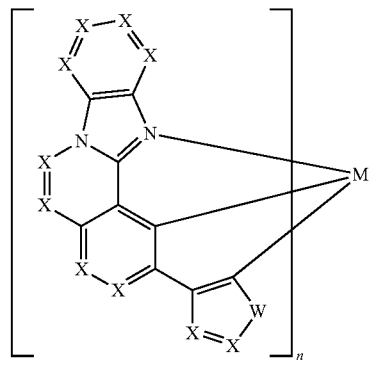
formula (41)

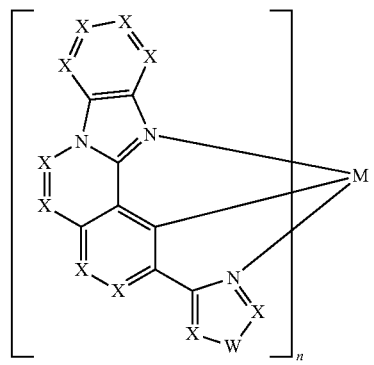
formula (42)

formula (43)

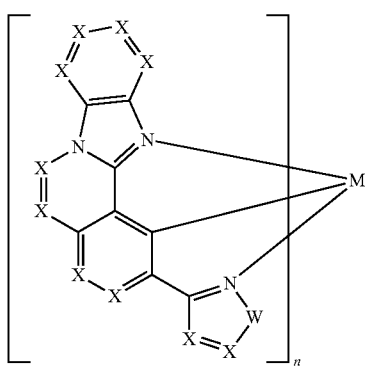

formula (44)

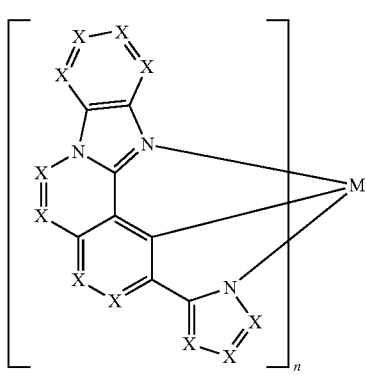

where the symbols and indices have the same meanings as described above, $X^1$ stands, oidentically or differently on each occurrence, for C or N and W stands, oidentically or differently on each occurrence, for S, O or $NR^2$.

Formulae (39) to (44) show, merely by way of example, how the substituent R can additionally coordinate to the metal. Other groups R which coordinate to the metal, for example also carbenes, are also accessible entirely analogously without further inventive step.

As described above, a bridging unit V which links this ligand L to one or more further ligands L or L' may also be present instead of one of the radicals R. In a preferred embodiment of the invention, a bridging unit V is present instead of one of the radicals R, in particular instead of the radicals R which are in the ortho- or meta-position to the coordinating atom, so that the ligands have a tridentate or polydentate or polypodal character. It is also possible for two such bridging units V to be present. This results in the formation of macrocyclic ligands or in the formation of cryptates.

Preferred structures containing polydentate ligands are the metal complexes of the following formulae (45) to (50), formula (45)

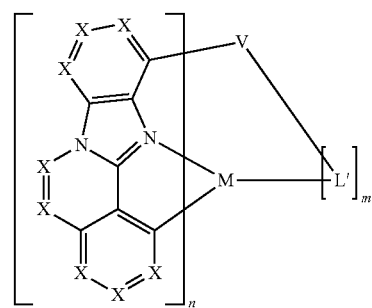

formula (46)

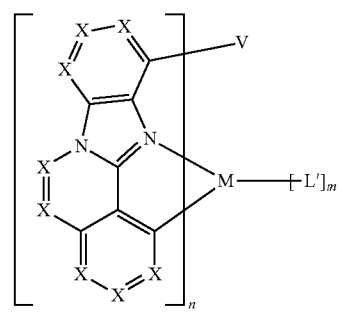

formula (47)

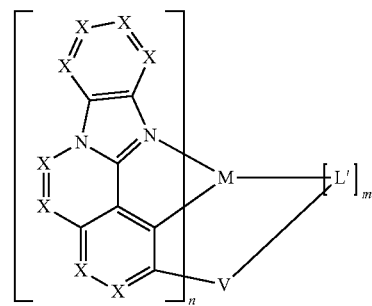

formula (48)

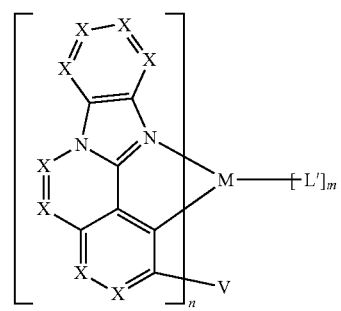

formula (49)

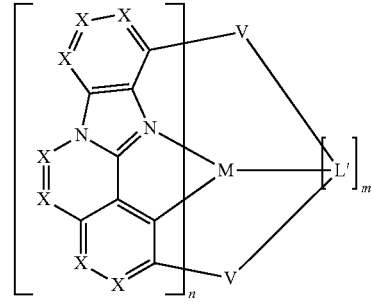

formula (50)

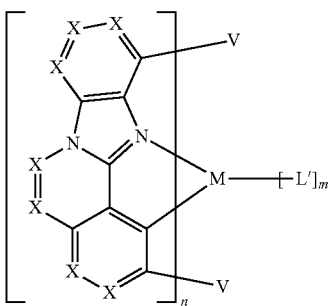

where the symbols used have the meanings given above, where V preferably represents a single bond or a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged, particularly preferably neutral. The charge of V is preferably selected so that overall a neutral complex forms. The preferences mentioned above for the moiety $ML_n$ apply to the ligands, and n is preferably at least 2.

It is also possible for two ligands $L^1$ additionally to be linked to one another via a further divalent bridge apart from via a single bond. This gives rise to structures of the following formula (45a):

formula (45a)

where the symbols used have the meanings given above and $V^1$ stands for $CR_2$, NR, O or S.

The precise structure and chemical composition of the group V does not have a significant effect on the electronic properties of the complex since the job of this group is essentially to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^2)^-$, $B(C(R^2)_2)_3$, $(R^2)B(C(R^2)_2)_3^-$, $B(O)_3$, $(R^2)B(O)_3^-$, $B(C(R^2)_2C(R^2)_2)_3$, $(R^2)B(C(R^2)_2C(R^2)_2)_3^-$, $B(C(R^2)_2O)_3$, $(R^2)B(C(R^2)_2O)_3^-$, $B(OC(R^2)_2)_3$, $(R^2)B(OC(R^2)_2)_3^-$, $C(R^2)$, $CO^-$, $CN(R^2)_2$, $(R^2)C(C(R^2)_2)_3$, $(R^2)C(O)_3$, $(R^2)C(C(R^2)_2C(R^2)_2)_3$, $(R^2)C(C(R^2)_2O)_3$, $(R^2)C(OC(R^2)_2)_3$, $(R^2)C(Si(R^2)_2)_3$, $(R^2)C(Si(R^2)_2C(R^2)_2)_3$, $(R^2)C(C(R^2)_2Si(R^2)_2)_3$, $(R^2)C(Si(R^2)_2Si(R^2)_2)_3$, $Si(R^2)$, $(R^2)Si(C(R^2)_2)_3$, $(R^2)Si(O)_3$, $(R^2)Si(C(R^2)_2C(R^2)_2)_3$, $(R^2)Si(OC(R^2)_2)_3$, $(R^2)Si(C(R^2)_2O)_3$, $(R^2)Si(Si(R^2)_2)_3$, $(R^2)Si(Si(R^2)_2C(R^2)_2)_3$, $(R^2)Si(C(R^2)_2Si(R^2)_2)_3$, $(R^2)Si(Si(R^2)_2Si(R^2)_2)_3$, N, NO, $N(R^2)^+$, $N(C(R^2)_2)_3$, $(R^2)N(C(R^2)_2)_3^+$, $N(C=O)_3$, $N(C(R^2)_2C(R^2)_2)_3$, $(R^2)N(C(R^2)_2C(R^2)_2)^+$, P, $P(R^2)^+$, PO, PS, PSe, PTe, $P(O)_3$, $PO(O)_3$, $P(OC(R^2)_2)_3$, $PO(OC(R^2)_2)_3$, $P(C(R^2)_2)_3$, $P(R^2)(C(R^2)_2)_3^+$, $PO(C(R^2)_2)_3$, $P(C(R^2)_2C(R^2)_2)_3$, $P(R^2)(C(R^2)_2C(R^2)_2)_3^+$, $PO(C(R^2)_2C(R^2)_2)_3$, $S^+$, $S(C(R^2)_2)_3^+$, $S(C(R^2)_2C(R^2)_2)_3^+$, or a unit of the formula (51), (52), (53) or (54), formula (51)

formula (52)

formula (53)

formula (54)

where the dashed bonds in each case indicate the bond to the part-ligands L or L', and Z is selected, identically or differently on each occurrence, from the group consisting of a single bond, O, S, S(=O), $S(=O)_2$, $NR^2$, $PR^2$, $P(=O)R^2$, $P(=NR^2)$, $C(R^2)_2$, $C(=O)$, $C(=NR^2)$, $C(=C(R^2)_2)$, $Si(R^2)_2$ or $BR^2$. The other symbols used have the meanings given above.

If V stands for a group $CR_2$, the two radicals R may also be linked to one another, and consequently structures such as, for example, 9,9-fluorene, are also suitable groups V.

If V is a divalent group, i.e. bridges two ligands L to one another or one ligand L to L', V is preferably selected, identically or differently on each occurrence, from the group consisting of aus $BR^2$, $B(R^2)_2^-$, $C(R^2)_2$, $C(=O)$, $Si(R^2)_2$, $NR^2$, $PR^2$, $P(R^2)_2^+$, $P(=O)(R^2)$, $P(=S)(R^2)$, $AsR^2$, $As(=O)(R^2)$, $As(=S)(R^2)$, O, S, Se, or a unit of the formula (55) to (64), formula (55)
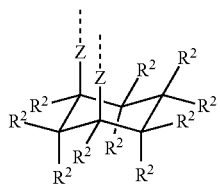

formula (56)
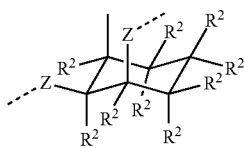

formula (57)
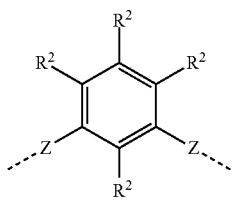

formula (58)
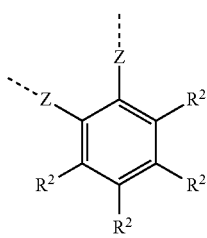

formula (59)
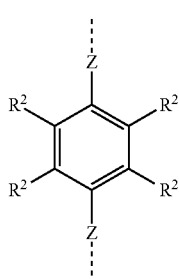

formula (60)
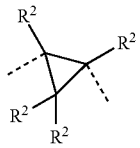

formula (61)
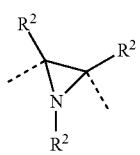

formula (62)

formula (63)
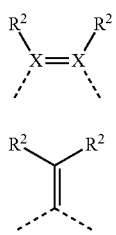

formula (64)

where the dashed bonds in each case indicate the bond to the part-ligands L or L', Y stands on each occurrence, identically or differently, for $C(R^2)_2$, $N(R^2)$, O or S, and the other symbols used each have the meanings indicated above.

Preferred ligands L' as occur in formula (1) are described below. The ligand groups L' can also be selected correspondingly if they are bonded to L via a bridging unit V, as indicated in formulae (45) to (50).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl)phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-C≡$C^-$, tert-butyl-C≡$C^-$, arylacetylides, such as, for example, phenyl-C≡$C^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino)ethyl]-pyridine, 2-[1-(ethylimino)ethyl]pyridine, 2-[1-(isopropylimino) ethyl]pyridine, 2-[1-(tert-butylimino)ethyl]pyridine, diimines, such as, for example, 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino)ethane, 1,2-bis(2,6-diisopropylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino) ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl)borate and tetrakis(1-pyrazolyl)borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (65) to (92) is generally particularly suitable for this purpose, where one group is preferably bonded via a neutral nitrogen atom or a carbene carbon atom and the other group is preferably bonded via a negatively charged carbon atom or a negatively charged nitrogen atom. The ligand L' can then be formed from the groups of the formulae (65) to (92) through these groups bonding to one another in each case at the position denoted by #. The position at which the groups coordinate to the metal is denoted by *. These groups may also be bonded to the ligand L via one or two bridging units V.

formula (65)

formula (66)

formula (67)

formula (68)

formula (69)

formula (70)

formula (71)

formula (72)

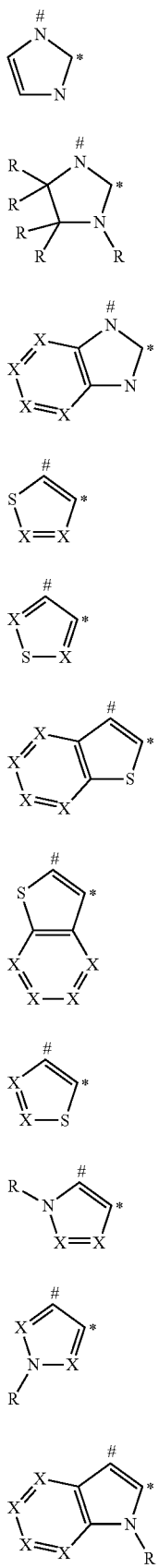

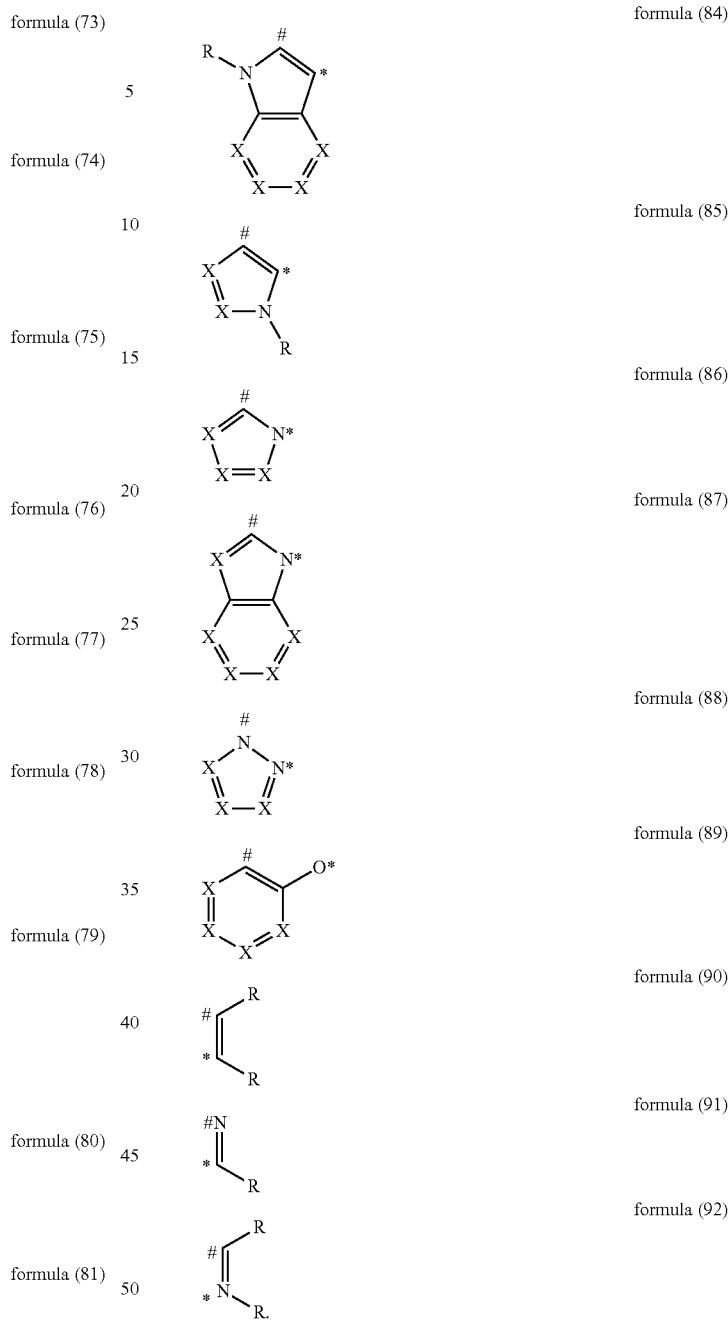

X here stands on each occurrence, identically or differently, for CR or N, and R has the same meaning as described above. Preferably, a maximum of three symbols X in each group stand for N, particularly preferably a maximum of two symbols X in each group stand for N, very particularly preferably a maximum of one symbol X in each group stands for N. Especially preferably, all symbols X stand for CR.

The formulae (76) to (80) may furthermore also contain oxygen instead of sulfur.

Likewise preferred ligands L' are $\eta^5$-cyclopentadienyl, $\eta^5$-pentamethyl-cyclopentadienyl, $\eta^6$-benzene or $\eta^7$-cycloheptatrienyl, each of which may be substituted by one or more radicals R.

Likewise preferred ligands L' are 1,3,5-cis,cis-cyclohexane derivatives, in particular of the formula (93), 1,1,1-tri (methylene)methane derivatives, in particular of the formula (94), and 1,1,1-trisubstituted methanes, in particular of the formula (95) and (96),

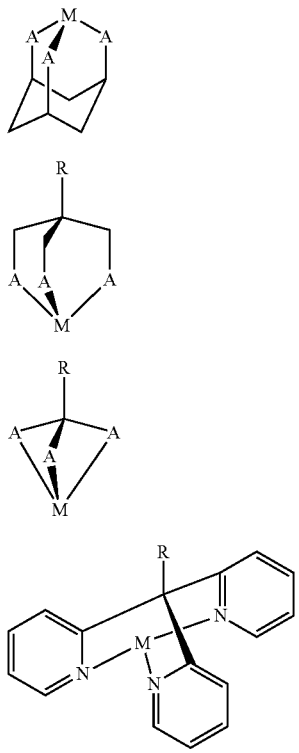

formula (93)

formula (94)

formula (95)

formula (96)

where the coordination to the metal M is shown in each of the formulae, R has the meaning given above, and A stands, identically or differently on each occurrence, for $O^-$, $S^-$, $COO^-$, $PR_2$ or $NR_2$.

Preferred radicals R in the structures shown above are selected on each occurrence, identically or differently, from the group consisting of H, D, F, Br, $N(R^2)_2$, CN, $B(OR^2)_2$, $C(=O)R^2$, $P(=O)(R^2)_2$, a straight-chain alkyl group having 1 to 10 C atoms or a straight-chain alkenyl or alkynyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 14 aromatic ring atoms, which may in each case be substituted by one or more radicals $R^1$; two or more adjacent radicals R here may also form a mono- or polycyclic, aliphatic, aromatic and/or benzo-fused ring system with one another. Particularly preferred radicals R are selected on each occurrence, identically or differently, from the group consisting of H, D, F, Br, CN, $B(OR^2)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^2$; two or more radicals R here may also form a mono- or polycyclic, aliphatic, aromatic and/or benzo-fused ring system with one another.

The complexes according to the invention can be facial or pseudofacial or they can be meridional or pseudomeridional.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (97), with metal ketoketonates of the formula (98), with metal halides of the formula (99) or with dimeric metal complexes of the formula (100), $M(OR)_n$  formula (97)

formula (98)

$MHal_n$  formula (99)

formula (100)

where the symbols M, m, n and R have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. [$IrCl_2(acac)_2$]$^-$, for example Na[$IrCl_2(acac)_2$], are particularly suitable. Metal complexes with acetylacetonate derivatives as ligand, for example Ir(acac)$_3$ or tris(2,2,6,6-tetramethylheptane-3,5-dionato)iridium, and $IrCl_3 \cdot xH_2O$, where x usually stands for a number between 2 and 4.

Suitable platinum starting materials are, for example, $PtCl_2$, $K_2[PtCl_4]$, $PtCl_2(DMSO)_2$, $Pt(Me)_2(DMSO)_2$ or $PtCl_2$(benzonitrile)$_2$.

The synthesis of the complexes is preferably carried out as described in WO 2002/060910, WO 2004/085449 and WO 2007/065523. Heteroleptic complexes can also be synthesised, for example, in accordance with WO 2005/042548. The synthesis here can also be activated, for example, thermally, photochemically and/or by microwave radiation.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quater-phenyl groups. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778 or the unpublished applications DE 102009048791.3 and DE 102010005697.9.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not essentially involved in charge transport, as described, for example, in WO 2010/108579.

It is furthermore preferred to employ a mixture of two or more triplet emitters emission spectrum serves as co-matrix for the triplett-emitter having the longer-wave emission spectrum. Thus, for example, the complexes of the formula (1) according to the invention can be employed as co-matrix for triplet emitters emitting at longer wavelength, for example for green- or red-emitting triplet emitters.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art:

1. Organic electroluminescent devices comprising compounds of the formula (1) as emitting materials have a very good lifetime.
2. Organic electroluminescent devices comprising compounds of the formula (1) as emitting materials have excellent efficiency.
3. The metal complexes according to the invention give access to organic electroluminescent devices which phosphoresce in the blue colour region. In particular, blue phosphorescence with good efficiencies and lifetimes can only be achieved with great difficulty in accordance with the prior art.
4. The metal complexes according to the invention are readily accessible synthetically and in high yields.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are carried out, unless indicated otherwise, under a protective-gas atmosphere in dried solvents. The metal complexes are additionally handled with exclusion of light. The solvents and reagents can be purchased, for example, from Sigma-ALDRICH or ABCR.

A: Synthesis of Synthones S 1) 3,5-Bisphenylbenzoyl chloride, S1

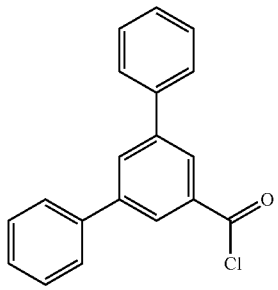 [SMILES: O=C(Cl)c1cc(-c2ccccc2)cc(-c2ccccc2)c1]

Preparation in accordance with Organikum [Practical Organic Chemistry], VEB Deutscher Verlag der Wissenschaften, Berlin, 5th Edition, 1965, page 409, by boiling 3,5-bisphenylbenzoic acid [99710-75-5] with 2 equivalents of thionyl chloride with addition of 2 drops of DMF. Yield: quantitative. Purity: >98% according to $^1$H-NMR.

2) 2-(2-Aminophenyl)benzimidazole derivatives

Preparation of
2-(2-amino-4-methylphenyl)benzimidazole, S2

Preparation analogous to B. Saha et al., Synth. Commun. 2007, 37, 19, 3455.

33.8 g (55 mmol) of oxone [70693-62-8] are added in portions to a solution of 13.5 g (100 mmol) of 2-nitro-4-methylbenzaldehyde [20357-22-6] and 11.9 g (110 mmol) of 1,2-diaminobenzene in a mixture of 150 ml of DMF and 5 ml of water with stirring and cooling to 20° C. at such a rate that the temperature does not exceed 35° C. The reaction mixture is subsequently stirred at room temperature until conversion of the aldehyde is complete (about 4 h). The reaction mixture is stirred into a solution of 40 g of potassium carbonate in 2000 ml of water, stirred for a further 15 min., extracted with three 300 ml portions of dichloromethane in each case, the organic phase is washed twice with 300 ml of water, once with 500 ml of sat. sodium chloride solution and dried over sodium sulfate. The dichloromethane solution is filtered through silica gel, and the dichloromethane is removed in vacuo. The yellow residue is taken up in 500 ml of methanol, blanketed with nitrogen with stirring, 3 g of 10% Pd/C are added, and the mixture is hydrogenated at room temperature in an autoclave at a hydrogen pressure of 2 bar. When the uptake of hydrogen is complete, the catalyst is filtered off via a Celite bed, and the methanol is removed in vacuo. Yield: 18.5 g (83 mmol), 83%. Purity: >95% according to $^1$H-NMR.

The following derivatives are prepared analogously:

| Ex. | Aldehyde | 1,2-Diamino-benzene | Product | Yield |
|---|---|---|---|---|
| S2 | 20357-22-6 | 95-54-5 | | 83% |
| S3 | 96864-00-5 | 95-54-5 | | 76% |
| S4 | 96864-00-5 | 3171-45-7 | | 67% |
| S5 | 96864-00-5 | 81927-47-1 | | 47% |

-continued

| Ex. | Aldehyde | 1,2-Diamino-benzene | Product | Yield |
|---|---|---|---|---|
| S6 | 515878-88-3 (O₂N, Ph-substituted benzaldehyde) | 95-54-5 | benzimidazole product with H₂N, Ph | 88% |
| S7 | 5858-27-5 (O₂N, methyl-substituted benzaldehyde) | 95-54-5 | benzimidazole product with H₂N, methyl | 77% |
| S8 | 2923-96-8 (O₂N, F-substituted benzaldehyde) | 95-54-5 | benzimidazole product with H₂N, F | 67% |

3) 2-(2-Bromophenyl)benzimidazole derivatives

3.1) Variant A, Oxone as Oxidant

Preparation analogous to B. Saha et al., Synth. Commun. 2007, 37, 3455. A solution of 100 mmol of the aldehyde and 110 mmol of the 1,2-diaminobenzene in a mixture of 150 ml of DMF and 5 ml of water is placed in a cold-water bath (about 1000 ml at about 10° C.), and 33.8 g (55 mmol) of oxone [70693-62-8] are then added in portions with stirring at such a rate that the temperature does not exceed 35° C. After the exothermic reaction has subsided, the mixture is stirred at room temperature until conversion of the aldehyde is complete (1-6 h). The reaction mixture is stirred into a solution of 40 g of potassium carbonate in 2000 ml of water and stirred for a further 15 min. Precipitated solids are filtered off with suction, washed three times with 100 ml of water each time and then sucked dry. Oils are extracted with three 300 ml portions of dichloromethane in each case, the organic phase is washed twice with 300 ml of water each time and once with 500 ml of sat. sodium chloride solution, and dried over sodium sulfate. The dichloromethane solution is filtered through a short silica-gel column, the dichloromethane is removed in vacuo, and the residue is recrystallised from ethyl acetate/ether or ethanol/water.

Preparation of
2-(2-bromo-4-fluorophenyl)-D4-benzimidazole, S9

33.8 g (55 mmol) of oxone [70693-62-8] are added in portions with stirring to a solution, cooled to 10° C., of 20.3 g (100 mmol) of 2-bromo-4-fluoro-benzaldehyde [59142-68-6] and 11.9 g (110 mmol) of 1,2-diaminobenzene-D4 [291765-93-0] in a mixture of 150 ml of DMF and 5 ml of water at such a rate that the temperature does not exceed 35° C. After the exothermic reaction has subsided, the mixture is stirred at room temperature until conversion of the aldehyde is complete (about 2 h). The reaction mixture is stirred into a solution of 40 g of potassium carbonate in 2000 ml of water, stirred for a further 15 min., the brown solid is filtered off with suction, washed three times with 100 ml of water each time and dried in vacuo. The solid is taken up in 200 ml of dichloromethane, filtered through a short silica-gel column, the dichloromethane is removed in vacuo, and the residue is recrystallised from ethyl acetate/ether. Yield: 12.2 g 42 mmol), 42%. Purity: >95% according to $^1$H-NMR.

3.2) Variant B, Nitrobenzene as Oxidant

Preparation analogous to D. Jerchel et al., Ann. Chem. 1952, 575, 162. A solution of 100 mmol of the aldehyde and 110 mmol of the 1,2-diaminobenzene in 100 ml of ethanol is placed in an apparatus consisting of a 500 ml flask with water separator and reflux condenser and stirred at room temperature for 30 min. 40 ml of nitrobenzene are subsequently added, and the reaction mixture is heated to weak reflux (oil-bath temperature about 220° C.), during which the ethanol and water formed are distilled off. After 45 min. under weak reflux, the mixture is allowed to cool, 40 ml of diethyl ether are added, the mixture is stirred for a further 30 min., the solid is filtered off with suction and washed once with 50 ml of diethyl ether. The solid is taken up in 200 ml of dichloromethane, filtered through a short silica-gel column, the dichloromethane is removed in vacuo, and the residue is recrystallised from ethyl acetate/ether or ethanol/water.

Preparation of
2-(2-bromo-4-fluorophenyl)-D4-benzimidazole, S9

A solution of 20.3 g (100 mmol) of 2-bromo-4-fluorobenzaldehyde [59142-68-6] and 11.9 g (110 mmol) of 1,2-diaminobenzene in 100 ml of ethanol is placed in an apparatus consisting of a 500 ml flask with water separator and reflux condenser and stirred at room temperature for 30 min. 40 ml of nitrobenzene are subsequently added, and the reaction mixture is heated to weak reflux (oil-bath temperature about 220° C.), during which the ethanol and water formed are distilled off. After 45 min. under weak reflux, the mixture is allowed to cool, 40 ml of diethyl ether are added, the mixture is stirred for a further 30 min., the solid is filtered off with suction and washed once with 50 ml of diethyl ether. The solid is taken up in 200 ml of dichloromethane, filtered through a short silica-gel column, the dichloromethane is removed in vacuo, and the residue is recrystallised from ethyl acetate/ether. Yield: 19.7 g (68 mmol), 68%. Purity: >95% according to $^1$H-NMR.

The following derivatives are prepared analogously:

| Ex | Variant | Aldehyde | 1,2-Diaminobenzene | Product | Yield |
|---|---|---|---|---|---|
| S9 | A | 2-bromo-4-fluorobenzaldehyde (59142-68-6) | perdeutero-1,2-diaminobenzene (291765-93-0) | 2-(2-bromo-4-fluorophenyl)-4,5,6,7-tetradeutero-1H-benzimidazole | 42% |
| S9 | B | 2-bromo-4-fluorobenzaldehyde (59142-68-6) | perdeutero-1,2-diaminobenzene (291765-93-0) | 2-(2-bromo-4-fluorophenyl)-4,5,6,7-tetradeutero-1H-benzimidazole | 68% |
| S10 | A | 2-bromo-4-fluorobenzaldehyde (59142-68-6) | 4,5-dimethyl-1,2-diaminobenzene (3171-45-7) | 2-(2-bromo-4-fluorophenyl)-5,6-dimethyl-1H-benzimidazole | 40% |
| S11 | A | 2-bromo-4-fluorobenzaldehyde (59142-68-6) | 3,4,5,6-tetramethyl-1,2-diaminobenzene (67130-14-7) | 2-(2-bromo-4-fluorophenyl)-4,5,6,7-tetramethyl-1H-benzimidazole | 31% |

-continued
| Ex | Variant | Aldehyde | 1,2-Diaminobenzene | Product | Yield |
|---|---|---|---|---|---|
| S12 | A | 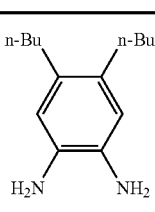 59142-68-6 | 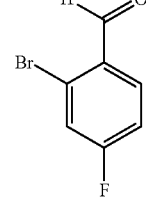 86723-73-1 | 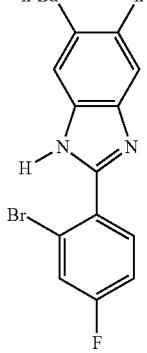 | 42% |
| S13 | A | 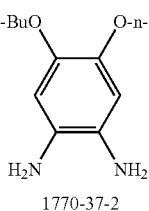 59142-68-6 | 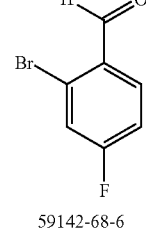 1770-37-2 | 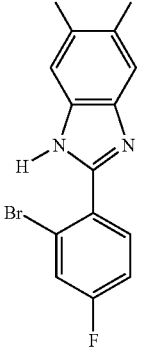 | 38% |
| S14 | B | 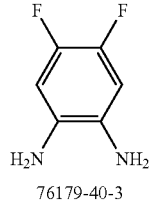 59142-68-6 | 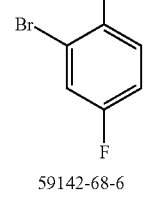 76179-40-3 | 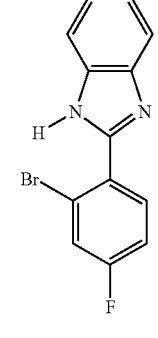 | 63% |
| S15 | A | 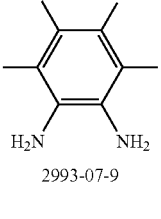 59142-68-6 | 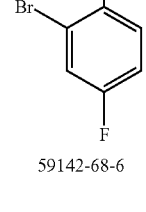 2993-07-9 |  | 37% |

| Ex | Variant | Aldehyde | 1,2-Diamino-benzene | Product | Yield |
|---|---|---|---|---|---|
| S16 | A | 2-bromo-4-fluorobenzaldehyde (59142-68-6) | 4,5-diphenylbenzene-1,2-diamine (117878-22-5) | 2-(2-bromo-4-fluorophenyl)-5,6-diphenyl-1H-benzimidazole | 47% |
| S16 | B | 2-bromo-4-fluorobenzaldehyde (59142-68-6) | 4,5-diphenylbenzene-1,2-diamine (117878-22-5) | 2-(2-bromo-4-fluorophenyl)-5,6-diphenyl-1H-benzimidazole | 61% |
| S17 | A | 2-bromo-3-cyanobenzaldehyde (446864-55-7) | benzene-1,2-diamine (95-54-5) | 2-(2-bromo-3-cyanophenyl)-1H-benzimidazole | 56% |

4) 2-(2-Aminophenyl)benzimidazole derivatives

Preparation of 2-(2-amino-4-fluorophenyl)-D4-benzimidazole, S18

Preparation analogous to N. Xiva et al, Angew. Chem. Int. Ed. 2009, 48, 337.

An autoclave is charged with 29.5 g (100 mmol) of 2-(2-bromo-4-fluorophenyl)-D4-benzimidazole (S9), 65.2 g (200 mmol) of caesium carbonate, 200 ml of DMF, 30 ml of conc. ammonia solution, 1.3 g (5 mmol) of copper(II) acetylacetonate and 2.1 ml (20 mmol) of acetylacetone and sealed. The reaction mixture is stirred at 90° C. for 24 h. After cooling, the reaction mixture is evaporated in vacuo, 500 ml of water are added to the residue, and the mixture is extracted five times with 200 ml of dichloromethane. The combined org. phases are washed three times with 200 ml of water each time and once with 300 ml of sat. sodium chloride solution and dried over sodium sulfate. After removal of the solvent, the residue is washed by stirring with diethyl ether. Yield: 16.9 g (73 mmol), 73%. Purity: >95% according to $^1$H-NMR.

The following derivatives are prepared analogously:
| Ex. | 2-(2-Bromo-phenyl)benz-imidazole | Product | Yield |
|---|---|---|---|
| S18 | 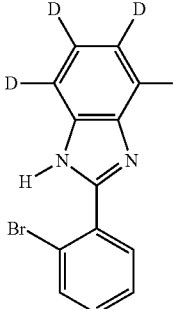 S9 | 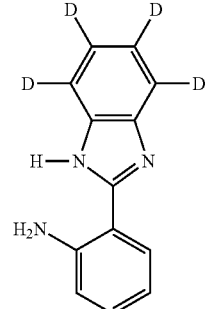 | 73% |
| S19 | 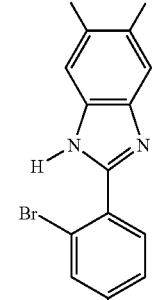 S10 | 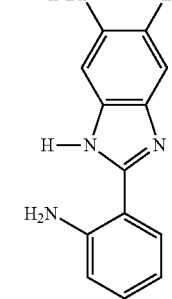 | 65% |
| S20 | 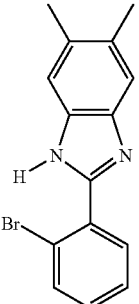 S11 | 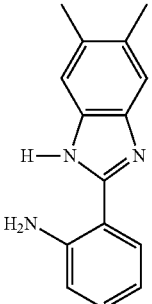 | 58% |
| S21 | 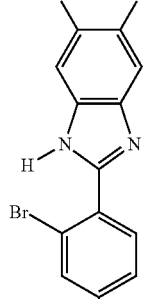 S12 | 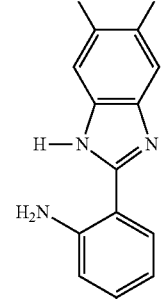 | 51% |
| S22 | 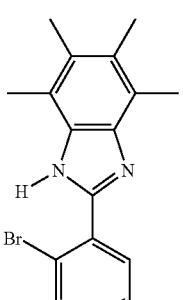 S13 | 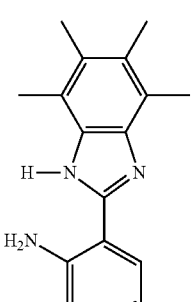 | 55% |
| S23 | 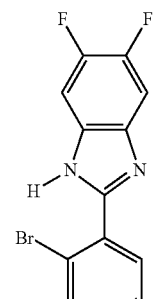 S14 | 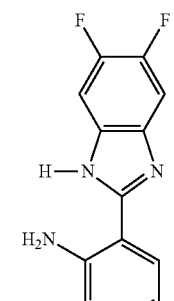 | 67% |

-continued

| Ex. | 2-(2-Bromo-phenyl)benz-imidazole | Product | Yield |
|---|---|---|---|
| S24 | S15 | | 61% |
| S25 | S16 | | 70% |
| S26 | S17 | | 24% |

5) 2-tert-Butyl-3-bromo-4-iodopyridine, S27

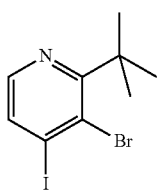

5.1) 2-tert-Butyl-3-bromo-6-trimethylsilylpyridine

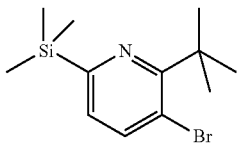

Procedure analogous to WO 2007/073303: 12.4 g (73 mmol) of silver nitrate are added to a mixture of 128.8 g (560 mmol) of 3-bromo-6-trimethylsilylpyridine [291312-74-8], 286.0 g (2.8 mol) of pivalic acid [75-98-9] and 400 ml of water, and the mixture is stirred at room temperature for min. 1000 ml of 10% by weight sulfuric acid are added dropwise to the reaction mixture over the course of 15 min., the mixture is warmed to 70° C., and a solution of 168.5 g (730 mmol) of ammonium peroxodisulfate in 300 ml of water is added dropwise over the course of 30 min. When the evolution of carbon dioxide is complete, the mixture is stirred at 70° C. for a further 3 h, the reaction mixture is allowed to cool, 500 ml of ethyl acetate are added, the aqueous phase is separated off, extracted again with 500 ml of ethyl acetate, the organic phases are combined, washed ten times with 300 ml of sat. sodium hydrogencarbonate solution each time, finally washed once with 500 ml of sat. sodium chloride solution, dried over magnesium sulfate, the solvent is removed in vacuo, and the oil obtained in this way is dried at 60° C. in an oil-pump vacuum. Yield: 59.4 g (207 mmol), 37%. Purity: >95% according to $^1$H-NMR.

5.2) 2-tert-Butyl-3-bromo-4-iodo-6-trimethylsilylpyridine

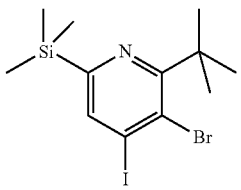 [SMILES: CC(C)(C)c1nc([Si](C)(C)C)cc(I)c1Br]

Procedure analogous to P. N. W. Baxter, Chem. Eur. J. 2003, 9, 2531: 65.6 ml (105 mmol) of n-BuLi, 1.6 M in hexane, are added dropwise over the course of 15 min. to a vigorously stirred mixture, cooled to −78° C., of 14.0 ml (100 mmol) of diisopropylamine and 500 ml of THF. The reaction mixture is stirred at −78° C. for 45 min. and then cooled to −90° C. A solution, pre-cooled to −90° C., of 30.1 g (105 mmol) of 2-tert-butyl-3-bromo-6-trimethylsilylpyridine in 100 ml of THF is added dropwise at such a rate that the temperature does not exceed −80° C. After stirring at −90° C. for a further 1 h, the reaction mixture is warmed to −75° C., stirred at −75° C. for a further 15 min. and then re-cooled to −90° C. A solution of 30.5 g (120 mmol) of iodine in 80 ml of THF is then added dropwise at such a rate that the temperature does not exceed −75° C., the reaction mixture is stirred at −75° C. for a further 4 h and allowed to warm to room temperature. After addition of 10 ml of water and removal of the THF in vacuo, 1000 ml of tert-butyl methyl ether are added, and 100 ml of saturated sodium sulfite solution are added dropwise to the mixture in order to reduce excess iodine. The org. phase is separated off, washed three times with 300 ml of water each time, dried over sodium sulfate, the solvent is removed in vacuo, and the residue is recrystallised once from cyclohexane. Yield: 14.8 g (36 mmol), 34%. Purity: >95% according to $^1$H-NMR.

5.3) 2-tert-Butyl-3-bromo-4-iodopyridine

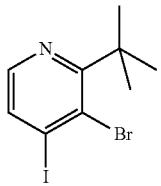

A solution of 14.8 g (36 mmol) of 2-tert-butyl-3-bromo-4-iodo-6-trimethylsilylpyridine and 14.0 g (40 mmol) of tetrabutylammonium fluoride trihydrate in 150 ml of THF is heated under reflux for 5 min. After cooling and removal of the THF in vacuo, the residue is taken up in 200 ml of dichloromethane, the org. phase is washed five times with 100 ml of water each time and dried over sodium sulfate. After removal of the dichloromethane in vacuo, the residue is recrystallised from ethanol. Yield: 9.2 g (27 mmol), 75%. Purity: >95% according to $^1$H-NMR.

6) 2-Chloro-3-cyano-6-tert-butylpyridine, S28

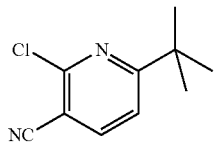

Procedure analogous to 5.1, using 77.6 g (560 mmol) of 2-chloro-3-cyanopyridine [6602-54-6] instead of 128.8 g (560 mmol) of 3-bromo-6-trimethylsilylpyridine. Yield: 92.5 g (475 mmol), 85%. Purity: >95% according to $^1$H-NMR.

7)
2-(2-Chloro-6-tert-butylpyridin-3-yl)benzimidazole derivatives

Preparation of 2-(2-chloro-6-tert-butylpyridin-3-yl)benzimidazole, S29

A mixture, homogenised in a mortar, of 19.5 g (100 mmol) of 2-chloro-3-cyano-6-tert-butylpyridine (S28), 36.2 g (200 mmol) of o-phenylenediamine and 38.0 g (200 mmol) of p-toluenesulfonic acid monohydrate is heated at 220° C. (oil-bath temperature) for 3 h. After cooling, the black, glassy sinter cake is taken up in a mixture of 100 ml of ethanol and 100 ml of 1N hydrochloric acid with vigorous stirring. After stirring for 30 min., the grey-green solid is filtered off with suction, washed three times with 50 ml of water each time and dried in vacuo. The solid is taken up in 200 ml of ethyl acetate, chromatographed on silica gel (ethyl acetate/heptane 1:1, Rf about 0.7) in order to remove 2-tert-butyl-6,11-dihydrobenzo[b]pyrido[2,3-e]-1,4-diazepin-5-one and brown by-products. The crude product obtained in this way is dissolved in ethyl acetate at the boiling temperature, and four times the amount of cyclohexane is added dropwise. After stirring at room temperature for 18 h, the crystals formed are filtered off with suction, washed with n-heptane and dried in vacuo. Yield: 7.5 g (26 mmol), 26%. Purity: >95% according to $^1$H-NMR.

The following derivatives are prepared analogously:

| Ex. | Cyanopyridine | 1,2-Diamino-benzene | Product | Yield |
|---|---|---|---|---|
| S29 | Cl, NC, S28 (2-chloro-3-cyano-6-tert-butylpyridine) | H₂N, NH₂, 95-54-5 | benzimidazole linked to 2-chloro-6-tert-butylpyridin-3-yl | 26% |

-continued

| Ex. | Cyanopyridine | 1,2-Diamino-benzene | Product | Yield |
|---|---|---|---|---|
| S30 | S28 | 3171-45-7 | | 22% |
| S31 | S28 | 76179-40-3 | | 31% |

8) 3-Cyano-4-chloro-6-tert-butylpyridine, S32

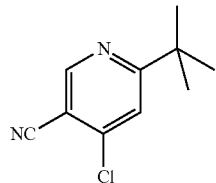

Procedure analogous to 5.1, using 77.6 g (560 mmol) of 3-cyano-4-chloropyridine [89284-61-7] instead of 128.8 g (560 mmol) of 3-bromo-6-trimethylsilylpyridine. Yield: 60.9 g (313 mmol), 56%. Purity: >95% according to $^1$H-NMR.

9) 2-(4-Chloro-6-tert-butylpyridin-3-yl)benzimidazole derivatives

Preparation of 2-(4-chloro-6-tert-butylpyridin-3-yl)benzimidazole, S33

A mixture, homogenised in a mortar, of 19.5 g (100 mmol) of 2-tert-butyl-3-chloro-4-cyanopyridine (S32), 36.2 g (200 mmol) of o-phenylenediamine and 38.0 g (200 mmol) of p-toluenesulfonic acid monohydrate is heated at 220° C. (oil-bath temperature) for 3 h. After cooling, the black, glassy sinter cake is taken up in a mixture of 100 ml of ethanol and 100 ml of 1N hydrochloric acid with vigorous stirring. After stirring for 30 min., the grey-green solid is filtered off with suction, washed three times with 50 ml of water each time and dried in vacuo. The solid is taken up in 200 ml of ethyl acetate, chromatographed on silica gel (ethyl acetate/heptane 1:1, Rf about 0.7) in order to remove 3-tert-butyl-5,10-dihydrobenzo[b]pyrido[4,3-e]-1,4-diazepin-11-one and brown by-products. The crude product obtained in this way is dissolved in ethyl acetate at the boiling temperature, and four times the amount of cyclohexane is added dropwise. After stirring at room temperature for 18 h, the crystals formed are filtered off with suction, washed with n-heptane and dried in vacuo. Yield: 7.5 g (26 mmol), 26%. Purity: >95% according to $^1$H-NMR.

The following derivatives are prepared analogously:

| Ex. | Cyanopyridine | 1,2-Diamino-benzene | Product | Yield |
|---|---|---|---|---|
| S33 | S32 | 95-54-5 | | 36% |
| S34 | S32 | 3171-45-7 | | 40% |
| S35 | S32 | 76179-40-3 | | 33% |

10) 2-tert-Butyl-5-chloro-1,6-naphthyridine, S36

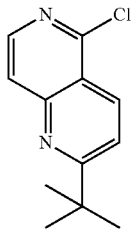

A mixture of 15.7 g (100 mmol) of 2-chloro-3-formyl-4-aminopyridine [338452-92-9], 37.6 ml (300 mmol) of tert-butyl methyl ketone, 1.0 ml (10 mmol) of piperidine and 100 ml of ethanol is heated under reflux for 60 h. After cooling, the reaction mixture is diluted with 500 ml of dichloromethane, washed five times with 500 ml of water each time, dried over magnesium sulfate, and the solvent is removed in vacuo. The residue is recrystallised from ethanol. Yield: 8.2 g (37 mmol), 37%. Purity: >95% according to $^1$H-NMR.

11) 8-Phenyl-5-chloro-1,6-naphthyridine, S37

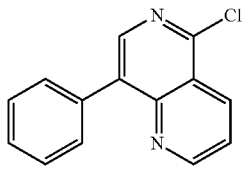 [SMILES: Clc1ncc(-c2ccccc2)c2ncccc12]

12.1 ml (130 mmol) of phosphoryl chloride are added dropwise at room temperature to a suspension of 22.2 g (100 mmol) of 8-phenyl-1,6-naphthyridin-5(6H)-one [173773-04-1] in 100 ml of toluene. After addition of 5 drops of N,N-dimethylaniline, the reaction mixture is heated under reflux for 5 h. After cooling, the reaction mixture is diluted with 300 ml of toluene, poured onto 1000 g of ice and rendered alkaline (pH about 9) by addition of 5 N NaOH. The organic phase is separated off, washed once with 300 ml of sat. sodium chloride solution, dried over magnesium sulfate, and the toluene is removed in vacuo. Yield: 22.9 g (95 mmol), 95%. Purity: >95% according to $^1$H-NMR.

12) 5-Amino-1,6-naphthyridine derivatives

Preparation of 2-tert-butyl-5-amino-1,6-naphthyridine, S38

A mixture of 22.1 g (100 mmol) of 2-tert-butyl-5-chloro-1,6-naphthyridine (S36), 32.1 g (600 mmol) of ammonium chloride in 100 ml of sulfolane is stirred at 200° C. for 20 h. 300 ml of water are added to the cooled mixture, which is then stirred at room temperature for 2 h. The solid is filtered off with suction, washed twice with 50 ml of water each time and subsequently suspended in a mixture of 50 ml of methanol and 150 ml of conc. ammonia solution. The suspension is stirred at room temperature for 20 h. The solid is filtered off, washed three times with 50 ml of water each time, dried in vacuo and subjected to sublimation (p about $1\times10^{-2}$ mbar, T=150° C.). Yield: 16.7 g (83 mmol), 83%. Purity: >97% according to $^1$H-NMR.

The following derivatives are prepared analogously:

| Ex. | 5-Chloro-1,6-naphthyridine | Product | Yield |
|---|---|---|---|
| S38 | 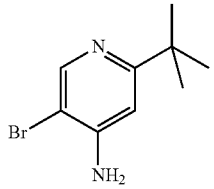 S36 | | 83% |
| S39 | | | 71% |

13) 3-Bromo-4-amino-6-tert-butylpyridine, S40

Procedure analogous to V. Canibano et al., Synthesis 2001, 14, 2175. 18.7 g (105 mmol) of N-bromosuccinimide are added in portions at 40° C. to a vigorously stirred, light-protected solution of 15.0 g (100 mmol) of 2-tertbutyl-4-aminopyridine [39919-69-2] in 500 ml of acetonitrile, and the mixture is stirred for a further 30 h. The solvent is removed in vacuo, the residue is taken up in 500 ml of dichloromethane, washed five times with 500 ml of water each time and once with 300 ml of sat. sodium chloride solution, the organic phase is dried over sodium sulfate, and the solvent is then removed in vacuo. The crude product is recrystallised from cyclohexane. Yield: 17.9 g (78 mmol), 78%. Purity: >95% according to $^1$H-NMR.

14) 1-Amino-6-tert-butyl-2,7-naphthyridine, S41

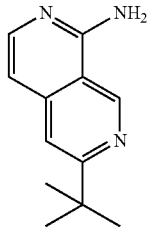

Procedure analogous to A. Zhang et al., J. Combi. Chem. 2007, 9, 6, 916: A mixture of 17.4 g (100 mmol) of 3-cyano- 4-methyl-6-tert-butylpyridine [942938-45-6], 14.0 ml (105 mmol) of N,N-dimethylformamind dimethyl acetal [4637-24-5] and 150 ml of DMF is heated under reflux for 16 h. The DMF is then removed at 70° C. in vacuo. 46.3 g (600 mmol) of anhydrous ammonium acetate are added to the oily residue, the mixture is homogenised, heated to melt ing in an oil bath (temperature about 135° C.) and stirred for 3 h. After cooling, the melt is taken up in a mixture of 200 ml of water and 100 ml of ethanol, rendered alkaline (pH about 9) by addition of conc. ammonia solution and extracted three times with 300 ml of dichloromethane each time. The combined org. phases are washed twice with 300 ml of water each time and dried over sodium sulfat e. Aft er evaporation of the org. phase in vacuo, the residue remaining is subjected to sublimation (p about $1 \times 10^{-2}$ mbar, T=150° C.). Yield: 13.7 g (68 mmol), 68%. Purity: >95% according to $^1$H-NMR.

15) 2-N-Pivaloylamido-3-cyano-6-tert-butylpyridine, S42

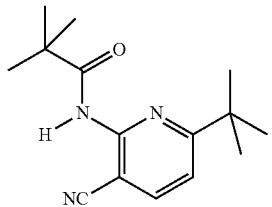 [SMILES: CC(C)(C)C(=O)Nc1nc(C(C)(C)C)ccc1C#N]

A mixture of 19.5 g (100 mmol) of 2-chloro-3-cyano-6-tert-butylpyridine (S28), 14.2 g (140 mmol) of pivalamide [754-10-9], 48.9 g (150 mmol) of caesium carbonate, 1.7 g (3 mmol) of 9,9-dimethyl-4,5-bis(diphenylphosphino)xanthene and 630 mg (2.8 mmol) of palladium(II) acetate in 400 ml of dioxane is stirred at 100° C. for 12 h. After cooling, the solvent is removed in vacuo, the residue is taken up in 1000 ml of ethyl acetate, the organic phase is washed three times with 300 ml of water each time and once with 300 ml of saturated sodium chloride solution and dried over magnesium sulfate. After removal of the solvent, a brown solid remains. Yield: 24.9 g (96 mmol), 96%. Purity: >95% according to $^1$H-NMR.

16)
2-(2-Amino-6-tert-butylpyridin-3-yl)benzimidazole derivatives

Preparation of
2-(2-amino-6-tert-butylpyridin-3-yl)benzimidazole, S43

A mixture, homogenised in a mortar, of 25.9 g (100 mmol) of 2-N-pivaloylamido-3-cyano-6-tert-butylpyridine (S42) and 90.5 g (500 mmol) of ophenylenediamine dihydrochloride [615-28-1] is put into an oil bath preheated to 240° C. and left at this temperature for 3.5 h. After cooling, the deep-blue melt is dissolved in a mixture of 150 ml of ethanol and 300 ml of water at elevated temperature, and a solution of 40 g of sodium carbonate in 200 ml of water is then added dropwise with vigorous stirring (note: foaming, evolution of carbon dioxide). When the addition is complete, the mixture is stirred for a further 30 min., the grey solid is then filtered off with suction, washed three times with 100 ml of water each time and dried in vacuo. Yield: 38.0 g, 86% of a 1:1 mixture of the product and 2-tert-butylbenzimidazole, which is reacted without further purification.

The following derivatives are prepared analogously:

| Ex. | Cyanopyridine | 1,2-Diamino-benzene | Product | Yield |
|---|---|---|---|---|
| S45 | 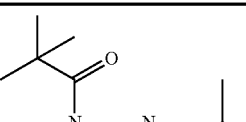<br>S42 | 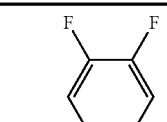<br>123470-46-2 | 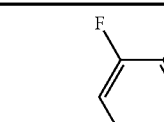 | 63% |

17)
3-Cyano-4-N-pivaloylamido-6-tert-butylpyridine, S46

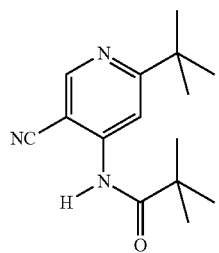 [SMILES: CC(C)(C)C(=O)Nc1cc(C(C)(C)C)ncc1C#N]

A mixture of 19.5 g (100 mmol) of 3-cyano-4-chloro-6-tert-butylpyridine, (S32), 14.2 g (140 mmol) of pivalamide [754-10-9], 48.9 g (150 mmol) of caesium carbonate, 1.7 g (3 mmol) of 9,9-dimethyl-4,5-bis(diphenylphosphino)xanthene and 630 mg (2.8 mmol) of palladium(II) acetate in 400 ml of dioxane is stirred at 100° C. for 12 h. After cooling, the solvent is removed in vacuo, the residue is taken up in 1000 ml of ethyl acetate, the org. phase is washed three times with 300 ml of water each time and once with 300 ml of sat. sodium chloride solution and dried over magnesium sulfate. After removal of the solvent, a brown solid remains. Yield: 24.4 g (94 mmol), 94%. Purity: >95% according to $^1$H-NMR.

18)
2-(4-Amino-6-tert-butylpyridin-3-yl)benzimidazole, S47

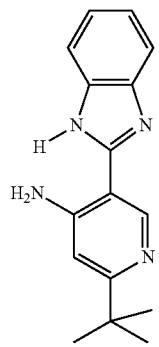

A mixture, homogenised in a mortar, of 25.9 g (100 mmol) of 3-cyano-4-N-pivaloylamido-6-tert-butylpyridine (S46), 90.5 g (500 mmol) of o-phenylenediamine dihydrochloride [615-28-1] is put into an oil bath pre-heated to 240° C. and left at this temperature for 3.5 h. After cooling, the deep-blue melt is dissolved in a mixture of 150 ml of ethanol and 300 ml of water at elevated temperature, and a solution of 40 g of sodium carbonate in 200 ml of water is then added dropwise with vigorous stirring (note: foaming, evolution of carbon dioxide). When the addition is complete, the mixture is stirred for a further 30 min., the grey solid is then filtered off with suction, washed three times with 100 ml of water each time and dried in vacuo. Yield: 33.5 g, 76% of a 1:1 mixture of the product and 2-tert-butylbenzimidazole, which is reacted without further purification.

19) 2-(2-tert-Butylpyrimidin-5-yl)benzimidazole, S48

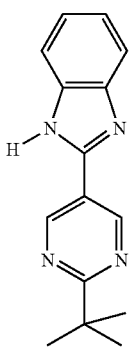 [SMILES: CC(C)(C)c1ncc(-c2nc3ccccc3[nH]2)cn1]

16.9 g (55 mmol) of oxone [70693-62-8] are added in portions with stirring at 10° C. to a solution of 16.4 g (100 mmol) of 2-tert-butylpyrimidine-5-carboxaldehyde [104461-06-5] and 11.9 g (110 mmol) of 1,2-diaminobenzene in a mixture of 100 ml of DMF and 3 ml of water, and the mixture is subsequently stirred at room temperature until conversion of the aldehyde is complete (about 2 h). The reaction mixture is stirred into a solution of 40 g of potassium carbonate solution in 2000 ml of water, stirred for a further 15 min., the solid formed is filtered off with suction, washed three times with 100 ml of water each time and dried in vacuo.

The solid is dissolved in about 50 ml of hot ethyl acetate, and, during cooling, diethyl ether is added until slightly cloudy, the mixture is stirred for a further 12 h, the crystals are filtered off with suction, washed once with 50 ml of diethyl ether and dried in vacuo. Yield: 16.6 g (66 mmol), 66%. Purity: >95% according to ¹H-NMR.

20) 4-Chloro-8-tert-butylquinazoline, S49

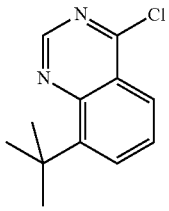

20.1) 8-tert-Butyl-4(3H)quinazolinone

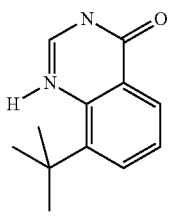

Procedure analogous to M. Berg et al., Chem. Med. Chem. 2009, 4, 2, 249: a mixture of 19.3 g (100 mmol) of 2-amino-3-tert-butylbenzoic acid [917874-35-2], 31.4 g (300 mmol) of formamidine acetate [3473-63-0] and 4.4 ml (110 mmol) of formamide is stirred at 160° C. for 12 h. After cooling to 60° C., a mixture of 200 ml of ethanol and 200 ml of 2 N sodium hydroxide solution is added dropwise, the mixture is filtered through a P4 frit covered with sea sand in order to remove polymeric material and then rendered neutral by addition of 2 N hydrochloric acid. After stirring for 12 h, the crystals formed are filtered off with suction and washed three times with 100 ml of water each time. Yield: 13.9 g (68 mmol), 68%. Purity: >95% according to ¹H-NMR.

20.2) 4-Chloro-8-tert-butylquinazoline, S49

18.6 ml (200 mmol) of phosphoryl chloride are added dropwise at room temperature to a suspension of 10.2 g (50 mmol) of 8-tert-butyl-4(3H)-quinazolinone in 100 ml of toluene. After addition of 5 drops of N,N-dimethylaniline, the reaction mixture is heated under reflux for 5 h. After cooling, the reaction mixture is diluted with 300 ml of toluene, poured onto 1000 g of ice and rendered alkaline (pH about 9) by addition of conc. ammonia solution. The organic phase is separated off, washed once with 300 ml of sat. sodium chloride solution, dried over magnesium sulfate, and the toluene is removed in vacuo. The residue is chromatographed on silica gel (n-heptane:ethyl acetate 3:1 v:v). Yield: 9.3 g (42 mmol), 84%. Purity: >95% according to ¹H-NMR.

21) 3,4-Diamino-6-tert-butylpyridine dihydrochloride, S50

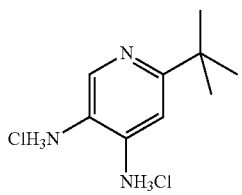

Procedure analogous to 4) S18 using 22.9 g (100 mmol) of 3-bromo-4-amino-6-tert-butylpyridine (S40) instead of 29.5 g (100 mmol) of 2-(2-bromo-4-fluorophenyl)-D4-benzimidazole (S9). The crude product is converted into the dihydrochloride by dissolution in 100 ml of ethanol and introduction of gaseous hydrochloric acid. The crystals obtained in this way are filtered off with suction and dried in vacuo. Yield: 13.3 g (56 mmol), 56%. Purity: >95% according to ¹H-NMR.

22) 2-(2-Amino-6-tert-butylpyridin-3-yl)-6-tert-butyl-3H-imidazo[4,5-c]pyridine, S51

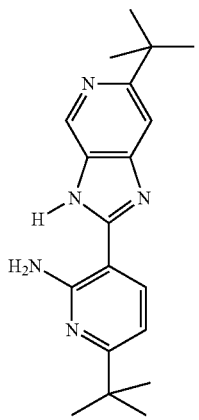 [SMILES: CC(C)(C)c1cc2nc(-c3ccc(C(C)(C)C)nc3N)[nH]c2cn1]

Procedure analogous to 16) S43, using 71.4 g (300 mmol) of 3,4-diamino-6-tert-butylpyridine dihydrochloride (S50) instead of 90.5 g (500 mmol) of o-phenylenediamine dihydrochloride. After cooling, the deep-blue melt is dissolved in a mixture of 150 ml of ethanol and 300 ml of water at elevated temperature, and a solution of 25 g of sodium carbonate in 100 ml of water is then added dropwise with vigorous stirring (note: foaming, evolution of carbon dioxide). When the addition is complete, the mixture is stirred for a further 30 min., the brown solid is then filtered off with suction, washed three times with 100 ml of water each time and dried in vacuo.

Yield: 43.8 g, 79% of a 1:1 mixture of the product and 2,6-di-tert-butyl-3H-imidazo[4,5-c]pyridine, which is reacted without further purification.

23) 2-(2-tert-Butylpyrimidin-5-yl)-6-tert-butyl-3H-imidazo[4,5-c]pyridine, S52

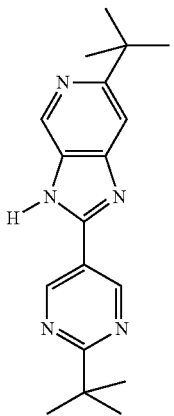 [SMILES: CC(C)(C)c1cc2nc(-c3cnc(C(C)(C)C)nc3)[nH]c2cn1]

Preparation analogous to 16), S43, using 16.1 g (100 mmol) of 2-tert-butyl-5-cyanopyrimidine [126230-72-6] and 71.4 g (300 mmol) of 3,4-diamino-6-tert-butylpyridine dihydrochloride (S50) instead of 25.9 g (100 mmol) of 2-N-pivaloylamido-3-cyano-6-tert-butylpyridine (S42) and 90.5 g (500 mmol) of o-phenylenediamine dihydrochloride [615-28-1]. After cooling, the violet melt is dissolved in a mixture of 150 ml of ethanol and 300 ml of water at elevated temperature, and a solution of 25 g of sodium carbonate in 100 ml of water is then added dropwise with vigorous stirring (note: foaming, evolution of carbon dioxide). When the addition is complete, the mixture is stirred for a further 30 min., the brown solid is then filtered off with suction, washed three times with 100 ml of water each time and dried in vacuo. Yield: 23.8 g (77 mmol), 77%. Purity: >95% according to $^1$H-NMR.

24) 2-(4-Amino-6-tert-butylpyridin-3-yl)-6-tert-butyl-3H-imidazo[4,5-c]pyridine, S53

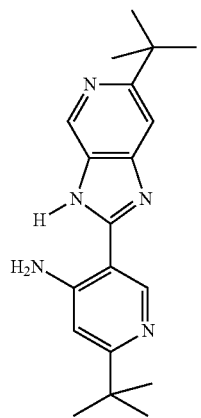

Procedure analogous to 18) S47, using 71.4 g (300 mmol) of 3,4-diamino-6-tert-butylpyridine dihydrochloride (S50) instead of 90.5 g (500 mmol) of o-phenylenediamine dihydrochloride. After cooling, the deep-blue melt is dissolved in a mixture of 150 ml of ethanol and 300 ml of water at elevated temperature, and a solution of 25 g of sodium carbonate in 100 ml of water is then added dropwise with vigorous stirring (note: foaming, evolution of carbon dioxide). When the addition is complete, the mixture is stirred for a further 30 min., the brown solid is then filtered off with suction, washed three times with 100 ml of water each time and dried in vacuo. Yield: 40.5 g, 74% of a 1:1 mixture of the product and 2,6-di-tert-butyl-3H-imidazo[4,5-c]pyridine, which is reacted without further purification.

25) Methyl 2-tert-butyl-4-(N-pivaloylamido)pyrimidine-5-carboxylate, S54

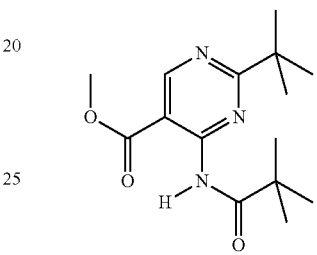

A mixture of 22.9 g (100 mmol) of methyl 2-tert-butyl-4-chloropyrimidine-5-carboxylate [897375-22-3], 14.2 g (140 mmol) of pivalamide [754-10-9], 48.9 g (150 mmol) of caesium carbonate, 1.7 g (3 mmol) of 9,9-dimethyl-4,5-bis(diphenylphosphino)xanthene and 630 mg (2.8 mmol) of palladium(II) acetate in 400 ml of dioxane is stirred at 100° C. for 12 h. After cooling, the solvent is removed in vacuo, the residue is taken up in 1000 ml of ethyl acetate, the org. phase is washed three times with 200 ml of water each time and once with 300 ml of sat. sodium chloride solution and dried over magnesium sulfate. After removal of the solvent, a brown solid remains. Yield: 28.2 g (96 mmol), 96%. Purity: >95% according to $^1$H-NMR.

26) 2-(2-tert-Butyl-4-aminopyrimidin-5-yl)benzimidazole, S55

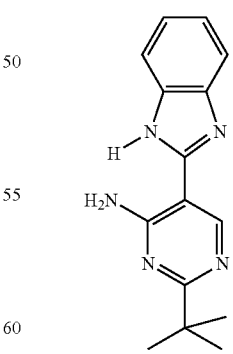

Preparation analogous to 16) S43, using 29.3 g (100 mmol) of methyl 2-tert-butyl-4-(N-pivaloylamido)pyrimidine-5-carboxylate (S54) instead of 25.9 g (100 mmol) of 2-N-pivaloylamido-3-cyano-6-tert-butylpyridine (S42). Methanol and water formed during the heating of the reaction mixture are expelled by a weak stream of argon. After cooling, the black melt is dissolved in a mixture of 150 ml of ethanol and 300 ml of water at elevated temperature, and a solution of 40 g of sodium carbonate in 2700 ml of water is then added dropwise with vigorous stirring (note: foaming, evolution of carbon dioxide). When the addition is complete, the mixture is stirred for a further 30 min., the brown solid is then filtered off with suction, washed three times with 100 ml of water each time and dried in vacuo. Yield: 28.3 g, 64% of a 1:1 mixture of the product and 2-tert-butylbenzimidazole, which is reacted without further purification.

27) 2-(2-tert-Butyl-4-aminopyrimidin-5-yl)-6-tert-butyl-3H-imidazo[4,5-c]pyridine, S56

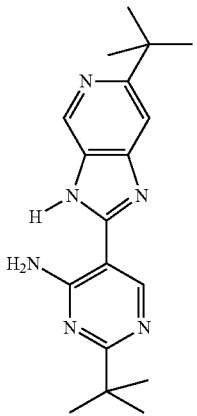

Preparation analogous to 16) S43, using 29.3 g (100 mmol) of methyl 2-tert-butyl-4-(N-pivaloylamido)pyrimidine-5-carboxylate (S54) instead of 25.9 g (100 mmol) of 2-N-pivaloylamido-3-cyano-6-tert-butylpyridine (S42) and 71.4 g (300 mmol) of 3,4-diamino-6-tert-butylpyridine di-hydrochloride (S50) instead of 90.5 g (500 mmol) of o-phenylenediamine dihydrochloride. Methanol and water formed during the heating of the reaction mixture are expelled by a weak stream of argon. After cooling, the black melt is dissolved in a mixture of 150 ml of ethanol and 300 ml of water at elevated temperature, and a solution of 25 g of sodium carbonate in 100 ml of water is added dropwise with vigorous stirring (note: foaming, evolution of carbon dioxide). When the addition is complete, the mixture is stirred for a further 30 min., the brown solid is then filtered off with suction, washed three times with 100 ml of water each time and dried in vacuo. Yield: 38.9 g, 70% of a 1:1 mixture of the product and 2,6-di-tert-butyl-3H-imidazo[4,5-c]pyridine, which is reacted without further purification.

28) 2-(N-Alkylamido)benzaldehyde derivatives

Preparation of 2-(N-pivaloylamido)-4-fluorobenzaldehyde, S57

A mixture of 20.3 g (100 mmol) of 2-bromo-4-fluorobenzaldehyde [59142-68-6], 14.2 g (140 mmol) of pivalamide [754-10-9], 81.5 g (250 mmol) of caesium carbonate, 1.7 g (3 mmol) of 9,9-dimethyl-4,5-bis(diphenyl-phosphino)xanthene and 630 mg (2.8 mmol) of palladium(II) acetate in 400 ml of dioxane is stirred at 100° C. for 4 h. After cooling, the solvent is removed in vacuo, the residue is taken up in 1000 ml of ethyl acetate, the organic phase is washed three times with 300 ml of water each time and once with 300 ml of sat. sodium chloride solution and filtered through a short silica-gel column. The solids obtained after the solvent has been stripped off in vacuo are reacted further. Yield: 20.8 g (93 mmol), 95%. Purity: >95% according to $^1$H-NMR.

The following derivatives are prepared analogously:

| Ex. | 2-Bromo-4-fluoro benzaldehyde | Amide | Product | Yield |
|---|---|---|---|---|
| S57 | 59142-68-6 | 754-10-9 | | 93% |
| S58 | 59142-68-6 | 926-04-5 | | 95% |

29) 2-(2-(N-Alkylamido)phenyl)benzimidazole derivatives

Preparation of 2-(2-(N-pivaloylamido)-4-fluorophenyl)benzimidazole, S59

A solution of 22.3 g (100 mmol) of 2-(N-pivaloylamido)-4-fluorobenzaldehyde (S57) and 11.9 g (110 mmol) of o-phenylenediamine [95-54-5] in 50 ml of ethanol is placed in a 500 ml round-bottomed flask with water separator and stirred at 50° C. for 30 min. 50 ml of nitrobenzene are then added, and the temperature is increased to gentle reflux of the nitrobenzene, with the ethanol and water formed being distilled off during the heating. After 2 h under gentle reflux, the mixture is allowed to cool to 50° C., 40 ml of methanol are added, the mixture is then allowed to cool completely with stirring, stirred at room temperature for a further 2 h, the crystals formed are then filtered off with suction, washed twice with 20 ml of methanol each time and dried in vacuo. Yield: 28.6 g (92 mmol), 92%. Purity: >95% according to $^1$H-NMR.

The following derivatives are prepared analogously:

30) 6-Chlorobenzo[4,5]imidazo[1,2-c]quinazoline, S61

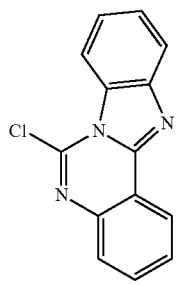 [SMILES: Clc1nc2ccccc2c2nc3ccccc3n12]

A mixture of 23.5 g (100 mmol) of benzimidazo[1,2-c]quinazolin-6(5H)-one [16367-99-0], 22.9 g (110 mmol) of phosphorus pentachloride and 250 ml of phosphoryl chloride is heated under reflux for 24 h. The excess phosphoryl chloride is removed in vacuo, 1000 ml of dichloromethane are added to the residue, the mixture is hydrolysed by addition of 1000 g of ice, rendered weakly alkaline by addition of 10% by weight sodium hydroxide solution, the organic phase is separated off, dried over sodium sulfate, and the dichloromethane is then removed in vacuo. Yield: 24.1 g (94 mmol), 94%. Purity: >95% according to $^1$H-NMR.

| Ex. | 2-(2-(N-Alkyl-amido)phenyl)-benzimidazole derivatives | Amine | Product | Yield |
|---|---|---|---|---|
| S59 | S57 | 95-54-5 | | 92% |
| S60 | S58 | 95-54-5 | | 79% |

31) 6-tert-Butyl-2-(3,3-dimethylbut-1-ynyl)nicotinonitrile, S62

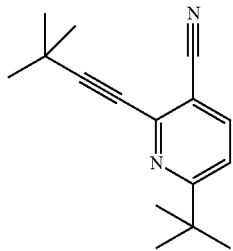 [SMILES: CC(C)(C)C#Cc1nc(C(C)(C)C)ccc1C#N]

15.7 g (60 mmol) of triphenylphosphine, 6.7 g (30 mmol) of palladium(II) acetate, 5.7 g (30 mmol) of copper(I) iodide and 155.6 g (1.9 mmol) of tert-butylacetylene are added consecutively to a solution of 194.7 g (1 mol) of 2-chloro-3-cyano-6-tert-butylpyridine, S28, in a mixture of 1800 ml of DMF and 1000 ml of triethylamine, and the mixture is stirred at 65° C. for 4 h. After cooling, the precipitated triethylammonium hydrochloride is filtered off with suction, rinsed with 300 ml of DMF. The filtrate is freed from the solvents in vacuo. The oily residue is taken up in 1000 ml of ethyl acetate, the solution is washed five times with 500 ml of water each time and once with 500 ml of saturated sodium chloride solution, and the organic phase is dried over magnesium sulfate. After removal of the ethyl acetate in vacuo, the black oily residue is subjected to bulb-tube distillation (p about $10^{-2}$ mbar, T=120-140° C.). Yield: 190.6 g (793 mmol), 79%. Purity: >97% according to $^1$H-NMR.

The following derivatives are prepared analogously:

| Ex. | Pyridine | Alkyne | Product | Yield |
|---|---|---|---|---|
| S63 | | 1066-4-2<br>The product is reacted further without bulb-tube distillation. | | 46% |
| S64 | | 74-99-7<br>The alkyne is introduced into the reaction mixture. | | 77% |
| S65 | | 6111-63-3<br>The alkyne is introduced into the reaction mixture. | | 74% |
| S66 | | 536-74-3 | | 86% |

| Ex. | Pyridine | Alkyne | Product | Yield |
|---|---|---|---|---|
| S67 | | 769-26-6 | | 81% |
| S68 | | 13361-63-2 | | 79% |

32) 6-tert-Butyl-2-(3,3-dimethylbut-1-ynyl)pyridine-3-carboxaldehyde, S69

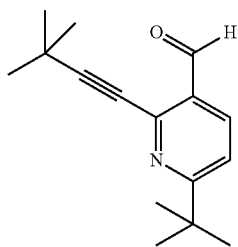 [SMILES: CC(C)(C)C#Cc1nc(C(C)(C)C)ccc1C=O]

310 ml (315 mmol) of diisobutylaluminium hydride, 1M in toluene, are added dropwise to a solution, cooled to −78° C., of 72.1 g (300 mmol) of 6-tert-butyl-2-(3,3-dimethylbut-1-ynyl)nicotinonitrile, S62, in 1500 ml of dichloromethane at such a rate that the temperature does not exceed −65° C. When the addition is complete, the reaction mixture is stirred at −78° C. for a further 2 h, then allowed to warm slowly to room temperature and stirred for a further 12 h. After re-cooling to −10° C., 300 ml of THF and then, with vigorous stirring, 400 ml of 2 N sulfuric acid (exothermic!) are added, and the mixture is stirred at room temperature for a further 12 h. After re-cooling to −10° C., a solution of 70 g of NaOH in 300 ml of water is added, the aqueous phase is separated off, the organic phase is washed three times with 1000 ml of water each time, once with 500 ml of saturated sodium chloride solution, dried over magnesium sulfate, and the solvent is removed in vacuo.

Yield: 69.6 g (286 mmol), 95%. Purity: >95% according to $^1$H-NMR.

The following derivatives are prepared analogously:

| Ex. | Nitrile | Product Pyridine-3-carbox-aldehydes | Yield |
|---|---|---|---|
| S70 | | | 87% |

-continued
| Ex. | Nitrile | Product Pyridine-3-carbox-aldehydes | Yield |
|---|---|---|---|
| S71 |  | 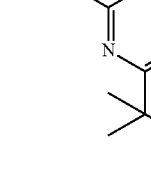 | 55% |
| S72 | 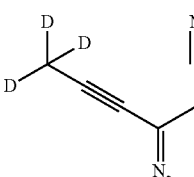 | 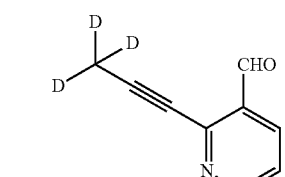 | 58% |
| S73 | 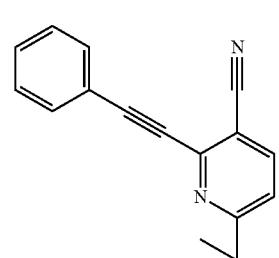 | 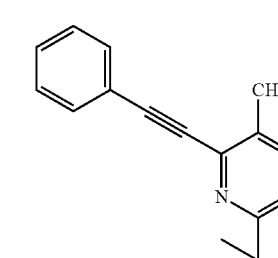 | 93% |
| S74 | 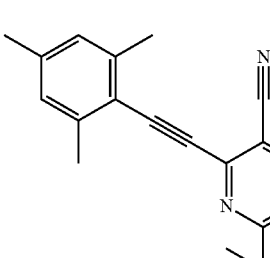 | 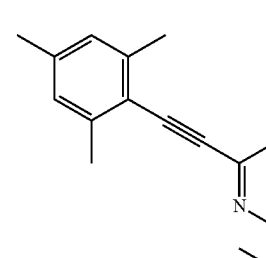 | 96% |
| S75 | 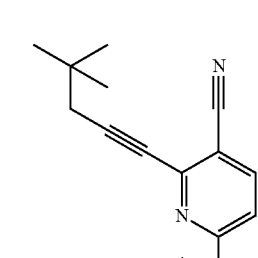 | 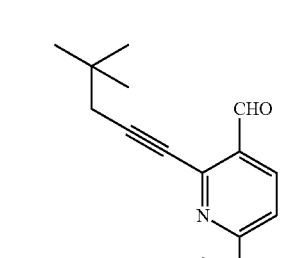 | 57% |

B. Synthesis of the Ligands L

1) Benzimidazo[1,2-c]quinazoline systems

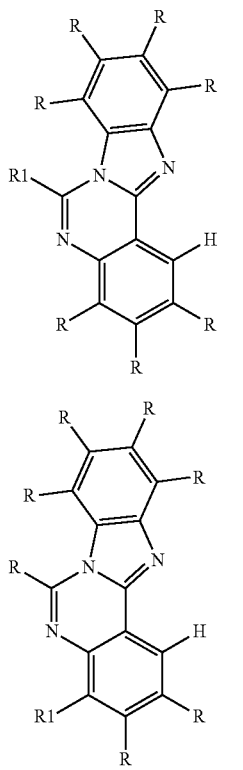

formula (6)

formula (7)

1.1) From 2-(2-aminophenyl)benzimidazole derivatives

General Ligand Synthesis Variant A

A vigorously stirred mixture of 100 mmol of the 2-(2-aminophenyl)benzimidazole derivative, 350 mmol of the carboxylic acid chloride and 300 mmol of the carboxylic acid is heated for 24 to 100 h under reflux in the case of carboxylic acid chlorides which boil below 150° C. or at 150° C. to 180° C. in the case of carboxylic acid chlorides which boil above 150° C., until the 2-(2-aminophenyl)benzimidazole derivative has reacted. After cooling, the reaction mixture is taken up in ethanol or ethyl acetate (50-200 ml). The reaction mixture is stirred into a mixture of 500 g of ice and 500 ml of aqueous conc. ammonia with vigorous stirring. If the product is produced as a solid, this is filtered off with suction, washed with water and sucked dry. If the product is produced as an oil, this is extracted with three portions of 300 ml of ethyl acetate in each case. The organic phase is separated off, washed with 500 ml of water and evaporated in vacuo. The crude product is taken up in ethyl acetate or dichloromethane, filtered through a short column containing aluminium oxide, basic, activity grade 1, or silica gel in order to remove brown impurities. After the product obtained in this way has been recrystallised twice (methanol, ethanol, acetone, dioxane, etc.), it is freed from low-boiling components and non-volatile secondary components by bulb-tube distillation or sublimation (p about $1 \times 10^{-5}$ mbar, T about 150-230° C.). Purity according to $^1$H-NMR typically >99.5%.

General Ligand Synthesis Variant B

Analogous procedure to variant A, but 50 mmol of water are added instead of the carboxylic acid.

General Ligand Synthesis Variant C

Analogous procedure to variant A, but no carboxylic acid is added.

Preparation of L13

A mixture of 20.9 g (100 mmol) of 2-(2-aminophenyl)benzimidazole, 42.2 g (350 mmol) of pivaloyl chloride and 30.6 g (300 mmol) of pivalic acid is heated under reflux for 50 h. The reaction mixture is allowed to cool to about 60° C., 100 ml of ethanol are added, the mixture obtained n this way is stirred into a mixture of 500 g of ice and 500 ml of conc. ammonia, the mixture is stirred for a further 15 min., the precipitated solid is then filtered off with suction, washed twice with 100 ml of water each time and sucked dry. The crude product is taken up in 200 ml of dichloromethane, filtered through a short silica-gel column, rinsed with 200 ml of dichloromethane, the dichloromethane is removed in vacuo, the residue is recrystallised twice from about 600 ml of ethanol, and the product is finally sublimed twice in vacuo (p=$1 \times 10^{-5}$ mbar, T=160° C.). Yield: 21.2 g (77 mmol), 77%. Purity: >99.5% according to $^1$H-NMR.

Preparation of L23

A mixture of 20.9 g (100 mmol) of 2-(2-aminophenyl)benzimidazole, 47.1 g (350 mmol) of 3,3-dimethylbutyryl chloride and 34.8 g (300 mmol) of 3,3-dimethylbutyric acid is heated under reflux for 20 h. The reaction mixture is allowed to cool to about 60° C., 100 ml of ethanol are added, the mixture obtained n this way is stirred into a mixture of 500 g of ice and 500 ml of conc. ammonia, the mixture is stirred for a further 15 min., the precipitated solid is then filtered off with suction, washed three times with 100 ml of water each time and sucked dry. The crude product is taken up in 200 ml of dichloromethane, filtered through a short silica-gel column, the silica-gel column is rinsed with 200 ml of dichloromethane, the dichloromethane is removed in vacuo, the residue is recrystallised twice from about 400 ml of ethanol, and the product is finally sublimed twice in vacuo (p=$1 \times 10^{-5}$ mbar, T=170° C.). Yield: 25.2 g (87 mmol), 87%. Purity: >99.5% according to $^1$H-NMR.

Preparation of L42

A mixture of 20.9 g (100 mmol) of 2-(2-aminophenyl)benzimidazole, 63.9 g (350 mmol) of 2,4,6-trimethylbenzoyl chloride and 0.9 ml of water is heated under reflux for 24 h. The reaction mixture is allowed to cool to about 40° C., 50 ml of ethyl acetate are added, the mixture obtained in this way is stirred into a mixture of 500 g of ice and 500 ml of conc. ammonia, the mixture is stirred for a further 15 min., the aqueous phase is extracted three times with 300 ml of ethyl acetate each time, the combined organic phases are dried over sodium sulfate, the organic phase is filtered through a short silica-gel column, the silica-gel column is rinsed with 200 ml of ethyl acetate, the ethyl acetate is removed in vacuo, the residue is recrystallised once from about 300 ml of methanol and once from about 100 ml of acetone, and the product is finally sublimed twice in vacuo (p=1×10⁻⁵ mbar, T=170° C.). Yield: 21.9 g (65 mmol), 65%. Purity: >99.5% according to ¹H-NMR.

1.2) From 2-(2-(N-alkylamido)phenyl)benzimidazole derivatives

General Ligand Synthesis Variant D

A vigorously stirred mixture of 100 mmol of the 2-(2-(N-alkylamido)phenyl)benzimidazole derivative and 350 mmol of the carboxylic acid chloride is heated under reflux—in the case of carboxylic acid chlorides which boil below 150° C.—or at 150° C. to 180° C.—in the case of carboxylic acid chlorides which boil above 150° C.—for 24 to 100 h until the 2-(2-(N-alkylamido)phenyl)benzimidazole derivative has reacted. If the reaction mixture is too pasty, it is diluted with an inert solvent whose boiling point matches the carboxylic acid chloride used, for example dioxane or diethylene glycol dimethyl ether. After cooling, the reaction mixture is taken up in dioxane (50-200 ml). The reaction mixture is stirred into a mixture of 500 g of ice and 500 ml of aqueous conc. ammonia with vigorous stirring. If the product is produced as a solid, this is filtered off with suction, washed with water and sucked dry. If the product is produced as an oil, this is extracted with three portions of 300 ml of ethyl acetate in each case. The organic phase is separated off, washed with water and evaporated in vacuo. The crude product is taken up in ethyl acetate or dichloromethane, filtered through a short containing aluminium oxide, basic, activity grade 1, or silica gel in order to remove brown impurities. After the product obtained n this way has been recrystallised twice (methanol, ethanol, acetone, dioxane, etc.), it is freed from low-boiling components and brown secondary components by bulb-tube distillation or sublimation (p about 1×10⁻⁵ mbar, T about 150-230° C.). Purity according to ¹H-NMR typically >99.5%.

1.3) From 6-chlorobenzo[4,5]imidazo[1,2-c]quinazoline derivatives

General Ligand Synthesis Variant E

A mixture of 25.4 g (100 mmol) of 6-chlorobenzo[4,5] imidazo[1,2-c]quinazoline, S61, and 200 mmol of the sodium alkoxide is heated under reflux in 200 ml of the corresponding alcohol until the 6-chlorobenzo[4,5]imidazo[1,2-c]quinazoline has reacted (2-12 h). The alcohol or solvent is distilled off, the solid is taken up in 300 ml of water and washed by stirring. After filtering off with suction, the solid is washed twice with 100 ml of water and once with 30 ml of cold methanol and then dried in vacuo. After the product obtained n this way has been recrystallised twice (ethanol, acetone, dioxane, etc.), it is freed from low-boiling components by bulb-tube distillation or sublimation (p about 1×10⁻⁵ mbar, T about 150-230° C.). Purity according to ¹H-NMR typically >99.5%.

The following derivatives are prepared analogously:

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L1 | A | 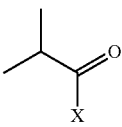<br>79-30-1<br>79-31-2 | 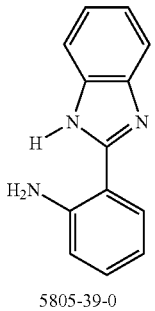<br>5805-39-0 | 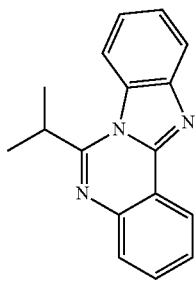 [SMILES: CC(C)c1nc2ccccc2c2nc3ccccc3n12] | 71% |
| L2 | A | 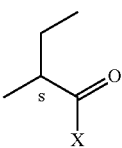<br>27763-54-8<br>1730-91-2 | 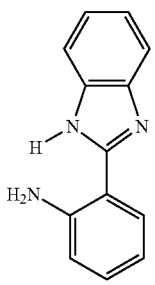<br>5805-39-0 | 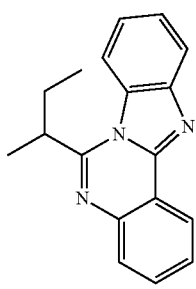 [SMILES: CCC(C)c1nc2ccccc2c2nc3ccccc3n12] | 70% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L3 | B | 2736-40-5 | 5805-39-0 | | 74% |
| L4 | B | 41693-47-4 | 5805-39-0 | | 61% |
| L5 | B | 29571-64-0 | 5805-39-0 | | 68% |
| L6 | A | 4023-34-1 1759-53-1 | 5805-39-0 | | 41% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L7 | C | 4524-93-0 | 5805-39-0 | | 70% |
| L8 | C | 2719-27-9 | 5805-39-0 | | 71% |
| L9 | B | 52912-50-2 | 5805-39-0 | | 65% |
| L10 | B | 29571-65-1 | 5805-39-0 | | 40% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L11 | B | 96188-83-9 | 5805-39-0 | | 66% |
| L12 | B | 54439-96-2 | 5805-39-0 | | 60% |
| L13 | A | 3282-30-2 75-98-9 | 5805-39-0 | | 78% |
| L14 | B | 5856-77-9 | 5805-39-0 | | 73% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L15 | B | 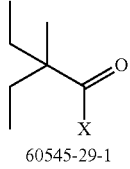 60545-29-1 | 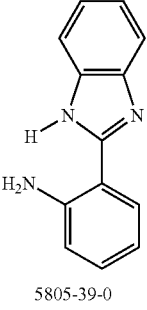 [SMILES: Nc1ccccc1-c1nc2ccccc2[nH]1] 5805-39-0 | 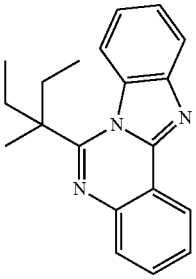 [SMILES: CCC(C)(CC)c1nc2ccccc2c2nc3ccccc3n12] | 73% |
| L16 | B | 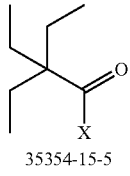 35354-15-5 | 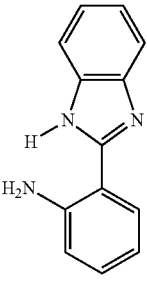 5805-39-0 | 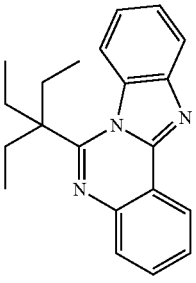 [SMILES: CCC(CC)(CC)c1nc2ccccc2c2nc3ccccc3n12] | 80% |
| L17 | B | 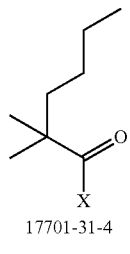 17701-31-4 | 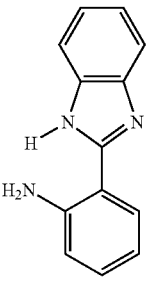 5805-39-0 | 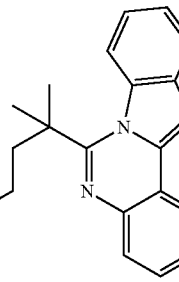 | 55% |
| L18 | B | 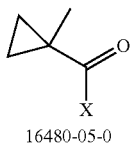 16480-05-0 | 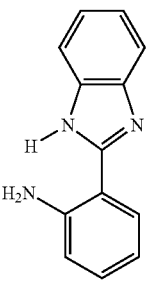 5805-39-0 | 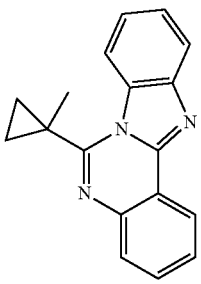 [SMILES: CC1(c2nc3ccccc3c3nc4ccccc4n23)CC1] | 51% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L19 | B | 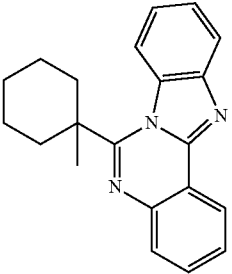 [SMILES: CC1(c2nc3ccccc3c3nc4ccccc4n23)CCCCC1]<br>2890-61-1 | 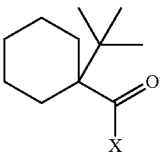<br>5805-39-0 | 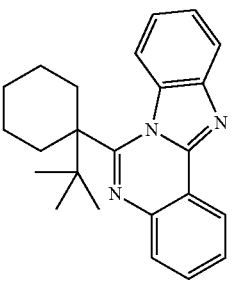 [SMILES: CC(C)(C)C1(c2nc3ccccc3c3nc4ccccc4n23)CCCCC1] | 57% |
| L20 | C | 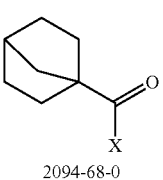<br>35618-41-8 | 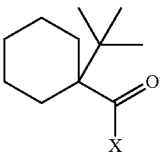<br>5805-39-0 | 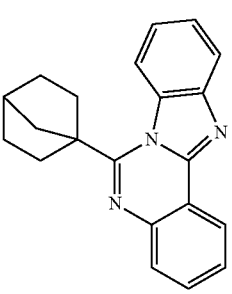 [SMILES: c1ccc2c(c1)nc(C13CCC(CC1)C3)n1c3ccccc3nc21] | 49% |
| L21 | B | 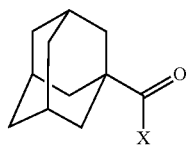<br>2094-68-0 | 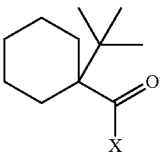<br>5805-39-0 | 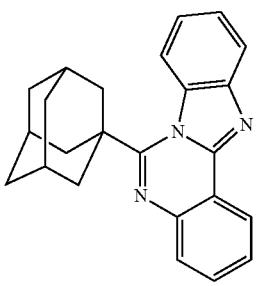 [SMILES: c1ccc2c(c1)nc(C13CC4CC(CC(C4)C1)C3)n1c3ccccc3nc21] | 65% |
| L22 | B | <br>2094-72-6 | 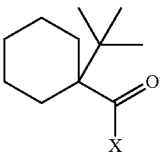<br>5805-39-0 |  | 67% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L23 | A | 7065-46-5<br>1070-83-3 | 5805-39-0 | | 69% |
| L24 | A | 79097-84-0<br>3177-74-0 | 5805-39-0 | | 66% |
| L25 | B | 115858-07-6 | 5805-39-0 | | 74% |
| L26 | B | 70079-84-4 | 5805-39-0 | | 36% |

-continued
| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L27 | B | 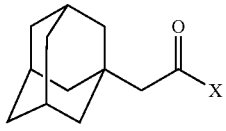 19835-38-2 | 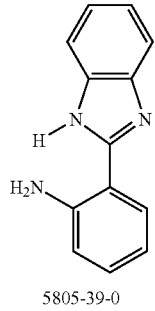 [SMILES: Nc1ccccc1-c1nc2ccccc2[nH]1] 5805-39-0 | 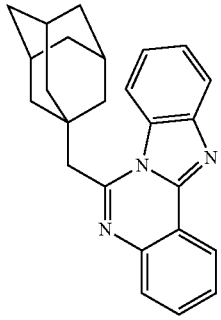 [SMILES: c1ccc2c(c1)nc(CC13CC4CC(CC(C4)C1)C3)n1c3ccccc3nc21] | 58% |
| L28 | B | 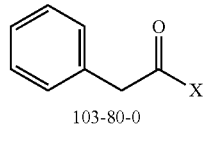 103-80-0 | 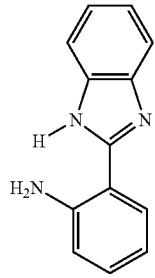 5805-39-0 | 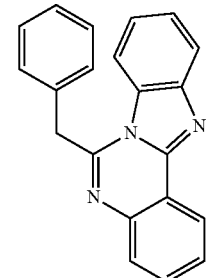 | 61% |
| L29 | B | 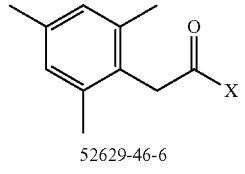 52629-46-6 | 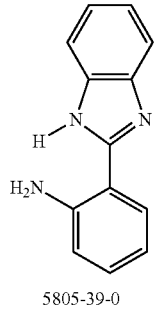 [SMILES: Nc1ccccc1-c1nc2ccccc2[nH]1] 5805-39-0 | 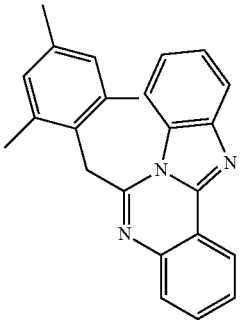 [SMILES: Cc1cc(C)c(Cc2nc3ccccc3c3nc4ccccc4n23)c(C)c1] | 67% |
| L30 | B | 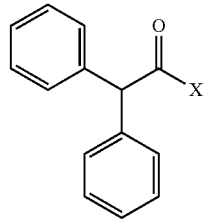 1871-76-7 | 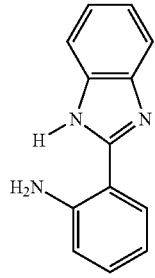 5805-39-0 | 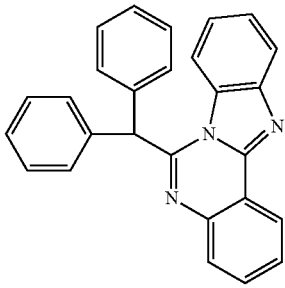 [SMILES: c1ccc(C(c2ccccc2)c2nc3ccccc3c3nc4ccccc4n23)cc1] | 65% |

-continued
| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L31 | B | 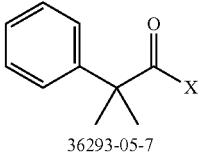 36293-05-7 | 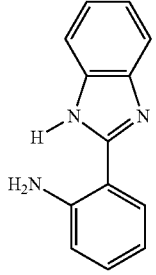 5805-39-0 | 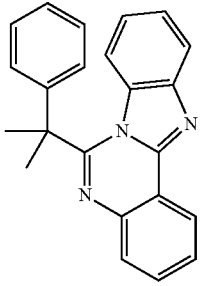 [SMILES: CC(C)(c1ccccc1)c1nc2ccccc2c2nc3ccccc3n12] | 70% |
| L32 | B | 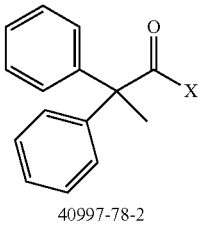 40997-78-2 | 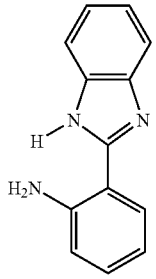 5805-39-0 | 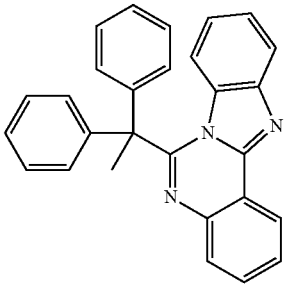 [SMILES: CC(c1ccccc1)(c1ccccc1)c1nc2ccccc2c2nc3ccccc3n12] | 62% |
| L33 | C | 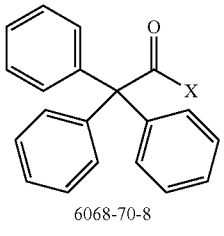 6068-70-8 | 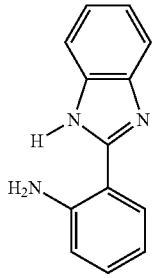 5805-39-0 | 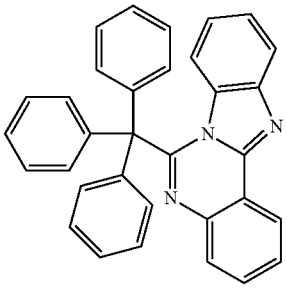 [SMILES: c1ccc(C(c2ccccc2)(c2ccccc2)c2nc3ccccc3c3nc4ccccc4n23)cc1] | 55% |
| L34 | B | 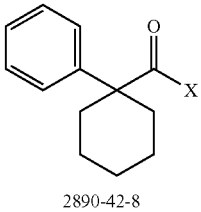 2890-42-8 | 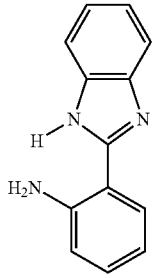 5805-39-0 | 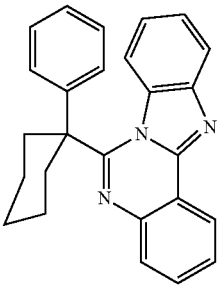 [SMILES: c1ccc(C2(c3nc4ccccc4c4nc5ccccc5n34)CCCCC2)cc1] | 60% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L35 | C | F$_3$C-C(=O)-X  354-32-5 | 2-(1H-benzimidazol-2-yl)aniline  5805-39-0 | 6-(trifluoromethyl)benzo[4,5]imidazo[1,2-c]quinazoline | 78% |
| L36 | C | F$_9$C$_4$-C(=O)-X  375-60-0 | 2-(1H-benzimidazol-2-yl)aniline  5805-39-0 | 6-(nonafluorobutyl)benzo[4,5]imidazo[1,2-c]quinazoline | 45% |
| L37 | C | CF$_3$-CH$_2$-C(=O)-X  41463-83-6 | 2-(1H-benzimidazol-2-yl)aniline  5805-39-0 | 6-(2,2,2-trifluoroethyl)benzo[4,5]imidazo[1,2-c]quinazoline | 52% |
| L38 | C | Ph-CF$_2$-C(=O)-X  312-24-3 | 2-(1H-benzimidazol-2-yl)aniline  5805-39-0 | 6-(difluoro(phenyl)methyl)benzo[4,5]imidazo[1,2-c]quinazoline | 66% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L39 | C | 63877-23-6 | 5805-39-0 | | 28% |
| L40 | B | 933-88-0 | 5805-39-0 | | 70% |
| L41 | B | 21900-37-8 | 5805-39-0 | | 61% |
| L42 | B | 938-18-1 | 5805-39-0 | | 48% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L43 | B | 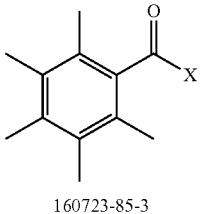 160723-85-3 | 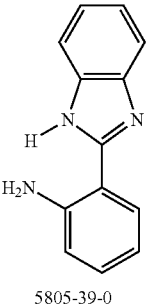 5805-39-0 | 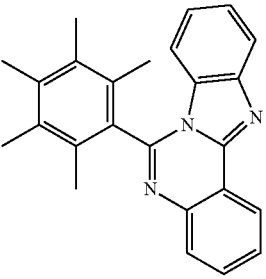 [SMILES: Cc1c(C)c(C)c(-c2nc3ccccc3c3nc4ccccc4n23)c(C)c1C] | 51% |
| L44 | B | 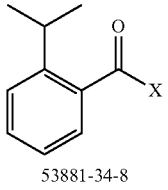 53881-34-8 | 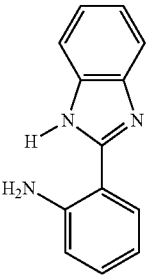 5805-39-0 | 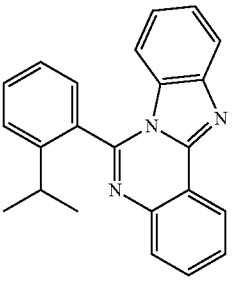 [SMILES: CC(C)c1ccccc1-c1nc2ccccc2c2nc3ccccc3n12] | 50% |
| L45 | B | 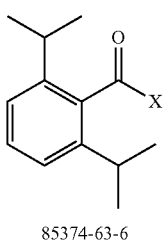 85374-63-6 | 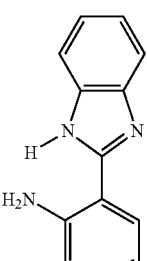 5805-39-0 | 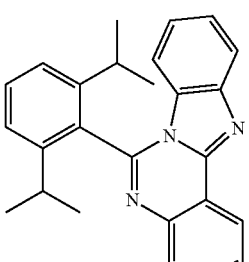 | 38% |
| L46 | B | 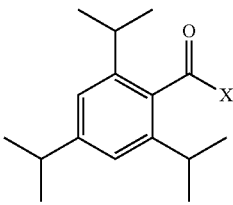 57199-00-5 | 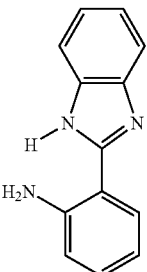 5805-39-0 | 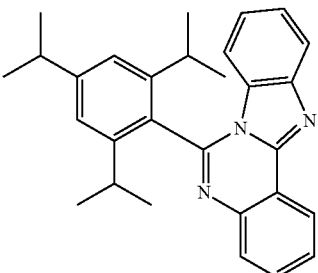 | 42% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L47 | B | 16372-51-3 | 5805-39-0 | | 54% |
| L48 | B | 20208-55-3 | 5805-39-0 | | 30% |
| L49 | B | 14002-52-9 | 5805-39-0 | | 56% |
| L50 | B | 167500-05-2 | 5805-39-0 | | 63% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L51 | B | 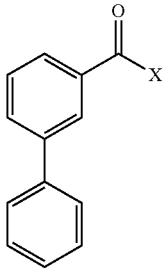<br>42498-44-2 | 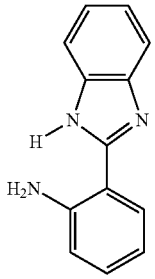<br>5805-39-0 | 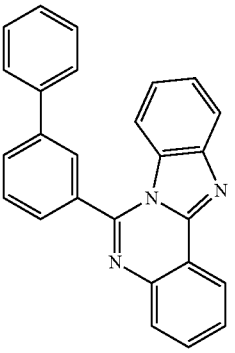 [SMILES: c1ccc(-c2cccc(-c3nc4ccccc4c4nc5ccccc5n34)c2)cc1] | 66% |
| L52 | C | 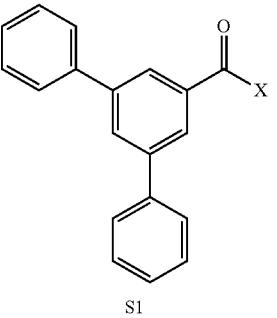<br>S1 | 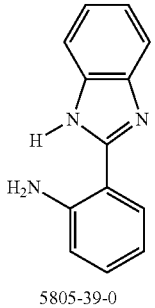<br>5805-39-0 | 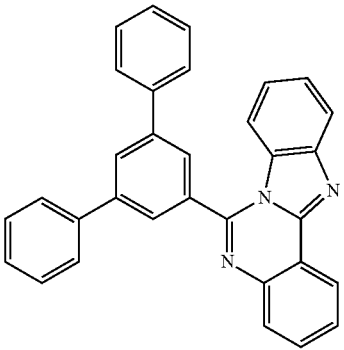 [SMILES: c1ccc(-c2cc(-c3ccccc3)cc(-c3nc4ccccc4c4nc5ccccc5n34)c2)cc1] | 72% |
| L53 | B | 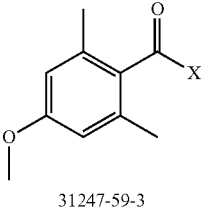<br>31247-59-3 | 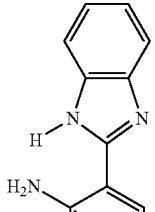<br>5805-39-0 | 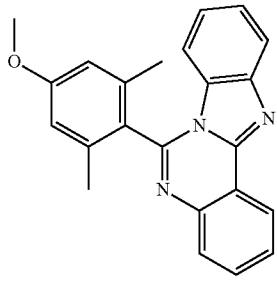 [SMILES: COc1cc(C)c(-c2nc3ccccc3c3nc4ccccc4n23)c(C)c1] | 65% |
| L54 | B | 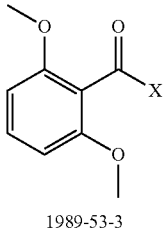<br>1989-53-3 | 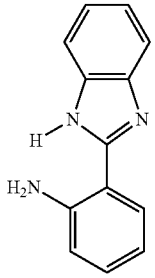<br>5805-39-0 | 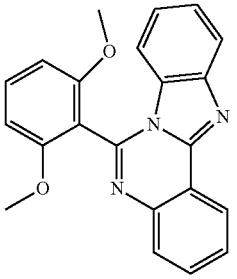 [SMILES: COc1cccc(OC)c1-c1nc2ccccc2c2nc3ccccc3n12] | 58% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L55 | B | 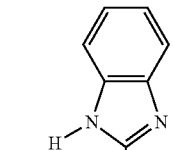 40501-36-8 | 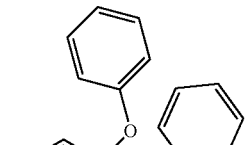 5805-39-0 | 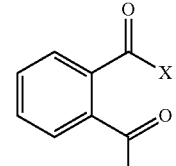 | 40% |
| L56 | B | 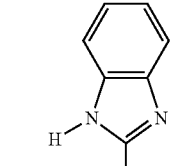 22103-85-1 | 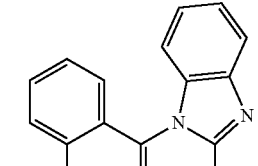 5805-39-0 | 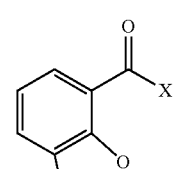 | 45% |
| L57 | C | 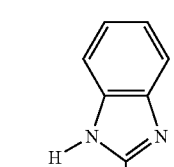 66283-60-1 | 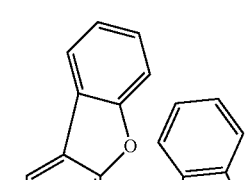 5805-39-0 | 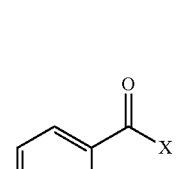 | 50% |
| L58 | C | 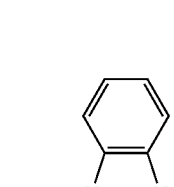 500589-01-5 | 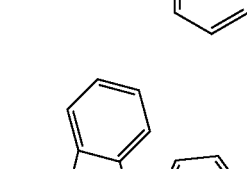 5805-39-0 | | 56 & |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L59 | C | 393-52-2 | 5805-39-0 | | 61% |
| L60 | C | 18063-02-0 | 5805-39-0 | | 57% |
| L61 | C | 79538-29-7 | 5805-39-0 | | 60% |
| L62 | C | 2251-50-5 | 5805-39-0 | | 45% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L63 | B | 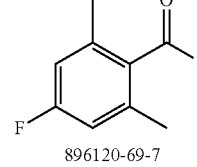 896120-69-7 | 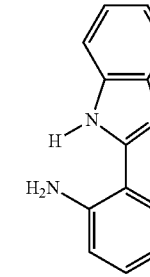 5805-39-0 | 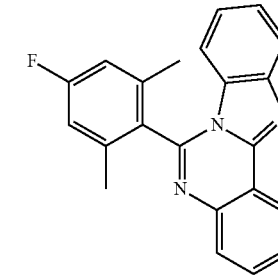 | 55% |
| L64 | B | 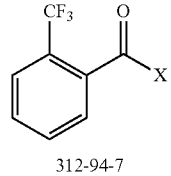 312-94-7 | 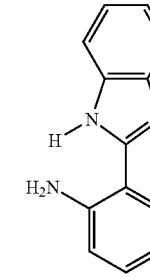 5805-39-0 | 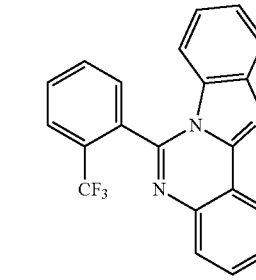 | 56% |
| L65 | B | 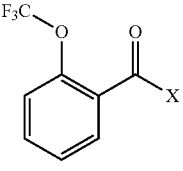 162046-61-9 | 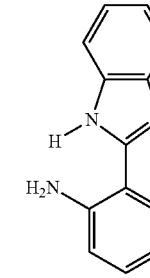 5805-39-0 | 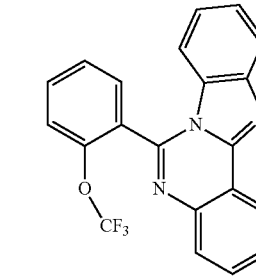 | 59% |
| L66 | B | 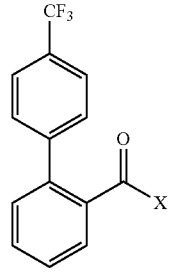 180340-74-3 | 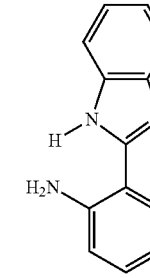 5805-39-0 | 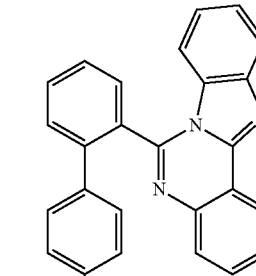 | 66% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L67 | A | 3282-30-2<br>75-98-9 | 10173-54-3 | | 70% |
| L68 | A | 7065-46-5<br>1070-83-3 | 10173-54-3 | | 76% |
| L69 | C | 938-18-1 | 10173-54-3 | | 68% |
| L70 | B | 115858-07-6 | 10173-54-3 | | 57% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L71 | B | 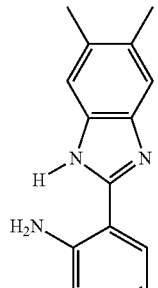 2094-72-6 | 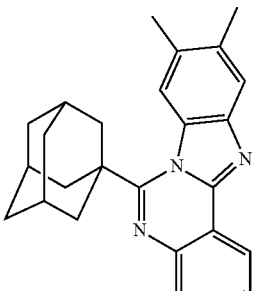 10173-54-3 | 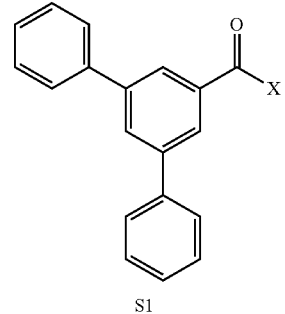 | 58% |
| L72 | C | 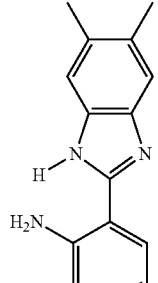 S1 | 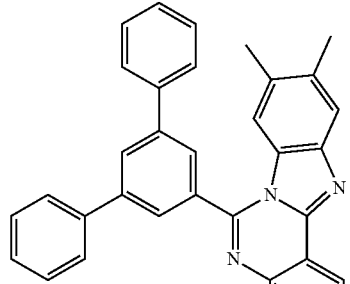 10173-54-3 | 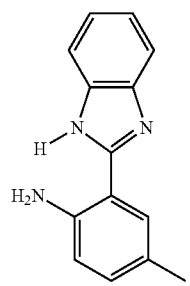 | 73% |
| L73 | A | 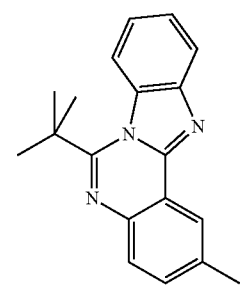 [SMILES: Cc1ccc2nc(C(C)(C)C)n3c4ccccc4nc3c2c1] 3282-30-2 75-98-9 | 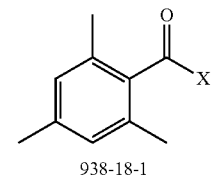 10173-57-6 | 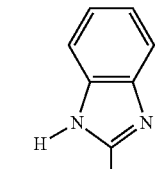 | 65% |
| L74 | B | 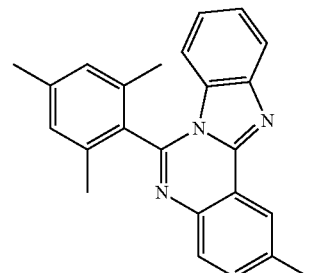 938-18-1 | (structure) 10173-57-6 | (structure) | 65% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L75 | C | 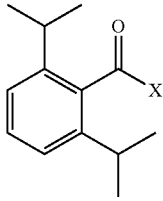<br>85374-63-6 | 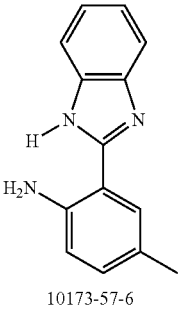<br>10173-57-6 | 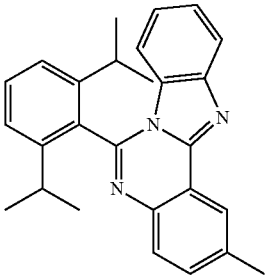 [SMILES: Cc1ccc2nc(-c3c(C(C)C)cccc3C(C)C)n3c4ccccc4nc3c2c1] | 44% |
| L76 | A | 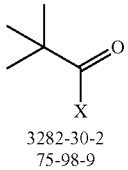<br>3282-30-2<br>75-98-9 | 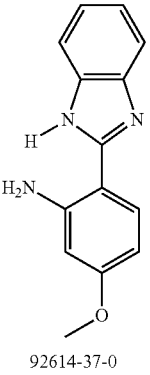 [SMILES: COc1ccc(-c2nc3ccccc3[nH]2)c(N)c1]<br>92614-37-0 | 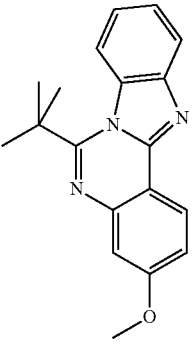 [SMILES: COc1ccc2c(c1)nc(C(C)(C)C)n1c3ccccc3nc21] | 52% |
| L77 | B | 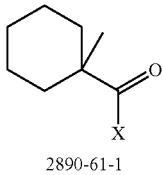<br>2890-61-1 | 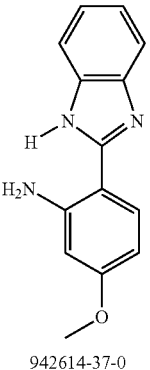<br>942614-37-0 | 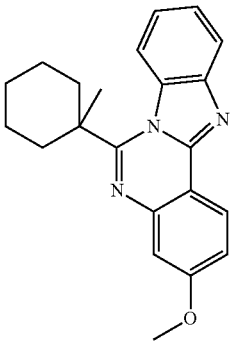 [SMILES: COc1ccc2c(c1)nc(C1(C)CCCCC1)n1c3ccccc3nc21] | 49% |
| L78 | A | 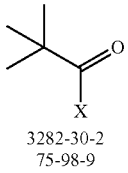<br>3282-30-2<br>75-98-9 | 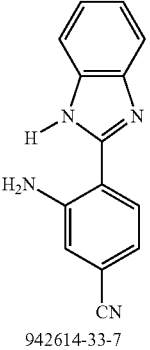<br>942614-33-7 | 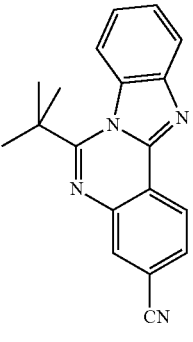 [SMILES: CC(C)(C)c1nc2cc(C#N)ccc2c2nc3ccccc3n12] | 51% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L79 | B | 16372-51-3 | 942614-33-7 | | 54% |
| L80 | C | 79538-29-7 | 942614-33-7 | | 63% |
| L81 | A | 3282-30-2 / 75-98-9 | S2 | | 74% |
| L82 | A | 3282-30-2 / 75-98-9 | S3 | | 72% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L83 | A | 3282-30-2 75-98-9 | S4 | | 74% |
| L84 | C | 938-18-1 | S5 | | 56% |
| L85 | C | 938-18-1 | S6 | | 75% |
| L86 | A | 3282-30-2 75-98-9 | S7 | | 65% |

-continued
| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L87 | C | 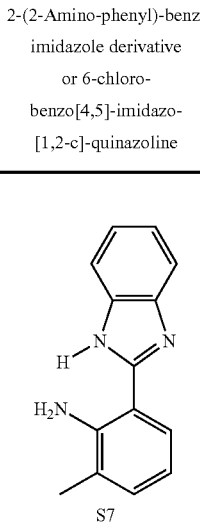<br>938-18-1 | 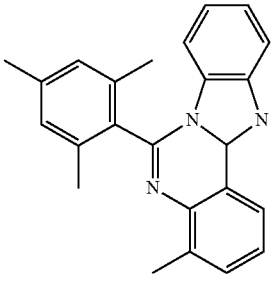 [SMILES: Cc1cc(C)c(C2=Nc3c(C)cccc3C3Nc4ccccc4N23)c(C)c1]<br>S7 | 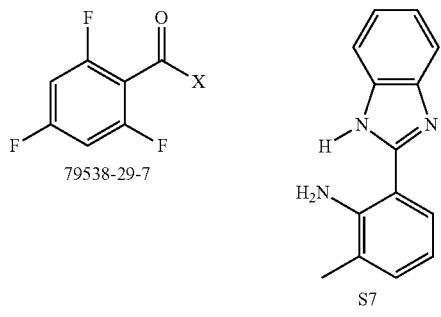 | 61% |
| L88 | C | 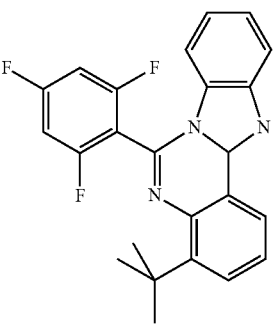 [SMILES: CC(C)(C)c1cccc2c1N=C(c1c(F)cc(F)cc1F)N1c3ccccc3NC21]<br>79538-29-7 | 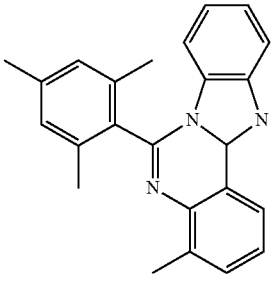 [SMILES: Cc1cc(C)c(C2=Nc3c(C)cccc3C3Nc4ccccc4N23)c(C)c1]<br>S7 | 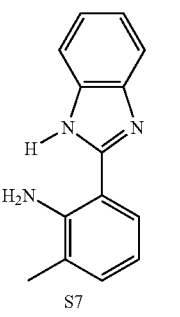 [SMILES: Cc1cccc(-c2nc3ccccc3[nH]2)c1N ; "S7"] | 65% |
| L89 | B | 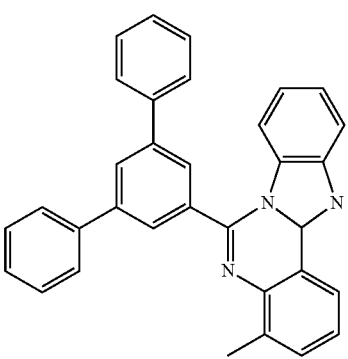 [SMILES: Cc1cccc2c1N=C(c1cc(-c3ccccc3)cc(-c3ccccc3)c1)N1c3ccccc3NC21]<br>S1 | 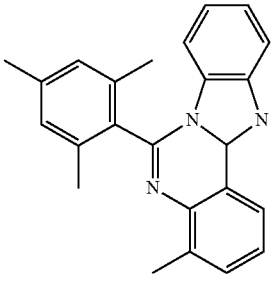 [SMILES: Cc1cc(C)c(C2=Nc3c(C)cccc3C3Nc4ccccc4N23)c(C)c1]<br>S7 | 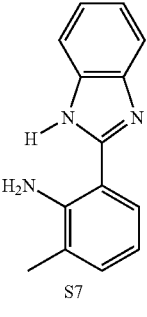 [SMILES: Cc1cccc(-c2nc3ccccc3[nH]2)c1N ; "S7"] | 67% |
| L90 | B | H$_{31}$C$_{15}$—C(=O)—X<br>112-67-4 | 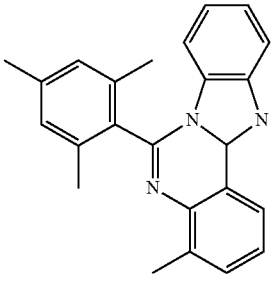 [SMILES: Cc1cc(C)c(C2=Nc3c(C)cccc3C3Nc4ccccc4N23)c(C)c1]<br>S7 | 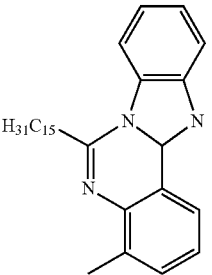 | 35% |

-continued
| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L91 | A | 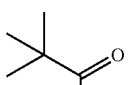<br>3282-30-2<br>75-98-9 | 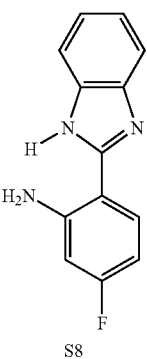 [SMILES: Nc1cc(F)ccc1-c1nc2ccccc2[nH]1 ; "S8"]<br>S8 | 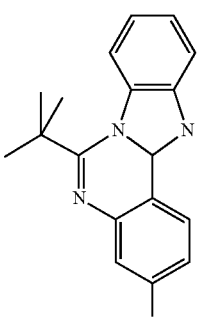 | 74% |
| L92 | C | 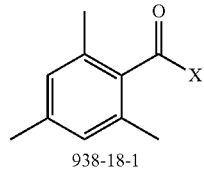<br>938-18-1 | 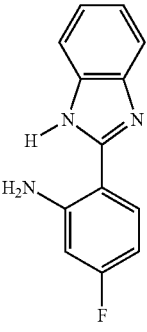<br>S8 | 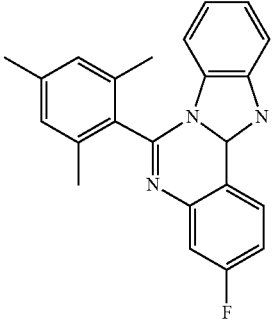 [SMILES: Cc1cc(C)c(C2=Nc3cc(F)ccc3C3Nc4ccccc4N23)c(C)c1] | 58% |
| L93 | C | 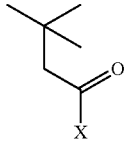<br>7065-46-5 | 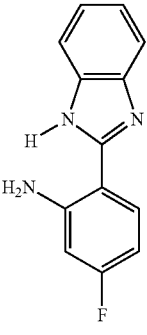<br>S8 | 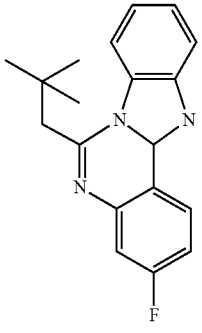 [SMILES: CC(C)(C)CC1=Nc2cc(F)ccc2C2Nc3ccccc3N12] | 72% |
| L94 | C | 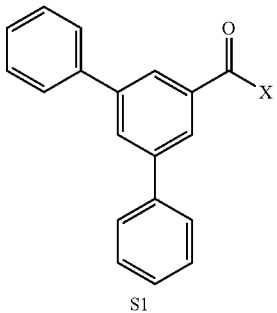<br>S1 | 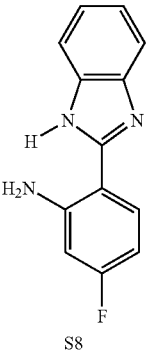 [SMILES: Nc1cc(F)ccc1-c1nc2ccccc2[nH]1 ; "S8"]<br>S8 | 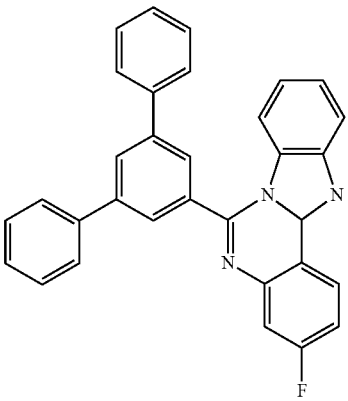 [SMILES: Fc1ccc2c(c1)N=C(c1cc(-c3ccccc3)cc(-c3ccccc3)c1)N1c3ccccc3NC21] | 59% |

-continued

| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L95 | B | 3282-30-2 | S18 | | 70% |
| L96 | A | 3282-30-2 75-98-9 | S19 | | 68% |
| L97 | A | 7065-46-5 1070-83-3 | S20 | | 69% |

-continued
| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L98 | A | 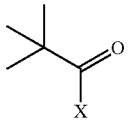 3282-30-2 75-98-9 | 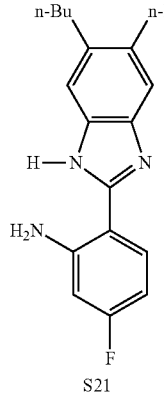 S21 | 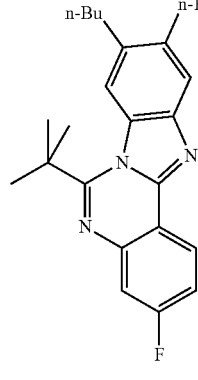 | 46% |
| L99 | A | 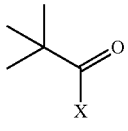 3282-30-2 75-98-9 | 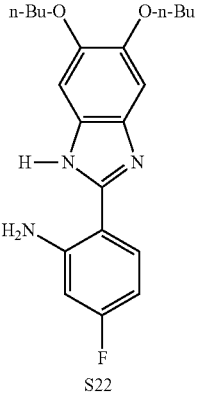 S22 | 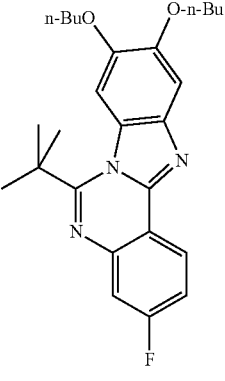 | 55% |
| L100 | A | 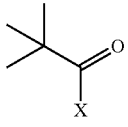 3282-30-2 75-98-9 | 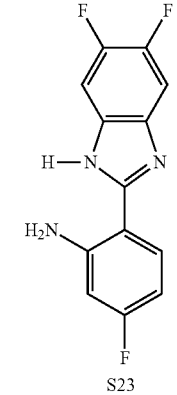 S23 | 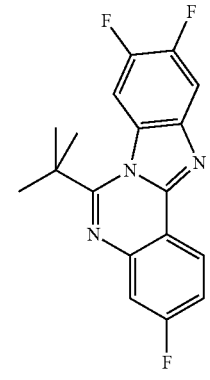 [SMILES: CC(C)(C)c1nc2cc(F)ccc2c2nc3cc(F)c(F)cc3n12] | 68% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L101 | A | 7065-46-5 1070-83-3 | S24 | | 68% |
| L102 | A | 7065-46-5 1070-83-3 | S25 | | 71% |
| L103 | C | 3282-30-2 | S26 | | 76% |
| L104 | B | 42983-08-4 | S18 | | 70% |

-continued
| Ex. | Variant | Carbonyl components X = Cl [CAS] OH [CAS] | 2-(2-Amino-phenyl)-benzimidazole derivative or 6-chloro-benzo[4,5]-imidazo-[1,2-c]-quinazoline | Product | Yield |
|---|---|---|---|---|---|
| L91 | D | 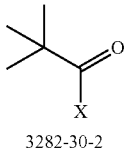 3282-30-2 | 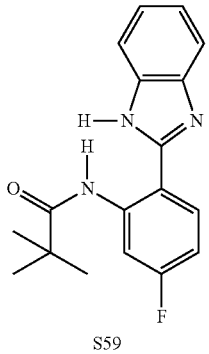 S59 | 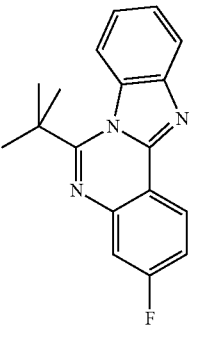 [SMILES: CC(C)(C)c1nc2cc(F)ccc2c2nc3ccccc3n12] | 74% |
| L93 | D | 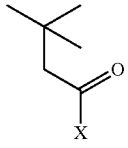 7065-46-5 | 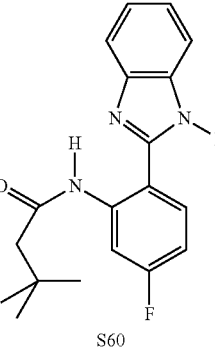 S60 | 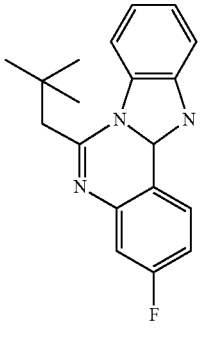 [SMILES: CC(C)(C)CC1=Nc2cc(F)ccc2C2Nc3ccccc3N12] | 76% |
| L159 | E | 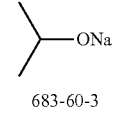 683-60-3 | 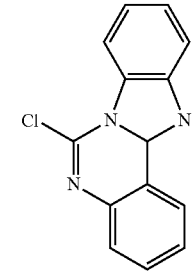 | 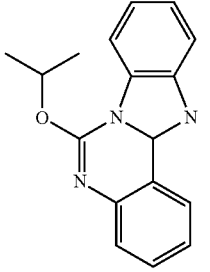 [SMILES: CC(C)OC1=Nc2ccccc2C2Nc3ccccc3N12] | 64% |
| L160 | E | 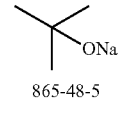 865-48-5 | 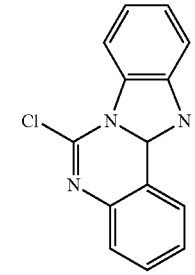 | 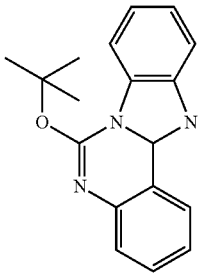 [SMILES: CC(C)(C)OC1=Nc2ccccc2C2Nc3ccccc3N12] | 67% |

-continued

| Ex. | Variant | Carbonyl components X = Cl [CAS] OH [CAS] | 2-(2-Amino-phenyl)-benz-imidazole derivative or 6-chloro-benzo[4,5]-imidazo-[1,2-c]-quinazoline | Product | Yield |
|---|---|---|---|---|---|
| L161 | E | 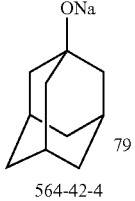<br>ONa<br>79<br>564-42-4 | 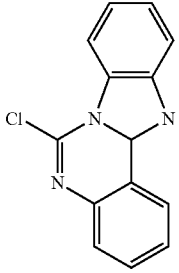 [SMILES: ClC1=Nc2ccccc2C2Nc3ccccc3N12] | 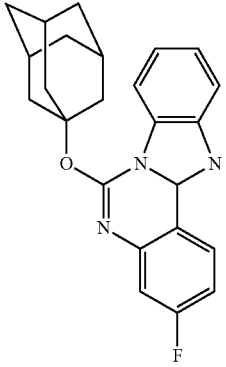 [SMILES: Fc1ccc2c(c1)N=C(OC13CC4CC(CC(C4)C1)C3)N1c3ccccc3NC21] | 42% |

2) 2,6a,11-Triazabenzo[a]fluorene systems

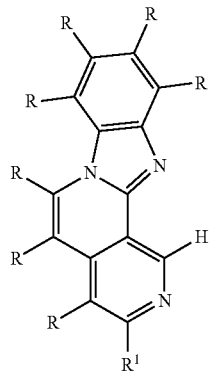

formula (8)

2.1) From 2-(4-chloropyridin-3-yl)benzimidazoles and terminal alkynes

A mixture of 14.3 g (50 mmol) of the 2-(4-chloro-6-tert-butylpyridin-3-yl)benzimidazole derivative, 55 mmol of the terminal alkyne, 191 mg (1 mmol) of copper(I) iodide, 112 mg (0.5 mmol) of palladium(II) acetate, 315 mg (1.2 mmol) of triphenylphosphine, 100 ml of triethylamine and 100 ml of dioxane is stirred at 120° C. in an autoclave for 16 h. After cooling, the solvent is removed in vacuo, the residue is taken up in 300 ml of ethyl acetate, the org. phase is washed three times with 100 ml of water each time and once with 100 ml of sat. sodium chloride solution, dried over sodium sulfate and filtered through a short silica-gel column. After removal of the solvent in vacuo, the residue is recrystallised twice from methanol. The solids obtained in this way are freed from low-boiling components and non-volatile secondary components by sublimation (p about $1\times10^{-5}$ mbar, T about 180-230° C.). Purity according to $^1$H-NMR typically >99.5%.

The following derivatives are prepared:

| Ex. | Imidazole derivative | Alkyne | Product | Yield |
|---|---|---|---|---|
| L105 | 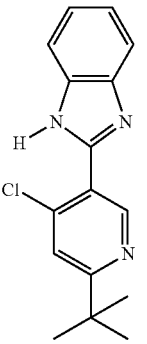ature<br>S33 | <br>917-92-0 | 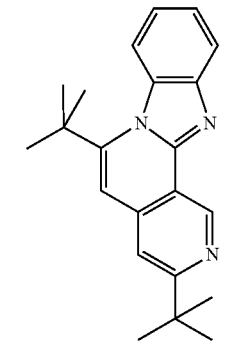 [SMILES: CC(C)(C)c1cc2cc(C(C)(C)C)n3c4ccccc4nc3c2cn1] | 46% |

-continued
| Ex. | Imidazole derivative | Alkyne | Product | Yield |
|---|---|---|---|---|
| L106 | 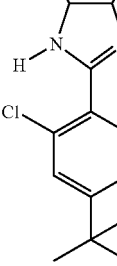 S33 | 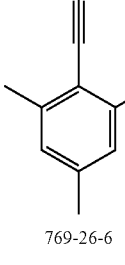 769-26-6 | 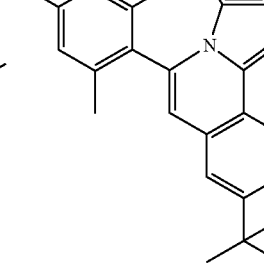 | 51% |
| L107 | 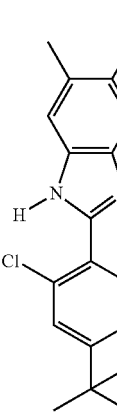 S34 |  917-92-0 | 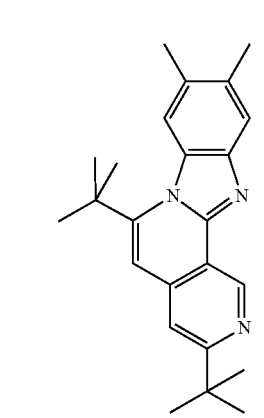 [SMILES: Cc1cc2nc3c4cnc(C(C)(C)C)cc4cc(C(C)(C)C)n3c2cc1C] | 33% |
| L108 | 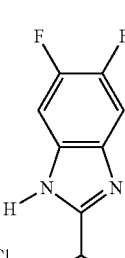 S35 | 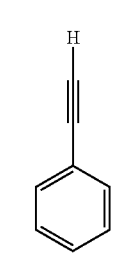 536-74-3 | 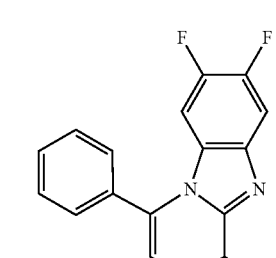 | 47% |

3) 4,6a,11-Triazabenzo[a]fluorene systems formula (11)

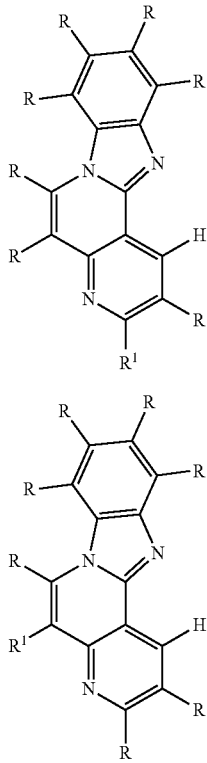

formula (10)

3.1) From 2-(2-chloropyridin-3-yl)benzimidazoles and terminal alkynes

A mixture of 14.3 g (50 mmol) of the 2(2-chloro-6-tert-butylpyridin-3-yl)benzimidazole derivative, 55 mmol of the terminal alkyne, 191 mg (1 mmol) of copper(I) iodide, 112 mg (0.5 mmol) of palladium(II) acetate, 315 mg (1.2 mmol) of triphenylphosphine, 100 ml of triethylamine and 100 ml of dioxane is stirred at 120° C. in an autoclave for 16 h. After cooling, the solvent is removed in vacuo, the residue is taken up in 300 ml of ethyl acetate, the organic phase is washed three times with 100 ml of water each time and once with 100 ml of saturated sodium chloride solution, dried over sodium sulfate and filtered through a short silica-gel column. After removal of the solvent in vacuo, the residue is recrystallised twice from methanol. The solids obtained in this way are freed from low-boiling components and non-volatile secondary components by sublimation (p about $1 \times 10^{-5}$ mbar, T about 180-230° C.). Purity according to $^1$H_NMR typically >99.5%.

The following derivatives are prepared:

| Ex. | Imidazole derivative | Alkyne | Product | Yield |
|---|---|---|---|---|
| L109 | (S29) | 917-92-0 | | 47% |
| L110 | (S29) | 769-26-6 | | 31% |

| Ex. | Imidazole derivative | Alkyne | Product | Yield |
|---|---|---|---|---|

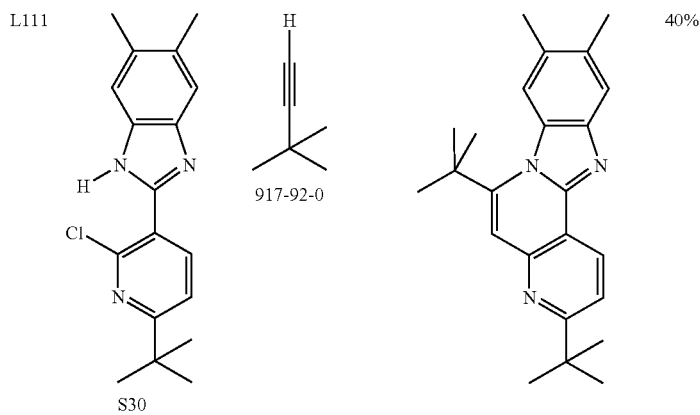

L111, S30, 917-92-0, 40%

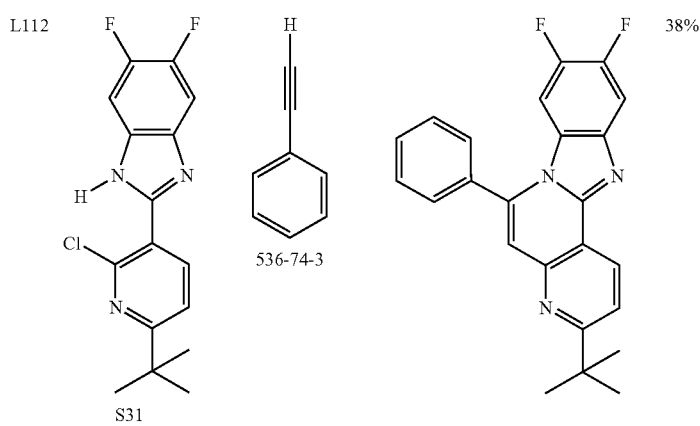

L112, S31, 536-74-3, 38%

3.2) From 2-(2-chloropyridin-3-yl)benzimidazoles and internal alkynes

A mixture of 14.3 g (50 mmol) of the 2(2-chloro-6-tert-butylpyridin-3-yl)benzimidazole derivative, 55 mmol of the internal alkyne, 225 mg (1 mmol) of palladium(II) acetate, 1.1 g (4 mmol) of triphenylphosphine, 14 g (100 mmol) of potassium carbonate and 200 ml of xylene is heated under reflux for 16 h. After cooling, the solid is filtered off via a silica-gel bed, rinsed with 500 ml of THF, and the filtrate is evaporated to dryness. The residue is dissolved in 50 ml of ethyl acetate at the boiling temperature, and 200 ml of n-heptane are slowly added. After cooling, solid which has crystallised out is filtered off with suction, washed twice with 50 ml of n-heptane each time and dried in vacuo. The solids obtained in this way are freed from low-boiling components and non-volatile secondary components by sublimation (p about $1 \times 10^{-5}$ mbar, T about 200-250° C.). Purity according to $^1$H-NMR typically >99.5%.

The following derivatives are prepared:

| Ex. | Imidazole derivative | Alkyne | Product | Yield |
|---|---|---|---|---|
| L113 | S29 | 501-65-5 | | 40% |
| L114 | S29 | 5806-58-6 | | 31% |

3.3) From pyridine-3-carboxaldehydes and 1,2-diaminobenzenes

A solution of 500 mmol of pyridine-3-carboxaldehyde and 550 mmol of 1,2-diaminobenzene in 1000 ml of nitrobenzene is placed in an apparatus consisting of a 2000 ml one-necked flask with stopcock part and attached distillation bridge and stirred at 200° C. for 2 h, during which the water formed distils off. The temperature is then increased to about 215° C., and the nitrobenzene is distilled off in a stream of argon. Towards the end of the distillation, a vacuum of about 100 mbar is applied in order to remove final residues of nitrobenzene, the reaction mixture is then allowed to cool.

If the crude product is produced in glassy form, the glass is comminuted mechanically, oils are mixed directly with 200-400 ml of methanol, and the mixture is heated under reflux, during which the glass or oil dissolves and the product crystallises out. The crude products obtained in this way already have high purity ($^1$H-NMR typically 97-99%). They are optionally recrystallised again and then freed from low-boiling components and non-volatile secondary components by sublimation (p about $1 \times 10^{-5}$ mbar, T about 200-250° C.). Purity according to $^1$H-NMR typically >99.5%.

The following derivatives are prepared:
| Ex. | Pyridine-3-carboxaldehyde | 1,2-Diamino-benzene | Product | Yield |
|---|---|---|---|---|
| L109 | 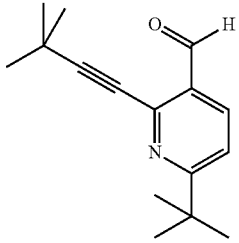 S69 | 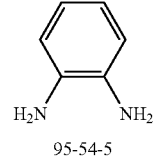 95-54-5 | 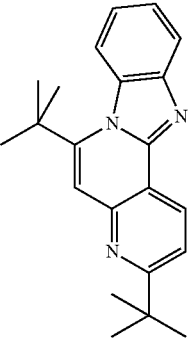 [SMILES: CC(C)(C)c1ccc2c(cc(C(C)(C)C)n3c4ccccc4nc23)n1] | 64% |
| L163 | 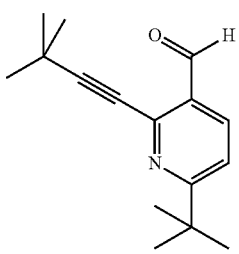 S69 | 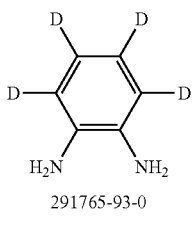 291765-93-0 | 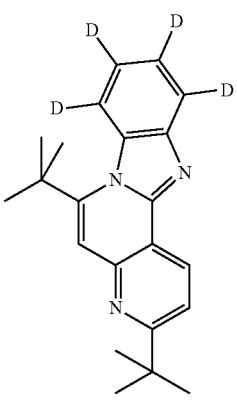 [SMILES: [2H]c1c([2H])c([2H])c2c(nc3c4ccc(C(C)(C)C)nc4cc(C(C)(C)C)n32)c1[2H]] | 66% |
| L111 | 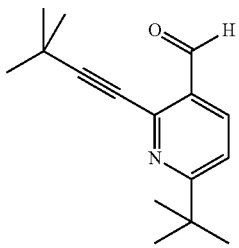 S69 | 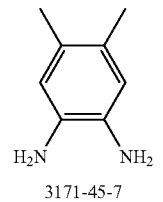 3171-45-7 | 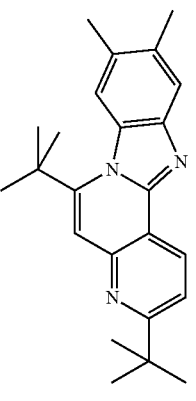 [SMILES: Cc1cc2nc3c4ccc(C(C)(C)C)nc4cc(C(C)(C)C)n3c2cc1C] | 58% |
| L165 | 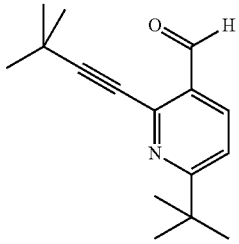 S69 | 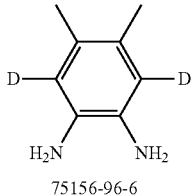 75156-96-6 | 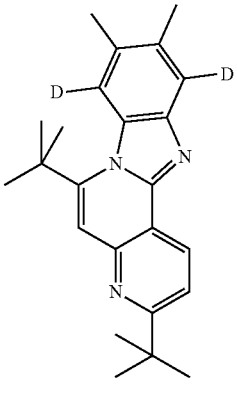 [SMILES: [2H]c1c(C)c(C)c([2H])c2c1nc1c3ccc(C(C)(C)C)nc3cc(C(C)(C)C)n12] | 55% |

-continued
| Ex. | Pyridine-3-carboxaldehyde | 1,2-Diamino-benzene | Product | Yield |
|---|---|---|---|---|
| L166 | 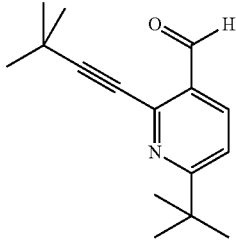 S69 | 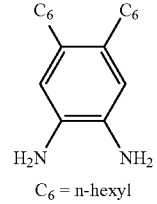 C₆ = n-hexyl 86723-75-3 | 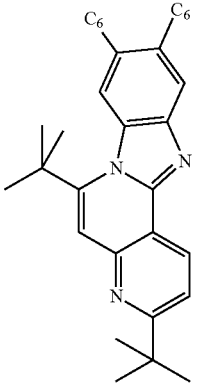 | 55% |
| L167 | 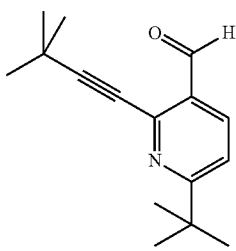 S69 | 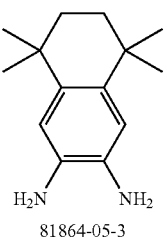 81864-05-3 | 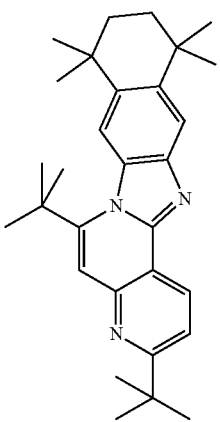 [SMILES: CC(C)(C)c1ccc2c(cc(C(C)(C)C)n3c4cc5c(cc4nc23)C(C)(C)CCC5(C)C)n1] | 63% |
| L168 | 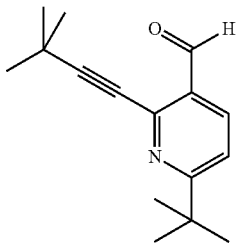 S69 | 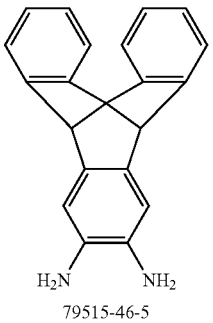 [SMILES: Nc1cc2c(cc1N)C1c3ccccc3C13c1ccccc1C23] 79515-46-5 | 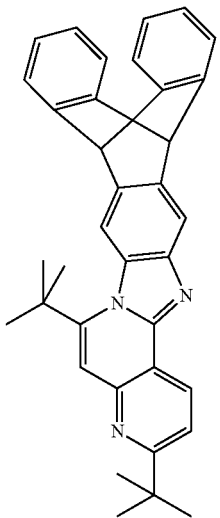 [SMILES: CC(C)(C)c1ccc2c(cc(C(C)(C)C)n3c4cc5c(cc4nc23)C2c3ccccc3C23c2ccccc2C53)n1] | 59% |

-continued
| Ex. | Pyridine-3-carboxaldehyde | 1,2-Diamino-benzene | Product | Yield |
|---|---|---|---|---|
| L169 | 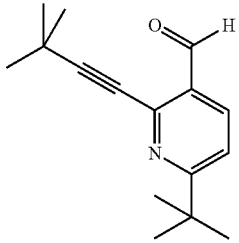<br>S69 | 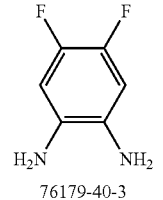<br>76179-40-3 | 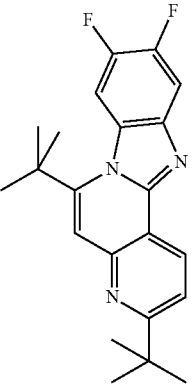 [SMILES: CC(C)(C)c1ccc2c(cc(C(C)(C)C)n3c4cc(F)c(F)cc4nc23)n1] | 67% |
| L170 | 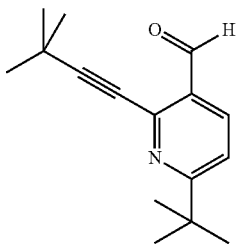<br>S69 | 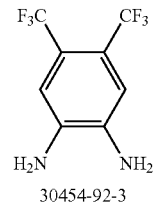<br>30454-92-3 | 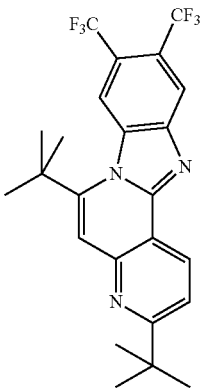 [SMILES: CC(C)(C)c1ccc2c(cc(C(C)(C)C)n3c4cc(C(F)(F)F)c(C(F)(F)F)cc4nc23)n1] | 46% |
| L171 | 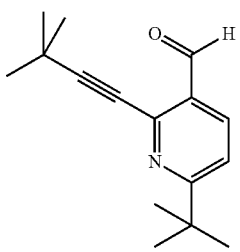<br>S69 | 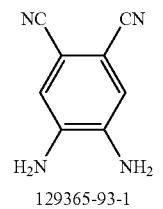<br>129365-93-1 | 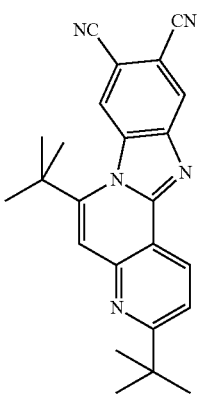 [SMILES: CC(C)(C)c1ccc2c(cc(C(C)(C)C)n3c4cc(C#N)c(C#N)cc4nc23)n1] | 30% |

| Ex. | Pyridine-3-carboxaldehyde | 1,2-Diaminobenzene | Product | Yield |
|---|---|---|---|---|
| L172 | 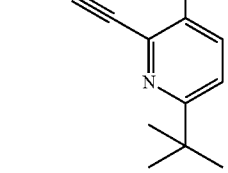<br>S69 | 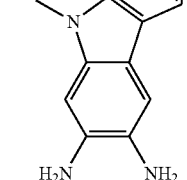<br>701284-83-5 | 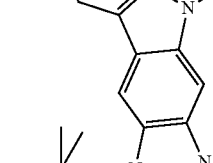 | 23% |
| L173 | 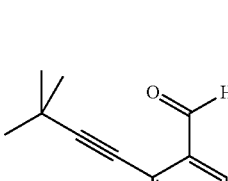<br>S69 | 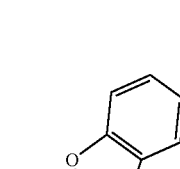<br>24258-73-9 | 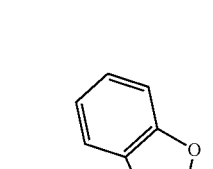 | 21% |
| L174 | <br>S69 | <br>106020-19-3 | 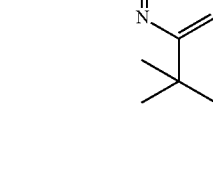 | 33% |

-continued
| Ex. | Pyridine-3-carboxaldehyde | 1,2-Diamino-benzene | Product | Yield |
|---|---|---|---|---|
| L175 | 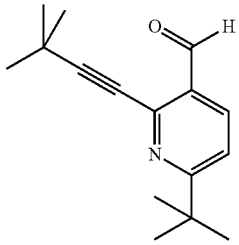 S69 | 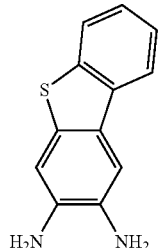 106020-19-3 Isolated from the mother liquor of L174 by chromatography | 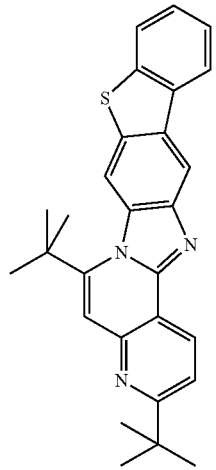 [SMILES: CC(C)(C)c1ccc2c(cc(C(C)(C)C)n3c4cc5sc6ccccc6c5cc4nc23)n1] | 14% |
| L176 | 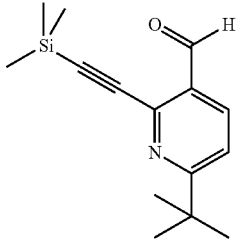 S70 | 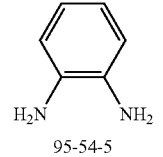 95-54-5 | 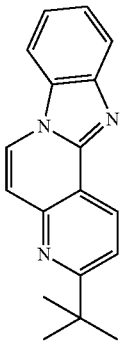 [SMILES: CC(C)(C)c1ccc2c(ccn3c4ccccc4nc23)n1] | 71% |
| L177 | 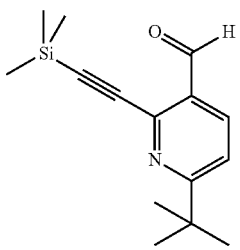 S70 | 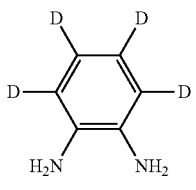 291765-93-0 | 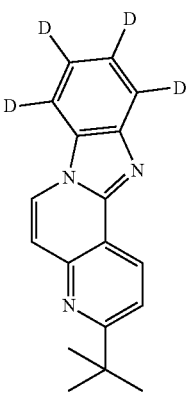 [SMILES: [2H]c1c([2H])c([2H])c2c(nc3c4ccc(C(C)(C)C)nc4ccn32)c1[2H]] | 68% |

-continued
| Ex. | Pyridine-3-carboxaldehyde | 1,2-Diamino-benzene | Product | Yield |
|---|---|---|---|---|
| L178 | 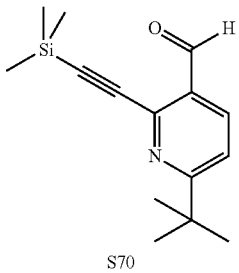 S70 | 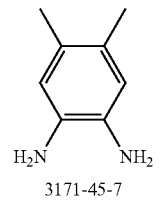 3171-45-7 | 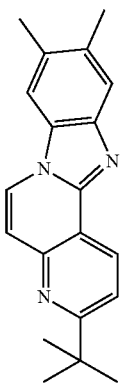 [SMILES: Cc1cc2nc3c4ccc(C(C)(C)C)nc4ccn3c2cc1C] | 59% |
| L179 | 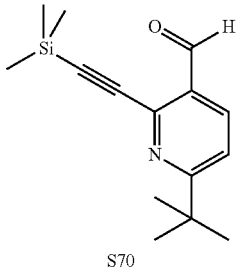 S70 | 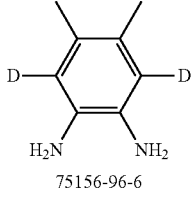 75156-96-6 | 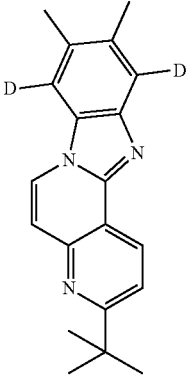 [SMILES: [2H]c1c(C)c(C)c([2H])c2c1nc1c3ccc(C(C)(C)C)nc3ccn12] | 60% |
| L180 | 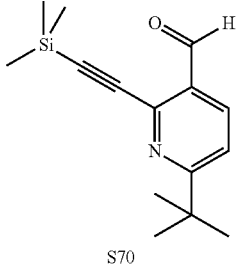 S70 | 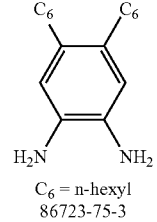 $C_6$ = n-hexyl 86723-75-3 | 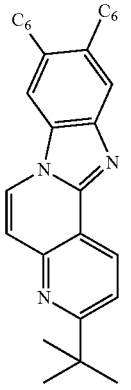 | 47% |
| L181 | 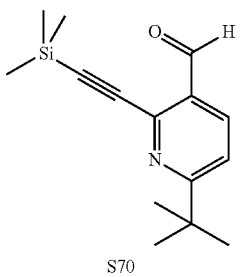 S70 | 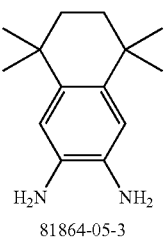 81864-05-3 | 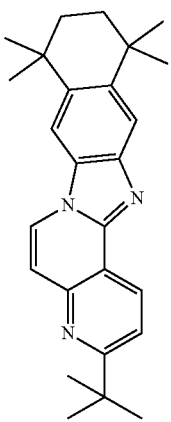 | 65% |

-continued

| Ex. | Pyridine-3-carboxaldehyde | 1,2-Diaminobenzene | Product | Yield |
|---|---|---|---|---|
| L182 | S70 | 79515-46-5 | | 70% |
| L183 | S70 | 76179-40-3 | | 62% |
| L184 | S70 | 30454-92-3 | | 53% |

-continued

| Ex. | Pyridine-3-carboxaldehyde | 1,2-Diamino-benzene | Product | Yield |
|---|---|---|---|---|
| L185 | S70 | 129365-93-1 | | 39% |
| L186 | S70 | 701284-83-5 | | 38% |
| L187 | S70 | 24258-73-9 | | 27% |

-continued

| Ex. | Pyridine-3-carboxaldehyde | 1,2-Diaminobenzene | Product | Yield |
|---|---|---|---|---|
| L188 | S70 | 106020-19-3 | | 30% |
| L189 | S70 | 858427-33-5 | | 34% |
| L190 | S70 | 412312-12-0 | | 39% |

-continued
| Ex. | Pyridine-3-carboxaldehyde | 1,2-Diamino-benzene | Product | Yield |
|---|---|---|---|---|
| L191 | 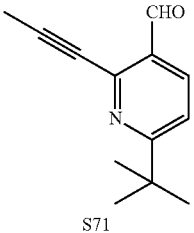<br>S71 | 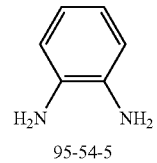<br>95-54-5 | 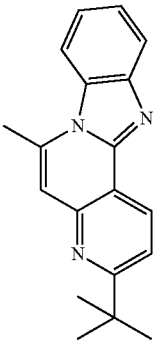 [SMILES: Cc1cc2nc(C(C)(C)C)ccc2c2nc3ccccc3n12] | 62% |
| L192 | 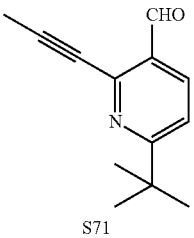<br>S71 | 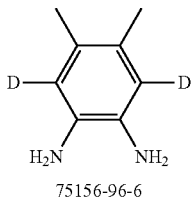<br>75156-96-6 | 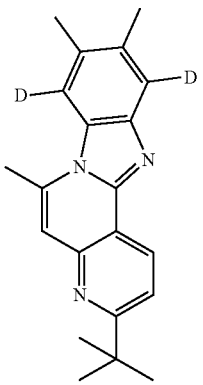 [SMILES: [2H]c1c(C)c(C)c([2H])c2c1nc1c3ccc(C(C)(C)C)nc3cc(C)n12] | 62% |
| L193 | 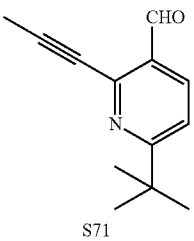<br>S71 | 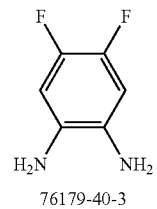<br>76179-40-3 | 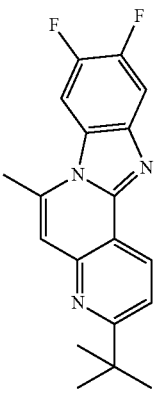 [SMILES: Cc1cc2nc(C(C)(C)C)ccc2c2nc3cc(F)c(F)cc3n12] | 57% |
| L194 | 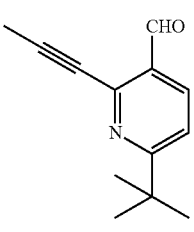<br>S71 | 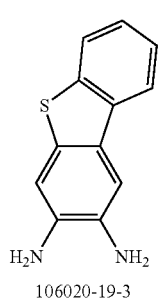<br>106020-19-3 | 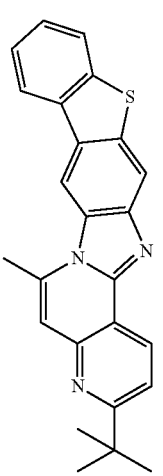 [SMILES: Cc1cc2nc(C(C)(C)C)ccc2c2nc3cc4sc5ccccc5c4cc3n12] | 27% |

-continued
| Ex. | Pyridine-3-carboxaldehyde | 1,2-Diamino-benzene | Product | Yield |
|---|---|---|---|---|
| L195 | 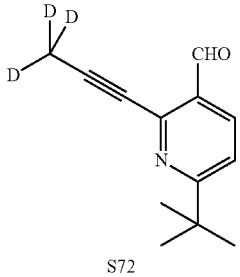 S72 | 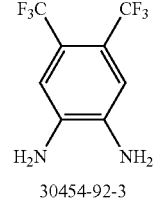 30454-92-3 | 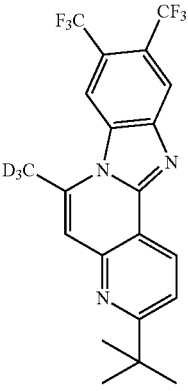 | 49% |
| L196 | 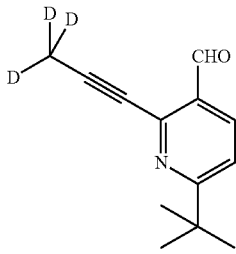 S72 | 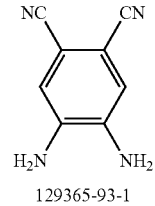 129365-93-1 | 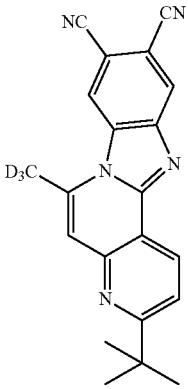 [SMILES: [2H]C([2H])([2H])c1cc2nc(C(C)(C)C)ccc2c2nc3cc(C#N)c(C#N)cc3n12] | 28% |
| L197 | 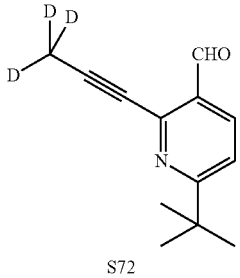 S72 | 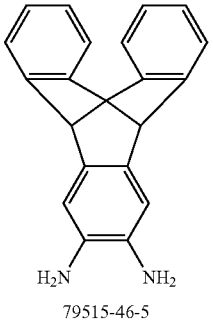 [SMILES: Nc1cc2c(cc1N)C1c3ccccc3C13c1ccccc1C23] 79515-46-5 | 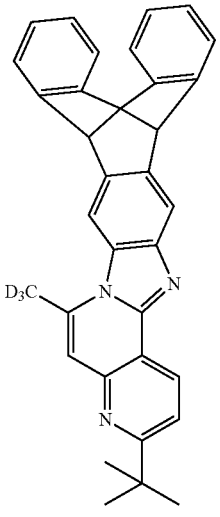 [SMILES: [2H]C([2H])([2H])c1cc2nc(C(C)(C)C)ccc2c2nc3cc4c(cc3n12)C1c2ccccc2C12c1ccccc1C42] | 66% |

-continued

| Ex. | Pyridine-3-carboxaldehyde | 1,2-Diaminobenzene | Product | Yield |
|---|---|---|---|---|
| L198 | S72 | 701284-83-5 | | 34% |
| L199 | S73 | 110966-18-2 | | 69% |
| L200 | S73 | $C_6$ = n-hexyl 86723-75-3 | | 64% |
| L201 | S73 | 76179-40-3 | | 60% |

-continued
| Ex. | Pyridine-3-carboxaldehyde | 1,2-Diamino-benzene | Product | Yield |
|---|---|---|---|---|
| L202 | 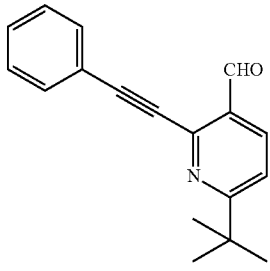<br>S73 | 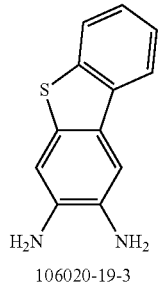<br>106020-19-3 | 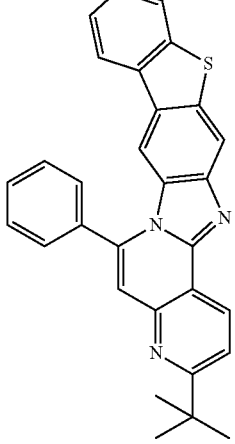 | 37% |
| L203 | 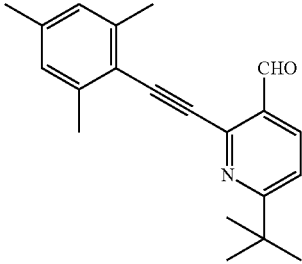<br>S74 | 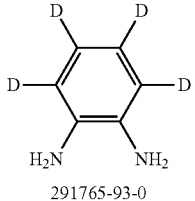<br>291765-93-0 | 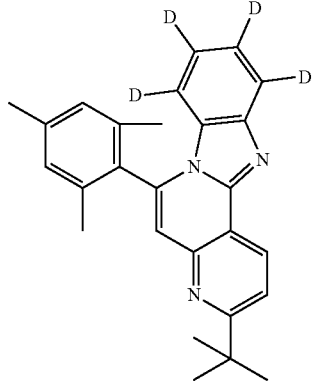 [SMILES: [2H]c1c([2H])c([2H])c2c(nc3c4ccc(C(C)(C)C)nc4cc(-c4c(C)cc(C)cc4C)n32)c1[2H]] | 63% |
| L204 | 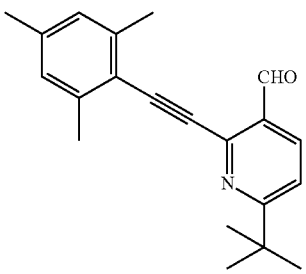<br>S74 | 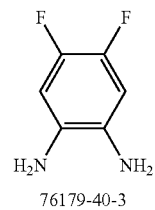<br>76179-40-3 | 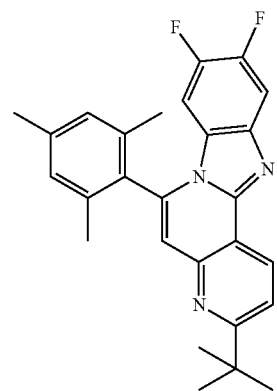 [SMILES: Cc1cc(C)c(-c2cc3nc(C(C)(C)C)ccc3c3nc4cc(F)c(F)cc4n23)c(C)c1] | 67% |

-continued

| Ex. | Pyridine-3-carboxaldehyde | 1,2-Diamino-benzene | Product | Yield |
|---|---|---|---|---|
| L205 | S74 | 129365-93-1 | | 35% |
| L206 | S74 | $C_6$ = n-hexyl 86723-75-3 | | 57% |
| L207 | S75 | 291765-93-0 | | 51% |
| L208 | S75 | $C_6$ = n-hexyl 86723-75-3 | | 47% |

-continued

| Ex. | Pyridine-3-carboxaldehyde | 1,2-Diamino-benzene | Product | Yield |
|---|---|---|---|---|
| L209 | S75 | 701284-83-5 | | 25% |
| L210 | S75 | 412312-12-0 | | 22% |
| L211 | S69 | 71625-27-9<br>230 mmol | | 47% |

US 9,273,080 B2
187 188
-continued
| Ex. | Pyridine-3-carboxaldehyde | 1,2-Diamino-benzene | Product | Yield |
|---|---|---|---|---|
| L212 | 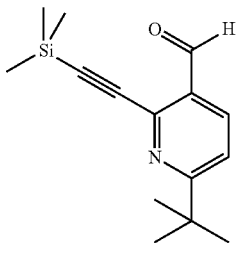<br>S70 | 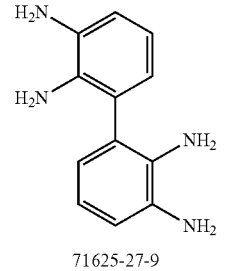<br>71625-27-9<br>230 mmol | 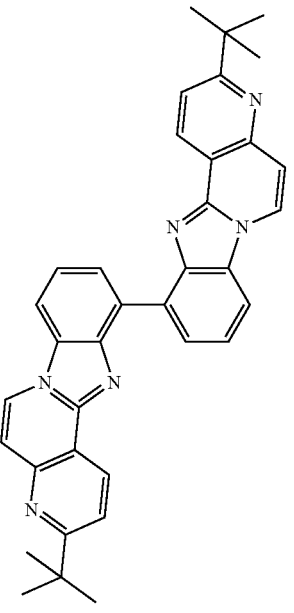 | 41% |
| L213 | 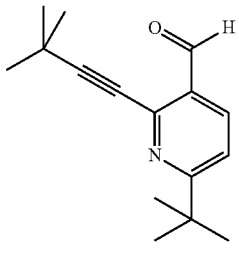<br>S69 | 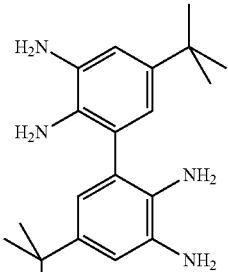<br>117110-91-5<br>230 mmol | 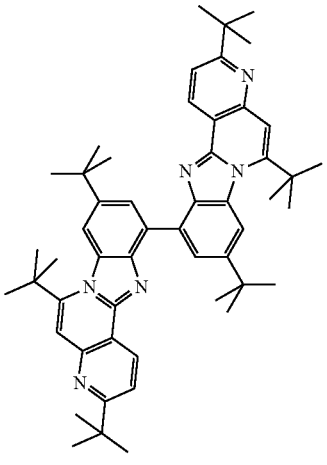 | 45% |

-continued

| Ex. | Pyridine-3-carboxaldehyde | 1,2-Diamino-benzene | Product | Yield |
|---|---|---|---|---|
| L214 | S70 | 117110-91-5 230 mmol | | 43% |
| L215 | S74 | 117110-91-5 230 mmol | | 39% |

4) 6a,8,1'-Triazabenzo[a]fluorene systems

4.1) From 1-aminoisoquinoline derivatives

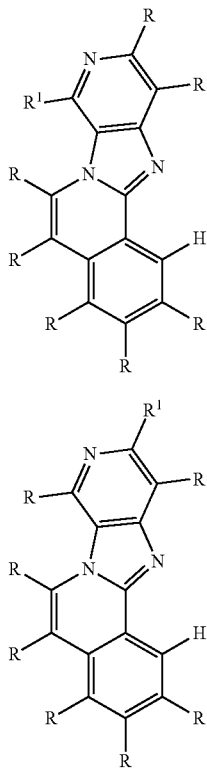

formula (12)

formula (13)

Procedure analogous to K. T. J. Loones, et al. Tetrahedron 2007, 63, 3818: a vigorously stirred mixture of 100 mmol of the 1-aminoisoquinoline derivative, 37.4 g (110 mmol) of 2-tert-butyl-3-bromo-4-iodopyridine (S27) or 27.9 g (110 mmol) of 2-trifluoromethyl-4-iodo-5-chloropyridine, 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 1-aminoisoquinoline derivative has been consumed (typically 3-30 h). After cooling, the solid is filtered off via a silica-gel bed, rinsed with 1000 ml of THF, and the filtrate is evaporated to dryness. The residue is dissolved in 100 ml of ethyl acetate at the boiling temperature, and 250 ml of n-heptane are slowly added. After cooling, the solid which has crystallised out is filtered off with suction, washed twice with 50 ml of n-heptane each time and dried in vacuo. The solids obtained in this way are freed from low-boiling components and non-volatile secondary components by sublimation (p about $1\times10^{-5}$ mbar, T about 180-230° C.). Purity according to $^1$H-NMR typically >99.5%.

The following derivatives are prepared:

| Ex. | 1-Amino-isoquinoline derivative | Pyridine derivative | Product | Yield |
|---|---|---|---|---|
| L115 | 1532-84-9 | S27 | | 61% |
| L116 | DE102009 007038.9 | S27 | | 28% |

-continued
| Ex. | 1-Amino-isoquinoline derivative | Pyridine derivative | Product | Yield |
|---|---|---|---|---|
| L117 | 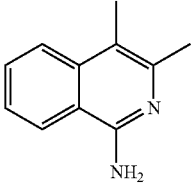<br>DE102009 007038.9 | 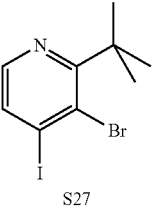<br>S27 | 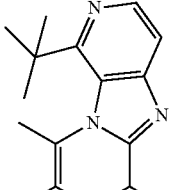 | 23% |
| L118 | 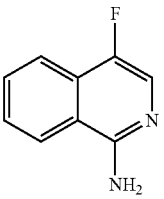<br>55270-26-3 | 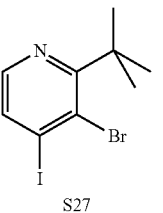<br>S27 | 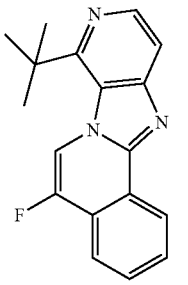 [SMILES: CC(C)(C)c1nccc2nc3c4ccccc4ccn3c12] | 34% |
| L119 | 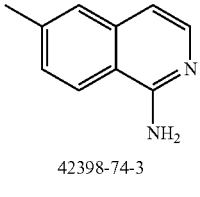<br>42398-74-3 | 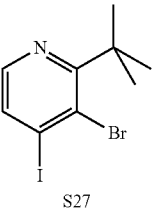<br>S27 | 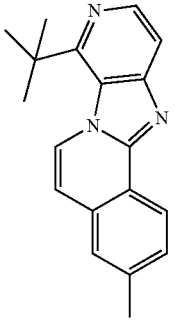 [SMILES: Cc1ccc2c(ccn3c2nc2ccnc(C(C)(C)C)c23)c1] | 60% |
| L120 | 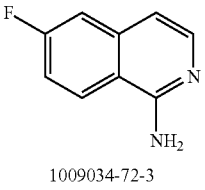 [SMILES: Nc1nccc2cc(F)ccc12]<br>1009034-72-3 | 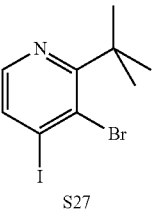<br>S27 | 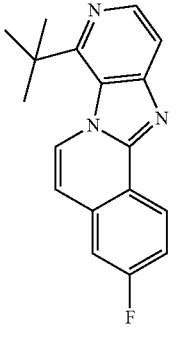 [SMILES: CC(C)(C)c1nccc2nc3c4ccc(F)cc4ccn3c12] | 55% |
| L121 | 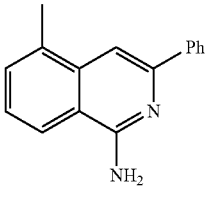<br>58814-44-1 | 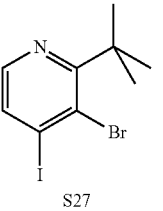<br>S27 | 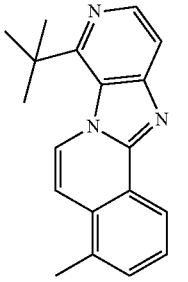 | 58% |

| Ex. | 1-Amino-isoquinoline derivative | Pyridine derivative | Product | Yield |
|---|---|---|---|---|
| L122 | 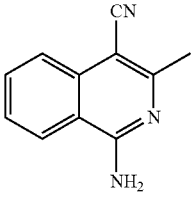<br>161468-33-3 | 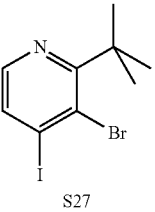<br>S27 | 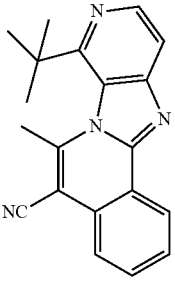 [SMILES: Cc1c(C#N)c2ccccc2c2nc3ccnc(C(C)(C)C)c3n12] | 66% |
| L123 | 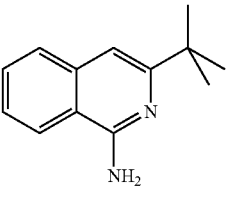<br>58814-44-8 | 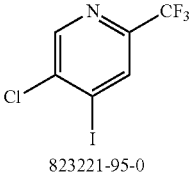<br>823221-95-0 | 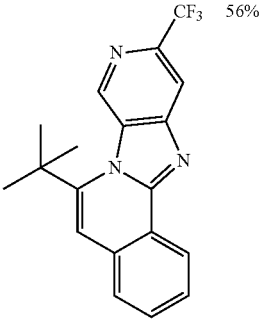 | 56% |

4.2) From 1-chloroisoquinoline derivatives

A vigorously stirred mixture of 100 mmol of the 1-chloroisoquinoline derivative, 29.8 g (130 mmol) of 3-bromo-4-amino-6-tert-butylpyridine (S40), 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 1-chloroisoquinoline derivative has been consumed (typically 3-30 h). After cooling, the solid is filtered off via a silica-gel bed, rinsed with 1000 ml of THF, and the filtrate is evaporated to dryness. The residue is dissolved in 75 ml of ethyl acetate at the boiling temperature, and 250 ml of n-heptane are slowly added. After cooling, the solid which has crystallised out is filtered off with suction, washed twice with 50 ml of n-heptane each time and dried in vacuo. The solids obtained in this way are freed from low-boiling components and non-volatile secondary components by sublimation (p about $1 \times 10^{-5}$ mbar, T about 150-230° C.). Purity according to $^1$H-NMR typically >99.5%.

The following derivatives are prepared:

| Ex. | 1-Chloro-iso-quinoline derivative | Pyridine | Product | Yield |
|---|---|---|---|---|
| L124 | 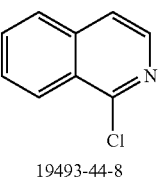 [SMILES: Clc1nccc2ccccc12]<br>19493-44-8 | 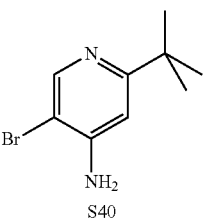<br>S40 | 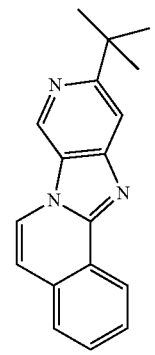 [SMILES: CC(C)(C)c1cc2nc3c4ccccc4ccn3c2cn1] | 73% |

-continued
| Ex. | 1-Chloro-iso-quinoline derivative | Pyridine | Product | Yield |
|---|---|---|---|---|
| L125 | 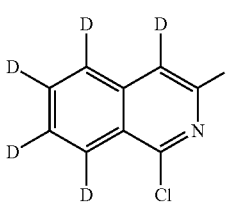<br>1003195-34-3 | 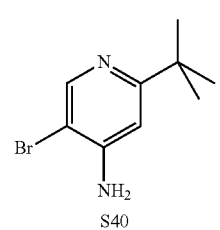<br>S40 | 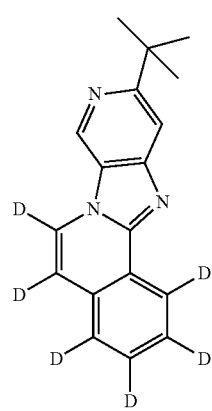 [SMILES: [2H]c1c([2H])c([2H])c2c(c1[2H])c([2H])c([2H])n1c3cnc(C(C)(C)C)cc3nc21] | 67% |
| L126 | 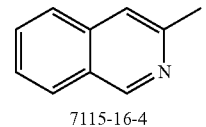<br>7115-16-4 | 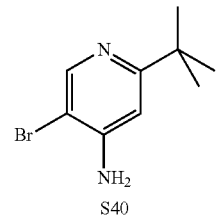<br>S40 | 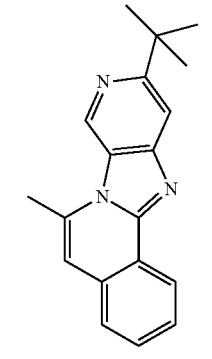 [SMILES: Cc1cc2ccccc2c2nc3cc(C(C)(C)C)ncc3n12] | 73% |
| L127 | 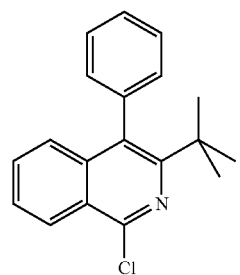<br>55792-01-3 | 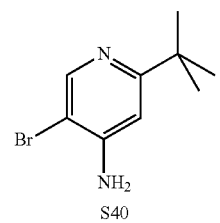<br>S40 | 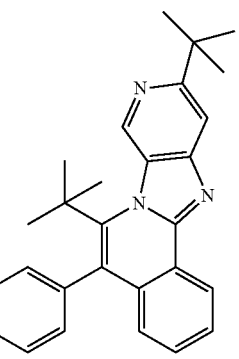 | 58% |
| L128 | 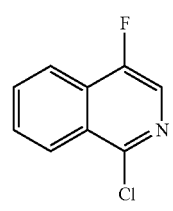<br>435278-06-1 | 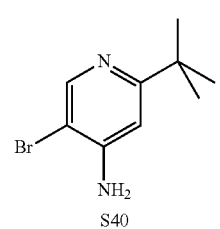<br>S40 | 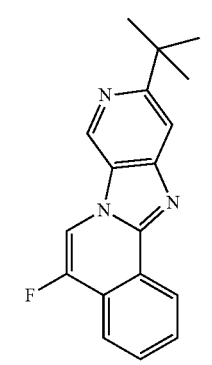 [SMILES: CC(C)(C)c1cc2nc3c4ccccc4c(F)cn3c2cn1] | 61% |

-continued
| Ex. | 1-Chloro-iso-quinoline derivative | Pyridine | Product | Yield |
|---|---|---|---|---|
| L129 | 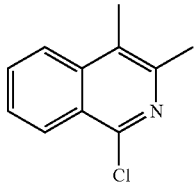<br>15787-20-9 | 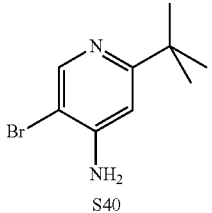<br>S40 | 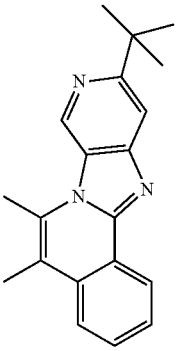 [SMILES: Cc1c(C)n2c3cnc(C(C)(C)C)cc3nc2c2ccccc12] | 65% |
| L130 | 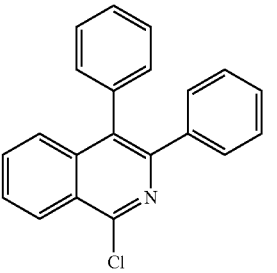<br>102183-41-5 | 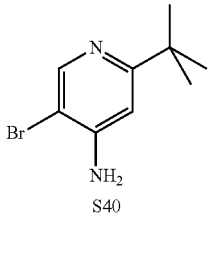<br>S40 | 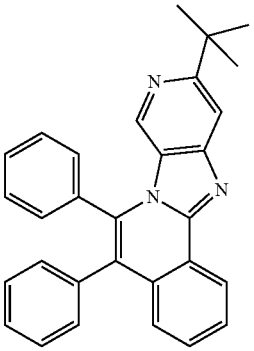 [SMILES: CC(C)(C)c1cc2nc3c4ccccc4c(-c4ccccc4)c(-c4ccccc4)n3c2cn1] | 46% |
| L131 | 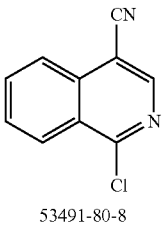 [SMILES: N#Cc1cnc(Cl)c2ccccc12]<br>53491-80-8 | 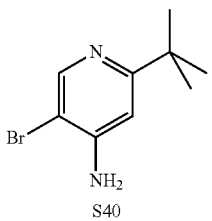<br>S40 | 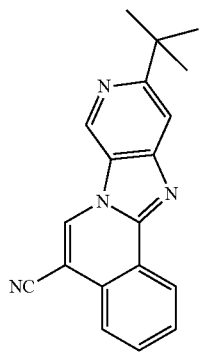 [SMILES: CC(C)(C)c1cc2nc3c4ccccc4c(C#N)cn3c2cn1] | 50% |

5) 4,6a,8,11-Tetraazabenzo[a]fluorene systems formula (14)

formula (15)

formula (16)

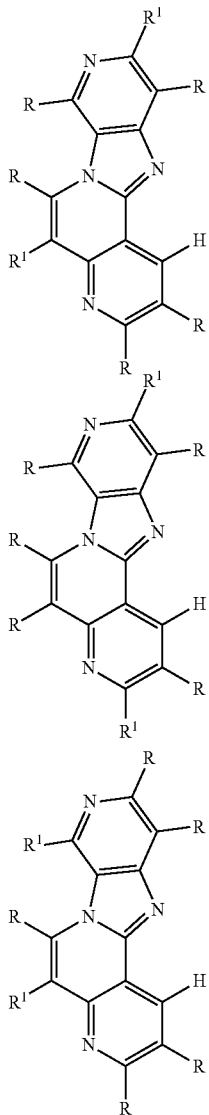

formula (17)

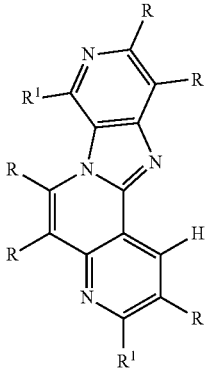

5.1) From 5-chloro-1,6-naphthyridine derivatives

A vigorously stirred mixture of 100 mmol of the 5-chloro-1,6-naphthyridine derivative, 29.8 g (130 mmol) of 2-tert-butyl-4-amino-5-bromopyridine (S40), 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 5-chloro-1,6-naphthyridine derivative has been consumed (typically 3-30 h). After cooling, the solid is filtered off via a silica-gel bed, rinsed with 1000 ml of THF, and the filtrate is evaporated to dryness. The residue is dissolved in 75 ml of ethyl acetate at the boiling temperature, and 250 ml of n-heptane are slowly added. After cooling, the solid which has crystallised out is filtered off with suction, washed twice with 50 ml of n-heptane each time and dried in vacuo. The solids obtained in this way are freed from low-boiling components and non-volatile secondary components by sublimation (p about $1 \times 10^{-5}$ mbar, T about 180-230° C.). Purity according to $^1$H-NMR typically >99.5%.

The following derivatives are prepared:

| Ex. | 5-Chloro-1,6-naphthyridine derivatives | Pyridine | Product | Yield |
|---|---|---|---|---|
| L132 | S36 | S40 | | 73% |

| Ex. | 5-Chloro-1,6-naphthyridine derivatives | Pyridine | Product | Yield |
|---|---|---|---|---|
| L133 | S37 | S40 | | 67% |

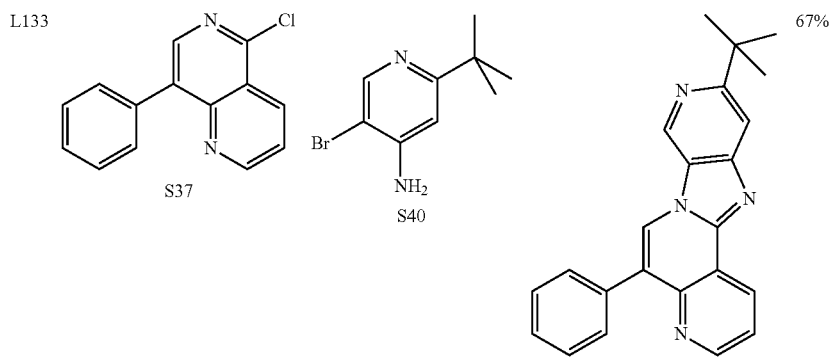

5.2) From 5-amino-1,6-naphthyridine derivatives

A vigorously stirred mixture of 100 mmol of the 5-amino-1,6-naphthyridine derivative, 37.4 g (110 mmol) of 2-tert-butyl-3-bromo-4-iodopyridine (S27) or 27.9 g (110 mmol) of 2-trifluoromethyl-4-iodo-5-chloropyridine [823221-95-0], 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 5-amino-1,6-naphthyridine derivative has been consumed (typically 3-30 h). After cooling, the solid is filtered off via a silica-gel bed, rinsed with 1000 ml of THF, and the filtrate is evaporated to dryness. The residue is dissolved in 75 ml of ethyl acetate at the boiling temperature, and 250 ml of n-heptane are slowly added. After cooling, the solid which has crystallised out is filtered off with suction, washed twice with 50 ml of n-heptane each time and dried in vacuo. The solids obtained in this way are freed from low-boiling components and non-volatile secondary components by sublimation (p about $1\times10^{-5}$ mbar, T about 180-230° C.). Purity according to $^1$H-NMR typically >99.5%.

The following derivatives are prepared:

| Ex. | 5-Amino-1,6-naphthyridine derivative | Pyridine derivative | Product | Yield |
|---|---|---|---|---|
| L134 | S38 | S27 | | 67% |

| Ex. | 5-Amino-1,6-naphthyridine derivative | Pyridine derivative | Product | Yield |
|---|---|---|---|---|
| L135 | S38 | 823221-95-0 | | 50% |
| L136 | S39 | S27 | | 47% |

6) 2,6a,8,11-Tetraazabenzo[a]fluorene systems formula (18)

formula (19)

A vigorously stirred mixture of 20.1 g (100 mmol) of 1-amino-6-tert-butyl-2,7-naphthyridine S41, 37.4 g (110 mmol) of 2-tert-butyl-3-bromo-4-iodopyridine (S27) or 27.9 g (110 mmol) of 2-trifluoromethyl-4-iodo-5-chloropyridine, 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 1-amino-6-tert-butyl-2,7-naphthyridine has been consumed (typically 3-30 h). After cooling, the solid is filtered off via a silica-gel bed, rinsed with 1000 ml of THF, and the filtrate is evaporated to dryness. The residue is dissolved in 75 ml of ethyl acetate at the boiling temperature, and 250 ml of n-heptane are slowly added. After cooling, the solid which has crystallised out is filtered off with suction, washed twice with 50 ml of n-heptane each time and dried in vacuo. The solids obtained in this way are freed from low-boiling components and non-volatile secondary components by sublimation (p about $1 \times 10^{-5}$ mbar, T about 170-200° C.). Purity according to $^1$H-NMR typically >99.5%.

The following derivatives are prepared:

7) 4,5,6a,11-Tetraazabenzo[a]fluorene systems

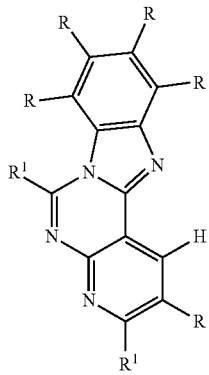

formula (20)

| Ex. | 1-Amino-6-tert-butyl-2,7-naphthyridine | Pyridine derivative | Product | Yield |
|---|---|---|---|---|
| L137 | S41 | S27 | | 56% |
| L138 | S41 | 823221-95-0 | | 48% |

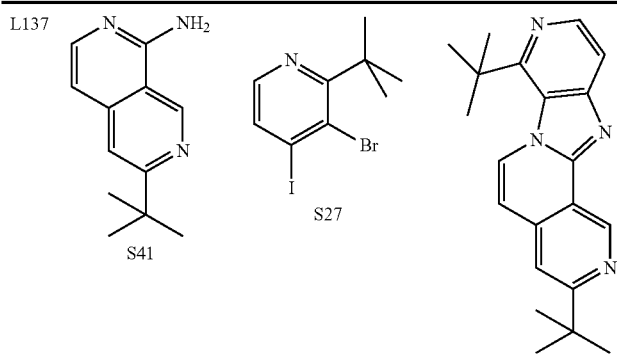

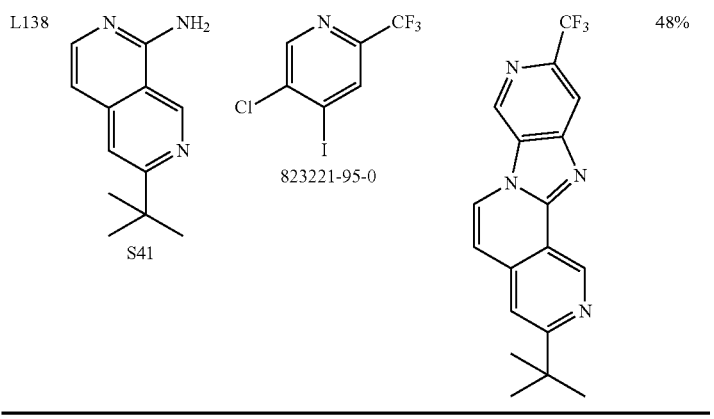

A mixture of 100 mmol of the 2-(2-aminopyridin-3-yl) benzimidazole derivative (employed as equimolar mixture with the corresponding 2-tert-butylbenzimidazole derivative as obtained from synthesis 16)) and 1 mol of the corresponding carboxylic acid chloride is heated for 8 to 40 h under reflux in the case of carboxylic acid chlorides which boil below 150° C. or at 150° C. to 180° C. in the case of carboxylic acid chlorides which boil above 150° C., until the 2-(2-aminopyridin-3-yl)benzimidazole derivative has reacted. The reaction mixture is allowed to cool to 80° C., optionally diluted with 100 ml of dioxane, then stirred into a mixture of 500 ml of conc. ammonia solution and 500 g of ice and stirred for a further 3 h. The solid is subsequently filtered off with suction, washed twice with 100 ml of water in each case and dried in vacuo. The solid is taken up in 1000 ml of ethyl acetate, filtered through a short silica-gel column, rinsed with 500 ml of ethyl acetate, the ethylacetate is removed in vacuo, and the brown residue is recrystallised from methanol. The solids obtained in this way are freed from low-boiling components and non-volatile secondary components by sublimation (p about $1 \times 10^{-5}$ mbar, T about 170-200° C.). Purity according to $^1$H-NMR typically >99.5%.

The following derivatives are prepared:

| Ex. | 2-(2-Amino-pyridin-3-yl)-benzimidazole derivative | Carboxylic acid chloride | Product | Yield |
|---|---|---|---|---|
| L139 | S43 | 3282-30-2 | | 38% |
| L140 | S43 | 938-18-1 | | 35% |

-continued
| Ex. | 2-(2-Amino-pyridin-3-yl)-benzimidazole derivative | Carboxylic acid chloride | Product | Yield |
|---|---|---|---|---|
| L141 | S44 | 3282-30-2 | | 41% |
| L142 | S45 | 3282-30-2 | | 27% |
8) 2,5,6a,11-Tetraazabenzo[a]fluorene systems
formula (21)
formula (22)
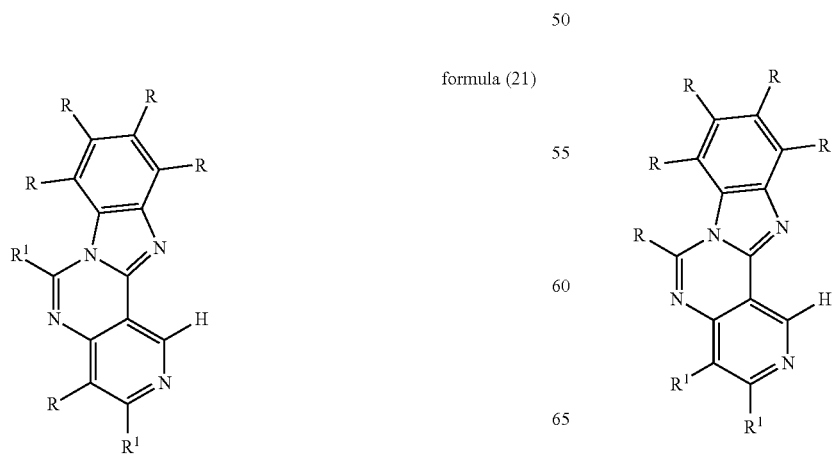

A mixture of 26.6 g (100 mmol) of 2-(4-amino-6-tert-butylpyridin-3-yl)benzimidazole (employed as equimolar mixture with 2-tert-butylbenzimidazole as obtained from synthesis 18)) and 1 mol of the corresponding carboxylic acid chloride is heated for 8 to 40 h under reflux in the case of carboxylic acid chlorides which boil below 150° C. or at 150° C. to 180° C. in the case of carboxylic acid chlorides which boil above 150° C., until the 2-(4-aminopyridin-3-yl)benzimidazole derivative has reacted. The reaction mixture is allowed to cool to 80° C., optionally diluted with 100 ml of dioxane, then stirred into a mixture of 500 ml of conc. ammonia solution and 500 g of ice and stirred for a further 3 h. The solid is subsequently filtered off with suction, washed twice with 100 ml of water each time and dried in vacuo. The solid is taken up in 1000 ml of ethyl acetate, filtered through a short silica-gel column, rinsed with 500 ml of ethyl acetate, the ethyl acetate is removed in vacuo, and the brown residue is recrystallised from methanol. The solids obtained in this way are freed from low-boiling components and non-volatile secondary components by sublimation (p about $1 \times 10^{-5}$ mbar, T about 180-220° C.). Purity according to $^1$H-NMR typically >99.5%.

The following derivatives are prepared:

9) 2,4,6a,11-Tetraazabenzo[a]fluorene systems

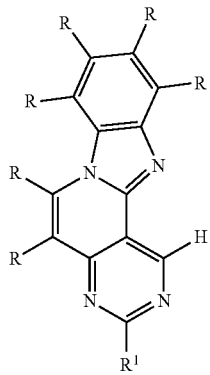

formula (23)

Preparation analogous to N. Umeda et al., Angew. Chem. Int. Ed. 2008, 47, 4019: a solution of 25.2 g (100 mmol) of 2-(2-tert-butylpyrimidin-5-yl)benzimidazole (S48) and 110 mmol of the alkyne in 400 ml of DMF is initially introduced in a pressure Schlenk tube, 1.5 g (4 mmol) of tetraphenylcyclopentadiene, 547 mg (1 mmol) of pentamethylcyclopentadienyl-rhodium chloride dimer and 21.0 (105 mmol) of copper(II) acetate monohydrate are added, and the mixture is stirred in the sealed tube at 100° C. for 18 h. After cooling, the DMF is removed in vacuo, the residue is taken up in 1000 ml of THF and filtered through a short silica-gel column. After removal of the THF in vacuo, the oily residue is taken up in hot methanol (about 75 ml). After cooling, the crystals formed are filtered off with suction and recrystallised again from methanol with addition of a little ethyl acetate. The solids obtained in this way are freed from low-boiling components and non-volatile secondary components by sublimation (p about $1 \times 10^{-5}$ mbar, T about 180-220° C.). Purity according to $^1$H-NMR typically >99.5%.

| Ex. | 2-(2-tert-Butyl-pyrimidin-5-yl)-benzimidazole | Alkyne | Product | Yield |
|---|---|---|---|---|
| L145 | S48 | 501-65-5 | | 31% |
| L146 | S48 | 503-17-3 | | 26% |

10) 5,6a,8,11-Tetraazabenzo[a]fluorene systems

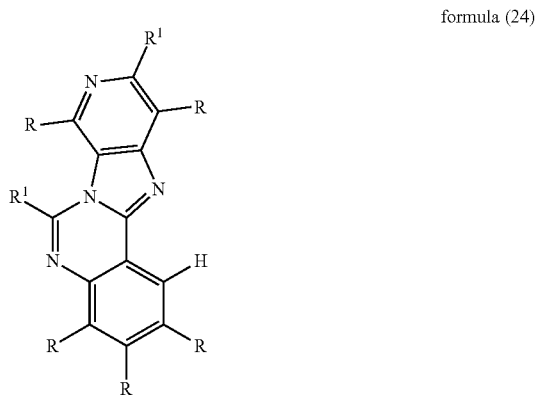

formula (24)

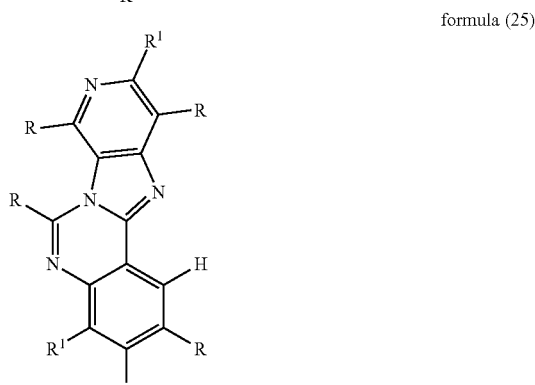

formula (25)

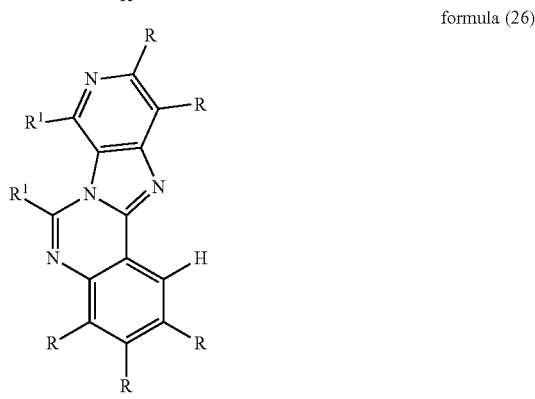

formula (26)

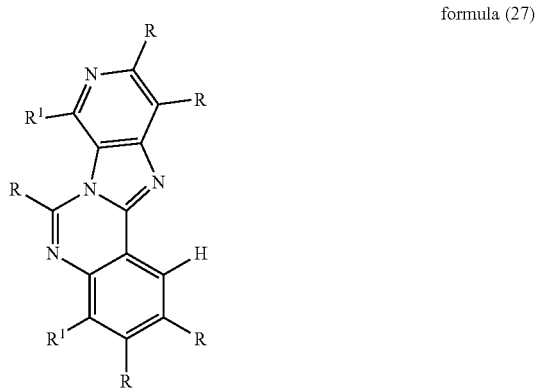

formula (27)

A vigorously stirred mixture of 100 mmol of the 4-chloroquinazoline derivative, 29.8 g (130 mmol) of 3-bromo-4- amino-6-tert-butylpyridine (S40), 35.0 g (250 mmol) of potassium carbonate, 200 g of glass beads (diameter 3 mm), 2.6 g (10 mmol) of triphenylphosphine and 450 mg (2 mmol) of palladium(II) acetate in 500 ml of o-xylene is heated under reflux until the 4-chloroquinazoline derivative has been consumed (typically 16 h). After cooling, the solid is filtered off via a silica-gel bed, rinsed with 1000 ml of THF, and the filtrate is evaporated to dryness. The residue is dissolved in 75 ml of ethyl acetate at the boiling temperature, and 250 ml of n-heptane are slowly added. After cooling, the solid which has crystallised out is filtered off with suction, washed twice with 50 ml of n-heptane each time and dried in vacuo and subsequently passed through a silica-gel column (heptane:ethyl acetate, 3:1 vv). The solids obtained in this way are freed from low-boiling components and non-volatile secondary components by sublimation (p about $1 \times 10^{-5}$ mbar, T about 150-230° C.). Purity according to $^1$H-NMR typically >99.5%.

The following derivatives are prepared:

11) 4,5,6a,8,1'-Pentaazabenzo[a]fluorene

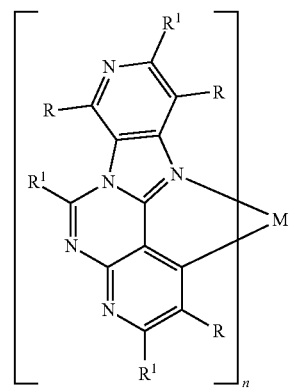

formula (28)

| Ex. | 4-Chloro-quinazoline derivative | Pyridine | Product | Yield |
|---|---|---|---|---|
| L147 | S49 | S40 | | 33% |
| L148 | 403612-89-5 | S40 | | 41% |

-continued

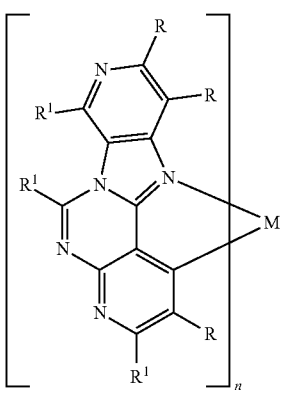

formula (29)

Preparation analogous to 7), using 32.3 g (100 mmol) of 2-(2-amino-6-tert-butylpyridin-3-yl)-6-tert-butyl-3H-imidazo[4,5-c]pyridine (S51) (employed as equimolar mixture with 2,6-di-tert-butyl-3H-imidazo[4,5-c]pyridine as obtained from synthesis 22)) instead of 100 mmol of the 2-(2-aminopyridin-3-yl)benzimidazole derivative. After crystallisation from methanol, the crude products are passed through a silica-gel column (heptane:ethyl acetate, 3:1 vv). The solids obtained in this way are freed from low-boiling components and non-volatile secondary components by sublimation (p about $1 \times 10^{-5}$ mbar, T about 200-240° C.). Purity according to $^1$H-NMR typically >99.5%.

The following derivatives are prepared:

12) 2,4,6a,8,11-Pentaazabenzo[a]fluorene

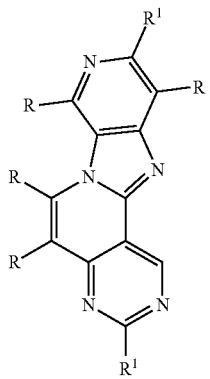

formula (30)

Preparation analogous to 9), using 30.9 g (100 mmol) of 2-(2-tert-butylpyrimidin-5-yl)-6-tert-butyl-3H-imidazo[4,5-c]pyridine (S52) instead of 25.2 g (100 mmol) of 2-(2-tert-butylpyrimidin-5-yl)benzimidazole (S48). After crystallisation from methanol, the crude products are passed through a silica-gel column (heptane:ethyl acetate, 3:1 vv). The solids obtained in this way are freed from low-boiling components and non-volatile secondary components by sublimation (p about $1\times10^{-5}$ mbar, T about 200-240° C.). Purity according to $^1$H-NMR typically >99.5%.

The following derivatives are prepared:

| Ex. | 2-(Pyrimidin-5-yl)-3H-imidazo-[4,5-c]pyridine derivative | Alkyne | Product | Yield |
|---|---|---|---|---|
| L151 | S52 | 501-65-5 | | 19% |
| L152 | S52 | 503-17-3 | | 16% |

13) 2,5,6a,8,1'-Pentaazabenzo[a]fluorene

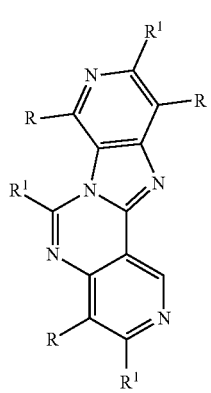

formula (32)

-continued formula (33)

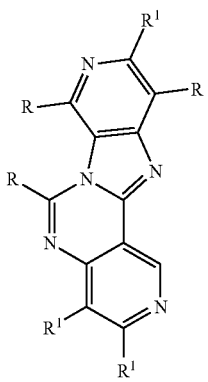

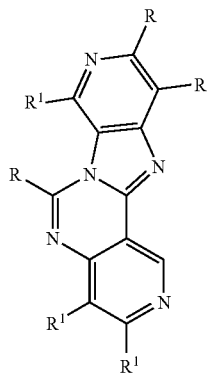

formula (34)

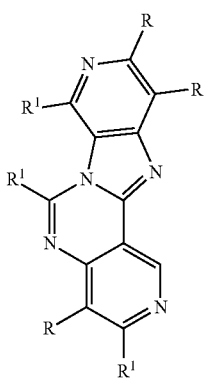

-continued formula (35)

Preparation analogous to 7), using 32.3 g (100 mmol) of 2-(4-amino-6-tertbutylpyridin-3-yl)-6-tert-butyl-3H-imidazo[4,5-c]pyridine (S53) (employed as equimolar mixture with 2,6-di-tert-butyl-3H-imidazo[4,5-c]pyridine as obtained from synthesis 24)) instead of 100 mmol of the 2-(2-aminopyridin-3-yl)benzimidazole derivative. After crystallisation from methanol, the crude products are passed through a silica-gel column (heptane:ethyl acetate, 3:1 vv). The solids obtained in this way are freed from low-boiling components and non-volatile secondary components by sublimation (p about $1 \times 10^{-5}$ mbar, T about 200-240° C.). Purity according to $^1$H-NMR typically >99.5%.

The following derivatives are prepared:

| Ex. | 2-(4-Amino-pyridin-3-yl)-3H-imidazo-[4,5-c]pyridine derivative | Carboxylic acid chloride | Product | Yield |
|---|---|---|---|---|
| L153 | 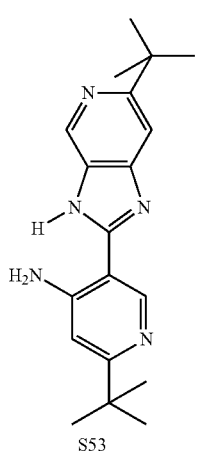<br>S53 | 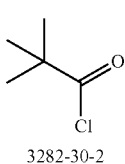<br>3282-30-2 | 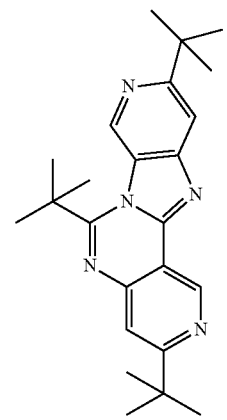 [SMILES: CC(C)(C)c1cc2nc(C(C)(C)C)n3c4cnc(C(C)(C)C)cc4nc3c2cn1] | 25% |

-continued

| Ex. | 2-(4-Amino-pyridin-3-yl)-3H-imidazo-[4,5-c]pyridine derivative | Carboxylic acid chloride | Product | Yield |
|---|---|---|---|---|
| L154 | S53 | 938-18-1 | | 27% |

14)) 2,4,5,6a,11-Pentaazabenzo[a]fluorene formula (36)

Preparation analogous to 7), using 26.7 g (100 mmol) of 2-(2-tert-butyl-4-aminopyrimidin-5-yl)benzimidazole (S55) (employed as equimolar mixture with 2-tert-butylbenzimidazole as obtained from synthesis 26)) instead of 100 mmol of the 2-(2-aminopyridin-3-yl)benzimidazole derivative. After crystallisation from methanol, the crude products are passed through a silica-gel column (heptane:ethyl acetate, 3:1 vv). The solids obtained in this way are freed from low-boiling components and non-volatile secondary components by sublimation (p about $1\times10^{-5}$ mbar, T about 200-240° C.). Purity according to $^1$H-NMR typically >99.5%.

The following derivatives are prepared:

| Ex. | 2-(4-Amino-pyrimidin-5-yl)-benzimidazole derivative | Carboxylic acid chloride | Product | Yield |
|---|---|---|---|---|
| L155 | S55 | 3282-30-2 | | 20% |

| Ex. | 2-(4-Amino-pyrimidin-5-yl)-benzimidazole derivative | Carboxylic acid chloride | Product | Yield |
|---|---|---|---|---|
| L156 | S55 | 938-18-1 | | 25% |

15) 2,4,5,6a,8,11-Hexaazabenzo[a]fluorene

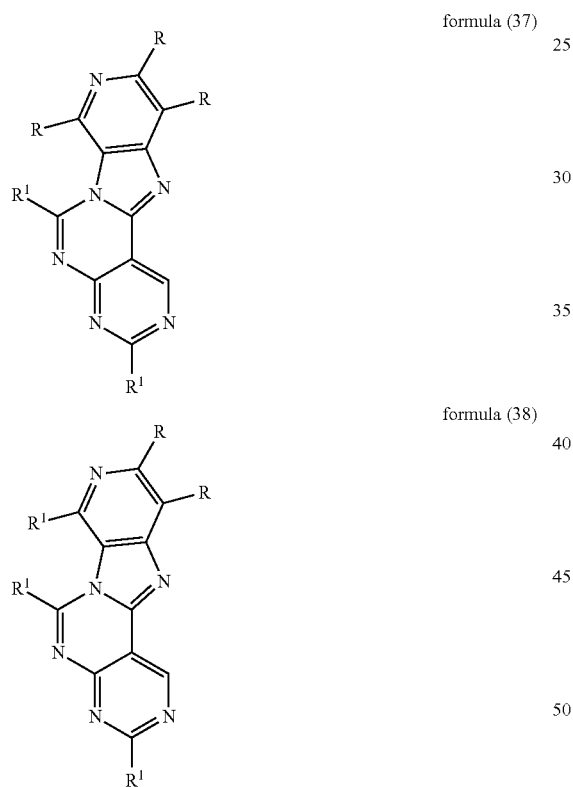

formula (37)

formula (38)

Preparation analogous to 7), using 32.4 g (100 mmol) of 2-(2-tert-butyl-4-aminopyrimidin-5-yl)-6-tert-butyl-3H-imidazo[4,5-c]pyridine (S56) (employed as equimolar mixture with 2,6-di-tert-butyl-3H-imidazo[4,5-c]-pyridine as obtained from synthesis 27)) instead of 100 mmol of the 2-(2-aminopyridin-3-yl)benzimidazole derivative. After crystallisation from methanol, the crude products are passed through a silica-gel column (heptane:ethyl acetate, 3:1 vv). The solids obtained in this way are freed from low-boiling components and non-volatile secondary components by sublimation (p about $1 \times 10^{-5}$ mbar, T about 200-240° C.). Purity according to $^1$H-NMR typically >99.5%.

The following derivatives are prepared:
| Ex. | 2-(4-Amino-pyrimidin-5-yl)-3H-imidazo-[4,5-c]pyridine derivative | Carboxylic acid chloride | Product | Yield |
|---|---|---|---|---|
| L157 | S56 | 3282-30-2 | | 27% |
| L158 | S56 | 938-18-1 | | 19% |
16) Tetradentate Ligands
A) 9,9'-Dibromo-3,6,8,3',6',8'-hexa-tert-butyl[10,10]bi[4,6a,1'-triazabenzo[a]fluorenyl], S76
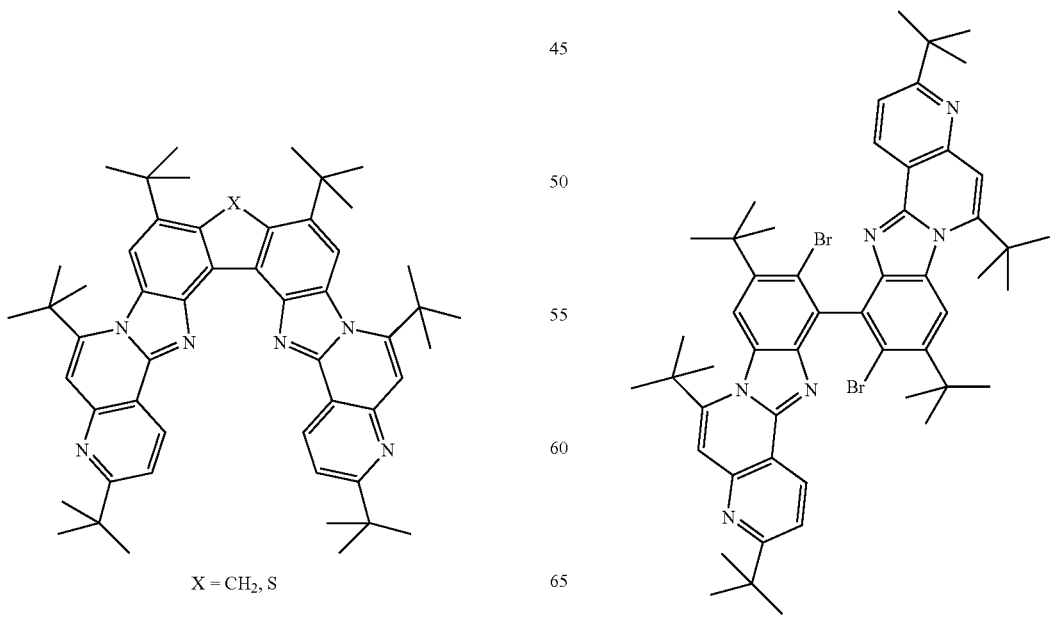
X = CH₂, S 39.2 g (220 mmol) of NBS are added in portions to a solution, warmed to 100° C., of 77.3 g (100 mmol) of 3,6,8,3',6',8'-hexa-tert-butyl[10,10]bi[4,6a,11-triazabenzo[a]fluorenyl], L213, in 300 ml of DMF, and the mixture is subsequently stirred for a further 6 h. The reaction mixture is evaporated to about 100 ml in vacuo, 200 ml of methanol are added dropwise, the mixture is stirred for a further 2 h, the precipitated crystals are then filtered off with suction and finally washed twice with 50 ml of methanol each time. Yield: 67.0 g (72 mmol), 72%. Purity: 97% according to $^1$H-NMR.

B) L216, X=S 22.0 ml (55 mmol) of n-butyllithium (2.5 M in hexane) are added dropwise with stirring to a solution, cooled to –78° C., of 23.3 g (25 mmol) of 9,9'-dibromo-3,6,8,3',6',8'-hexa-tert-butyl[10,10]bi[4,6a,11-triazabenzo[a]-fluorenyl] in 1000 of THF, and the mixture is subsequently stirred for a further 1 h. A mixture of 2.8 ml (35 mmol) of disulfur dichloride and 50 ml of THF is then added dropwise. After slow warming to room temperature, the THF is removed in vacuo, the residue is washed by stirring once with 200 ml of hot methanol and then recrystallised twice from DMF. The solid is freed from low-boiling components and non-volatile secondary components by sublimation (p about $1\times10^{-5}$ mbar, T about 340° C.). Yield: 8.4 g (10.5 mmol), 42%. Purity: 99% according to $^1$H-NMR.

C) L217, X=CH$_2$ 22.0 ml (55 mmol) of n-butyllithium (2.5 M in hexane) are added dropwise with stirring to a solution, cooled to –78° C., of 23.3 g (25 mmol) of 9,9'-dibromo-3,6,8,3',6',8'-hexa-tert-butyl[10,10]bi[4,6a,11-triazabenzo[a]fluorenyl] in 1000 of THF, and the mixture is subsequently stirred for a further 1 h. A mixture of 2.7 ml (35 mmol) of methyl chloroformate and 50 ml of THF is then added dropwise. After slow warming to room temperature, the THF is removed in vacuo. The solid is taken up in 100 ml of diethylene glycol, 4 ml of hydrazine hydrate are added, and the mixture is slowly heated to 190° C. on a water separator. After 16 h, the mixture is allowed to cool to room temperature, diluted with 50 ml of methanol, the precipitated crystals are filtered off with suction, washed three times with 30 ml of methanol each time and recrystallised twice from DMF. The solid is freed from low-boiling components and non-volatile secondary components by sublimation (p about $1\times10^{-5}$ mbar, T about 340° C.). Yield: 7.3 g (9.3 mmol), 39%. Purity: 99% according to $^1$H-NMR.

17) Hexadentate Ligands

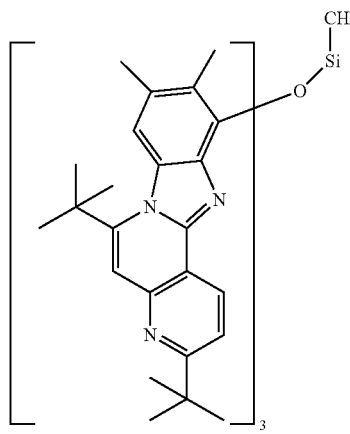

A) 10-Bromo-3,6-di-tert-butyl-8,9-dimethyl-4,6a,11-triazabenzo[a]-fluorene, S77

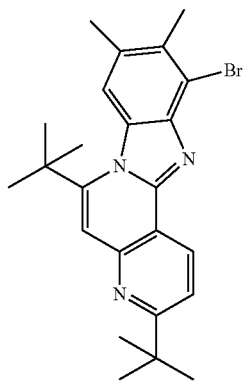 [SMILES: Cc1cc2c(nc3c4ccc(C(C)(C)C)nc4cc(C(C)(C)C)n23)c(Br)c1C]

19.6 g (110 mmol) of NBS are added in portions to a solution, warmed to 100° C., of 36.0 g (100 mmol) of 3,6-di-tert-butyl-8,9-dimethyl-4,6a,11-triazabenzo[a]fluorene, L111, in 300 ml of DMF, and the mixture is subsequently stirred for a further 6 h. The reaction mixture is evaporated to about 150 ml in vacuo, stirred for a further 2 h, the precipitated crystals are filtered off with suction and finally washed twice with 50 ml of methanol each time. Yield: 33.8 g (77 mmol), 77%. Purity: 97% according to $^1$H-NMR.

B) 10-Hydroxy-3,6-di-tert-butyl-8,9-dimethyl-4,6a,11-triazabenzo[a]-fluorene, S78

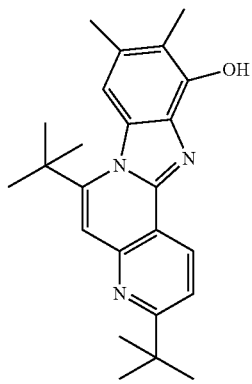 [SMILES: Cc1cc2c(nc3c4ccc(C(C)(C)C)nc4cc(C(C)(C)C)n23)c(O)c1C]

13.2 ml (33 mmol) of n-butyllithium (2.5 M in hexane) are added dropwise with vigorous stirring to a solution, cooled to –78° C., of 13.2 g (30 mmol) of 10-bromo-3,6-di-tert-butyl-8,9-dimethyl-4,6a,11-triazabenzo[α]fluorene in 300 ml of THF, and the mixture is stirred for a further 30 min. 4.7 ml (42 mmol) of trimethyl borate are added to this solution in one portion, the mixture is stirred for a further 1 h and then allowed to warm to room temperature. The solvent is removed in vacuo, the residue is taken up in 1000 ml of ethyl acetate, the solution is cooled to 5° C., 19 ml of aqueous H$_2$O$_2$ solution (30% by weight) are added with vigorous stirring, and a solution of 825 mg of NaOH in 20 ml of water is then added dropwise. After stirring for 3 h, 300 ml of saturated ammonium chloride solution are added, the organic phase is separated off, washed twice with 200 ml of water each time, dried over magnesium sulfate, and the org. phase is then evaporated to a volume of about 50 ml in vacuo. 200 ml of methanol are added to the crystal slurry, the crystals are filtered off with suction and washed once with 50 ml of methanol and dried in vacuo.

Yield: 8.1 g (22 mmol), 72%. Purity: 95% according to $^1$H-NMR.

C) L218

0.5 ml of a 1N sodium methoxide solution in methanol is added to a suspension of 5.63 g (15 mmol) of 10-hydroxy-3, 6-di-tert-butyl-8,9-dimethyl-4,6a,11-triazabenzo[a]fluorene in a mixture of 100 ml of toluene and 50 ml of methanol, and the mixture is stirred at 50° C. for 1 h. 681 mg of trimethoxymethylsilane are then added, the mixture is stirred for a further 2 h, and the methanol is then slowly distilled off, the temperature is then increased until all the toluene has also distilled off. Towards the end, a vacuum is applied in order to remove final residues of toluene. The colourless foam obtained in this way is reacted further without purification. Yield: 5.82 g (5 mmol), quantitative. Purity: 90% according to $^1$H-NMR.

18) Macrocyclic Tetradentate Ligands, L219

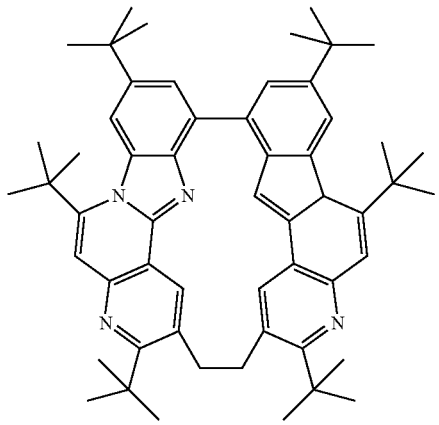 [SMILES: CC(C)(C)C1=Cc2nc(C(C)(C)C)c3cc2C2=Cc4c(cc(C(C)(C)C)cc4C21)-c1cc(C(C)(C)C)cc2c1nc1c4cc(c(C(C)(C)C)nc4cc(C(C)(C)C)n21)CC3]

A) 6-tert-Butyl-2-chloro-5-methylnicotinonitrile, S79

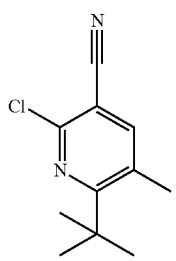

Procedure analogous to 5.1, using 85.4 g (560 mmol) of 2-chloro-3-cyano-5-methylpyridine [66909-34-0] instead of 128.8 g (560 mmol) of 3-bromo-6-trimethylsilylpyridine. Yield: 78.4 g (376 mmol), 67%. Purity: >95% according to $^1$H-NMR.

B) 6-tert-Butyl-2-(3,3-dimethylbut-1-ynyl)-5-methylnicotinonitrile, S80

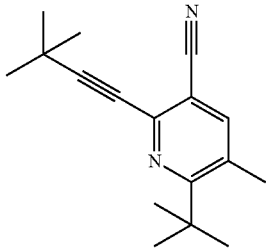 [SMILES: Cc1cc(C#N)c(C#CC(C)(C)C)nc1C(C)(C)C]

Procedure analogous to 31, using 62.6 g (300 mmol) of 6-tert-butyl-2-chloro-5-methylnicotinonitrile, S79, instead of 194.7 g (1 mol) of 2-chloro-3-cyano-6-tert-butylpyridine, S28, and scaling the remaining reagents correspondingly on a molar level. Yield: 68.9 g (271 mmol), 90%. Purity: >95% according to $^1$H-NMR.

c) 6-tert-Butyl-2-(3,3-dimethylbut-1-ynyl)-5-methylpyridine-3-carboxaldehyde, S81

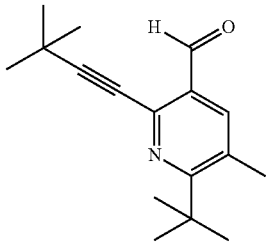 [SMILES: Cc1cc(C=O)c(C#CC(C)(C)C)nc1C(C)(C)C]

Procedure analogous to 32, using 63.6 g (250 mmol) of 6-tert-butyl-2-(3,3-dimethylbut-1-ynyl)-5-methylnicotinonitrile, S80, instead of 72.1 g (300 mmol) of 6-tert-butyl-2-(3,3-dimethylbut-1-ynyl)nicotinonitrile, S62, and scaling the remaining reagents correspondingly on a molar level. Yield: 57.7 g (224 mmol), 90%. Purity: >95% according to $^1$H-NMR.

D) 3,6,8,3',6',8'-Hexa-tert-butyl-2,2'-dimethyl[10,10]bi[4,6a,1'-triazabenzo[a]fluorenyl], S82

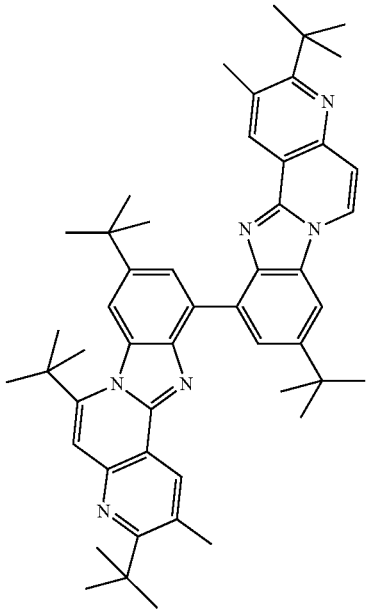 [SMILES: Cc1cc2c(ccn3c4cc(C(C)(C)C)cc(-c5cc(C(C)(C)C)cc6c5nc5c7cc(C)c(C(C)(C)C)nc7cc(C(C)(C)C)n65)c4nc23)nc1C(C)(C)C]

Procedure analogous to 3.3, L213. Yield 38%.

E) L219

200 g of glass beads (diameter 5 mm) are added to a suspension, cooled to −5° C., of 40.0 g (50 mmol) of 3,6,8,3',6',8'-hexa-tert-butyl-2,2'-dimethyl[10,10]bi[4,6a,11-triazabenzo[a]fluorenyl], S82, in 1000 ml of diethylether. 40 ml (100 mmol) of n-butyllithium (2.5 M in n-hexane) are slowly added dropwise with vigorous stirring, the mixture is stirred for a further 30 min., and 10.3 ml (120 mmol) of 1,2-dibromoethane are then added in one portion, and the mixture is allowed to warm to room temperature with stirring. 50 ml of ethanol are added, the mixture is decanted off from the glass beads, the org. phase is washed once with 200 ml of water and evaporated to about 200 ml in vacuo. After addition of 100 ml of methanol, the solid is filtered off with suction, washed twice with 200 ml of methanol and dried in vacuo. The solid is recrystallised three times from DMF, freed from low-boiling components and non-volatile secondary components by sublimation (p about 1×10⁻⁵ mbar, T about 350° C.). Yield: 20.8 g (26 mmol), 52%. Purity: 99% according to ¹H-NMR.

C. Synthesis of the Metal Complexes

1) Homoleptic Tris-Facial Iridium Complexes

Variant A: Trisacetylacetonatoiridium(III) as Iridium Starting Material

A mixture of 10 mmol of trisacetylacetonatoiridium(III) [15635-87-7] and 60 mmol of the ligand L is melted into a 50 ml glass ampoule in vacuo (10⁻⁵ mbar). The ampoule is heated at the temperature indicated for the time indicated, during which the molten mixture is stirred with the aid of a magnetic stirrer. After cooling (NOTE: the ampoules are usually under pressure!), the ampoule is opened, the sinter cake is stirred for 3 h with 100 g of glass beads (diameter 3 mm) in 100 ml of the suspension medium indicated and mechanically digested at the same time. The fine suspension is decanted off from the glass beads, the solid is filtered off with suction and dried in vacuo. The dry solid is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about 10⁻⁶ mbar). The sublimation is carried out in the temperature range from about 320 to about 400° C. in a high vacuum (p about 10⁻⁶ mbar), where the sublimation is preferably carried out in the form of a fractional sublimation. In the case of ligands in point group C1, the derived metal complexes are obtained as diastereomer mixture.

Variant B: Tris(2,2,6,6-tetramethyl-3,5-heptanedionato)iridium as Iridium Starting Material Procedure analogous to variant A, using 10 mmol of tris(2,2,6,6-tetramethyl-3,5-heptanedionato)iridium instead of 10 mmol of trisacetylacetonatoiridium(III) [15635-87-7].

| Ex. | Ligand L | Ir complex | Variant<br>Reaction temp./reaction time<br>Suspension medium<br>Extraction medium | Yield |
|---|---|---|---|---|
| Ir(L1)₃ | L1 | 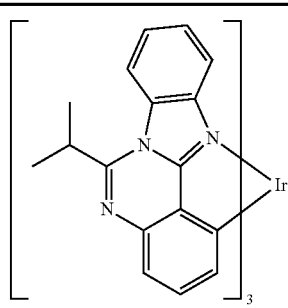<br>Ir(L1)₃ | A<br>270° C./100 h<br>DCM THF | 46% |
| Ir(L2)₃ | L2 | Ir(L2)₃ | as Ex. Ir(L1)₃ | 51% |
| Ir(L3)₃ | L3 | Ir(L3)₃ | as Ex. Ir(L1)₃ | 38% |
| Ir(L4)₃ | L4 | Ir(L4)₃ | as Ex. Ir(L1)₃ | 37% |
| Ir(L5)₃ | L5 | Ir(L5)₃ | A<br>270° C./100 h<br>DCM/EtOH, 2:1 THF | 46% |
| Ir(L6)₃ | L6 | Ir(L6)₃ | as Ex. Ir(L5)₃ | 18% |
| Ir(L7)₃ | L7 | Ir(L7)₃ | as Ex. Ir(L1)₃ | 31% |
| Ir(L8)₃ | L8 | Ir(L8)₃ | as Ex. Ir(L1)₃ | 47% |
| Ir(L9)₃ | L9 | Ir(L9)₃ | as Ex. Ir(L1)₃ | 30% |
| Ir(L10)₃ | L10 | Ir(L10)₃ | as Ex. Ir(L1)₃ | 35% |
| Ir(L11)₃ | L11 | Ir(L11)₃ | as Ex. Ir(L1)₃ | 36% |
| Ir(L12)₃ | L12 | Ir(L12)₃ | as Ex. Ir(L1)₃ | 39% |

-continued

| Ex. | Ligand L | Ir complex | Variant Reaction temp./reaction time Suspension medium Extraction medium | Yield |
|---|---|---|---|---|
| Ir(L13)₃ | L13 | Ir(L13)₃ | as Ex. Ir(L1)₃ | 42% |
| Ir(L13)₃ | L13 | Ir(L13)₃ | B 270° C./120 h DCM/THF | 52% |
| Ir(L14)₃ | L14 | Ir(L14)₃ | as Ex. Ir(L5)₃ | 41% |
| Ir(L15)₃ | L15 | Ir(L15)₃ | as Ex. Ir(L5)₃ | 41% |
| Ir(L16)₃ | L16 | Ir(L16)₃ | as Ex. Ir(L5)₃ | 40% |
| Ir(L17)₃ | L17 | Ir(L17)₃ | as Ex. Ir(L5)₃ | 35% |
| Ir(L18)₃ | L18 | Ir(L18)₃ | as Ex. Ir(L5)₃ | 22% |
| Ir(L19)₃ | L19 | Ir(L19)₃ | as Ex. Ir(L5)₃ | 33% |
| Ir(L20)₃ | L20 | Ir(L20)₃ | as Ex. Ir(L5)₃ | 27% |
| Ir(L21)₃ | L21 | Ir(L21)₃ | as Ex. Ir(L5)₃ | 36% |
| Ir(L22)₃ | L22 | Ir(L22)₃ | as Ex. Ir(L5)₃ | 41% |
| Ir(L23)₃ | L23 | Ir(L23)₃ | as Ex. Ir(L5)₃ | 50% |
| Ir(L24)₃ | L24 | Ir(L24)₃ | as Ex. Ir(L5)₃ | 30% |
| Ir(L25)₃ | L25 | Ir(L25)₃ | as Ex. Ir(L5)₃ | 32% |
| Ir(L26)₃ | L26 | Ir(L26)₃ | as Ex. Ir(L5)₃ | 35% |
| Ir(L27)₃ | L27 | Ir(L27)₃ | as Ex. Ir(L5)₃ | 38% |
| Ir(L28)₃ | L28 | Ir(L28)₃ | as Ex. Ir(L5)₃ | 48% |
| Ir(L29)₃ | L29 | Ir(L29)₃ | as Ex. Ir(L5)₃ | 20% |
| Ir(L30)₃ | L30 | Ir(L30)₃ | as Ex. Ir(L5)₃ | 26% |
| Ir(L31)₃ | L31 | Ir(L31)₃ | as Ex. Ir(L5)₃ | 34% |
| Ir(L32)₃ | L32 | Ir(L32)₃ | as Ex. Ir(L5)₃ | 37% |
| Ir(L33)₃ | L33 | Ir(L33)₃ | as Ex. Ir(L5)₃ | 17% |
| Ir(L34)₃ | L34 | Ir(L34)₃ | as Ex. Ir(L5)₃ | 41% |

| Ex. | Ligand L | Ir complex | Variant Reaction temp./reaction time Suspension medium Extraction medium | Yield |
|---|---|---|---|---|
| Ir(L35)₃ | L35 | Ir(L35)₃ | as Ex. Ir(L5)₃ | 43% |
| Ir(L36)₃ | L36 | Ir(L36)₃ | as Ex. Ir(L1)₃ | 35% |
| Ir(L37)₃ | L37 | Ir(L37)₃ | as Ex. Ir(L1)₃ | 30% |
| Ir(L38)₃ | L38 | Ir(L38)₃ | as Ex. Ir(L1)₃ | 32% |
| Ir(L39)₃ | L39 | Ir(L39)₃ | as Ex. Ir(L5)₃ | 9% |
| Ir(L40)₃ | L40 | Ir(L40)₃ | as Ex. Ir(L1)₃ | 27% |
| Ir(L41)₃ | L41 | Ir(L41)₃ | as Ex. Ir(L1)₃ | 36% |
| Ir(L42)₃ | L42 | Ir(L42)₃ | as Ex. Ir(L1)₃ | 35% |
| Ir(L43)₃ | L43 | Ir(L43)₃ | as Ex. Ir(L5)₃ | 38% |
| Ir(L44)₃ | L44 | Ir(L44)₃ | as Ex. Ir(L5)₃ | 40% |
| Ir(L45)₃ | L45 | Ir(L45)₃ | as Ex. Ir(L5)₃ | 45% |
| Ir(L46)₃ | L46 | Ir(L46)₃ | as Ex. Ir(L5)₃ | 40% |
| Ir(L47)₃ | L47 | Ir(L47)₃ | as Ex. Ir(L5)₃ | 42% |
| Ir(L48)₃ | L48 | Ir(L48)₃ | as Ex. Ir(L5)₃ | 38% |
| Ir(L49)₃ | L49 | Ir(L49)₃ | as Ex. Ir(L5)₃ | 45% |
| Ir(L50)₃ | L50 | Ir(L50)₃ | as Ex. Ir(L5)₃ | 44% |
| Ir(L51)₃ | L51 | Ir(L51)₃ | as Ex. Ir(L5)₃ | 28% |
| Ir(L52)₃ | L52 | Ir(L52)₃ | as Ex. Ir(L5)₃ | 43% |
| Ir(L53)₃ | L53 | Ir(L53)₃ | as Ex. Ir(L5)₃ | 32% |
| Ir(L54)₃ | L54 | Ir(L54)₃ | as Ex. Ir(L5)₃ | 34% |
| Ir(L55)₃ | L55 | Ir(L55)₃ | as Ex. Ir(L5)₃ | 25% |
| Ir(L56)₃ | L56 | Ir(L56)₃ | as Ex. Ir(L5)₃ | 20% |

-continued

| Ex. | Ligand L | Ir complex | Variant Reaction temp./reaction time Suspension medium Extraction medium | Yield |
|---|---|---|---|---|
| Ir(L57)₃ | L57 | Ir(L57)₃ | as Ex. Ir(L5)₃ | 39% |
| Ir(L58)₃ | L58 | Ir(L58)₃ | as Ex. Ir(L5)₃ | 37% |
| Ir(L59)₃ | L59 | Ir(L59)₃ | as Ex. Ir(L5)₃ | 34% |
| Ir(L60)₃ | L60 | Ir(L60)₃ | as Ex. Ir(L5)₃ | 45% |
| Ir(L61)₃ | L61 | Ir(L61)₃ | as Ex. Ir(L5)₃ | 48% |
| Ir(L62)₃ | L62 | Ir(L62)₃ | as Ex. Ir(L5)₃ | 40% |
| Ir(L63)₃ | L63 | Ir(L63)₃ | as Ex. Ir(L5)₃ | 39% |
| Ir(L64)₃ | L64 | Ir(L64)₃ | as Ex. Ir(L5)₃ | 36% |
| Ir(L65)₃ | L65 | Ir(L65)₃ | as Ex. Ir(L5)₃ | 40% |
| Ir(L66)₃ | L66 | Ir(L66)₃ | as Ex. Ir(L5)₃ | 41% |
| Ir(L67)₃ | L67 | Ir(L67)₃ | as Ex. Ir(L1)₃ | 44% |
| Ir(L67)₃ | L67 | Ir(L67)₃ | B 270° C./110 h DCM THF | 53% |
| Ir(L68)₃ | L68 | Ir(L68)₃ | as Ex. Ir(L1)₃ | 42% |
| Ir(L69)₃ | L69 | Ir(L69)₃ | as Ex. Ir(L1)₃ | 43% |
| Ir(L70)₃ | L70 | Ir(L70)₃ | as Ex. Ir(L5)₃ | 35% |
| Ir(L71)₃ | L71 | Ir(L71)₃ | as Ex. Ir(L5)₃ | 36% |
| Ir(L72)₃ | L72 | Ir(L72)₃ | as Ex. Ir(L5)₃ | 32% |

-continued

| Ex. | Ligand L | Ir complex | Variant Reaction temp./reaction time Suspension medium Extraction medium | Yield |
|---|---|---|---|---|
| Ir(L73)₃ | L73 | Ir(L73)₃ | as Ex. Ir(L1)₃ | 17% |
| Ir(L74)₃ | L74 | Ir(L74)₃ | as Ex. Ir(L5)₃ | 15% |
| Ir(L75)₃ | L75 | Ir(L75)₃ | as Ex. Ir(L5)₃ | 11% |
| Ir(L76)₃ | L76 | Ir(L76)₃ | as Ex. Ir(L5)₃ | 16% |
| Ir(L77)₃ | L77 | Ir(L77)₃ | as Ex. Ir(L5)₃ | 19% |
| Ir(L78)₃ | L78 | Ir(L78)₃ | as Ex. Ir(L5)₃ | 47% |
| Ir(L79)₃ | L79 | Ir(L79)₃ | as Ex. Ir(L5)₃ | 41% |
| Ir(L80)₃ | L80 | Ir(L80)₃ | as Ex. Ir(L5)₃ | 46% |
| Ir(L81)₃ | L81 | Ir(L81)₃ | as Ex. Ir(L5)₃ | 36% |

-continued

| Ex. | Ligand L | Ir complex | Variant Reaction temp./reaction time Suspension medium Extraction medium | Yield |
|---|---|---|---|---|
| Ir(L82)$_3$ | L82 | Ir(L82)$_3$ | as Ex. Ir(L5)$_3$ | 47% |
| Ir(L83)$_3$ | L83 | Ir(L83)$_3$ | as Ex. Ir(L5)$_3$ | 45% |
| Ir(L84)$_3$ | L84 | Ir(L84)$_3$ | as Ex. Ir(L5)$_3$ | 50% |
| Ir(L85)$_3$ | L85 | Ir(L85)$_3$ | as Ex. Ir(L5)$_3$ | 49% |
| Ir(L86)$_3$ | L86 | Ir(L86)$_3$ | as Ex. Ir(L5)$_3$ | 44% |
| Ir(L87)$_3$ | L87 | Ir(L87)$_3$ | as Ex. Ir(L5)$_3$ | 45% |
| Ir(L88)$_3$ | L88 | Ir(L88)$_3$ | as Ex. Ir(L5)$_3$ | 39% |
| Ir(L89)$_3$ | L89 | Ir(L89)$_3$ | as Ex. Ir(L5)$_3$ | 32% |
| Ir(L90)$_3$ | L90 | Ir(L90)$_3$ | as Ex. Ir(L5)$_3$ | 22% |
| Ir(L91)$_3$ | L91 | Ir(L91)$_3$ | as Ex. Ir(L5)$_3$ | 50% |
| Ir(L92)$_3$ | L92 | Ir(L92)$_3$ | as Ex. Ir(L5)$_3$ | 56% |
| Ir(L93)$_3$ | L93 | Ir(L93)$_3$ | as Ex. Ir(L5)$_3$ | 45% |
| Ir(L94)$_3$ | L94 | Ir(L94)$_3$ | as Ex. Ir(L5)$_3$ | 46% |
| Ir(L95)$_3$ | L95 | Ir(L95)$_3$ | as Ex. Ir(L5)$_3$ | 48% |
| Ir(L96)$_3$ | L96 | Ir(L96)$_3$ | as Ex. Ir(L5)$_3$ | 36% |
| Ir(L97)$_3$ | L97 | Ir(L97)$_3$ | as Ex. Ir(L5)$_3$ | 47% |
| Ir(L98)$_3$ | L98 | Ir(L98)$_3$ | as Ex. Ir(L5)$_3$ | 28% |
| Ir(L99)$_3$ | L99 | Ir(L99)$_3$ | as Ex. Ir(L5)$_3$ | 31% |
| Ir(L100)$_3$ | L100 | Ir(L100)$_3$ | as Ex. Ir(L5)$_3$ | 39% |
| Ir(L101)$_3$ | L101 | Ir(L101)$_3$ | as Ex. Ir(L5)$_3$ | 41% |
| Ir(L102)$_3$ | L102 | Ir(L102)$_3$ | as Ex. Ir(L5)$_3$ | 35% |

-continued

| Ex. | Ligand L | Ir complex | Variant<br>Reaction temp./reaction time<br>Suspension medium<br>Extraction medium | Yield |
|---|---|---|---|---|
| Ir(L103)$_3$ | L103 | Ir(L103)$_3$ | as Ex. Ir(L5)$_3$ | 30% |
| Ir(L104)$_3$ | L104 | Ir(L104)$_3$ | as Ex. Ir(L5)$_3$ | 49% |
| Ir(L105)$_3$ | L105 | Ir(L105)$_3$ | A<br>290° C./100 h<br>DCM/EtOH, 2:1 THF | 23% |
| Ir(L106)$_3$ | L106 | Ir(L106)$_3$ | as Ex. Ir(L105)$_3$ | 19% |
| Ir(L107)$_3$ | L107 | Ir(L107)$_3$ | as Ex. Ir(L105)$_3$ | 17% |
| Ir(L108)$_3$ | L108 | Ir(L108)$_3$ | A<br>300° C./100 h<br>DCM/EtOH, 2:1 THF | 9% |
| Ir(L109)$_3$ | L109 | Ir(L109)$_3$ | as Ex. Ir(L105)$_3$ | 17% |
| Ir(L110)$_3$ | L110 | Ir(L110)$_3$ | as Ex. Ir(L105)$_3$ | 15% |
| Ir(L111)$_3$ | L111 | Ir(L111)$_3$ | as Ex. Ir(L105)$_3$ | 19% |
| Ir(L112)$_3$ | L112 | Ir(L112)$_3$ | as Ex. Ir(L108)$_3$ | 8% |
| Ir(L113)$_3$ | L113 | Ir(L113)$_3$ | as Ex. Ir(L105)$_3$ | 23% |
| Ir(L114)$_3$ | L114 | Ir(L114)$_3$ | A<br>300° C./100 h<br>Toluene/EtOH, 1:1 DCM | 24% |
| Ir(L115)$_3$ | L115 | Ir(L115)$_3$ | A<br>280° C./130 h<br>DCM/EtOH, 2:1 THF | 34% |
| Ir(L116)$_3$ | L116 | Ir(L116)$_3$ | as Ex. Ir(L115)$_3$ | 35% |
| Ir(L117)$_3$ | L117 | Ir(L117)$_3$ | as Ex. Ir(L115)$_3$ | 41% |

-continued

| Ex. | Ligand L | Ir complex | Variant Reaction temp./reaction time Suspension medium Extraction medium | Yield |
|---|---|---|---|---|
| Ir(L118)₃ | L118 | Ir(L118)₃ | as Ex. Ir(L115)₃ | 30% |
| Ir(L119)₃ | L119 | Ir(L119)₃ | as Ex. Ir(L115)₃ | 32% |
| Ir(L120)₃ | L120 | Ir(L120)₃ | as Ex. Ir(L115)₃ | 25% |
| Ir(L121)₃ | L121 | Ir(L121)₃ | as Ex. Ir(L115)₃ | 27% |
| Ir(L122)₃ | L122 | Ir(L122)₃ | as Ex. Ir(L115)₃ | 23% |
| Ir(L123)₃ | L123 | Ir(L123)₃ | as Ex. Ir(L115)₃ | 9% |
| Ir(L124)₃ | L124 | 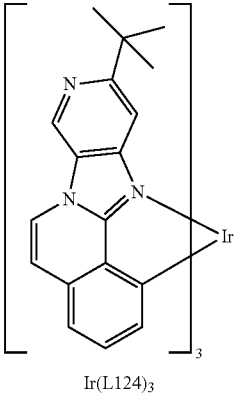<br>Ir(L124)₃ | as Ex. Ir(L115)₃ | 20% |
| Ir(L125)₃ | L125 | Ir(L125)₃ | as Ex. Ir(L115)₃ | 19% |
| Ir(L126)₃ | L126 | Ir(L126)₃ | as Ex. Ir(L115)₃ | 22% |
| Ir(L127)₃ | L127 | Ir(L127)₃ | as Ex. Ir(L115)₃ | 20% |
| Ir(L128)₃ | L128 | Ir(L128)₃ | as Ex. Ir(L115)₃ | 16% |
| Ir(L129)₃ | L129 | Ir(L129)₃ | as Ex. Ir(L115)₃ | 24% |
| Ir(L130)₃ | L130 | Ir(L130)₃ | as Ex. Ir(L114)₃ | 21% |
| Ir(L131)₃ | L131 | Ir(L131)₃ | as Ex. Ir(L115)₃ | 10% |
| Ir(L132)₃ | L132 | 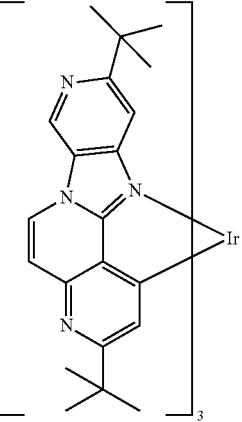<br>Ir(L132)₃ | A<br>315° C./130 h<br>DCM/EtOH, 2:1 THF | 17% |
| Ir(L133)₃ | L133 | Ir(L133)₃ | as Ex. Ir(L132)₃ | 17% |
| Ir(L134)₃ | L134 | Ir(L134)₃ | as Ex. Ir(L132)₃ | 24% |
| Ir(L135)₃ | L135 | Ir(L135)₃ | as Ex. Ir(L132)₃ | 11% |
| Ir(L136)₃ | L136 | Ir(L136)₃ | as Ex. Ir(L132)₃ | 22% |

-continued
| Ex. | Ligand L | Ir complex | Variant Reaction temp./reaction time Suspension medium Extraction medium | Yield |
|---|---|---|---|---|
| Ir(L137)₃ | L137 | 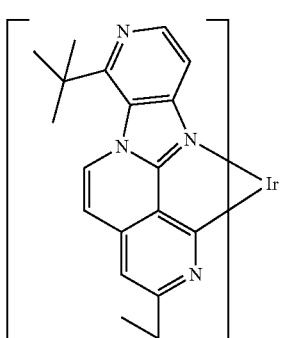<br>Ir(L137)₃ | as Ex. Ir(L132)₃ | 9% |
| Ir(L138)₃ | L138 | Ir(L138)₃ | as Ex. Ir(L132)₃ | 5% |
| Ir(L139)₃ | L139 | 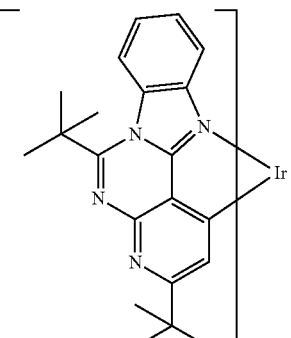<br>Ir(L139)₃ | as Ex. Ir(L132)₃ | 10% |
| Ir(L140)₃ | L140 | Ir(L140)₃ | as Ex. Ir(L132)₃ | 12% |
| Ir(L141)₃ | L141 | Ir(L141)₃ | as Ex. Ir(L132)₃ | 9% |
| Ir(L142)₃ | L142 | Ir(L142)₃ | as Ex. Ir(L132)₃ | 7% |
| Ir(L143)₃ | L143 | 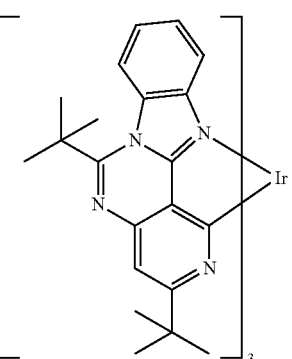<br>Ir(L143)₃ | A<br>320° C./120 h<br>DCM/EtOH, 2:1 THF | 9% |
| Ir(L144)₃ | L144 | Ir(L144)₃ | as Ex. Ir(L143)₃ | 11% |

| Ex. | Ligand L | Ir complex | Variant<br>Reaction temp./reaction time<br>Suspension medium<br>Extraction medium | Yield |
|---|---|---|---|---|
| Ir(L145)₃ | L145 | Ir(L145)₃ | A<br>320° C./130 h<br>Toluene THF | 11% |
| Ir(L146)₃ | L146 | Ir(L146)₃ | as Ex. Ir(L143)₃ | 13% |
| Ir(L147)₃ | L147 | Ir(L147)₃ | as Ex. Ir(L115)₃ | 17% |
| Ir(L148)₃ | L148 | Ir(L148)₃ | as Ex. Ir(L115)₃ | 20% |
| Ir(L149)₃ | L149 | Ir(L149)₃ | A<br>315° C./130 h<br>DCM THF | 7% |
| Ir(L150)₃ | L150 | Ir(L150)₃ | as Ex. Ir(L149)₃ | 9% |

-continued
| Ex. | Ligand L | Ir complex | Variant Reaction temp./reaction time Suspension medium Extraction medium | Yield |
|---|---|---|---|---|
| Ir(L151)₃ | L151 | 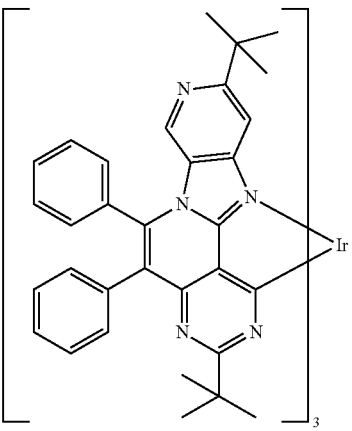<br>Ir(L151)₃ | as Ex. Ir(L145)₃ | 5% |
| Ir(L152)₃ | L152 | Ir(L152)₃ | as Ex. Ir(L145)₃ | 6% |
| Ir(L153)₃ | L153 | 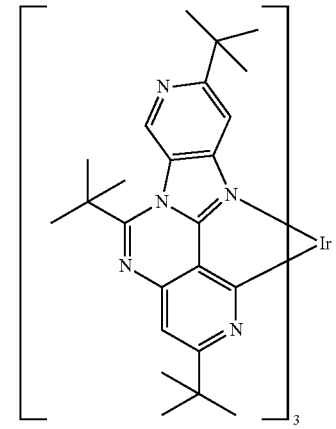<br>Ir(L153)₃ | as Ex. Ir(L149)₃ | 5% |
| Ir(L154)₃ | L154 | Ir(L154)₃ | as Ex. Ir(L149)₃ | 8% |
| Ir(L155)₃ | L155 | 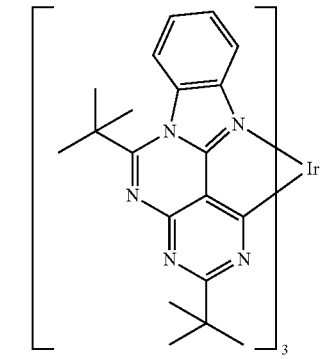<br>Ir(L155)₃ | as Ex. Ir(L143)₃ | 4% |
| Ir(L156)₃ | L156 | Ir(L156)₃ | as Ex. Ir(L143)₃ | 6% |

-continued

| Ex. | Ligand L | Ir complex | Variant Reaction temp./reaction time Suspension medium Extraction medium | Yield |
|---|---|---|---|---|
| Ir(L157)₃ | L157 | Ir(L157)₃ | A 325° C./80 h DCM THF | 7% |
| Ir(L158)₃ | L158 | Ir(L158)₃ | as Ex. Ir(L157)₃ | 6% |
| Ir(L159)₃ | L159 | Ir(L159)₃ | A 265° C./80 h DCM THF | 37% |
| Ir(L160)₃ | L160 | Ir(L160)₃ | as Ex. Ir(L159)₃ | 43% |
| Ir(L161)₃ | L161 | Ir(L161)₃ | as Ex. Ir(L159)₃ | 30% |
| Ir(L162)₃ | L162 | Ir(L162)₃ | B 305° C./130 h Acetone Toluene | 46% |
| Ir(L163)₃ | L163 | Ir(L163)₃ | as Ex. Ir(L162)₃ | 44% |
| Ir(L164)₃ | L164 | Ir(L164)₃ | B 305° C./130 h Acetone Cyclohexane | 41% |
| Ir(L165)₃ | L165 | Ir(L165)₃ | as Ex. Ir(L164)₃ | 43% |
| Ir(L166)₃ | L166 | Ir(L166)₃ | as Ex. Ir(L164)₃ | 43% |
| Ir(L167)₃ | L167 | Ir(L167)₃ | as Ex. Ir(L164)₃ | 32% |
| Ir(L168)₃ | L168 | Ir(L168)₃ | as Ex. Ir(L162) | 39% |
| Ir(L169)₃ | L169 | Ir(L169)₃ | as Ex. Ir(L162) | 40% |
| Ir(L170)₃ | L170 | Ir(L170)₃ | as Ex. Ir(L162) | 40% |
| Ir(L171)₃ | L171 | Ir(L171)₃ | as Ex. Ir(L162) | 19% |

-continued

| Ex. | Ligand L | Ir complex | Variant Reaction temp./reaction time Suspension medium Extraction medium | Yield |
|---|---|---|---|---|
| Ir(L172)$_3$ | L172 | Ir(L172)$_3$ | as Ex. Ir(L162) | 31% |
| Ir(L173)$_3$ | L173 | Ir(L173)$_3$ | as Ex. Ir(L162) | 36% |
| Ir(L174)$_3$ | L174 | Ir(L174)$_3$ | as Ex. Ir(L162) | 35% |
| Ir(L175)$_3$ | L175 | Ir(L175)$_3$ | as Ex. Ir(L162) | 33% |
| Ir(L176)$_3$ | L176 | Ir(L176$_3$ | as Ex. Ir(L162) | 45% |
| Ir(L177)$_3$ | L177 | Ir(L177)$_3$ | as Ex. Ir(L162) | 44% |
| Ir(L178)$_3$ | L178 | Ir(L178)$_3$ | as Ex. Ir(L162) | 41% |
| Ir(L179)$_3$ | L179 | Ir(L179)$_3$ | as Ex. Ir(L162) | 42% |
| Ir(L180)$_3$ | L180 | Ir(L180)$_3$ | as Ex. Ir(L162) | 29% |
| Ir(L181)$_3$ | L181 | Ir(L181)$_3$ | as Ex. Ir(L162) | 36% |
| Ir(L182)$_3$ | L182 | Ir(L182)$_3$ | as Ex. Ir(L162) | 44% |
| Ir(L183)$_3$ | L183 | Ir(L183)$_3$ | as Ex. Ir(L162) | 38% |
| Ir(L184)$_3$ | L184 | Ir(L184)$_3$ | as Ex. Ir(L162) | 37% |
| Ir(L185)$_3$ | L185 | Ir(L185)$_3$ | as Ex. Ir(L162) | 26% |
| Ir(L186)$_3$ | L186 | Ir(L186)$_3$ | as Ex. Ir(L162) | 40% |
| Ir(L187)$_3$ | L187 | Ir(L187)$_3$ | as Ex. Ir(L162) | 35% |
| Ir(L188)$_3$ | L188 | Ir(L188)$_3$ | as Ex. Ir(L162) | 36% |
| Ir(L189)$_3$ | L189 | Ir(L189)$_3$ | as Ex. Ir(L162) | 39% |
| Ir(L190)$_3$ | L190 | Ir(L190)$_3$ | as Ex. Ir(L162) | 30% |
| Ir(L191)$_3$ | L191 | Ir(L191)$_3$ | as Ex. Ir(L162) | 39% |
| Ir(L192)$_3$ | L192 | Ir(L192)$_3$ | as Ex. Ir(L164)$_3$ | 41% |
| Ir(L193)$_3$ | L192 | Ir(L193)$_3$ | as Ex. Ir(L162) | 36% |
| Ir(L194)$_3$ | L194 | Ir(L194)$_3$ | as Ex. Ir(L162) | 28% |
| Ir(L195)$_3$ | L192'5 | Ir(L195)$_3$ | as Ex. Ir(L162) | 37% |
| Ir(L196)$_3$ | L196 | Ir(L196)$_3$ | as Ex. Ir(L162) | 22% |
| Ir(L197)$_3$ | L197 | Ir(L197)$_3$ | as Ex. Ir(L162) | 34% |
| Ir(L198)$_3$ | L198 | Ir(L198)$_3$ | as Ex. Ir(L162) | 36% |
| Ir(L199)$_3$ | L199 | Ir(L199)$_3$ | as Ex. Ir(L162) | 35% |
| Ir(L200)$_3$ | L200 | Ir(L200)$_3$ | as Ex. Ir(L164) | 27% |
| Ir(L201)$_3$ | L201 | Ir(L201)$_3$ | as Ex. Ir(L162) | 40% |
| Ir(L202)$_3$ | L202 | Ir(L202)$_3$ | as Ex. Ir(L162) | 30% |
| Ir(L203)$_3$ | L203 | Ir(L203)$_3$ | as Ex. Ir(L162) | 35% |
| Ir(L204)$_3$ | L204 | Ir(L204)$_3$ | as Ex. Ir(L162) | 39% |
| Ir(L205)$_3$ | L205 | Ir(L205)$_3$ | as Ex. Ir(L162) | 25% |
| Ir(L206)$_3$ | L206 | Ir(L206)$_3$ | as Ex. Ir(L164)$_3$ | 21% |
| Ir(L207)$_3$ | L207 | Ir(L207)$_3$ | as Ex. Ir(L164) | 43% |
| Ir(L208)$_3$ | L208 | Ir(L208)$_3$ | as Ex. Ir(L162) | 26% |
| Ir(L209)$_3$ | L209 | Ir(L209)$_3$ | as Ex. Ir(L162) | 30% |
| Ir(L210)$_3$ | L210 | Ir(L210)$_3$ | as Ex. Ir(L162) | 29% |
| Ir(L218)$_3$ | L218 | 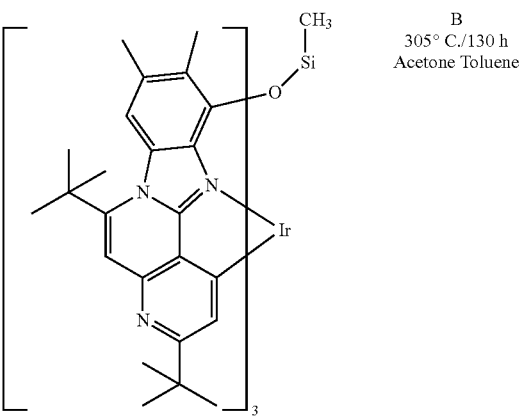 Tris(2,2,6,6-tetramethyl-3,5-heptanedionato)iridium: L218 1:1 Addition of 3 ml of tridecane | B 305° C./130 h Acetone Toluene | 12% |

2) Heteroleptic Iridium Complexes

Variant A

Step 1

A mixture of 10 mmol of sodium bisacetylacetonatodichloroiridate(III) [770720-50-8] and 24 mmol of ligand L is melted into a 50 ml glass ampoule in vacuo ($10^{-3}$ mbar). The ampoule is heated at the temperature indicated for the time indicated, during which the molten mixture is stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated and mechanically digested at the same time. The fine suspension is decanted off from the glass beads, the solid is filtered off with suction and dried in vacuo.

Step 2

The crude chloro dimer of the formula $[Ir(L)_2Cl]_2$ obtained in this way is suspended in a mixture of 75 ml of 2-ethoxyethanol and 25 ml of water, 13 mmol of the co-ligand CL or the co-ligand compound CL and 15 mmol of sodium carbonate are added. After 20 h under reflux, a further 75 ml of water are added dropwise, after cooling the solid is filtered off with suction, washed three times with 50 ml of water each time and three times with 50 ml of methanol each time and dried in vacuo. The dry solid is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 300 to about 390° C. in a high vacuum (p about $10^{-6}$ mbar), where the sublimation is preferably carried out in the form of a fractional sublimation.

| Ex. | Ligand L | Co-ligand CL | Ir complex  Step 1: reaction temp./reaction time/suspension medium  Step 2: extraction medium | Yield |
|---|---|---|---|---|
| $Ir(L1)_2(CL1)$ | L1 | ![CL1 structure] 123-54-6 CL1 | 260° C./60 h/DCM THF | 68% |
| $Ir(L13)_2(CL1)$ | L13 | CL1 | as Ex. $Ir(L1)_2(CL1)$ | 65% |

-continued
| Ex. | Ligand L | Co-ligand CL | Ir complex Step 1: reaction temp./reaction time/suspension medium Step 2: extraction medium | Yield |
|---|---|---|---|---|
| Ir(L23)₂(CL1) | L23 | CL1 | 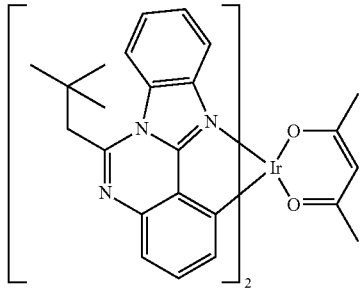 as Ex. Ir(L1)₂(CL1) | 56% |
| Ir(L41)₂(CL2) | L41 | 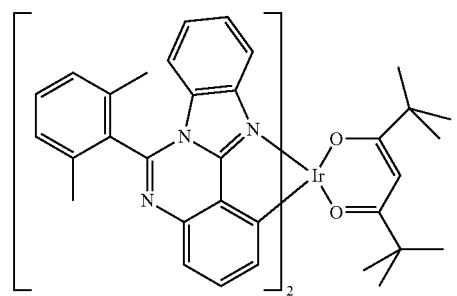 1118-71-4 CL2 | as Ex. Ir(L1)₂(CL1) | 64% |
| Ir(L91)₂(CL2) | L91 | CL2 | 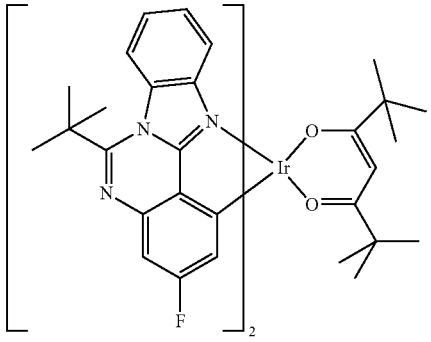 as Ex. Ir(L1)₂(CL1) | 60% |
| Ir(L91)₂(CL3) | L91 | 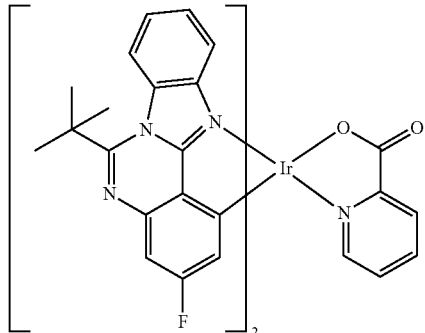 98-98-6 CL3 | as Ex. Ir(L1)₂(CL1) | 58% |

-continued
| Ex. | Li-gand L | Co-ligand CL | Ir complex<br>Step 1: reaction temp./reaction time/suspension medium<br>Step 2: extraction medium | Yield |
|---|---|---|---|---|
| Ir(L91)₂(CL4) | L91 | 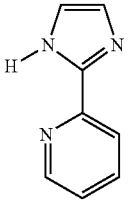<br>18653-75-3<br>CL4 | 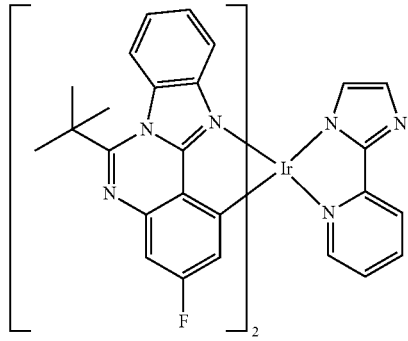<br>as Ex. Ir(L1)₂(CL1) | 47% |
| Ir(L91)₂(CL5) | L91 | 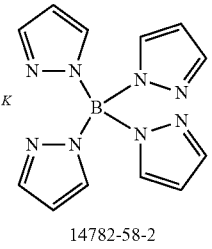<br>14782-58-2<br>CL5 | 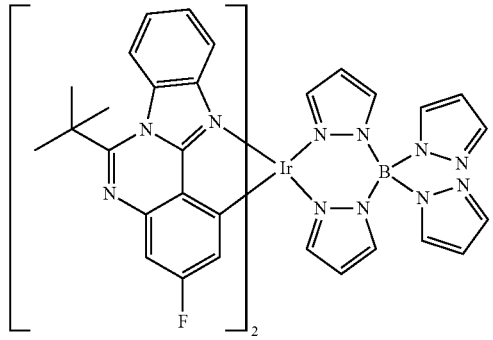<br>as Ex. Ir(L1)₂(CL1) | 50% |
| Ir(L92)₂(CL6) | L92 | 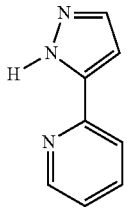<br>75415-03-1<br>CL6 | 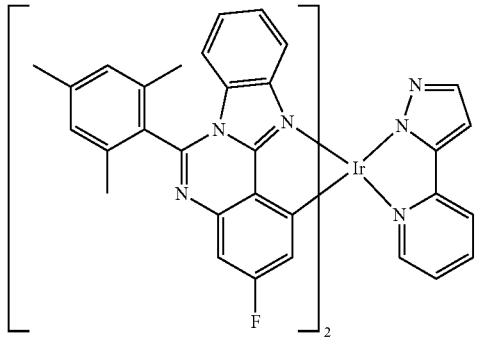<br>as Ex. Ir(L1)₂(CL1) | 56% |

-continued
| Ex. | Ligand L | Co-ligand CL | Ir complex<br>Step 1: reaction temp./reaction time/suspension medium<br>Step 2: extraction medium | Yield |
|---|---|---|---|---|
| Ir(L111)₂(CL3) | L111 | CL3 | 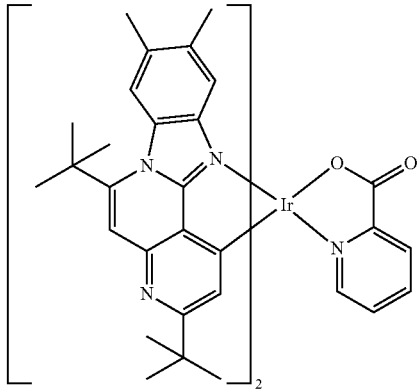<br>275° C./70 h/DCM THF | 35% |
| Ir(L120)₂(CL3) | L120 | CL3 | 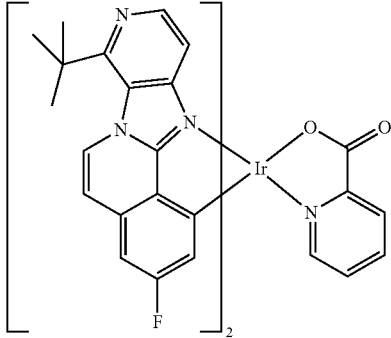<br>270° C./70 h/Toluene THF | 52% |
| Ir(L141)₂(CL1) | L141 | CL1 | 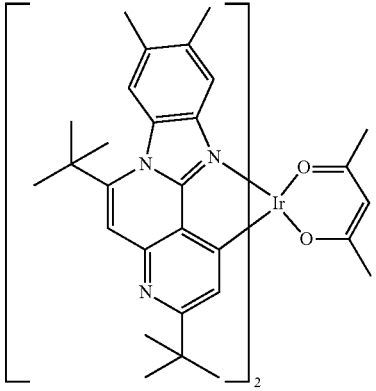<br>300° C./80 h/DCM THF | 23% |

-continued

| Ex. | Ligand L | Co-ligand CL | Ir complex Step 1: reaction temp./reaction time/suspension medium Step 2: extraction medium | Yield |
|---|---|---|---|---|
| Ir(L13)₂(CL17) | L13 | (structure) 219508-27-7 CL17 | (structure) as Ex. Ir(L1)₂(CL1) | 55% |

Variant B

Step 1

See variant A, step 1.

Step 2

The crude chloro dimer of the formula $[Ir(L)_2Cl]_2$ is reacted further in accordance with WO 2007/065523, Example 5, in the presence of 80 mmol of co-ligand CL and 75 mmol of N,N-dimethylglycine in 1000 ml of a dioxane/water mixture (1:1, vv). The solid obtained in this way is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 300 to about 390° C. in a high vacuum (p about $10^{-6}$ mbar), where the sublimation is preferably carried out in the form of a fractional sublimation.

| Ex. | Ligand L | Co-ligand CL | Ir complex Step 1: reaction temp./reaction time/suspension medium Step 2: extraction medium | Yield |
|---|---|---|---|---|
| Ir(L1)₂(CL7) | L1 | (structure) 391604-55-0 CL7 | (structure) 260° C./60 h/DCM THF | 61% |

-continued

| Ex. | Ligand L | Co-ligand CL | Ir complex<br>Step 1: reaction temp./reaction time/suspension medium<br>Step 2: extraction medium | Yield |
|---|---|---|---|---|
| Ir(L13)₂(CL7) | L13 | CL7 | as Ex. Ir(L1)₂(CL7) | 55% |
| Ir(L23)₂(CL7) | L23 | CL7 | as Ex. Ir(L1)₂(CL7) | 43% |
| Ir(L91)₂(CL7) | L91 | CL7 | as Ex. Ir(L1)₂(CL7) | 48% |
| Ir(L91)₂(CL8) | L91 | 1093072-00-4<br>CL8 | as Ex. Ir(L1)₂(CL7) | 39% |

-continued

| Ex. | Ligand L | Co-ligand CL | Ir complex<br>Step 1: reaction temp./reaction time/suspension medium<br>Step 2: extraction medium | Yield |
|---|---|---|---|---|
| Ir(L91)₂(CL8) | L92 | CL8 | as Ex. Ir(L1)₂(CL7) | 42% |
| Ir(L111)₂(CL9) | L111 | 3475-07-8<br>CL9 | 280° C./50 h/DCM THF | 45% |
| Ir(L120)₂(CL7) | L120 | CL7 | 270° C./50 h/DCM THF | 37% |

-continued

| Ex. | Ligand L | Co-ligand CL | Ir complex<br>Step 1: reaction temp./reaction time/suspension medium<br>Step 2: extraction medium | Yield |
|---|---|---|---|---|
| Ir(L147)$_2$(CL9) | L147 | CL9 | 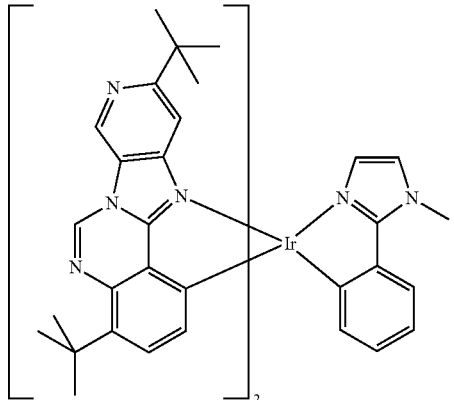<br>275° C./80 h/DCM THF | 29% |

Variant C

Step 1

See variant a, step 1.

Step 2

The crude chloro dimer of the formula [Ir(L)$_2$Cl]$_2$ obtained in this way is suspended in 100 ml of THF, 40 mmol of co-ligand CL, 20 mmol of silver(I) trifluoroacetate and 80 mmol of potassium carbonate are added to the suspension, and the mixture is heated under reflux for 24 h. After cooling, the THF is removed in vacuo. The residue is taken up in 200 ml of a mixture of ethanol and conc. ammonia solution (1:1, vv). The suspension is stirred at room temperature for 1 h, the solid is filtered off with suction, washed twice with 50 ml of a mixture of ethanol and conc. ammonia solution (1:1, vv) each time and twice with 50 ml of ethanol each time and then dried in vacuo. The solid obtained in this way is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 300 to about 390° C. in a high vacuum (p about $10^{-6}$ mbar), where the sublimation is preferably carried out in the form of a fractional sublimation.

| Ex. | Ligand L | Co-ligand CL | Ir complex<br>Step 1: reaction temp./reaction time/suspension medium<br>Step 2: extraction medium | Yield |
|---|---|---|---|---|
| Ir(L9)$_2$(CL7) | L9 | CL7 | 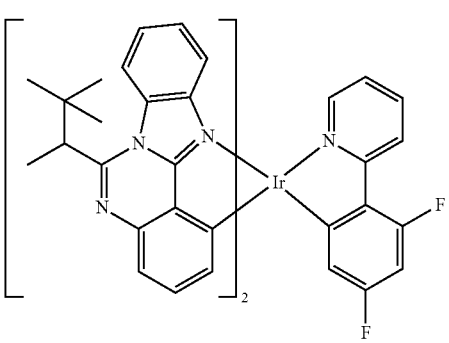<br>260° C./70 h/DCM THF | 40% |

-continued

| Ex. | Ligand L | Co-ligand CL | Ir complex Step 1: reaction temp./reaction time/suspension medium Step 2: extraction medium | Yield |
|---|---|---|---|---|
| Ir(L22)$_2$(CL7) | L22 | CL7 | as Ex. Ir(L9)$_2$(CL7) | 46% |
| Ir(L52)$_2$(CL10) | L52 | 4350-51-0 CL10 | as Ex. Ir(L9)$_2$(CL7) | |
| Ir(L91)$_2$(CL11) | L91 | 5957-90-4 CL11 | as Ex. Ir(L9)$_2$(CL7) | 47% |
| Ir(L91)$_2$(CL8) | L91 | CL8 | as Ex. Ir(L9)$_2$(CL7) | 45% |

-continued

| Ex. | Ligand L | Co-ligand CL | Ir complex Step 1: reaction temp./reaction time/suspension medium Step 2: extraction medium | Yield |
|---|---|---|---|---|
| Ir(L92)$_2$(CL12) | L92 | 7941-27-83 CL12 | as Ex. Ir(L9)$_2$(CL7) | 34% |
| Ir(L91)$_2$(CL11) | L91 | 5957-90-4 CL11 | as Ex. Ir(L9)$_2$(CL7) | 47% |
| Ir(L91)$_2$(CL8) | L91 | CL8 | as Ex. Ir(L9)$_2$(CL7) | 45% |

-continued

| Ex. | Ligand L | Co-ligand CL | Ir complex  Step 1: reaction temp./reaction time/suspension medium  Step 2: extraction medium | Yield |
|---|---|---|---|---|
| Ir(L92)₂(CL12) | L92 | 7941-27-83 CL12 | as Ex. Ir(L9)₂(CL7) | 34% |
| Ir(L111)₂(CL9) | L111 | CL9 | as Ex. Ir(L111)₂(CL9) | 36% |
| Ir(L120)₂(CL7) | L120 | CL7 | 270° C./40 h/DCM THF | 33% |

-continued

| Ex. | Ligand L | Co-ligand CL | Ir complex Step 1: reaction temp./reaction time/suspension medium Step 2: extraction medium | Yield |
|---|---|---|---|---|
| Ir(L124)$_2$(CL13) | L124 | 152536-39-5 CL13 | 270° C./75 h DCM/THF | 24% |

Variant D

Step 1

See variant a, step 1.

Step 2

The crude chloro dimer of the formula [Ir(L)$_2$Cl]$_2$ obtained in this way is suspended in 1000 ml of dichloromethane and 150 ml of ethanol, 40 mmol of silver(I) trifluoromethanesulfonate are added to the suspension, and the mixture is stirred at room temperature for 24 h. The precipitated solid (AgCl) is filtered off with suction via a short Celite bed, and the filtrate is evaporated to dryness in vacuo. The solid obtained in this way is taken up in 100 ml of ethanol, 30 mmol of co-ligand CL are added, and the mixture is then heated under reflux for 30 h. After cooling, the solid is filtered off with suction, washed twice with 50 ml of ethanol each time and dried in vacuo. The solid obtained in this way is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 300 to about 390° C. in a high vacuum (p about $10^{-6}$ mbar), where the sublimation is preferably carried out in the form of a fractional sublimation. In the case of ionic metal complexes, aluminium oxide is replaced by Celite in the hot-extraction step.

| Ex. | Ligand L | Co-ligand CL | Ir complex Step 1: reaction temp./reaction time/suspension medium Step 2: extraction medium | Yield |
|---|---|---|---|---|
| Ir(L91)$_2$(CL14) | L91 | 914306-48-2 CL14 | as Ex. Ir(L9)$_2$(CL7) | 56% |

-continued
| Ex. | Li-gand L | Co-ligand CL | Ir complex Step 1: reaction temp./reaction time/suspension medium Step 2: extraction medium | Yield |
|---|---|---|---|---|
| Ir(L91)₂(CL15) | L91 | 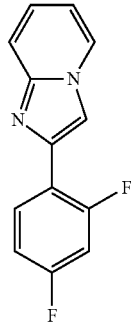<br>769093-92-7<br>CL15 | 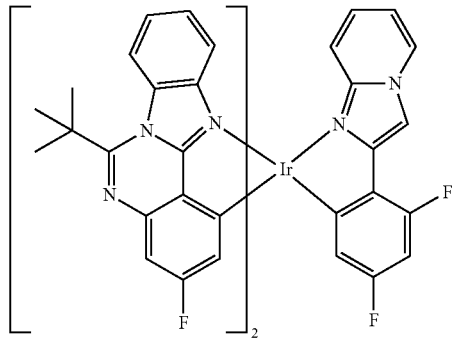<br>as Ex. Ir(L9)₂(CL7) | 38% |
| Ir(L111)₂(CL16) | L111 | 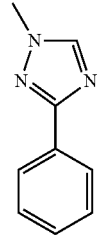<br>39696-58-7<br>CL16 | 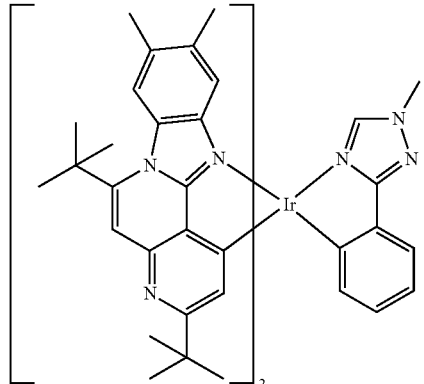<br>as Ex. Ir(L111)₂(CL9) | 44% |
| [Ir(L91)₂(CL18)]OTf | L91 | 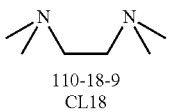<br>110-18-9<br>CL18 | 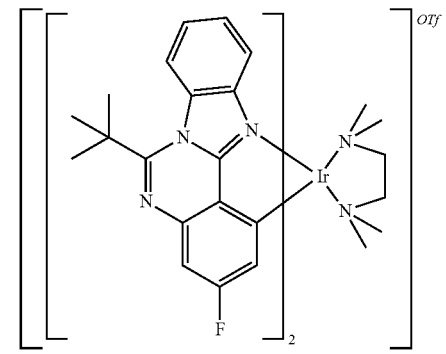<br>as Ex. Ir(L9)₂(CL7) | 27% |

-continued

| Ex. | Ligand L | Co-ligand CL | Ir complex Step 1: reaction temp./reaction time/suspension medium Step 2: extraction medium | Yield |
|---|---|---|---|---|
| [Ir(L91)₂(CL19)]OTf | L91 | <br>23936-60-9<br>CL19 | 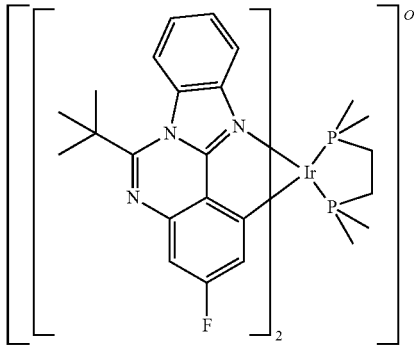<br>as Ex. Ir(L9)₂(CL7) | 49% |
| [Bu₄N][Ir(L91)₂(CL20)] | L91 | 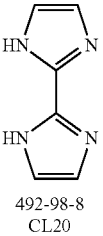<br>492-98-8<br>CL20 | 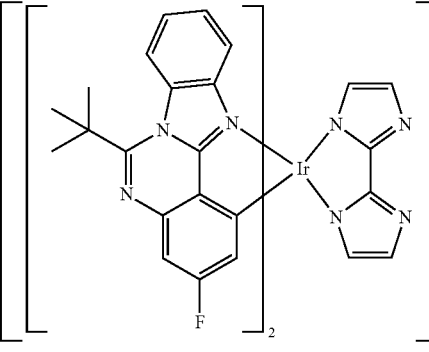<br>as Ex. Ir(L9)₂(CL7)<br>Addition of 30 mmol of Bu₄NCl and 30 mml NaCO₃ in step 2 | 23% |
| [Bu₄N][Ir(L91)₂(CL19)] | L91 | 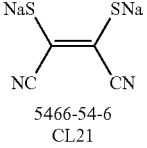<br>5466-54-6<br>CL21 | 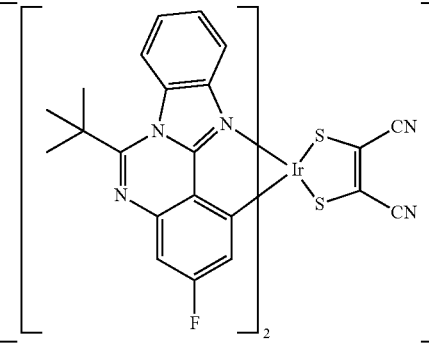<br>as Ex. Ir(L9)₂(CL7)<br>Addition of 30 mmol of Bu₄NCl in step 2 | 37% |

Variant E

A mixture of 10 mmol of the Ir complex Ir(L)₂(CL) and 30 mmol of ligand L is melted into a 50 ml glass ampoule in vacuo (10⁻⁵ mbar). The ampoule is heated at the temperature indicated for the time indicated, during which the molten mixture is stirred with the aid of a magnetic stirrer. After cooling (NOTE: the ampoules are usually under pressure!), the ampoule is opened, the sinter cake is stirred for 3 h with 100 g of glass beads (diameter 3 mm) in 100 ml of the suspension medium indicated and mechanically digested at the same time. The fine suspension is decanted off from the glass beads, the solid is filtered off with suction and dried in vacuo. The dry solid is placed on an aluminium oxide bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 340 to about 400° C. in a high vacuum (p about $10^{-6}$ mbar), where the sublimation is preferably carried out in the form of a fractional sublimation.

| Ex. | Ir complex Ir(L)$_2$(CL) | Ligand L | Ir complex Step 1: reaction temp./reaction time/suspension medium Step 2: extraction medium | Yield |
|---|---|---|---|---|
| Ir(L13)$_2$(L23) | Ir(L13)$_2$(CL1) | L23 | as Ex. Ir(L1)$_3$ | 35% |
| Ir(L23)$_2$(L13) | Ir(L23)$_2$(CL1) | L13 | as Ex. Ir(L1)$_3$ | 28% |
| Ir(L41)$_2$(L13) | Ir(L41)$_2$(CL2) | L13 | as Ex. Ir(L1)$_3$ | 34% |

-continued

| Ex. | Ir complex Ir(L)₂(CL) | Li-gand L | Ir complex Step 1: reaction temp./reaction time/suspension medium Step 2: extraction medium | Yield |
|---|---|---|---|---|
| Ir(L91)₂(L111) | Ir(L91)₂(CL2) | L111 | as Ex. Ir(L105)₃ | 26% |

Variant F

Step 1

A mixture of 10 mmol of iridium(III) chloride hydrate, 21 mmol of ligand L, 60 ml of 2-ethoyxethanol and 30 ml of water is heated under reflux for 160 h. After cooling, the solid is filtered off with suction, washed once with 20 ml of a mixture of ethanol and water (1:1, vv) and three times with 10 ml of ethanol each time and dried in vacuo.

Step 2

The crude chloro dimer of the formula [Ir(L)₂Cl]₂ obtained in this way can be employed as starting material in variant A, B, C and D step 2.

3) Heteroleptic Platinum Complexes

A mixture of 10 mmol of platinum(II) chloride, 12 mmol of ligand L, 1 mmol of tetra-n-butylammonium chloride in 30 ml of dichloromethane is heated under reflux for 12 h. After dropwise addition of 100 ml of methanol, the fine solid is filtered off with suction, washed twice with 25 ml of methanol and dried in vacuo. The crude chloro dimer of the formula [Pt(L)Cl]₂ obtained in this way is suspended in a mixture of 60 ml of 2-ethoxyethanol and 20 ml of water, and 12 mmol of co-ligand CL or co-ligand compound CL and 12 mmol of sodium carbonate are added. After 20 h under reflux, a further 100 ml of water are added dropwise, after cooling the solid is filtered off with suction, washed three times with 50 ml of water each time and three times with 50 ml of methanol each time and dried in vacuo. The solid obtained in this way is placed on a Celite bed (aluminium oxide, basic activity grade 1) with a depth of 10 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range 200-300° C. in a high vacuum (p about $10^{-6}$ mbar). The sublimation is carried out in the temperature range from about 300 to about 390° C. in a high vacuum (p about $10^{-6}$ mbar), where the sublimation is preferably carried out in the form of a fractional sublimation.

| Ex. | Li-gand L | Co-ligand CL | Pt complex | Yield |
|---|---|---|---|---|
| Pt(L13)(CL1) | L13 | CL1 | | 20% |

| Ex. | Ligand L | Co-ligand CL | Pt complex | Yield |
|---|---|---|---|---|
| Pt(L91)(CL17) | L91 | CL17 | 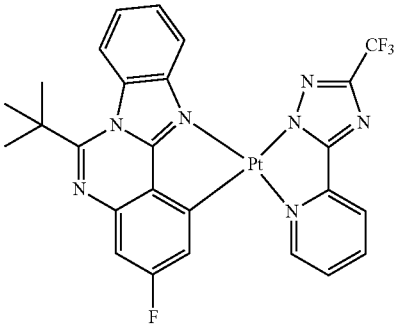 | 23% |

4) Platinum Complexes of Tetradentate Ligands

Variant A

A mixture of 10 mmol of potassium tetrachloroplatinate, 10 mmol of ligand L, 50 mmol of lithium acetate, anhydrous in 100 ml of glacial acetic acid, is heated under reflux for 60 h. After dropwise addition of 100 ml of methanol and 100 ml of water to the cooled reaction mixture, the solid is filtered off with suction, washed five times with 25 ml of methanol each time and dried in vacuo. The solid obtained in this way is placed on a Celite bed (aluminium oxide, basic activity grade 1) with a depth of 3 cm in a hot extractor and then extracted with the extraction medium indicated (initially introduced amount about 300 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC.

If the purity is below 99.5%, the hot-extraction step is repeated; if a purity of 99.5-99.9% has been reached, the Pt complex is sublimed. The sublimation is carried out in the temperature range from about 350 to about 390° C. in a high vacuum (p about $10^{-6}$ mbar), where the sublimation is preferably carried out in the form of a fractional sublimation.

Variant B

A mixture of 10 mmol of bis(benzonitrile)platinum(II) dichloride and 10 mmol of ligand L in 50 ml of benzonitrile is heated under reflux for 24 h. After dropwise addition of 100 ml of methanol to the cooled reaction mixture, the solid is filtered off with suction, washed five times with 25 ml of methanol each time and dried in vacuo. Remainder of the work-up as described in the case of variant A.

| Ex. | Ligand L | Pt complex | Variant Extraction medium | Yield |
|---|---|---|---|---|
| Pt(L211) | L211 | 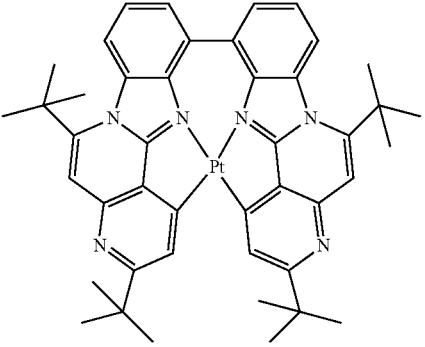<br>Pt(L211) | A p-Xylene | 43% |
| Pt(L212) | L212 | Pt(L212) | as Ex. Pt(L211) | 39% |
| Pt(L213) | L213 | Pt(L213) | A Toluene | 28% |
| Pt(L214) | L214 | Pt(L214) | as Ex. Pt(L211) | 33% |
| Pt(L215) | L215 | Pt(L215) | as Ex. Pt(L213) | 34% |

-continued

| Ex. | Ligand L | Pt complex | Variant Extraction medium | Yield |
|---|---|---|---|---|
| Pt(L216) | L216 | 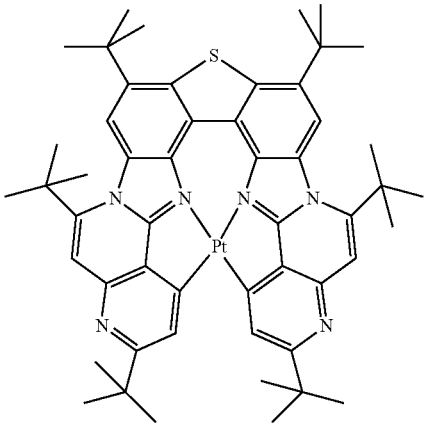Pt(L216) | B p-Xylene | 20% |
| Pt(L217) | L217 | Pt(L217) | as Ex. Pt(L216) | 31% |
| Pt(L219) | L219 | 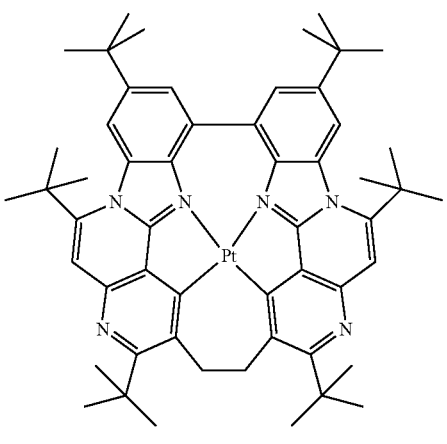Pt(L219) | as Ex. Pt(L216) | 18% |

Example

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in Examples 1 to 146 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL)/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M3:M2:Ir(L1)$_3$ (55%:35%:10%) here means that material M3 is present in the layer in a proportion by volume of 55%, M2 is present in the layer in a proportion of 35% and Ir(L1)$_3$ is present in the layer in a proportion of 10%. Analogously, the electron-transport layer may also consist of a mixture of two materials. The precise structure of the OLEDs is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LD50 means that the lifetime given is the time at which the luminous density has dropped to 50% of the initial luminous density, i.e. from, for example, 4000 cd/m$^2$ to 2000 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

Use of Compounds According to the Invention as Emitter Materials in Phosphorescent OLEDs The compounds according to the invention can be employed, inter alia, as phosphorescent emitter materials in the emission layer in OLEDs. The metal complexes with the central atoms Ir and Pt are used here. The compounds Ir(ref)$_3$ is used as comparison in accordance with the prior art. The results for the OLEDs are summarised in Table 2. In the case of the OLEDs, it is apparent here that the materials according to the invention result in efficient blue- and green-emitting OLEDs.

TABLE 1

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 1 | HIM 20 nm | HTM 5 nm | EBM2 15 nm | M2:M3:Ir(L1)$_3$ (80%:10%:10%) 40 nm | — | ETM1 30 nm | LiQ 2 nm |
| 2 | HIM 20 nm | HTM 5 nm | EBM2 15 nm | M2:M3:Ir(L2)$_3$ (80%:10%:10%) 40 nm | — | ETM1 30 nm | LiQ 2 nm |
| 3 | HIM 20 nm | HTM 5 nm | EBM2 15 nm | M2:M3:Ir(L3)$_3$ (80%:10%:10%) 40 nm | — | ETM1 30 nm | LiQ 2 nm |
| 4 | HIM 20 nm | HTM 5 nm | EBM2 15 nm | M2:M3:Ir(L6)$_3$ (80%:10%:10%) 40 nm | — | ETM1 30 nm | LiQ 2 nm |
| 5 | HIM 20 nm | HTM 5 nm | EBM2 15 nm | M2:M3:Ir(L7)$_3$ (80%:10%:10%) 40 nm | — | ETM1 30 nm | LiQ 2 nm |
| 6 | HIM 20 nm | HTM 5 nm | EBM1 15 nm | M2:M3:Ir(L9)$_3$ (80%:10%:10%) 40 nm | — | ETM1 30 nm | LiQ 2 nm |
| 7 | HIM 20 nm | HTM 5 nm | EBM2 15 nm | M2:M3:Ir(L10)$_3$ (80%:10%:10%) 40 nm | — | ETM1 30 nm | LiQ 2 nm |
| 8 | HIM 20 nm | HTM 5 nm | EBM2 15 nm | M2:M3:Ir(L13)$_3$ (80%:10%:10%) 40 nm | — | ETM1 30 nm | LiQ 2 nm |
| 9 | HIM 20 nm | HTM 5 nm | EBM2 15 nm | EBM2:M3:Ir(L13)$_3$ (60%:30%:10%) 40 nm | — | ETM1 30 nm | LiQ 2 nm |
| 10 | HIM 20 nm | HTM 5 nm | EBM2 15 nm | M1:Ir(L13)$_3$ (90%:10%) 40 nm | — | ETM1 30 nm | LiQ 2 nm |
| 11 | HIM 20 nm | HTM 5 nm | EBM2 15 nm | M2:M3:Ir(L13)$_3$ (85%:10%:5%) 40 nm | — | ETM1 30 nm | LiQ 2 nm |
| 12 | HIM 20 nm | HTM 5 nm | EBM2 15 nm | M4:M3:Ir(L14)$_3$ (80%:10%:10%) 40 nm | — | ETM1 30 nm | LiQ 2 nm |
| 13 | HIM 20 nm | HTM 5 nm | EBM2 15 nm | M4:M3:Ir(L15)$_3$ (80%:10%:10%) 40 nm | — | ETM1 30 nm | LiQ 2 nm |
| 14 | HIM 20 nm | HTM 5 nm | EBM2 15 nm | M4:M3:Ir(L18)$_3$ (80%:10%:10%) 40 nm | — | ETM1 30 nm | LiQ 2 nm |
| 15 | HIM 20 nm | HTM 5 nm | EBM2 15 nm | M4:M3:Ir(L21)$_3$ (80%:10%:10%) 40 nm | — | ETM1 30 nm | LiQ 2 nm |
| 16 | HIM 20 nm | HTM 5 nm | EBM1 15 nm | M2:M3:Ir(L22)$_3$ (80%:10%:10%) 40 nm | — | ETM1 30 nm | LiQ 2 nm |
| 17 | HIM 20 nm | HTM 5 nm | EBM2 15 nm | M2:M3:Ir(L23)$_3$ (80%:10%:10%) 40 nm | — | ETM1 30 nm | LiQ 2 nm |
| 18 | HIM 20 nm | HTM 5 nm | EBM2 15 nm | M2:M3:Ir(L23)$_3$ (85%:10%:5%) 40 nm | — | ETM1 30 nm | LiQ 2 nm |
| 19 | HIM 20 nm | HTM 5 nm | EBM2 15 nm | M2:M3:Ir(L24)$_3$ (85%:10%:5%) 40 nm | — | ETM1 30 nm | LiQ 2 nm |
| 20 | HIM 20 nm | HTM 5 nm | EBM2 15 nm | M2:M3:Ir(L25)$_3$ (85%:10%:5%) 40 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 21 | HIM 20 nm | HTM 5 nm | EBM2 15 nm | M2:M3:Ir(L26)$_3$ (85%:10%:5%) 40 nm | — | ETM1 30 nm | LiQ 2 nm |
| 22 | HIM 20 nm | HTM 5 nm | EBM2 15 nm | M2:M3:Ir(L27)$_3$ (85%:10%:5%) 40 nm | — | ETM1 30 nm | LiQ 2 nm |
| 23 | HIM 20 nm | HTM 5 nm | EBM2 15 nm | M2:M3:Ir(L28)$_3$ (85%:10%:5%) 40 nm | — | ETM1 30 nm | LiQ 2 nm |
| 24 | HIM 20 nm | HTM 5 nm | EBM1 15 nm | M4:M3:Ir(L31)$_3$ (85%:10%:5%) 40 nm | — | ETM1 30 nm | LiQ 2 nm |
| 25 | HIM 20 nm | HTM 5 nm | EBM2 15 nm | M3:Ir(L35)$_3$ (90%:10%) 40 nm | — | ETM1 30 nm | LiQ 2 nm |
| 26 | HIM 20 nm | HTM 5 nm | EBM2 15 nm | M3:Ir(L36)$_3$ (90%:10%) 40 nm | — | ETM1 30 nm | LiQ 2 nm |
| 27 | HIM 20 nm | HTM 5 nm | EBM2 15 nm | M3:Ir(L37)$_3$ (90%:10%) 40 nm | — | ETM1 30 nm | LiQ 2 nm |
| 28 | HIM 20 nm | HTM 5 nm | EBM1 15 nm | M4:M3:Ir(L39)$_3$ (85%:10%:5%) 40 nm | — | ETM1 30 nm | LiQ 2 nm |
| 29 | HIM 20 nm | HTM 5 nm | EBM1 15 nm | M4:M3:Ir(L40)$_3$ (85%:10%:5%) 40 nm | — | ETM1 30 nm | LiQ 2 nm |
| 30 | HIM 20 nm | HTM 5 nm | EBM1 15 nm | M4:M3:Ir(L41)$_3$ (85%:10%:5%) 40 nm | — | ETM1 30 nm | LiQ 2 nm |
| 31 | HIM 20 nm | HTM 5 nm | EBM1 15 nm | M4:M3:Ir(L42)$_3$ (85%:10%:5%) 40 nm | — | ETM1 30 nm | LiQ 2 nm |
| 32 | HIM 20 nm | HTM 5 nm | EBM1 15 nm | M4:M3:Ir(L43)$_3$ (85%:10%:5%) 40 nm | — | ETM1 30 nm | LiQ 2 nm |
| 33 | HIM 20 nm | HTM 5 nm | EBM1 15 nm | M4:M3:Ir(L44)$_3$ (85%:10%:5%) 40 nm | — | ETM1 30 nm | LiQ 2 nm |
| 34 | HIM 20 nm | HTM 5 nm | EBM2 15 nm | M2:M3:Ir(L59)$_3$ (85%:10%:5%) 40 nm | — | ETM1 30 nm | LiQ 2 nm |
| 35 | HIM 20 nm | HTM 5 nm | EBM2 15 nm | M2:M3:Ir(L60)$_3$ (85%:10%:5%) 40 nm | — | ETM1 30 nm | LiQ 2 nm |
| 36 | HIM 20 nm | HTM 5 nm | EBM2 15 nm | M2:M3:Ir(L61)$_3$ (85%:10%:5%) 40 nm | — | ETM1 30 nm | LiQ 2 nm |
| 37 | HIM 20 nm | HTM 5 nm | EBM2 15 nm | M2:M3:Ir(L62)$_3$ (85%:10%:5%) 40 nm | — | ETM1 30 nm | LiQ 2 nm |
| 38 | HIM 20 nm | HTM 5 nm | EBM2 15 nm | M2:M3:Ir(L63)$_3$ (85%:10%:5%) 40 nm | — | ETM1 30 nm | LiQ 2 nm |
| 39 | HIM 20 nm | HTM 5 nm | EBM2 15 nm | M2:M3:Ir(L64)$_3$ (85%:10%:5%) 40 nm | — | ETM1 30 nm | LiQ 2 nm |
| 40 | HIM 20 nm | HTM 5 nm | EBM2 15 nm | M2:M3:Ir(L67)$_3$ (85%:10%:5%) 40 nm | — | ETM1 30 nm | LiQ 2 nm |
| 41 | HIM 20 nm | HTM 5 nm | EBM2 15 nm | M2:M3:Ir(L68)$_3$ (85%:10%:5%) 40 nm | — | ETM1 30 nm | LiQ 2 nm |
| 42 | HIM 20 nm | HTM 5 nm | EBM2 15 nm | M2:M3:Ir(L69)$_3$ (85%:10%:5%) 40 nm | — | ETM1 30 nm | LiQ 2 nm |
| 43 | HIM 20 nm | HTM 5 nm | EBM2 15 nm | M2:M3:Ir(L71)$_3$ (85%:10%:5%) 40 nm | — | ETM1 30 nm | LiQ 2 nm |
| 44 | HIM 20 nm | HTM 5 nm | EBM2 15 nm | M2:M3:Ir(L73)$_3$ (85%:10%:5%) 40 nm | — | ETM1 30 nm | LiQ 2 nm |
| 45 | HIM 20 nm | HTM 5 nm | EBM2 15 nm | M2:M3:Ir(L74)$_3$ (85%:10%:5%) 40 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 46 | HIM 20 nm | HTM 5 nm | EBM2 15 nm | M2:M3:Ir(L75)$_3$ (85%:10%:5%) 40 nm | — | ETM1 30 nm | LiQ 2 nm |
| 47 | HIM 20 nm | HTM 5 nm | EBM2 15 nm | M2:M3:Ir(L78)$_3$ (85%:10%:5%) 40 nm | — | ETM1 30 nm | LiQ 2 nm |
| 48 | HIM 20 nm | HTM 5 nm | EBM2 15 nm | M2:M3:Ir(L79)$_3$ (85%:10%:5%) 40 nm | — | ETM1 30 nm | LiQ 2 nm |
| 49 | HIM 20 nm | HTM 5 nm | EBM2 15 nm | M2:M3:Ir(L80)$_3$ (85%:10%:5%) 40 nm | — | ETM1 30 nm | LiQ 2 nm |
| 50 | HIM 20 nm | HTM 5 nm | EBM2 15 nm | M2:M3:Ir(L81)$_3$ (85%:10%:5%) 40 nm | — | ETM1 30 nm | LiQ 2 nm |
| 51 | HIM 20 nm | HTM 5 nm | EBM2 15 nm | M2:M3:Ir(L82)$_3$ (85%:10%:5%) 40 nm | — | ETM1 30 nm | LiQ 2 nm |
| 52 | HIM 20 nm | HTM 5 nm | EBM2 15 nm | M2:M3:Ir(L83)$_3$ (85%:10%:5%) 40 nm | — | ETM1 30 nm | LiQ 2 nm |
| 53 | HIM 20 nm | HTM 5 nm | EBM2 15 nm | M2:M3:Ir(L85)$_3$ (85%:10%:5%) 40 nm | — | ETM1 30 nm | LiQ 2 nm |
| 54 | HIM 20 nm | HTM 5 nm | EBM2 15 nm | M2:M3:Ir(L86)$_3$ (85%:10%:5%) 40 nm | — | ETM1 30 nm | LiQ 2 nm |
| 55 | HIM 20 nm | HTM 5 nm | EBM2 15 nm | M4:M3:Ir(L87)$_3$ (85%:10%:5%) 40 nm | — | ETM1 30 nm | LiQ 2 nm |
| 56 | HIM 20 nm | HTM 5 nm | EBM2 15 nm | M4:M3:Ir(L88)$_3$ (85%:10%:5%) 40 nm | — | ETM1 30 nm | LiQ 2 nm |
| 57 | HIM 20 nm | HTM 5 nm | EBM2 15 nm | M4:M3:Ir(L91)$_3$ (85%:10%:5%) 40 nm | — | ETM1 30 nm | LiQ 2 nm |
| 58 | HIM 20 nm | HTM 5 nm | EBM2 15 nm | M4:M3:Ir(L92)$_3$ (85%:10%:5%) 40 nm | — | ETM1 30 nm | LiQ 2 nm |
| 59 | HIM 20 nm | HTM 5 nm | EBM2 15 nm | M4:M3:Ir(L93)$_3$ (85%:10%:5%) 40 nm | — | ETM1 30 nm | LiQ 2 nm |
| 60 | HIM 20 nm | HTM 5 nm | EBM2 15 nm | M4:M3:Ir(L95)$_3$ (85%:10%:5%) 40 nm | — | ETM1 30 nm | LiQ 2 nm |
| 61 | HIM 20 nm | HTM 5 nm | EBM2 15 nm | M4:M3:Ir(L96)$_3$ (85%:10%:5%) 40 nm | — | ETM1 30 nm | LiQ 2 nm |
| 62 | HIM 20 nm | HTM 5 nm | EBM2 15 nm | M4:M3:Ir(L97)$_3$ (85%:10%:5%) 40 nm | — | ETM1 30 nm | LiQ 2 nm |
| 63 | HIM 20 nm | HTM 5 nm | EBM2 15 nm | M4:M3:Ir(L100)$_3$ (85%:10%:5%) 40 nm | — | ETM1 30 nm | LiQ 2 nm |
| 64 | HIM 20 nm | HTM 5 nm | EBM2 15 nm | M4:M3:Ir(L101)$_3$ (85%:10%:5%) 40 nm | — | ETM1 30 nm | LiQ 2 nm |
| 65 | HIM 20 nm | HTM 5 nm | EBM2 15 nm | M4:M3:Ir(L103)$_3$ (85%:10%:5%) 40 nm | — | ETM1 30 nm | LiQ 2 nm |
| 66 | HIM 20 nm | HTM 5 nm | EBM2 15 nm | M4:M3:Ir(L104)$_3$ (85%:10%:5%) 40 nm | — | ETM1 30 nm | LiQ 2 nm |
| 67 | HIM 20 nm | HTM 5 nm | EBM2 15 nm | M4:M3:Ir(L105)$_3$ (85%:10%:5%) 40 nm | — | ETM1 30 nm | LiQ 2 nm |
| 68 | HIM 20 nm | HTM 5 nm | EBM2 15 nm | M4:M3:Ir(L106)$_3$ (85%:10%:5%) 40 nm | — | ETM1 30 nm | LiQ 2 nm |
| 69 | HIM 20 nm | HTM 5 nm | EBM2 15 nm | M4:M3:Ir(L107)$_3$ (85%:10%:5%) 40 nm | — | ETM1 30 nm | LiQ 2 nm |
| 70 | HIM 20 nm | HTM 5 nm | EBM2 15 nm | M4:M3:Ir(L108)$_3$ (85%:10%:5%) 40 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 71 | HIM 20 nm | HTM 5 nm | EBM2 15 nm | M4:M3:Ir(L109)$_3$ (85%:10%:5%) 40 nm | — | ETM1 30 nm | LiQ 2 nm |
| 72 | HIM 20 nm | HTM 5 nm | EBM2 15 nm | M4:M3:Ir(L110)$_3$ (85%:10%:5%) 40 nm | — | ETM1 30 nm | LiQ 2 nm |
| 73 | HIM 20 nm | HTM 5 nm | EBM2 15 nm | M4:M3:Ir(L111)$_3$ (85%:10%:5%) 40 nm | — | ETM1 30 nm | LiQ 2 nm |
| 74 | HIM 20 nm | HTM 5 nm | EBM2 15 nm | M4:M3:Ir(L112)$_3$ (85%:10%:5%) 40 nm | — | ETM1 30 nm | LiQ 2 nm |
| 75 | HIM 20 nm | HTM 5 nm | EBM2 15 nm | M4:M3:Ir(L115)$_3$ (85%:10%:5%) 40 nm | — | ETM1 30 nm | LiQ 2 nm |
| 76 | HIM 20 nm | HTM 5 nm | EBM2 15 nm | M4:M3:Ir(L116)$_3$ (85%:10%:5%) 40 nm | — | ETM1 30 nm | LiQ 2 nm |
| 77 | HIM 20 nm | HTM 5 nm | EBM2 15 nm | M4:M3:Ir(L117)$_3$ (85%:10%:5%) 40 nm | — | ETM1 30 nm | LiQ 2 nm |
| 78 | HIM 20 nm | HTM 5 nm | EBM2 15 nm | M4:M3:Ir(L118)$_3$ (85%:10%:5%) 40 nm | — | ETM1 30 nm | LiQ 2 nm |
| 79 | HIM 20 nm | HTM 5 nm | EBM2 15 nm | M4:M3:Ir(L119)$_3$ (85%:10%:5%) 40 nm | — | ETM1 30 nm | LiQ 2 nm |
| 80 | HIM 20 nm | HTM 5 nm | EBM2 15 nm | M4:M3:Ir(L120)$_3$ (85%:10%:5%) 40 nm | — | ETM1 30 nm | LiQ 2 nm |
| 81 | HIM 20 nm | HTM 5 nm | EBM2 15 nm | M4:M3:Ir(L121)$_3$ (85%:10%:5%) 40 nm | — | ETM1 30 nm | LiQ 2 nm |
| 82 | HIM 20 nm | HTM 5 nm | EBM2 15 nm | M4:M3:Ir(L122)$_3$ (85%:10%:5%) 40 nm | — | ETM1 30 nm | LiQ 2 nm |
| 83 | HIM 20 nm | HTM 5 nm | EBM2 15 nm | M4:M3:Ir(L123)$_3$ (85%:10%:5%) 40 nm | — | ETM1 30 nm | LiQ 2 nm |
| 84 | HIM 20 nm | HTM 5 nm | EBM2 15 nm | M4:M3:Ir(L124)$_3$ (85%:10%:5%) 40 nm | — | ETM1 30 nm | LiQ 2 nm |
| 85 | HIM 20 nm | HTM 20 nm | EBM2 15 nm | M4:M3:Ir(L125)$_3$ (85%:10%:5%) 40 nm | — | ETM1 30 nm | LiQ 2 nm |
| 86 | HIM 20 nm | HTM 20 nm | EBM2 15 nm | M4:M3:Ir(L126)$_3$ (85%:10%:5%) 40 nm | — | ETM1 30 nm | LiQ 2 nm |
| 87 | HIM 20 nm | HTM 5 nm | EBM2 15 nm | M4:M3:Ir(L128)$_3$ (85%:10%:5%) 40 nm | — | ETM1 30 nm | LiQ 2 nm |
| 88 | HIM 20 nm | HTM 5 nm | EBM2 15 nm | M4:M3:Ir(L129)$_3$ (85%:10%:5%) 40 nm | — | ETM1 30 nm | LiQ 2 nm |
| 89 | HIM 20 nm | HTM 5 nm | EBM2 15 nm | M4:M3:Ir(L131)$_3$ (85%:10%:5%) 40 nm | — | ETM1 30 nm | LiQ 2 nm |
| 90 | HIM 20 nm | HTM 5 nm | EBM2 15 nm | M4:M3:Ir(L132)$_3$ (85%:10%:5%) 40 nm | — | ETM1 30 nm | LiQ 2 nm |
| 91 | HIM 20 nm | HTM 5 nm | EBM2 15 nm | M4:M3:Ir(L134)$_3$ (85%:10%:5%) 40 nm | — | ETM1 30 nm | LiQ 2 nm |
| 92 | HIM 20 nm | HTM 5 nm | EBM2 15 nm | M4:M3:Ir(L135)$_3$ (85%:10%:5%) 40 nm | — | ETM1 30 nm | LiQ 2 nm |
| 93 | HIM 20 nm | HTM 5 nm | EBM2 15 nm | M4:M3:Ir(L137)$_3$ (85%:10%:5%) 40 nm | — | ETM1 30 nm | LiQ 2 nm |
| 94 | HIM 20 nm | HTM 5 nm | EBM2 15 nm | M4:M3:Ir(L138)$_3$ (85%:10%:5%) 40 nm | — | ETM1 30 nm | LiQ 2 nm |
| 95 | HIM 20 nm | HTM 5 nm | EBM2 15 nm | M4:M3:Ir(L139)$_3$ (85%:10%:5%) 40 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 96 | HIM 20 nm | HTM 5 nm | EBM2 15 nm | M4:M3:Ir(L140)$_3$ (85%:10%:5%) 40 nm | — | ETM1 30 nm | LiQ 2 nm |
| 97 | HIM 20 nm | HTM 5 nm | EBM2 15 nm | M4:M3:Ir(L141)$_3$ (85%:10%:5%) 40 nm | — | ETM1 30 nm | LiQ 2 nm |
| 98 | HIM 20 nm | HTM 5 nm | EBM2 15 nm | M4:M3:Ir(L142)$_3$ (85%:10%:5%) 40 nm | — | ETM1 30 nm | LiQ 2 nm |
| 99 | HIM 20 nm | HTM 5 nm | EBM2 15 nm | M4:M3:Ir(L143)$_3$ (85%:10%:5%) 40 nm | — | ETM1 30 nm | LiQ 2 nm |
| 100 | HIM 20 nm | HTM 5 nm | EBM2 15 nm | M4:M3:Ir(L144)$_3$ (85%:10%:5%) 40 nm | — | ETM1 30 nm | LiQ 2 nm |
| 101 | HIM 20 nm | HTM 5 nm | EBM2 15 nm | M4:M3:Ir(L146)$_3$ (85%:10%:5%) 40 nm | — | ETM1 30 nm | LiQ 2 nm |
| 102 | HIM 20 nm | HTM 5 nm | EBM2 15 nm | M4:M3:Ir(L147)$_3$ (85%:10%:5%) 40 nm | — | ETM1 30 nm | LiQ 2 nm |
| 103 | HIM 20 nm | HTM 5 nm | EBM2 15 nm | M4:M3:Ir(L148)$_3$ (85%:10%:5%) 40 nm | — | ETM1 30 nm | LiQ 2 nm |
| 104 | HIM 20 nm | HTM 5 nm | EBM2 15 nm | M4:M3:Ir(L149)$_3$ (85%:10%:5%) 40 nm | — | ETM1 30 nm | LiQ 2 nm |
| 105 | HIM 20 nm | HTM 5 nm | EBM2 15 nm | M4:M3:Ir(L150)$_3$ (85%:10%:5%) 40 nm | — | ETM1 30 nm | LiQ 2 nm |
| 106 | HIM 20 nm | HTM 5 nm | EBM2 15 nm | M4:M3:Ir(L152)$_3$ (85%:10%:5%) 40 nm | — | ETM1 30 nm | LiQ 2 nm |
| 107 | HIM 20 nm | HTM 5 nm | EBM2 15 nm | M4:M3:Ir(L153)$_3$ (85%:10%:5%) 40 nm | — | ETM1 30 nm | LiQ 2 nm |
| 108 | HIM 20 nm | HTM 5 nm | EBM2 15 nm | M4:M3:Ir(L154)$_3$ (85%:10%:5%) 40 nm | — | ETM1 30 nm | LiQ 2 nm |
| 109 | HIM 20 nm | HTM 5 nm | EBM2 15 nm | M4:M3:Ir(L155)$_3$ (85%:10%:5%) 40 nm | — | ETM1 30 nm | LiQ 2 nm |
| 110 | HIM 20 nm | HTM 5 nm | EBM2 15 nm | M4:M3:Ir(L156)$_3$ (85%:10%:5%) 40 nm | — | ETM1 30 nm | LiQ 2 nm |
| 111 | HIM 20 nm | HTM 5 nm | EBM1 15 nm | M2:M3:Ir(L1)$_2$(CL1) (88%:12%) 30 nm | — | ETM1 30 nm | LiQ 2 nm |
| 112 | HIM 20 nm | HTM 5 nm | EBM1 15 nm | M2:M3:Ir(L13)$_2$(CL1) (88%:12%) 30 nm | — | ETM1 30 nm | LiQ 2 nm |
| 113 | HIM 20 nm | HTM 5 nm | EBM1 15 nm | M2:M3:Ir(L23)$_2$(CL1) (88%:12%) 30 nm | — | ETM1 30 nm | LiQ 2 nm |
| 114 | HIM 20 nm | HTM 5 nm | EBM1 15 nm | M2:M3:Ir(L41)$_2$(CL2) (88%:12%) 30 nm | — | ETM1 30 nm | LiQ 2 nm |
| 115 | HIM 20 nm | HTM 5 nm | EBM1 15 nm | M2:M3:Ir(L91)$_2$(CL2) (88%:12%) 30 nm | — | ETM1 30 nm | LiQ 2 nm |
| 116 | HIM 20 nm | HTM 5 nm | EBM2 15 nm | M4:M3:Ir(L91)$_2$(CL3) (85%:10%:5%) 40 nm | — | ETM1 30 nm | LiQ 2 nm |
| 117 | HIM 20 nm | HTM 5 nm | EBM2 15 nm | M4:M3:Ir(L91)$_2$(CL4) (85%:10%:5%) 40 nm | — | ETM1 30 nm | LiQ 2 nm |
| 118 | HIM 20 nm | HTM 5 nm | EBM2 15 nm | M4:M3:Ir(L91)$_2$(CL5) (85%:10%:5%) 40 nm | — | ETM1 30 nm | LiQ 2 nm |
| 119 | HIM 20 nm | HTM 5 nm | EBM2 15 nm | M4:M3:Ir(L92)$_2$(CL6) (85%:10%:5%) 40 nm | — | ETM1 30 nm | LiQ 2 nm |
| 120 | HIM 20 nm | HTM 5 nm | EBM2 15 nm | M4:M3:Ir(L111)$_2$(CL3) (85%:10%:5%) 40 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 121 | HIM 20 nm | HTM 5 nm | EBM2 15 nm | M4:M3:Ir(L120)$_2$(CL3) (85%:10%:5%) 40 nm | — | ETM1 30 nm | LiQ 2 nm |
| 122 | HIM 20 nm | HTM 5 nm | EBM1 15 nm | M4:M3:Ir(L141)$_2$(CL1) (88%:12%) 30 nm | — | ETM1 30 nm | LiQ 2 nm |
| 123 | HIM 20 nm | HTM 5 nm | EBM2 15 nm | M4:M3:Ir(L13)$_2$(CL17) (85%:10%:5%) 40 nm | — | ETM1 30 nm | LiQ 2 nm |
| 124 | HIM 20 nm | HTM 5 nm | EBM2 15 nm | M4:M3:Ir(L1)$_2$(CL7) (85%:10%:5%) 40 nm | — | ETM1 30 nm | LiQ 2 nm |
| 125 | HIM 20 nm | HTM 5 nm | EBM2 15 nm | M4:M3:Ir(L13)$_2$(CL7) (85%:10%:5%) 40 nm | — | ETM1 30 nm | LiQ 2 nm |
| 126 | HIM 20 nm | HTM 5 nm | EBM2 15 nm | M4:M3:Ir(L23)$_2$(CL7) (85%:10%:5%) 40 nm | — | ETM1 30 nm | LiQ 2 nm |
| 127 | HIM 20 nm | HTM 5 nm | EBM2 15 nm | M4:M3:Ir(L91)$_2$(CL7) (85%:10%:5%) 40 nm | — | ETM1 30 nm | LiQ 2 nm |
| 128 | HIM 20 nm | HTM 5 nm | EBM2 15 nm | M4:M3:Ir(L91)$_2$(CL8) (85%:10%:5%) 40 nm | — | ETM1 30 nm | LiQ 2 nm |
| 129 | HIM 20 nm | HTM 5 nm | EBM2 15 nm | M4:M3:Ir(L92)$_2$(CL8) (85%:10%:5%) 40 nm | — | ETM1 30 nm | LiQ 2 nm |
| 130 | HIM 20 nm | HTM 5 nm | EBM2 15 nm | M4:M3:Ir(L111)$_2$(CL9) (85%:10%:5%) 40 nm | — | ETM1 30 nm | LiQ 2 nm |
| 131 | HIM 20 nm | HTM 5 nm | EBM2 15 nm | M4:M3:Ir(L120)$_2$(CL7) (85%:10%:5%) 40 nm | — | ETM1 30 nm | LiQ 2 nm |
| 132 | HIM 20 nm | HTM 5 nm | EBM2 15 nm | M4:M3:Ir(L147)$_2$(CL9) (85%:10%:5%) 40 nm | — | ETM1 30 nm | LiQ 2 nm |
| 133 | HIM 20 nm | HTM 5 nm | EBM2 15 nm | M4:M3:Ir(L9)$_2$(CL7) (85%:10%:5%) 40 nm | — | ETM1 30 nm | LiQ 2 nm |
| 134 | HIM 20 nm | HTM 5 nm | EBM2 15 nm | M4:M3:Ir(L22)$_2$(CL7) (85%:10%:5%) 40 nm | — | ETM1 30 nm | LiQ 2 nm |
| 135 | HIM 20 nm | HTM 5 nm | EBM2 15 nm | M4:M3:Ir(L91)$_2$(CL11) (85%:10%:5%) 40 nm | — | ETM1 30 nm | LiQ 2 nm |
| 136 | HIM 20 nm | HTM 5 nm | EBM2 15 nm | M4:M3:Ir(L92)$_2$(CL12) (85%:10%:5%) 40 nm | — | ETM1 30 nm | LiQ 2 nm |
| 137 | HIM 20 nm | HTM 5 nm | EBM2 15 nm | M4:M3:Ir(L124)$_2$(CL13) (85%:10%:5%) 40 nm | — | ETM1 30 nm | LiQ 2 nm |
| 138 | HIM 20 nm | HTM 5 nm | EBM2 15 nm | M4:M3:Ir(L91)$_2$(CL14) (85%:10%:5%) 40 nm | — | ETM1 30 nm | LiQ 2 nm |
| 139 | HIM 20 nm | HTM 5 nm | EBM2 15 nm | M4:M3:Ir(L91)$_2$(CL15) (85%:10%:5%) 40 nm | — | ETM1 30 nm | LiQ 2 nm |
| 140 | HIM 20 nm | HTM 5 nm | EBM2 15 nm | M4:M3:Ir(L111)$_2$(CL16) (85%:10%:5%) 40 nm | — | ETM1 30 nm | LiQ 2 nm |
| 141 | HIM 20 nm | HTM 5 nm | EBM2 15 nm | M4:M3:Ir(L13)$_2$(L23) (85%:10%:5%) 40 nm | — | ETM1 30 nm | LiQ 2 nm |
| 142 | HIM 20 nm | HTM 5 nm | EBM2 15 nm | M4:M3:Ir(L23)$_2$(L13) (85%:10%:5%) 40 nm | — | ETM1 30 nm | LiQ 2 nm |
| 143 | HIM 20 nm | HTM 5 nm | EBM2 15 nm | M4:M3:Ir(L41)$_2$(L13) (85%:10%:5%) 40 nm | — | ETM1 30 nm | LiQ 2 nm |
| 144 | HIM 20 nm | HTM 5 nm | EBM2 15 nm | M4:M3:Ir(L91)$_2$(L111) (85%:10%:5%) 40 nm | — | ETM1 30 nm | LiQ 2 nm |
| 145 | HIM 20 nm | HTM 5 nm | EBM2 15 nm | M4:M3:Pt(L13)$_2$(CL1) (88%:12%) 30 nm | — | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 146 | HIM 20 nm | HTM 5 nm | EBM2 15 nm | M4:M3:Pt(L91)$_2$(CL17) (85%:10%:5%) 30 nm | — | ETM1 30 nm | LiQ 2 nm |
| Vgl. | HIM 20 nm | HTM 5 nm | EBM2 15 nm | M2:Ir(ref) (85%:15%) 40 nm | M3 10 nm | Alq$_3$ 20 nm | LiF |
| 203 | HIM 20 nm | HTM 5 nm | EBM2 15 nm | M5:M2:Ir(L163)$_3$ (10%:85%:5%) 40 nm | M5 10 nm | ETM1 30 nm | LiQ 2 nm |
| 204 | HIM 20 nm | HTM 5 nm | EBM2 15 nm | M5:M2:Ir(L165)$_3$ (10%:85%:5%) 40 nm | M5 10 nm | ETM1 30 nm | LiQ 2 nm |
| 205 | HIM 20 nm | HTM 5 nm | EBM2 15 nm | M5:M2:Ir(L167)$_3$ (10%:85%:5%) 40 nm | M5 10 nm | ETM1 30 nm | LiQ 2 nm |
| 206 | HIM 20 nm | HTM 5 nm | EBM2 15 nm | M5:M2:Ir(L168)$_3$ (10%:85%:5%) 40 nm | M5 10 nm | ETM1 30 nm | LiQ 2 nm |
| 207 | HIM 20 nm | HTM 5 nm | EBM2 15 nm | M5:M2:Ir(L169)$_3$ (10%:85%:5%) 40 nm | M5 10 nm | ETM1 30 nm | LiQ 2 nm |
| 208 | HIM 20 nm | HTM 5 nm | EBM2 15 nm | M5:M2:Ir(L170)$_3$ (10%:85%:5%) 40 nm | M5 10 nm | ETM1 30 nm | LiQ 2 nm |
| 209 | HIM 20 nm | HTM 5 nm | EBM2 15 nm | M5:M2:Ir(L171)$_3$ (10%:85%:5%) 40 nm | M5 10 nm | ETM1 30 nm | LiQ 2 nm |
| 210 | HIM 20 nm | HTM 5 nm | EBM2 15 nm | M5:M2:Ir(L172)$_3$ (10%:85%:5%) 40 nm | M5 10 nm | ETM1 30 nm | LiQ 2 nm |
| 211 | HIM 20 nm | HTM 5 nm | EBM2 15 nm | M5:M2:Ir(L173)$_3$ (10%:85%:5%) 40 nm | M5 10 nm | ETM1 30 nm | LiQ 2 nm |
| 212 | HIM 20 nm | HTM 5 nm | EBM2 15 nm | M5:M2:Ir(L174)$_3$ (10%:85%:5%) 40 nm | M5 10 nm | ETM1 30 nm | LiQ 2 nm |
| 213 | HIM 20 nm | HTM 5 nm | EBM2 15 nm | M5:M2:Ir(L175)$_3$ (10%:85%:5%) 40 nm | M5 10 nm | ETM1 30 nm | LiQ 2 nm |
| 214 | HIM 20 nm | HTM 5 nm | EBM2 15 nm | M5:M2:Ir(L176)$_3$ (10%:85%:5%) 40 nm | M5 10 nm | ETM1 30 nm | LiQ 2 nm |
| 215 | HIM 20 nm | HTM 5 nm | EBM2 15 nm | M5:M2:Ir(L177)$_3$ (10%:85%:5%) 40 nm | M5 10 nm | ETM1 30 nm | LiQ 2 nm |
| 216 | HIM 20 nm | HTM 5 nm | EBM2 15 nm | M5:M2:Ir(L178)$_3$ (10%:85%:5%) 40 nm | M5 10 nm | ETM1 30 nm | LiQ 2 nm |
| 217 | HIM 20 nm | HTM 5 nm | EBM2 15 nm | M5:M2:Ir(L179)$_3$ (10%:85%:5%) 40 nm | M5 10 nm | ETM1 30 nm | LiQ 2 nm |
| 218 | HIM 20 nm | HTM 5 nm | EBM2 15 nm | M5:M2:Ir(L181)$_3$ (10%:85%:5%) 40 nm | M5 10 nm | ETM1 30 nm | LiQ 2 nm |
| 219 | HIM 20 nm | HTM 5 nm | EBM2 15 nm | M5:M2:Ir(L183)$_3$ (10%:85%:5%) 40 nm | M5 10 nm | ETM1 30 nm | LiQ 2 nm |
| 220 | HIM 20 nm | HTM 5 nm | EBM2 15 nm | M5:M2:Ir(L184)$_3$ (10%:85%:5%) 40 nm | M5 10 nm | ETM1 30 nm | LiQ 2 nm |
| 221 | HIM 20 nm | HTM 5 nm | EBM2 15 nm | M5:M2:Ir(L185)$_3$ (10%:85%:5%) 40 nm | M5 10 nm | ETM1 30 nm | LiQ 2 nm |
| 222 | HIM 20 nm | HTM 5 nm | EBM2 15 nm | M5:M2:Ir(L186)$_3$ (10%:85%:5%) 40 nm | M5 10 nm | ETM1 30 nm | LiQ 2 nm |
| 223 | HIM 20 nm | HTM 5 nm | EBM2 15 nm | M5:M2:Ir(L187)$_3$ (10%:85%:5%) 40 nm | M5 10 nm | ETM1 30 nm | LiQ 2 nm |
| 224 | HIM 20 nm | HTM 5 nm | EBM2 15 nm | M5:M2:Ir(L188)$_3$ (10%:85%:5%) 40 nm | M5 10 nm | ETM1 30 nm | LiQ 2 nm |
| 225 | HIM 20 nm | HTM 5 nm | EBM2 15 nm | M5:M2:Ir(L189)$_3$ (10%:85%:5%) 40 nm | M5 10 nm | ETM1 30 nm | LiQ 2 nm |

TABLE 1-continued

Structure of the OLEDs

| Ex. | HTL1 Thickness | HTL2 Thickness | EBL Thickness | EML Thickness | HBL Thickness | ETL Thickness | EIL Thickness |
|---|---|---|---|---|---|---|---|
| 226 | HIM 20 nm | HTM 5 nm | EBM2 15 nm | M5:M2:Ir(L190)₃ (10%:85%:5%) 40 nm | M5 10 nm | ETM1 30 nm | LiQ 2 nm |
| 227 | HIM 20 nm | HTM 5 nm | EBM2 15 nm | M5:M2:Ir(L191)₃ (10%:85%:5%) 40 nm | M5 10 nm | ETM1 30 nm | LiQ 2 nm |
| 228 | HIM 20 nm | HTM 5 nm | EBM2 15 nm | M5:M2:Ir(L192)₃ (10%:85%:5%) 40 nm | M5 10 nm | ETM1 30 nm | LiQ 2 nm |
| 229 | HIM 20 nm | HTM 5 nm | EBM2 15 nm | M5:M2:Ir(L196)₃ (10%:85%:5%) 40 nm | M5 10 nm | ETM1 30 nm | LiQ 2 nm |
| 230 | HIM 20 nm | HTM 5 nm | EBM2 15 nm | M5:M2:Ir(L198)₃ (10%:85%:5%) 40 nm | M5 10 nm | ETM1 30 nm | LiQ 2 nm |
| 231 | HIM 20 nm | HTM 5 nm | EBM2 15 nm | M5:M2:Ir(L199)₃ (10%:85%:5%) 40 nm | M5 10 nm | ETM1 30 nm | LiQ 2 nm |
| 232 | HIM 20 nm | HTM 5 nm | EBM2 15 nm | M5:M2:Ir(L203)₃ (10%:85%:5%) 40 nm | M5 10 nm | ETM1 30 nm | LiQ 2 nm |
| 233 | HIM 20 nm | HTM 5 nm | EBM2 15 nm | M5:M2:Ir(L207)₃ (10%:85%:5%) 40 nm | M5 10 nm | ETM1 30 nm | LiQ 2 nm |
| 234 | HIM 20 nm | HTM 5 nm | EBM2 15 nm | M5:M2:Pt(L211) (45%:45%:10%) 40 nm | M5 10 nm | ETM1 30 nm | LiQ 2 nm |
| 235 | HIM 20 nm | HTM 5 nm | EBM2 15 nm | M5:M2:Pt(L212) (40%:55%:5%) 40 nm | M5 10 nm | ETM1 30 nm | LiQ 2 nm |
| 236 | HIM 20 nm | HTM 5 nm | EBM2 15 nm | M5:M2:Pt(L213) (40%:55%:5%) 40 nm | M5 10 nm | ETM1 30 nm | LiQ 2 nm |
| 237 | HIM 20 nm | HTM 5 nm | EBM2 15 nm | M5:M2:Pt(L214) (50%:45%:5%) 40 nm | M5 10 nm | ETM1 30 nm | LiQ 2 nm |
| 238 | HIM 20 nm | HTM 5 nm | EBM2 15 nm | M5:M2:Pt(L215) (40%:50%:10%) 40 nm | M5 10 nm | ETM1 30 nm | LiQ 2 nm |
| 239 | HIM 20 nm | HTM 5 nm | EBM2 15 nm | M5:M2:Pt(L216) (40%:50%:10%) 40 nm | M5 10 nm | ETM1 30 nm | LiQ 2 nm |
| 240 | HIM 20 nm | HTM 5 nm | EBM2 15 nm | M5:M2:Pt(L217) (40%:50%:10%) 40 nm | M5 10 nm | ETM1 30 nm | LiQ 2 nm |
| 241 | HIM 20 nm | HTM 5 nm | EBM2 15 nm | M5:M2:Ir(L218) (10%:85%:5%) 40 nm | M5 10 nm | ETM1 30 nm | LiQ 2 nm |
| 242 | HIM 20 nm | HTM 5 nm | EBM2 10 nm | M5:M2:Pt(L219) (40%:55%:5%) 30 nm | M5 10 nm | ETM1 30 nm | LiQ 2 nm |

TABLE 2

Use of compounds according to the invention as emitters in phosphorescent OLEDs

| Ex. | Efficiency (cd/A) at 1000 cd/m² | Voltage (V) 1000 cd/m² | CIE x/y at 1000 cd/m² | LT50 (h) at 1000 cd/m² |
|---|---|---|---|---|
| 1 | 13.2 | 6.9 | 0.15/0.28 | 750 |
| 2 | 12.5 | 5.5 | 0.15/0.29 | 260 |
| 3 | 8.7 | 8.5 | 0.16/0.31 | 40 |
| 4 | 15.4 | 5.8 | 0.15/0.30 | 560 |
| 5 | 11.0 | 6.7 | 0.14/0.29 | 430 |
| 6 | 7.9 | 6.5 | 0.15/0.31 | — |
| 7 | 6.5 | 8.2 | 0.16/0.31 | — |
| 8 | 26.8 | 7.2 | 0.15/0.30 | 1100 |
| 9 | 14.7 | 5.6 | 0.15/0.28 | 330 |
| 10 | 22.4 | 6.4 | 0.16/0.33 | — |
| 11 | 21.1 | 5.5 | 0.15/0.30 | 580 |
| 12 | 29.5 | 6.7 | 0.14/0.29 | 900 |
| 13 | 17.6 | 7.2 | 0.16/0.30 | 650 |
| 14 | 23.3 | 5.9 | 0.16/0.29 | 530 |
| 15 | 11.3 | 5.4 | 0.17/0.29 | — |
| 16 | 9.7 | 8.6 | 0.16/0.29 | — |
| 17 | 8.3 | 7.0 | 0.15/0.29 | 580 |
| 18 | 14.0 | 8.2 | 0.15/0.29 | 570 |
| 19 | 9.5 | 5.2 | 0.16/0.29 | 470 |
| 20 | 8.3 | 5.9 | 0.15/0.28 | — |
| 21 | 10.4 | 6.1 | 0.17/0.33 | — |
| 22 | 9.7 | 6.4 | 0.16/0.29 | — |

TABLE 2-continued

Use of compounds according to the invention as emitters in phosphorescent OLEDs

| Ex. | Efficiency (cd/A) at 1000 cd/m² | Voltage (V) 1000 cd/m² | CIE x/y at 1000 cd/m² | LT50 (h) at 1000 cd/m² |
|---|---|---|---|---|
| 23 | 16.1 | 6.4 | 0.15/0.28 | — |
| 24 | 12.0 | 7.3 | 0.17/0.32 | — |
| 25 | 48.1 | 4.0 | 0.36/0.60 | 29000 |
| 26 | 59.7 | 3.5 | 0.36/0.61 | 45000 |
| 27 | 35.2 | 3.8 | 0.17/0.35 | 2000 |
| 28 | 11.2 | 6.3 | 0.16/0.29 | 600 |
| 29 | 22.4 | 5.4 | 0.15/0.33 | 930 |
| 30 | 17.4 | 5.3 | 0.15/0.29 | 990 |
| 31 | 24.3 | 5.5 | 0.15/0.28 | 1000 |
| 32 | 26.3 | 6.3 | 0.15/0.29 | 640 |
| 33 | 12.4 | 5.9 | 0.15/0.30 | — |
| 34 | 30.9 | 5.7 | 0.14/0.28 | — |
| 35 | 11.3 | 6.1 | 0.15/0.29 | — |
| 36 | 9.8 | 7.3 | 0.15/0.29 | — |
| 37 | 6.5 | 7.1 | 0.15/0.30 | — |
| 38 | 24.4 | 5.5 | 0.15/0.28 | 1100 |
| 39 | 12.7 | 6.0 | 0.17/0.34 | 450 |
| 40 | 30.9 | 7.0 | 0.15/0.29 | 850 |
| 41 | 14.1 | 8.1 | 0.16/0.30 | 430 |
| 42 | 19.5 | 6.5 | 0.14/0.27 | 520 |
| 43 | 9.9 | 5.7 | 0.15/0.30 | — |
| 44 | 7.3 | 6.8 | 0.17/0.35 | 470 |
| 45 | 22.5 | 5.2 | 0.18/0.37 | 1500 |
| 46 | 6.4 | 7.6 | 0.18/0.38 | 1450 |
| 47 | 28.3 | 6.2 | 0.17/0.35 | 960 |
| 48 | 14.1 | 7.8 | 0.14/0.26 | 870 |
| 49 | 13.9 | 7.1 | 0.14/0.24 | 540 |
| 50 | 15.8 | 6.1 | 0.15/0.29 | — |
| 51 | 20.0 | 5.4 | 0.15/0.28 | 1050 |
| 52 | 21.2 | 5.4 | 0.15/0.33 | 780 |
| 53 | 17.9 | 5.6 | 0.15/0.28 | — |
| 54 | 16.3 | 5.7 | 0.14/0.26 | 560 |
| 55 | 6.3 | 6.8 | 0.17/0.38 | — |
| 56 | 21.7 | 6.2 | 0.17/0.35 | 350 |
| 57 | 15.7 | 5.3 | 0.15/0.23 | 550 |
| 58 | 16.9 | 5.6 | 0.15/0.21 | 560 |
| 59 | 21.9 | 5.4 | 0.15/0.20 | 680 |
| 60 | 16.3 | 8.1 | 0.15/0.28 | 720 |
| 61 | 25.7 | 6.1 | 0.15/0.26 | 910 |
| 62 | 19.9 | 5.9 | 0.15/0.28 | — |
| 63 | 15.7 | 6.1 | 0.15/0.24 | 620 |
| 64 | 13.4 | 5.7 | 0.15/0.25 | 710 |
| 65 | 19.8 | 5.6 | 0.15/0.26 | 450 |
| 66 | 17.7 | 8.5 | 0.14/0.23 | 680 |
| 67 | 25.7 | 4.8 | 0.16/0.35 | 1300 |
| 68 | 12.7 | 6.1 | 0.17/0.39 | 2100 |
| 69 | 19.6 | 5.2 | 0.17/0.35 | 2600 |
| 70 | 23.5 | 5.3 | 0.16/0.33 | 2300 |
| 71 | 16.5 | 4.8 | 0.15/0.23 | 1400 |
| 72 | 16.4 | 4.9 | 0.15/0.24 | 1500 |
| 73 | 18.3 | 4.7 | 0.15/0.22 | — |
| 74 | 14.8 | 5.5 | 0.15/0.25 | — |
| 75 | 29.6 | 4.8 | 0.15/0.29 | 970 |
| 76 | 7.6 | 6.8 | 0.16/0.31 | 150 |
| 77 | 12.5 | 6.7 | 0.15/0.30 | 540 |
| 78 | 24.6 | 6.3 | 0.14/0.26 | 360 |
| 79 | 16.7 | 5.2 | 0.15/0.29 | 720 |
| 80 | 16.5 | 6.3 | 0.15/0.23 | 250 |
| 81 | 13.1 | 5.2 | 0.15/0.28 | 760 |
| 82 | 14.9 | 5.5 | 0.15/0.22 | 110 |
| 83 | 9.0 | 5.8 | 0.15/0.25 | 730 |
| 84 | 6.5 | 7.8 | 0.16/0.29 | — |
| 85 | 8.8 | 7.3 | 0.16/0.30 | — |
| 86 | 8.6 | 7.4 | 0.16/0.31 | 810 |
| 87 | 11.1 | 7.4 | 0.15/0.24 | 170 |
| 88 | 16.4 | 7.3 | 0.15/0.32 | 870 |
| 89 | 13.1 | 6.4 | 0.15/0.25 | 210 |
| 90 | 18.4 | 5.8 | 0.16/0.29 | 590 |
| 91 | 23.1 | 6.2 | 0.15/0.30 | — |
| 92 | 12.3 | 7.6 | 0.15/0.28 | — |
| 93 | 6.4 | 8.0 | 0.16/0.33 | — |
| 94 | 9.7 | 7.1 | 0.16/0.31 | 180 |
| 95 | 13.4 | 6.5 | 0.15/0.20 | 220 |
| 96 | 12.9 | 5.8 | 0.15/0.24 | 250 |
| 97 | 10.7 | 6.1 | 0.15/0.23 | 270 |
| 98 | 16.4 | 5.7 | 0.15/0.21 | 160 |
| 99 | 6.3 | 5.2 | 0.15/0.25 | — |
| 100 | 9.6 | 5.6 | 0.15/0.24 | — |
| 101 | 6.1 | 6.5 | 0.15/0.14 | — |
| 102 | 26.8 | 5.7 | 0.15/0.29 | 330 |
| 103 | 18.3 | 5.6 | 0.15/0.28 | 370 |
| 104 | 5.5 | 6.0 | 0.15/0.20 | — |
| 105 | 7.8 | 6.3 | 0.15/0.28 | — |
| 106 | 11.0 | 7.5 | 0.15/0.19 | 190 |
| 107 | 6.5 | 7.4 | 0.15/0.22 | — |
| 108 | 7.3 | 7.6 | 0.15/0.21 | — |
| 109 | 6.2 | 8.1 | 0.15/0.18 | — |
| 110 | 4.5 | 8.3 | 0.15/0.22 | — |
| 111 | 24.1 | 6.3 | 0.15/0.29 | 670 |
| 112 | 22.7 | 5.9 | 0.15/0.30 | 1100 |
| 113 | 18.9 | 5.5 | 0.16/0.31 | 690 |
| 114 | 26.4 | 6.1 | 0.15/0.28 | 1200 |
| 115 | 23.1 | 5.7 | 0.16/0.32 | 270 |
| 116 | 17.2 | 5.1 | 0.15/0.26 | 180 |
| 117 | 14.3 | 5.7 | 0.15/0.28 | 240 |
| 118 | 16.8 | 6.7 | 0.15/0.29 | 170 |
| 119 | 11.2 | 6.2 | 0.15/0.31 | 210 |
| 120 | 16.0 | 5.1 | 0.15/0.29 | 350 |
| 121 | 14.3 | 5.9 | 0.15/0.25 | 430 |
| 122 | 15.8 | 6.1 | 0.15/0.26 | 2200 |
| 123 | 16.8 | 7.1 | 0.15/0.28 | 480 |
| 124 | 8.3 | 7.0 | 0.15/0.28 | 330 |
| 125 | 11.1 | 7.7 | 0.16/0.30 | 610 |
| 126 | 24.0 | 7.2 | 0.15/0.29 | 510 |
| 127 | 16.5 | 5.6 | 0.15/0.28 | 170 |
| 128 | 32.0 | 5.5 | 0.15/0.23 | 450 |
| 129 | 14.7 | 5.6 | 0.15/0.28 | — |
| 130 | 19.7 | 6.4 | 0.16/0.33 | — |
| 131 | 6.6 | 7.1 | 0.15/0.27 | — |
| 132 | 10.4 | 7.0 | 0.15/0.29 | 320 |
| 133 | 25.6 | 6.1 | 0.15/0.26 | 470 |
| 134 | 6.5 | 7.2 | 0.15/0.27 | 360 |
| 135 | 22.7 | 4.5 | 0.21/0.43 | — |
| 136 | 27.8 | 4.2 | 0.19/0.42 | — |
| 137 | 9.6 | 8.7 | 0.16/0.30 | — |
| 138 | 13.5 | 5.0 | 0.15/0.28 | — |
| 139 | 19.0 | 6.5 | 0.14/0.25 | — |
| 140 | 17.7 | 6.5 | 0.15/0.28 | — |
| 141 | 13.4 | 6.2 | 0.15/0.32 | 1200 |
| 142 | 17.6 | 5.3 | 0.15/0.30 | 990 |
| 143 | 8.8 | 7.0 | 0.16/0.34 | 870 |
| 144 | 6.4 | 6.9 | 0.17/0.35 | 890 |
| 145 | 28.0 | 5.0 | 0.16/0.31 | 360 |
| 146 | 16.0 | 6.3 | 0.15/0.28 | 780 |
| Vgl. | 6.7 | 9.6 | 0.18/0.30 | 300 |
| 203 | 15.8 | 4.8 | 0.15/0.23 | 950 |
| 204 | 9.8 | 5.3 | 0.15/0.22 | — |
| 205 | 10.2 | 5.4 | 0.15/0.22 | — |
| 206 | 13.3 | 4.8 | 0.15/0.22 | — |
| 207 | 14.7 | 4.6 | 0.15/0.26 | — |
| 208 | 7.3 | 6.2 | 0.15/0.21 | — |
| 209 | 14.0 | 5.0 | 0.16/0.22 | — |
| 210 | 21.5 | 4.8 | 0.17/0.26 | 1200 |
| 211 | 17.8 | 5.0 | 0.16/0.25 | — |
| 212 | 16.4 | 4.9 | 0.15/0.24 | — |
| 213 | 18.8 | 5.2 | 0.15/0.24 | — |
| 214 | 17.8 | 4.6 | 0.15/0.23 | — |
| 215 | 16.9 | 4.6 | 0.15/0.23 | — |
| 216 | 19.3 | 4.7 | 0.15/0.23 | — |
| 217 | 19.7 | 4.7 | 0.15/0.23 | — |
| 218 | 17.5 | 5.0 | 0.15/0.24 | — |
| 219 | 19.7 | 4.6 | 0.15/0.26 | — |
| 220 | 12.0 | 5.9 | 0.15/0.21 | — |
| 221 | 16.5 | 5.1 | 0.16/0.22 | — |
| 222 | 15.0 | 5.1 | 0.16/0.22 | — |
| 223 | 19.6 | 4.7 | 0.17/0.26 | — |

TABLE 2-continued
Use of compounds according to the invention as emitters in phosphorescent OLEDs
| Ex. | Efficiency (cd/A) at 1000 cd/m$^2$ | Voltage (V) 1000 cd/m$^2$ | CIE x/y at 1000 cd/m$^2$ | LT50 (h) at 1000 cd/m$^2$ |
|---|---|---|---|---|
| 224 | 19.0 | 4.8 | 0.16/0.25 | — |
| 225 | 19.5 | 4.8 | 0.15/0.24 | — |
| 226 | 17.6 | 4.7 | 0.15/0.24 | — |
| 227 | 15.9 | 4.7 | 0.15/0.23 | — |
| 228 | 16.0 | 4.9 | 0.15/0.23 | — |
| 229 | 14.5 | 5.0 | 0.16/0.22 | — |
| 230 | 10.1 | 5.6 | 0.17/0.26 | — |
| 231 | 17.8 | 4.8 | 0.15/0.23 | — |
| 232 | 17.5 | 4.8 | 0.15/0.23 | — |
| 233 | 17.3 | 4.9 | 0.15/0.23 | — |
| 234 | 68.0 | 4.3 | 0.30/0.65 | 8000 |
| 235 | 70.0 | 4.2 | 0.29/0.68 | 11000 |
| 236 | 65.3 | 4.2 | 0.30/0.65 | 9500 |
| 237 | 67.4 | 4.3 | 0.30/0.67 | 13000 |
| 238 | 69.0 | 4.3 | 0.30/0.66 | 12000 |
| 239 | 71.2 | 4.2 | 0.25/0.60 | 16000 |
| 240 | 64.6 | 4.4 | 0.27/0.62 | 15000 |
| 241 | 15.6 | 6.5 | 0.16/0.31 | — |
| 242 | 64.3 | 4.4 | 0.26/0.64 | 20000 |
TABLE 3
Structural formulae of the materials used
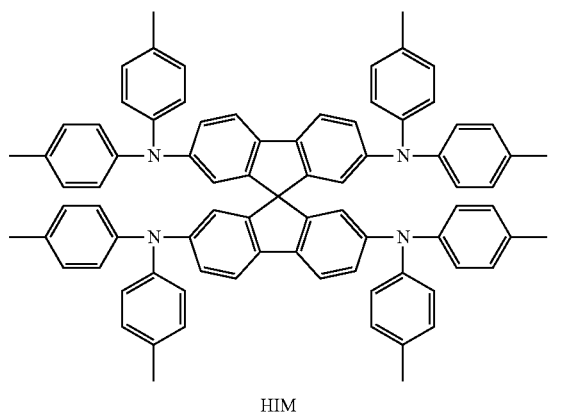
HIM
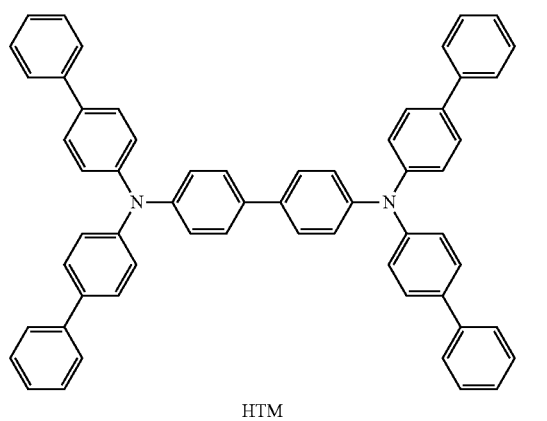
HTM
TABLE 3-continued
Structural formulae of the materials used
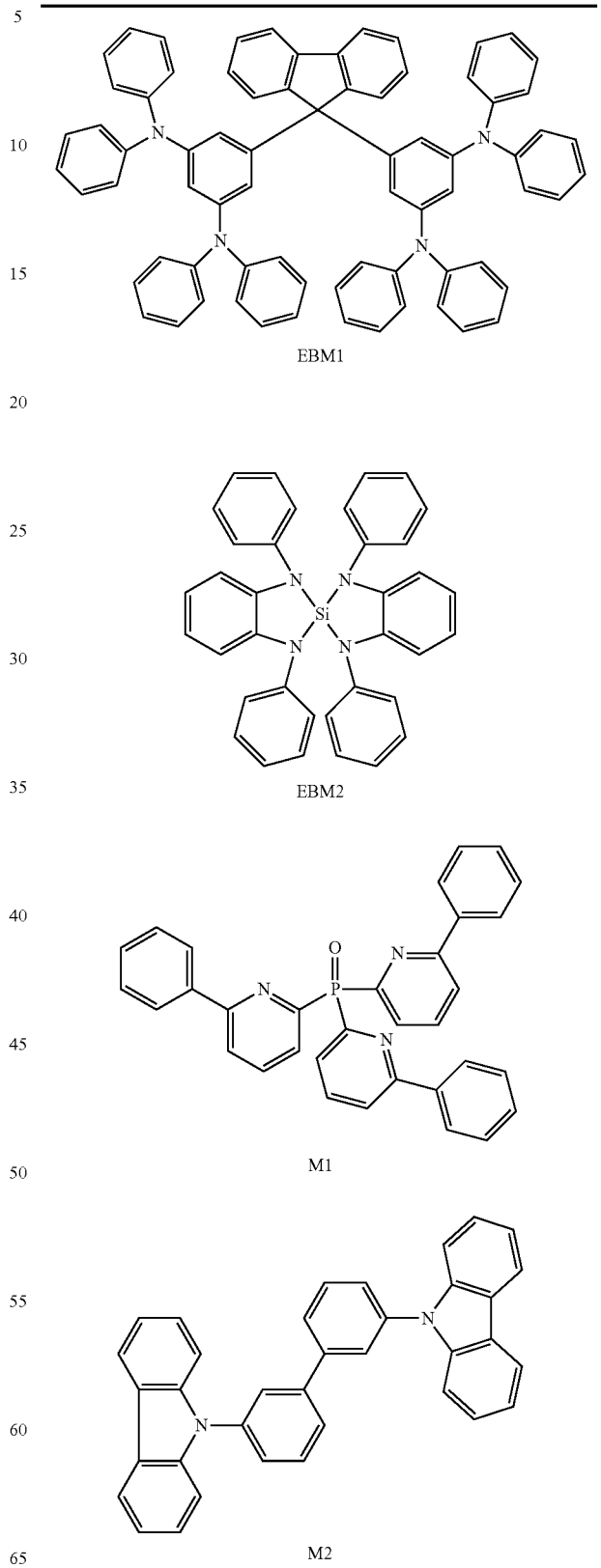
EBM1
EBM2
M1
M2

TABLE 3-continued

Structural formulae of the materials used

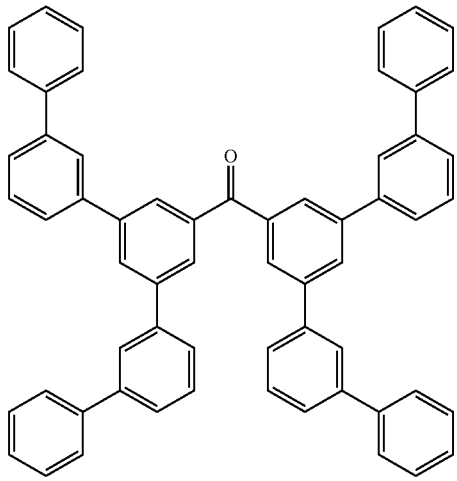

M3

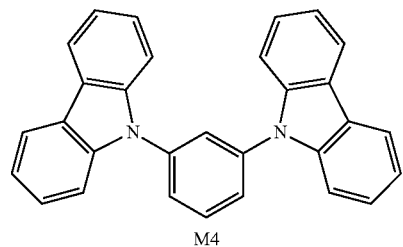

M4

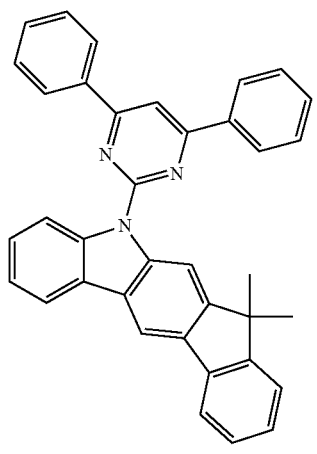

M5

TABLE 3-continued

Structural formulae of the materials used

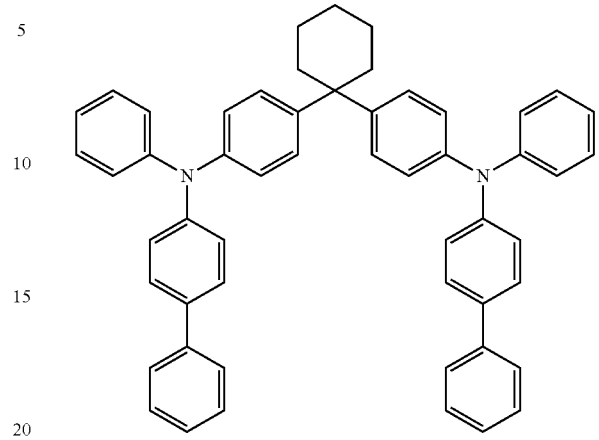

M6

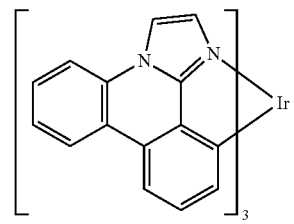

Ir(ref)

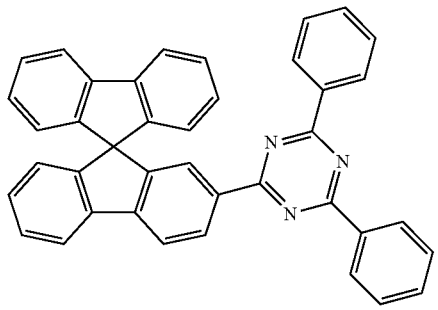

ETM1

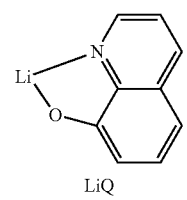

LiQ

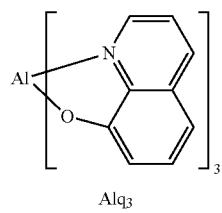

Alq$_3$

Materials according to the invention can also be used from solution, where they result in significantly simpler OLEDs compared with vacuum-processed OLEDs with nevertheless good properties. The production of components of this type is based on the production of polymeric light-emitting diodes (PLEDs), which has already been described many times in the literature (for example in WO 2004/037887). The structure is composed of substrate/ITO/PEDOT (80 nm)/interlayer/emission layer (80 nm)/cathode. The interlayer used serves for hole injection; in this case, HIL-012 from Merck is used. In the present case, the emitters according to the invention for the emission layer are dissolved in toluene along with the matrices. The typical solids content of such solutions is between 16 and 25 g/l if, as here, the typical layer thickness of 80 nm for a device is to be achieved by means of spin coating. The emission layer is applied by spin coating in an inert-gas atmosphere, in the present case argon, and dried by heating at 120° C. for 10 min. Finally, a cathode comprising barium and aluminium is applied by vacuum vapour deposition. The layers HBL and ETL used in the above-mentioned examples can also be applied by vapour deposition between EML and cathode, the interlayer may also be replaced by one or more layers which merely have to satisfy the condition of not being detached again by the subsequent processing step of EML deposition from solution. The solution-processed devices are characterised by standard methods in the matrices PS (polystyrene):M6:M1:Ir(LX)$_3$ (26%:14%:42%:20%), the OLED examples given have not yet been optimised. Table 4 summarises the data obtained. In the case of the processed OLEDs, its is apparent here that the materials according to the invention result in efficient blue-emitting OLEDs.

TABLE 4

Results with materials processed from solution

| Ex. | EML with emitter 80 nm | Voltage [V] at 100 cd/m$^2$ | Max. eff. [cd/A] | CIE (x, y) |
|---|---|---|---|---|
| 147 | Ir(L4)$_3$ | 8.3 | 9.6 | 0.15/0.32 |
| 148 | Ir(L5)$_3$ | 8.6 | 6.6 | 0.16/0.32 |
| 149 | Ir(L8)$_3$ | 7.9 | 10.4 | 0.16/0.33 |
| 150 | Ir(L11)$_3$ | 7.7 | 8.3 | 0.16/0.35 |
| 151 | Ir(L12)$_3$ | 8.6 | 19.1 | 0.16/0.36 |
| 152 | Ir(L16)$_3$ | 7.6 | 14.7 | 0.16/0.35 |
| 153 | Ir(L17)$_3$ | 6.5 | 6.4 | 0.16/0.33 |
| 154 | Ir(L19)$_3$ | 7.4 | 4.8 | 0.17/0.35 |
| 155 | Ir(L20)$_3$ | 8.6 | 9.1 | 0.16/0.35 |
| 156 | Ir(L29)$_3$ | 9.7 | 12.6 | 0.15/0.32 |
| 157 | Ir(L30)$_3$ | 8.0 | 7.6 | 0.15/0.30 |
| 158 | Ir(L32)$_3$ | 7.8 | 9.4 | 0.16/0.33 |
| 159 | Ir(L33)$_3$ | 7.9 | 13.4 | 0.16/0.33 |
| 160 | Ir(L34)$_3$ | 7.9 | 12.8 | 0.16/0.32 |
| 161 | Ir(L38)$_3$ | 7.3 | 28.0 | 0.17/0.40 |

TABLE 4-continued

Results with materials processed from solution

| Ex. | EML with emitter 80 nm | Voltage [V] at 100 cd/m$^2$ | Max. eff. [cd/A] | CIE (x, y) |
|---|---|---|---|---|
| 162 | Ir(L45)$_3$ | 8.1 | 20.3 | 0.16/0.30 |
| 163 | Ir(L46)$_3$ | 8.4 | 6.7 | 0.17/0.35 |
| 164 | Ir(L47)$_3$ | 8.7 | 25.7 | 0.17/0.36 |
| 165 | Ir(L48)$_3$ | 8.0 | 19.8 | 0.16/0.34 |
| 166 | Ir(L49)$_3$ | 7.9 | 8.4 | 0.15/0.34 |
| 167 | Ir(L50)$_3$ | 8.3 | 17.2 | 0.16/0.33 |
| 168 | Ir(L51)$_3$ | 9.5 | 11.2 | 0.15/0.32 |
| 169 | Ir(L52)$_3$ | 10.1 | 16.3 | 0.16/0.33 |
| 170 | Ir(L53)$_3$ | 7.4 | 10.5 | 0.15/0.30 |
| 171 | Ir(L54)$_3$ | 8.9 | 12.7 | 0.16/0.31 |
| 172 | Ir(L55)$_3$ | 7.8 | 21.3 | 0.16/.35 |
| 173 | Ir(L56)$_3$ | 8.1 | 9.0 | 0.16/0.33 |
| 174 | Ir(L57)$_3$ | 7.7 | 27.5 | 0.17/0.38 |
| 175 | Ir(L58)$_3$ | 8.1 | 31.2 | 0.17/0.37 |
| 176 | Ir(L65)$_3$ | 9.1 | 6.5 | 0.17/0.34 |
| 177 | Ir(L66)$_3$ | 7.7 | 5.2 | 0.15/0.30 |
| 178 | Ir(L70)$_3$ | 8.5 | 10.0 | 0.15/0.31 |
| 179 | Ir(L72)$_3$ | 8.5 | 9.9 | 0.15/0.29 |
| 180 | Ir(L76)$_3$ | 8.9 | 19.9 | 0.16/0.28 |
| 181 | Ir(L77)$_3$ | 8.5 | 8.6 | 0.16/0.27 |
| 182 | Ir(L84)$_3$ | 7.9 | 22.5 | 0.18/0.37 |
| 183 | Ir(L89)$_3$ | 9.1 | 4.5 | 0.16/0.33 |
| 184 | Ir(L90)$_3$ | 8.2 | 18.4 | 0.16/0.31 |
| 185 | Ir(L94)$_3$ | 7.8 | 12.1 | 0.15/0.27 |
| 186 | Ir(L98)$_3$ | 9.6 | 8.5 | 0.15/0.26 |
| 187 | Ir(L99)$_3$ | 10.5 | 20.1 | 0.16/0.31 |
| 188 | Ir(L102)$_3$ | 7.6 | 11.9 | 0.15/0.29 |
| 189 | Ir(L113)$_3$ | 9.2 | 14.1 | 0.15/0.30 |
| 190 | Ir(L114)$_3$ | 8.7 | 14.0 | 0.15/0.26 |
| 191 | Ir(L127)$_3$ | 7.8 | 4.5 | 0.16/0.31 |
| 192 | Ir(L130)$_3$ | 8.5 | 7.6 | 0.16/0.35 |
| 193 | Ir(L133)$_3$ | 9.9 | 21.1 | 0.16/0.32 |
| 194 | Ir(L136)$_3$ | 8.6 | 9.0 | 0.16/0.33 |
| 195 | Ir(L145)$_3$ | 7.9 | 5.5 | 0.15/0.30 |
| 196 | Ir(L151)$_3$ | 7.5 | 8.1 | 0.15/0.25 |
| 197 | Ir(L157)$_3$ | 9.4 | 17.1 | 0.15/0.18 |
| 198 | Ir(L158)$_3$ | 7.9 | 6.9 | 0.16/0.19 |
| 199 | Ir(L159)$_3$ | 8.4 | 21.0 | 0.15/0.23 |
| 200 | Ir(L160)$_3$ | 7.6 | 18.6 | 0.16/0.24 |
| 201 | Ir(L161)$_3$ | 7.1 | 20.1 | 0.15/0.24 |
| 202 | Ir(L52)$_2$(CL10) | 32.1 | 18.0 | 0.16/0.38 |

Example 243

White-Emitting OLEDs

A white-emitting OLED having the following layer structure is produced by the general process:

TABLE 5

Structure of the white OLEDs

| Ex. | HTL1 Thickness | HTL2 Thickness | EML Red Thickness | EML Blue Thickness | EML Green Thickness | HBL Thickness | ETL Thickness |
|---|---|---|---|---|---|---|---|
| 243 | HIM 250 nm | HTM 10 nm | EBM2:Ir—R (97%:3%) 9 nm | M2:M5:Ir(L13)$_3$ (45%:50%:5%) 8 nm | M5:Ir-G (90%:10%) 7 nm | M5 10 nm | ETM1:LiQ (50%:50%) 30 nm |

Device results

| Ex. | Efficiency (cd/A) at 1000 cd/m$^2$ | Voltage (V) 1000 cd/m$^2$ | CIE x/y at 1000 cd/m$^2$ CRI | LT50 (h) at 1000 cd/m$^2$ |
|---|---|---|---|---|
| 243 | 33.0 | 6.2 | 0.45/0.44/80 | 1500 |

TABLE 5-continued

Structural formulae of the materials used

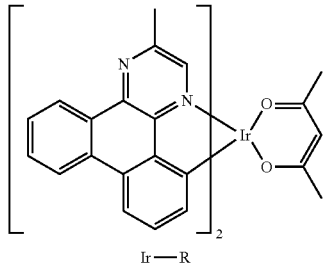
Ir—R

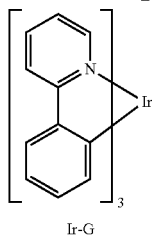
Ir-G

The invention claimed is:
1. A compound of the formula (1),

M(L)$_n$(L')$_m$      formula (1)

where the compound of the general formula (1) contains a moiety M(L)$_n$ of the formula (2):

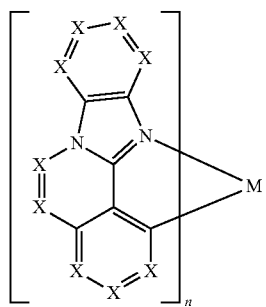

formula (2)

where the following applies to the symbols and indices used:

M is a metal;

X is selected on each occurrence, identically or differently, from the group consisting of CR, CR$^1$ and N, with the proviso that at least one X=N and that at least one X which is adjacent to this N stands for CR$^1$;

R is on each occurrence, identically or differently, H, D, F, Cl, Br, I, N(R$^2$)$_2$, CN, NO$_2$, OH, COOH, C(=O)N(R$^2$)$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals R$^2$, where one or more non-adjacent CH$_2$ groups is optionally replaced by R$^2$C=CR$^2$, C≡C, Si(R$^2$)$_2$, C=O, NR$^2$, O, S or CONR$^2$ and where one or more H atoms is optionally replaced by D, F, Cl, Br, I or CN, or an aromatic or heteroaromatic ring system having 5 to 60 aromatic ring atoms, which is optionally substituted by one or more radicals R$^2$, or an aryloxy or heteroaryloxy group having 5 to 40 aromatic ring atoms, which is optionally substituted by one or more radicals R$^2$, or an aralkyl or hetero-aralkyl group having 5 to 40 aromatic ring atoms, which is optionally substituted by one or more radicals R$^2$, or a diarylamino group, diheteroarylamino group or arylheteroarylamino group having 10 to 40 aromatic ring atoms, which is optionally substituted by one or more radicals R$^2$; or two adjacent radicals R or R with R' here may also form a mono- or polycyclic, aliphatic ring system with one another;

R$^1$ is on each occurrence, identically or differently, CF$_3$, OCF$_3$, a branched or cyclic alkyl or alkoxy group having 3 to 20 C atoms, which optionally in each case is substituted by one or more radicals R$^2$, where one or more non-adjacent CH$_2$ groups which are not bonded directly to the aromatic carbon atom of the ligand is optionally replaced by R$^2$C=CR$^2$, C≡C, Si(R$^2$)$_2$, C=O, NR$^2$, O, S or CONR$^2$ and where one or more H atoms is optionally replaced by D, F, Cl, Br, I or CN, or Si(R$^2$)$_3$, where R$^2$ is not equal to H or D, a dialkylamino group, where the alkyl groups each have 1 to 10 C atoms and is optionally linear, branched or cyclic, or an aromatic or heteroaromatic ring system having 5 to 60 aromatic ring atoms, which optionally in each case is substituted by one or more radicals R$^2$, or an aralkyl or heteroaralkyl group having 5 to 40 aromatic ring atoms, which is optionally substituted by one or more radicals R$^2$;

R$^2$ is on each occurrence, identically or differently, H, D, F, Cl, Br, I, N(R$^3$)$_2$, CN, NO$_2$, Si(R$^3$)$_3$, B(OR$^3$)$_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals R$^3$, where one or more non-adjacent CH$_2$ groups is optionally replaced by R$^3$C=CR$^3$, C≡C, Si(R$^3$)$_2$, C=O, NR$^3$, O, S or CONR$^3$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy or heteroaryloxy group having 5 to 40 aromatic ring atoms, which is optionally substituted by one or more radicals R³, or an aralkyl or heteroaralkyl group having 5 to 40 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³; two or more adjacent radicals R³ here may form a mono- or polycyclic, aliphatic ring system with one another;

R³ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R³ here may also form a mono- or polycyclic, aliphatic ring system with one another;

L' is, identically or differently on each occurrence, any desired co-ligand;

n is 1, 2 or 3;

m is 0, 1, 2, 3 or 4;

a plurality of ligands L is optionally linked to one another or L is optionally linked to L' via a single bond or any desired bridge V and thus form a tridentate, tetradentate, pentadentate or hexadentate ligand system;

a substituent R or R¹ may also additionally be coordinated to the metal;

with the proviso that R¹ stands for a branched or cyclic alkyl group having 4 to 20 C atoms, which optionally in each case is substituted by one or more radicals R², where one or more non-adjacent CH₂ groups which are not bonded directly to the aromatic carbon atom of the ligand is optionally replaced by R²C=CR², C≡C, Si(R²)₂, C=O, NR², O, S or CONR² and where one or more H atoms is optionally replaced by D, F, Cl, Br, I or CN, or for a bi- or oligoaryl or -heteroaryl group having 10 to 60 aromatic ring atoms or for an aryl or heteroaryl group which is substituted by a radical R² other than H or D in at least one ortho-position to the link to the ligand if the moiety conforms to one of the following formulae (3), (4), (5) or (6):

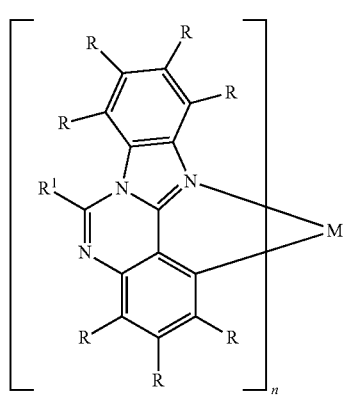

formula (3)

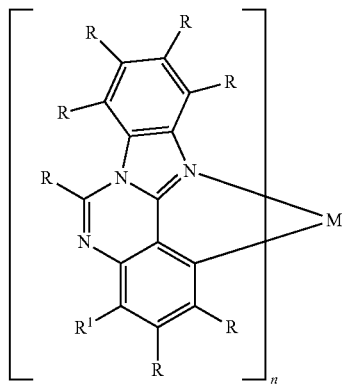

formula (4)

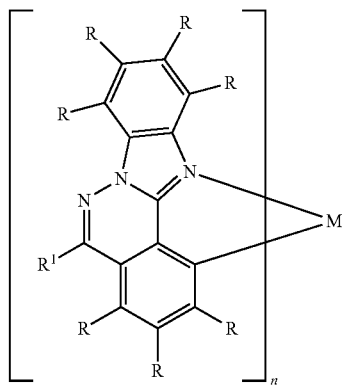

formula (5)

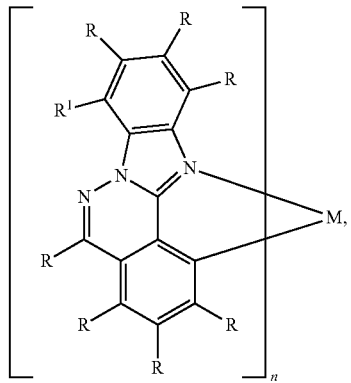

formula (6)

where the symbols and indices used have the above-mentioned meanings.

2. The compound according to claim 1, wherein it is uncharged.

3. The compound according to claim 1, wherein M is selected from the group consisting of chromium, molybdenum, tungsten, rhenium, ruthenium, osmium, rhodium, iridium, nickel, palladium, platinum, copper, silver and gold.

4. The compound according to claim 1, wherein, in the ligand L, one, two, three or four groups X stand for N.

5. The compound according to claim 1, wherein, in the ligand L, one, two, or three groups X, stand for N.

6. The compound according to claim 1, wherein, for each X which stands for N, at least one X which is adjacent to this N stands for CR¹.

7. The compound according to claim 1, wherein the moiety of the formula (2) is selected, identically or differently on each occurrence, from the moieties of the following formulae (7) to (38), formula (7)
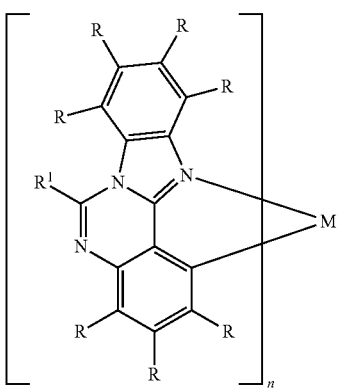
formula (8)
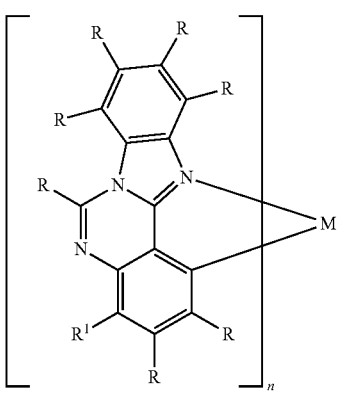
formula (9)
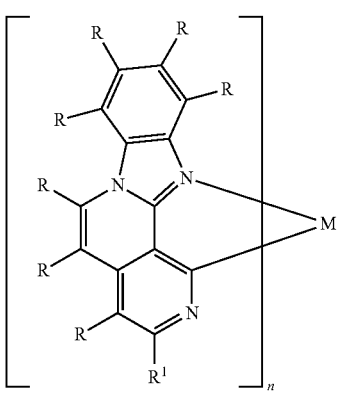
formula (10)
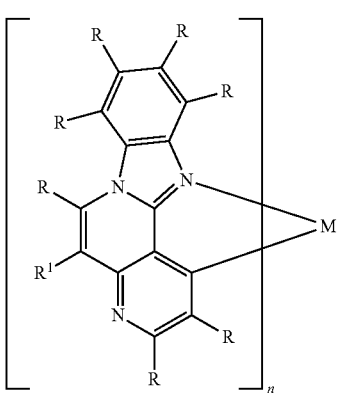
-continued
formula (11)
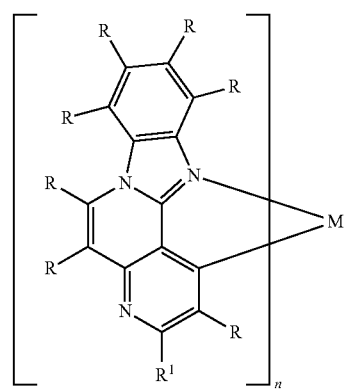
formula (12)
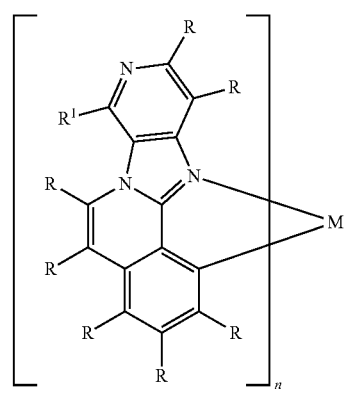
formula (13)
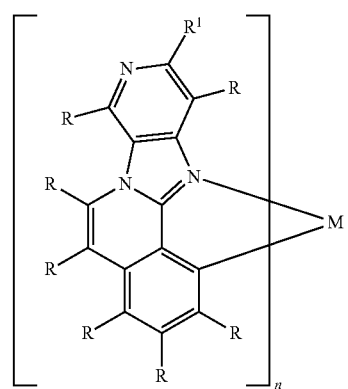
formula (14)
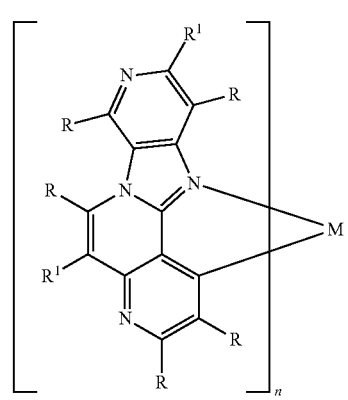

-continued
formula (15)
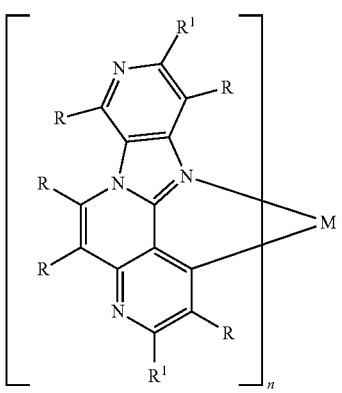
formula (16)
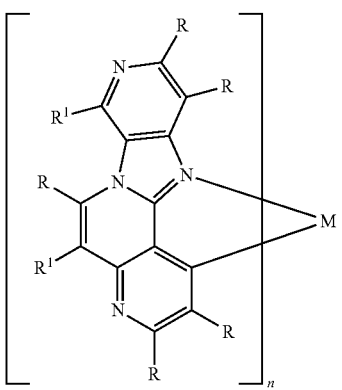
formula (17)
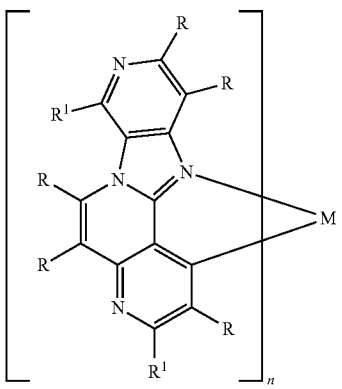
formula (18)
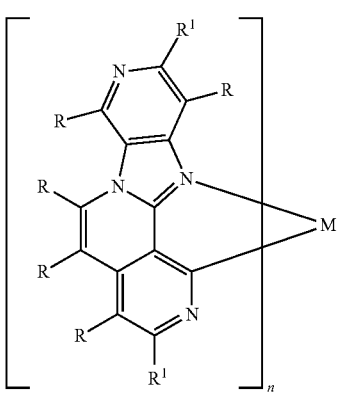
-continued
formula (19)
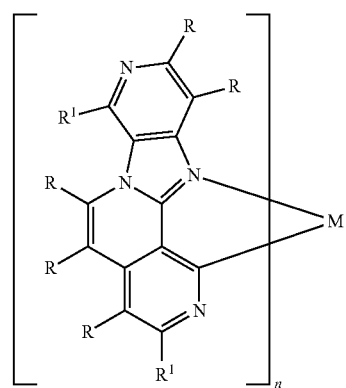
formula (20)
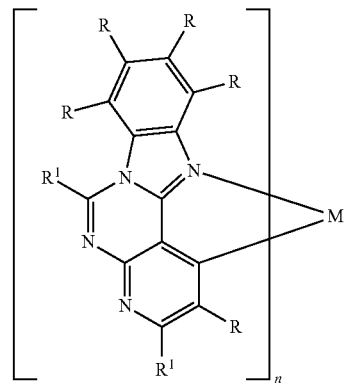
formula (21)
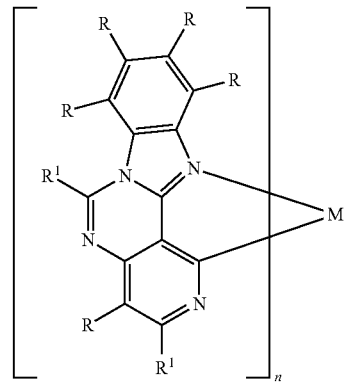
formula (22)
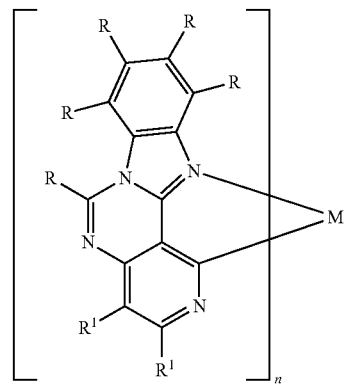

formula (23)
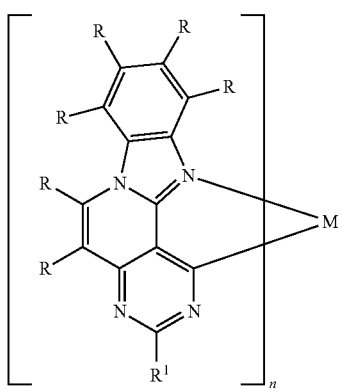
formula (27)
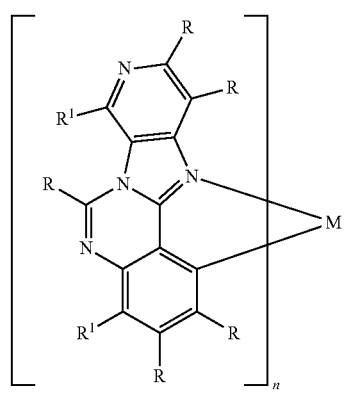
formula (24)
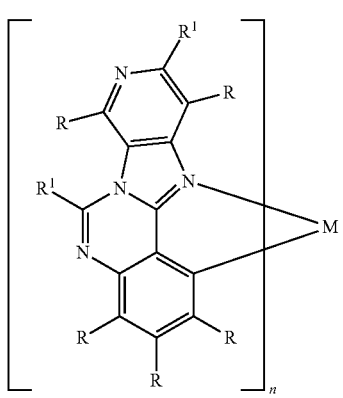
formula (28)
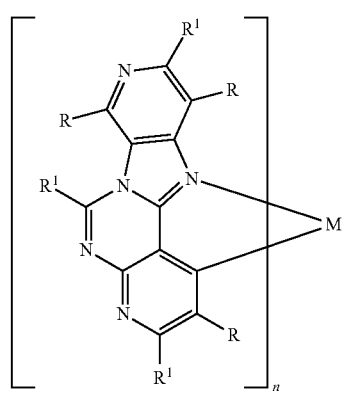
formula (25)
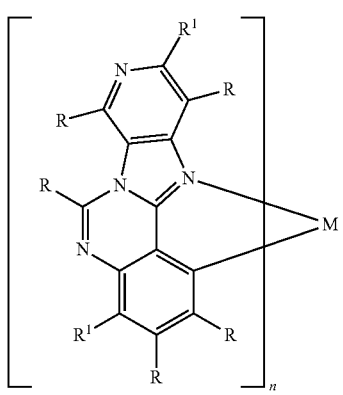
formula (29)
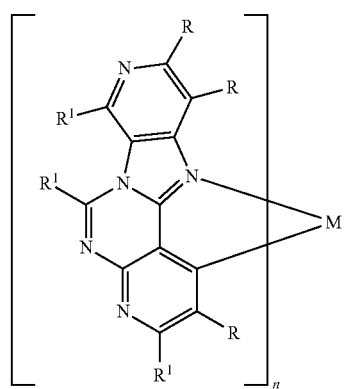
formula (26)
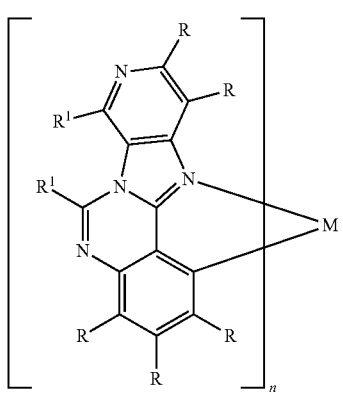
formula (30)
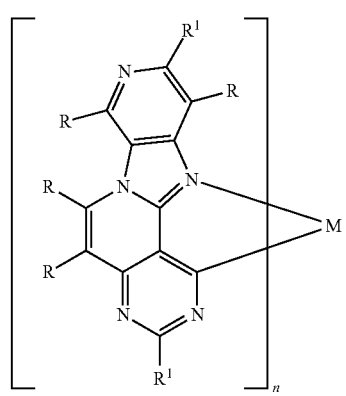

331
-continued
formula (31)
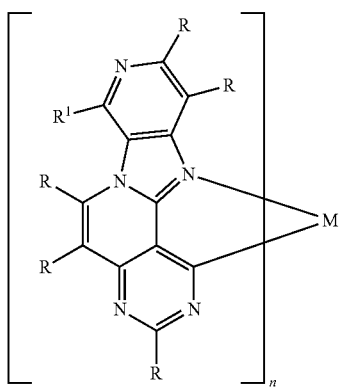
formula (32)
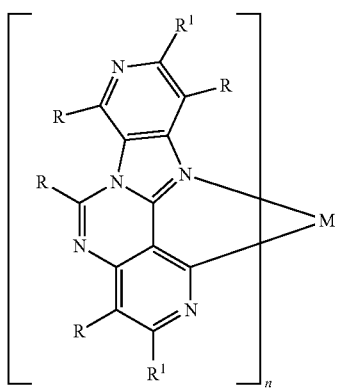
formula (33)
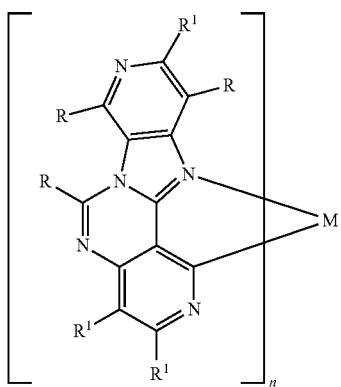
formula (34)
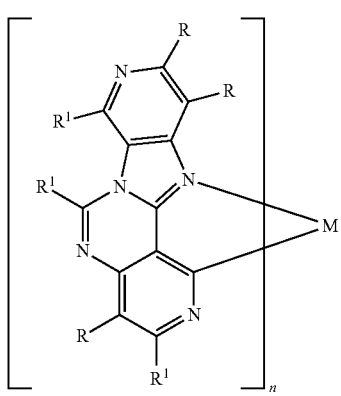
332
-continued
formula (35)
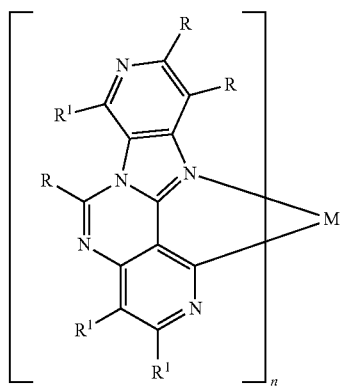
formula (36)
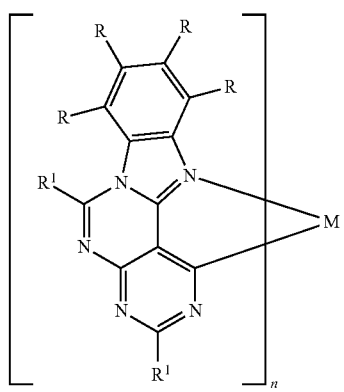
formula (37)
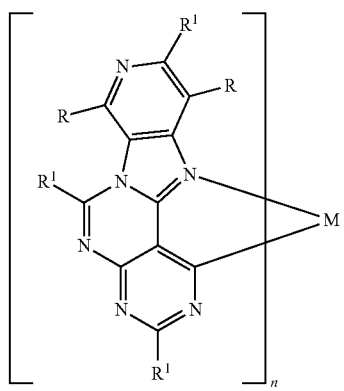
formula (38)
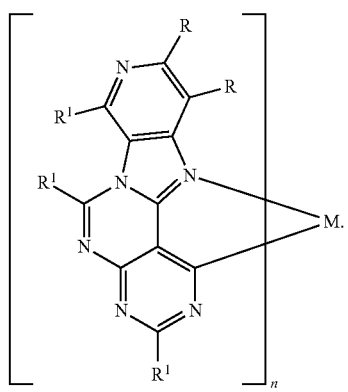
8. The compound according to claim 1, wherein $R^1$ is selected from the structures of the following formulae ($R^1$-1) to ($R^1$-112), where the linking of these groups to the ligand is in each case also drawn in:

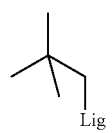 (R¹-1)
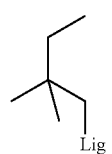 (R¹-2)
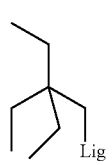 (R¹-3)
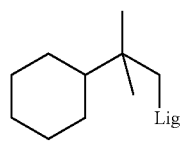 (R¹-4)
 (R¹-5)
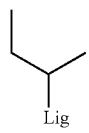 (R¹-6)
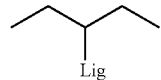 (R¹-7)
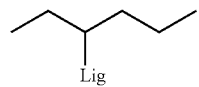 (R¹-8)
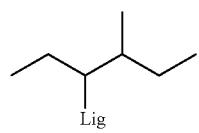 (R¹-9)
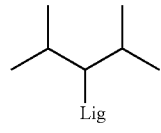 (R¹-10)
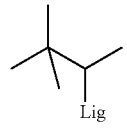 (R¹-11)
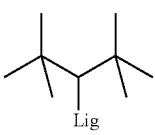 (R¹-12)
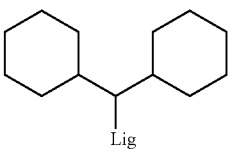 (R¹-13)
 (R¹-14)
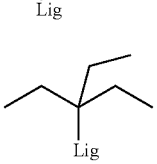 (R¹-15)
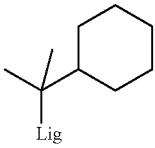 (R¹-16)
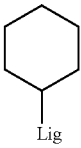 (R¹-17)
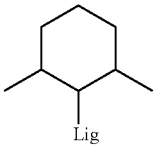 (R¹-18)
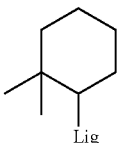 (R¹-19)
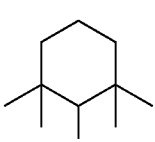 (R¹-20)
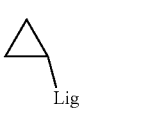 (R¹-21)
(R¹-22)

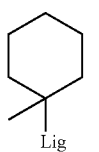 (R¹-23)
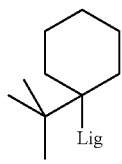 (R¹-24)
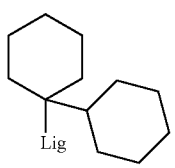 (R¹-25)
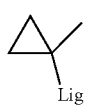 (R¹-26)
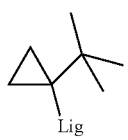 (R¹-27)
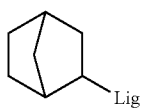 (R¹-28)
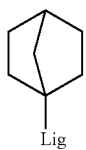 (R¹-29)
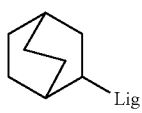 (R¹-30)
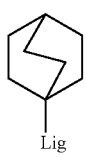 (R¹-31)
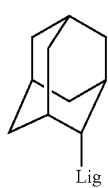 (R¹-32)
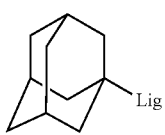 (R¹-33)
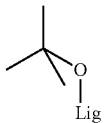 (R¹-34)
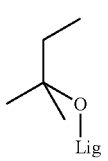 (R¹-35)
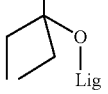 (R¹-36)
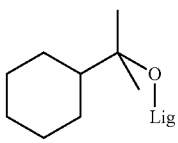 (R¹-37)
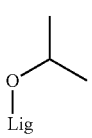 (R¹-38)
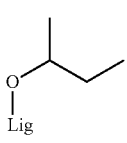 (R¹-39)
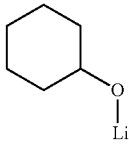 (R¹-40)
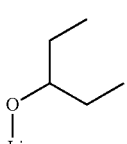 (R¹-41)
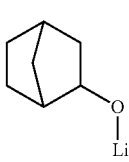 (R¹-42)

-continued
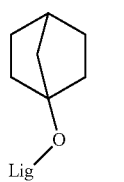 (R¹-43)
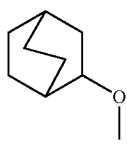 (R¹-44)
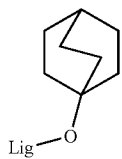 (R¹-45)
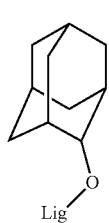 (R¹-46)
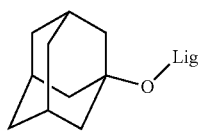 (R¹-47)
 (R¹-48)
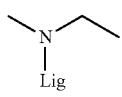 (R¹-49)
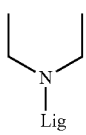 (R¹-50)
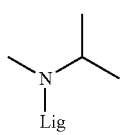 (R¹-51)
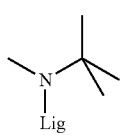 (R¹-52)
-continued
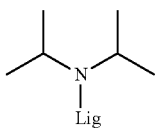 (R¹-53)
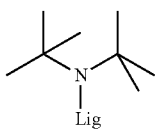 (R¹-54)
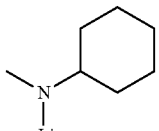 (R¹-55)
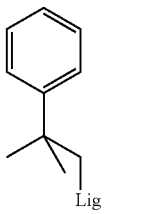 (R¹-56)
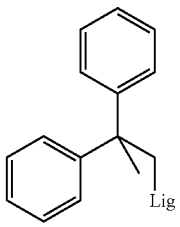 (R¹-57)
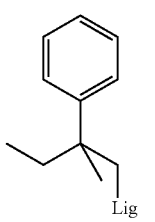 (R¹-58)
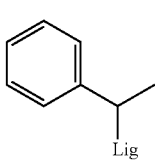 (R¹-59)
(R¹-60)

-continued
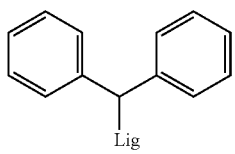 (R¹-61)
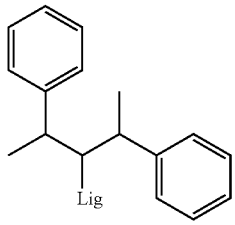 (R¹-62)
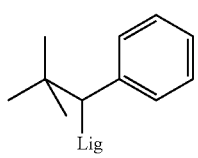 (R¹-63)
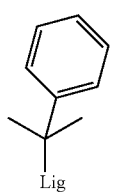 (R¹-64)
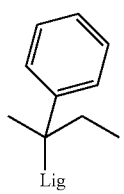 (R¹-65)
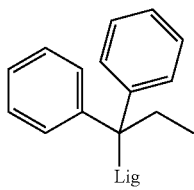 (R¹-66)
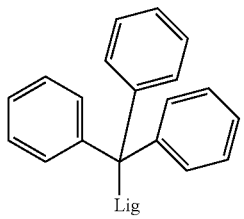 (R¹-67)
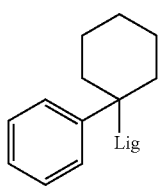 (R¹-68)
-continued
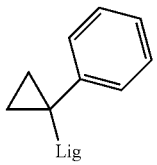 (R¹-69)
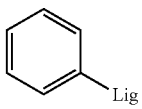 (R¹-70)
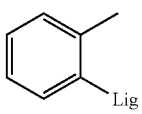 (R¹-71)
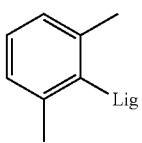 (R¹-72)
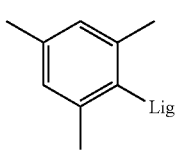 (R¹-73)
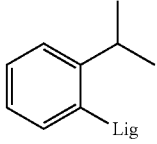 (R¹-74)
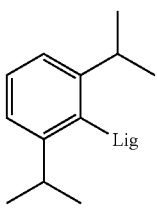 (R¹-75)
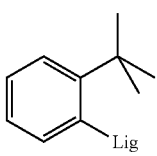 (R¹-76)
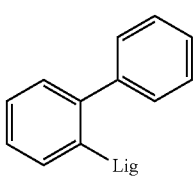 (R¹-77)

(R¹-78) 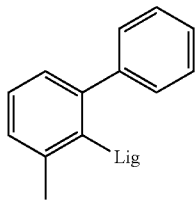
(R¹-79) 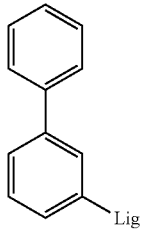
(R¹-80) 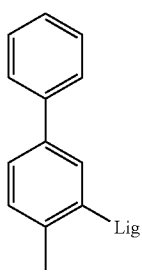
(R¹-81) 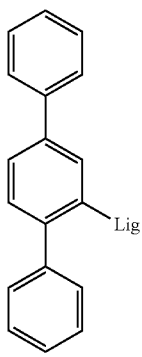
(R¹-82) 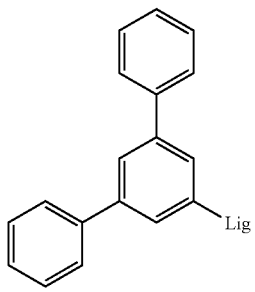
(R¹-83) 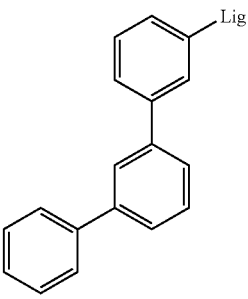
(R¹-84) 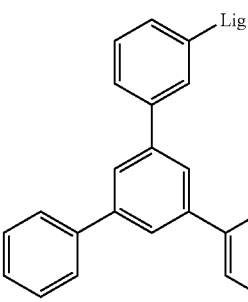
(R¹-85) 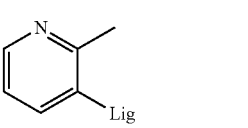
(R¹-86) 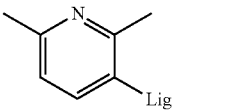
(R¹-87) 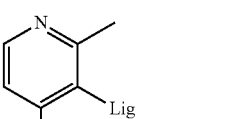
(R¹-88) 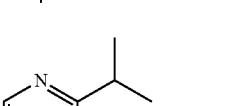
(R¹-89) 
(R¹-90) 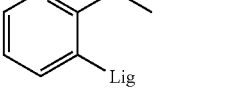
(R¹-91) 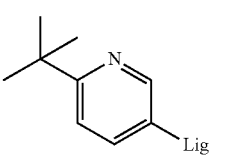

343
-continued
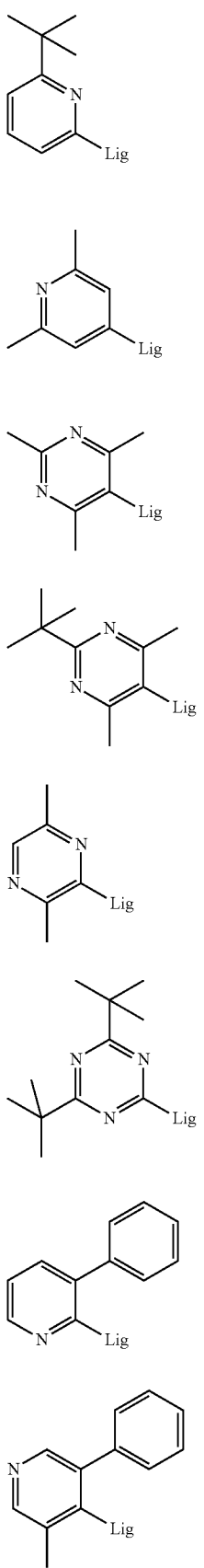
(R¹-92)
(R¹-93)
(R¹-94)
(R¹-95)
(R¹-96)
(R¹-97)
(R¹-98)
(R¹-99)
344
-continued
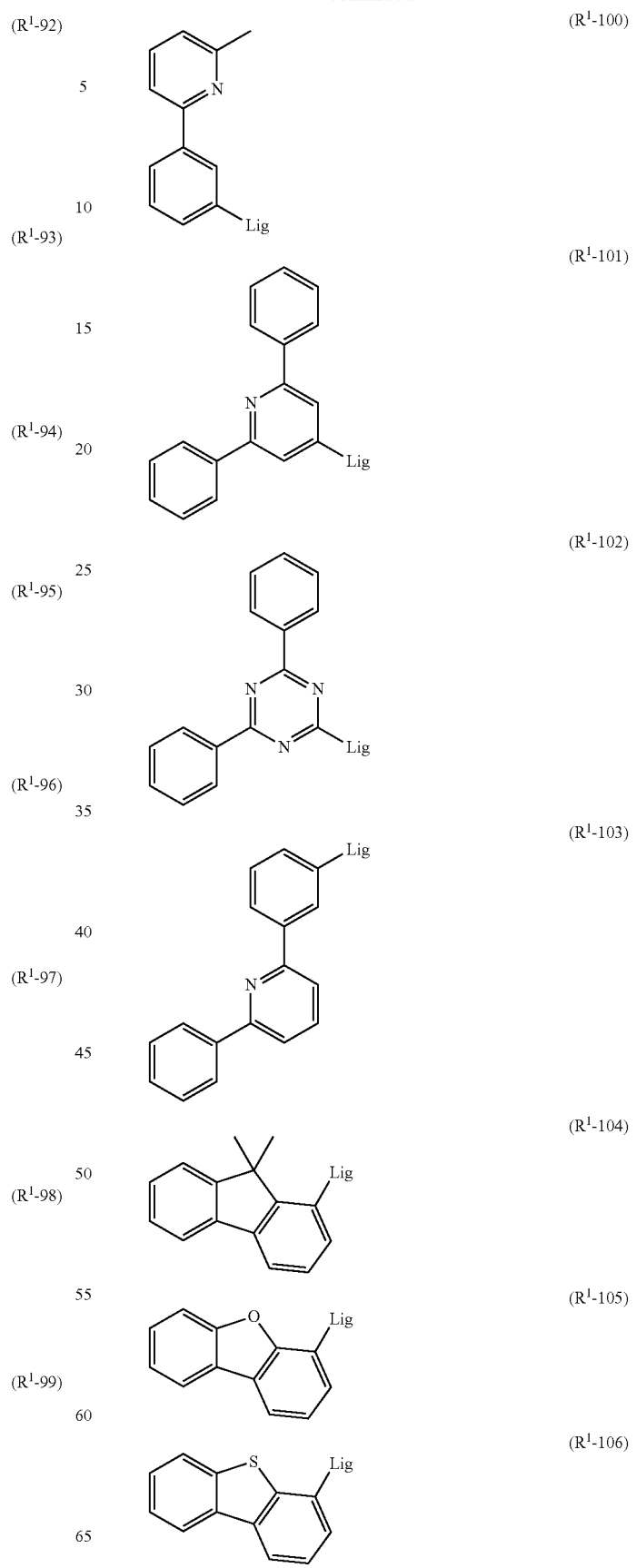
(R¹-100)
(R¹-101)
(R¹-102)
(R¹-103)
(R¹-104)
(R¹-105)
(R¹-106)

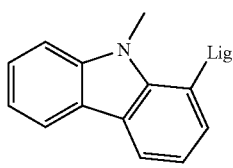
(R¹-107)

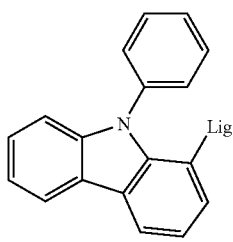
(R¹-108)

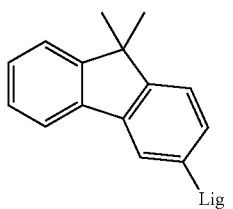
(R¹-109)

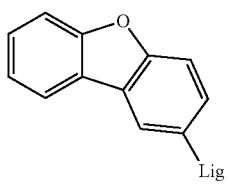
(R¹-110)

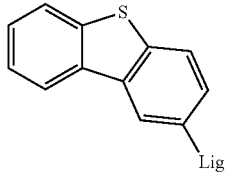
(R¹-111)

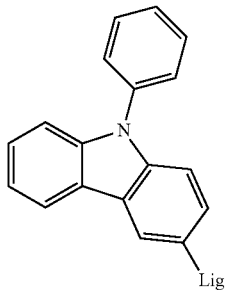
(R¹-112)

wherein Lig denotes the link to the ligand, and the aromatic and heteroaromatic groups optionally is substituted by one or more radicals R².

9. The compound according to claim 1, wherein, if further radicals R are bonded in the moiety of the formula (2) in addition to the radicals R¹, these radicals R are selected on each occurrence, identically or differently, from H, D, F, Br, I, N(R²)₂, CN, Si(R²)₃, B(OR²)₂, C(=O)R², a straight-chain alkyl group having 1 to 10 C atoms or an alkenyl group having 2 to 10 C atoms or a branched or cyclic alkyl group having 3 to 10 C atoms, each of which is optionally substituted by one or more radicals R², where one or more H atoms is optionally replaced by D or F, or an aromatic or heteroaromatic ring system having 5 to 30 aromatic ring atoms, which may in each case be substituted by one or more radicals R²; two adjacent radical R or R with R¹ here may also form a mono- or polycyclic, aliphatic ring system with one another.

10. The compound according to claim 1, wherein, if a substituent R which has a +M effect is bonded in the moiety of the formula (2) of the complex according to the invention, this is bonded to the ring which is bonded to the metal via the carbon in the meta-position to the metal, and in that, if a substituent R which has a −M effect is bonded in the moiety of the formula (2) of the complex according to the invention, this is bonded to the ring which is bonded to the metal via the carbon in the para-position to the metal.

11. The compound according to claim 1, wherein the substituent R which is in the ortho-position to the metal coordination represents a coordinating group which is likewise coordinated to the metal M, where the coordinating group R is selected from aryl or heteroaryl groups, aryl or alkyl cyanides, aryl or alkyl isocyanides, amines, amides, alcohols, alcoholates, thioalcohols, thioalcoholates, phosphines, phosphites, carbonyl functions, carboxylates, carbamides or aryl- or alkylacetylides.

12. The compound according to claim 1, wherein structures having polydentate ligands of the following formulae (45) to (50) or (45a) are involved,

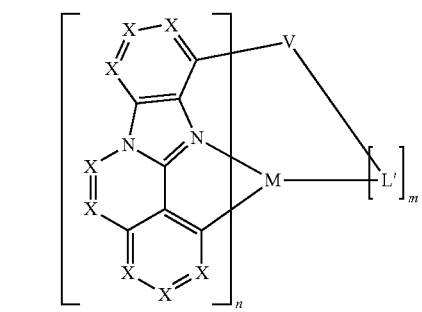
formula (45)

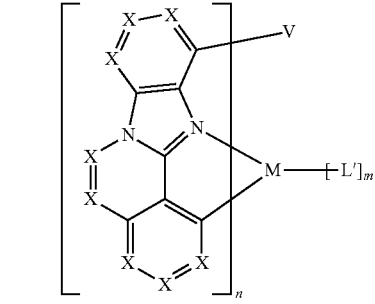
formula (46)

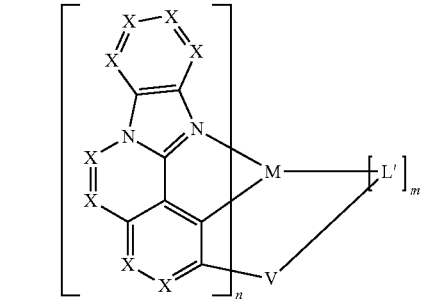
formula (47)

formula (48)
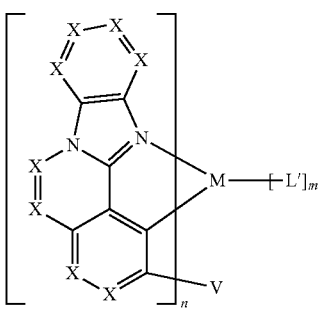

formula (49)
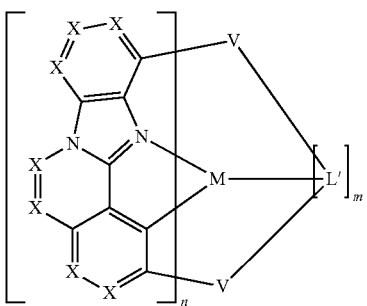

formula (50)
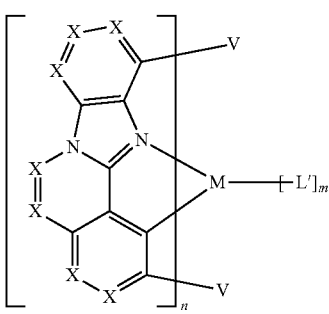

formula (45a)
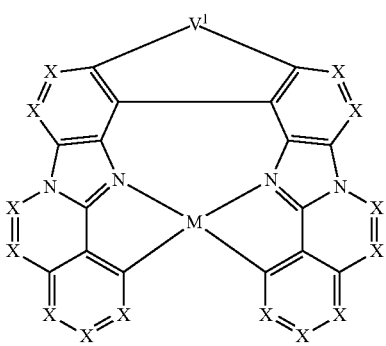

where the symbols used have the above-mentioned meanings, where $V^1$ stands for $CR_2$, NR, O or S and where V preferably represents a bridging unit containing 1 to 80 atoms from the third, fourth, fifth and/or sixth main group (group 13, 14, 15 or 16 in accordance with IUPAC) or a 3- to 6-membered homo- or heterocycle which covalently bonds the part-ligands L to one another or L to L' to one another.

13. The compound according to claim 1, wherein the ligands L' are selected, identically or differently on each occurrence, from carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, the halides F$^-$, Cl$^-$, Br$^-$ and I$^-$, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, O$^{2-}$, S$^{2-}$, carbides which result in coordination in the form nitrenes which result in coordination in the form R—N=M, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates, dithiolates, borates of nitrogen-containing heterocycles or bidentate monoanionic, neutral or dianionic ligands which, with the metal, form a cyclometallated five-membered ring or six-membered ring having at least one metal-carbon bond.

14. A process for the preparation of the compound according to claim 1 which comprises reacting the corresponding free ligand L with metal alkoxides of the formula (97), with metal ketoketonates of the formula (98), with metal halides of the formula (99) or with dimeric metal complexes of the formula (100), formula (97)
$$M(OR)_n$$

formula (98)
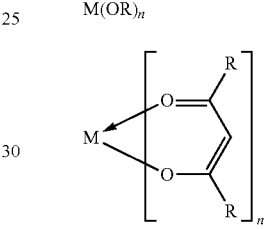

formula (99)
$$MHal_n$$

formula (100)
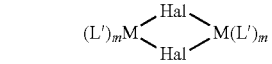

where the symbols M, m, n and R have the meanings indicated in claim 1, and Hal =F, Cl, Br or I.

15. An electronic device comprising at least one compound according to claim 1.

16. The electronic device according to claim 15, wherein the device is an organic electroluminescent device (OLED, PLED), organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC) or organic laser diode (O-laser).

17. The electronic device according to claim 16, wherein the device is an organic electroluminescent device and the compound according to claim 1 is employed as an emitting compound in one or more emitting layers.

18. The organic electroluminescent device according to claim 17, wherein the emitting compound is used together with one or more matrix materials, where the matrix material or matrix materials are ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives, zinc complexes, dibenzofuran derivatives or bridged carbazole derivatives.

* * * * *